US012778881B2

(12) United States Patent
Pala et al.

(10) Patent No.: US 12,778,881 B2
(45) Date of Patent: Nov. 3, 2026

(54) CILIA-TARGETING NANOPARTICLES

(71) Applicant: Chapman University, Orange, CA (US)

(72) Inventors: Rajasekharreddy Pala, Orange, CA (US); Surya M. Nauli, Orange, CA (US)

(73) Assignee: Chapman University, Orange, CA (US)

( * ) Notice: Subject to any disclaimer, the term of this patent is extended or adjusted under 35 U.S.C. 154(b) by 0 days.

(21) Appl. No.: 17/105,949

(22) Filed: Nov. 27, 2020

(65) Prior Publication Data

US 2021/0259954 A1 Aug. 26, 2021

Related U.S. Application Data

(60) Provisional application No. 62/941,208, filed on Nov. 27, 2019.

(51) Int. Cl.

| | |
|---|---|
| ***A61K 9/00*** | (2006.01) |
| ***A61K 9/50*** | (2006.01) |
| ***A61K 9/51*** | (2006.01) |
| ***A61K 31/55*** | (2006.01) |
| ***A61K 39/395*** | (2006.01) |
| ***A61P 9/12*** | (2006.01) |
| ***C07K 16/28*** | (2006.01) |
| *A61K 39/00* | (2006.01) |

(52) U.S. Cl.

CPC .......... *A61K 9/0009* (2013.01); *A61K 9/5015* (2013.01); *A61K 9/5031* (2013.01); *A61K 9/5115* (2013.01); *A61K 9/5153* (2013.01); *A61K 31/55* (2013.01); *A61K 39/39533* (2013.01); *A61P 9/12* (2018.01); *C07K 16/286* (2013.01); *A61K 2039/505* (2013.01)

(58) Field of Classification Search

CPC .. A61K 9/0009; A61K 9/5015; A61K 9/5031; A61K 9/5115; A61K 9/5153; A61K 31/55; A61K 39/39533; A61K 2039/505; A61K 9/5146; A61P 9/12; C07K 16/286; C07K 2317/34

See application file for complete search history.

(56) References Cited

U.S. PATENT DOCUMENTS

| | | | | |
|---|---|---|---|---|
| 6,420,347 B1 * | 7/2002 | Jacobus | A61K 31/70 | 514/47 |
| 2007/0128707 A1 * | 6/2007 | Rorrer | B82Y 5/00 | 359/245 |
| 2009/0191162 A1 * | 7/2009 | Lapidot | A61P 29/00 | 435/375 |
| 2010/0273190 A1 * | 10/2010 | Harris | C07K 14/705 | 530/387.9 |
| 2011/0081296 A1 * | 4/2011 | Barr | G01N 33/6842 | 424/9.2 |
| 2013/0123613 A1 * | 5/2013 | Trembly | A61B 6/12 | 600/12 |
| 2014/0023584 A1 * | 1/2014 | Yamauchi | G01N 33/53 | 435/7.1 |
| 2015/0157584 A1 * | 6/2015 | Guan | A61K 31/661 | 435/375 |
| 2018/0110887 A1 * | 4/2018 | Alphandery | A61K 49/1887 | |
| 2018/0128821 A1 * | 5/2018 | Bao | G01N 33/54306 | |
| 2018/0185511 A1 * | 7/2018 | Woodworth | A61K 47/6937 | |

FOREIGN PATENT DOCUMENTS

| | | | |
|---|---|---|---|
| WO | 2017/165663 * | 9/2017 | |
| WO | WO-2017165663 A1 * | 9/2017 | |
| WO | 2017/173103 * | 10/2017 | |
| WO | WO-2017173103 A1 * | 10/2017 | A61K 31/135 |

OTHER PUBLICATIONS

Wang. The effect of surface poly(ethylene glycol) length on in vivo drug delivery behaviors of polymeric nanoparticles. Biomaterials . 2018 (Year: 2018).*

Plouffe (Probing the Constitutive Activity Among Dopamine D1 and D5 Receptors and Their Mutants. Methods of Enzymology. 2010) (Year: 2010).*

Atkinson (Dopaminergic signaling within the primary cilia in the renovascular system. Frontiers in Physiology. Apr. 16, 2015). ( Year: 2015).*

Yallapu (PEG-Functionalized Magnetic Nanoparticles for Drug Delivery and Magnetic Resonance Imaging Applications. Pharm Res. 2010.) (Year: 2010).*

Weimbs (Emerging targeted strategies for the treatment of autosomal dominant polycystic kidney disease. CKJ Review. 2018.) ( Year: 2018).*

Kathem (Ciliotherapy: A Novel Intervention in Polycystic Kidney Disease. Pharmacy Faculty Articles and Research. 2014.) (Year: 2014).*

Pala et al., "Personalized Nanotherapy by Specifically Targeting Cell Organelles To Improve Vascular Hypertension"; Nano Lett. 2019, 9:904-914.

Pala et al., "Ciliotherapy: Remote Control of Primary Cilia Movement and Function by Magnetic Nanoparticles", ACS Nano 2019, 13:555-3572.

(Continued)

*Primary Examiner* — Michael G. Hartley

*Assistant Examiner* — Samantha L Mejias

(74) *Attorney, Agent, or Firm* — K&L Gates LLP; Brian J. Novak; Giorgios N. Kefallinos

(57) ABSTRACT

Disclosed herein are cilia-targeting nanoparticles and methods of treating ciliopathies.

15 Claims, 120 Drawing Sheets

Specification includes a Sequence Listing.

(56) References Cited

OTHER PUBLICATIONS

Zeier M et al. "Elevated blood pressure profile and left ventricular mass in children and young aduts with autosomal dominant polycystic kidney disease," J Am Soc Nephrol 3:1451-1457, 1993.
Oflaz H et al., "Biventricular diastolic dysfunction in patients with autosomal-dominant polycystic kidney disease," Kidney Int 68:2244-2249, 2005.
Bell Pe et al. "Hypertension in autosomal dominant polycystic kidney disease," Kidney Int 34:683-690, 1988.
Chapman AB et al. "The renin-angiotensin-aldosterone system and autosomal dominant polycystic kidney disease," New Eng J Med 323:1091-1096, 1990.
Ecder T and Schrier RW "Hypertension in autosomal-dominant polycystic kidney disease: early occurrence and unique aspects," J Am Soc Nephrol 12:194-200, 2001.
Almeida EA et al. "Tissue Doppler imaging in the evaluation of left ventricular function in young adults with autosomal dominant polycystic kidney disease," Am J Kidney Dis 47:587-592, 2006.
Cui W et al. "Self-assembled smart nanocarriers for targeted drug delivery," Adv Mater 28L1302-1311, 2016.
Polo E et al. "Advances toward more efficient targeted delivery of nanoparticles in vivo: understanding interactions between nanoparticles and cells," ACS Nano 11:2397-2402, 2017.

* cited by examiner

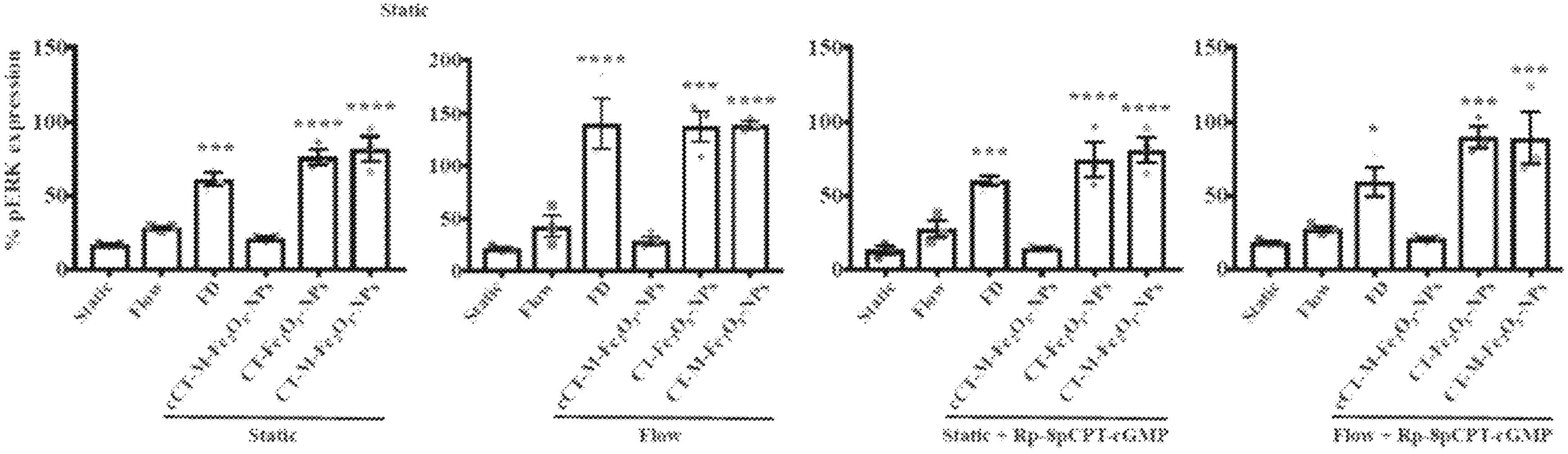
Figure 29D
Flow → Primary Cilia → Intracellular $Ca^{2+}$ → NO → cGMP → PKG → MAP kinase → [Cardiovascular Effect]
CT-$Fe_2O_3$-NPs ↗
Figure 29E
Figure 30A From Figure 34F-1

| | PI | annexin-V | PI/annexin |
|---|---|---|---|
| No Staining | 0.0±0.0 | 0.6±0.3 | 3.1±1.4 |
| Positive Ctrl | 0.0±0.0 | 1.1±1.1 | 98.9±1.1 |
| Negative Ctrl | 3.2±1.6 | 0.2±0.2 | 0.0±0.0 |
| CT-Fe$_2$O$_3$-NPs | 2.3±0.7 | 1.2±0.1 | 1.9±0.1 |

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:

-continued

```
<223> OTHER INFORMATION: Control scrambled morpholine sequence

<400> SEQUENCE: 1

cctcttacct cagttacaat ttata                                    25


<210> SEQ ID NO 2
<211> LENGTH: 24
<212> TYPE: DNA
<213> ORGANISM: Artificial Sequence
<220> FEATURE:
<223> OTHER INFORMATION: Pkd2 morpholino sequence

<400> SEQUENCE: 2

aggacgaacg cgactgggct catc                                     24
```

CILIA-TARGETING NANOPARTICLES

CROSS-REFERENCE TO RELATED APPLICATIONS

This application claims the benefit of U.S. Provisional Patent Application 62/941,208 filed Nov. 27, 2020, which is incorporated by reference herein in its entirety.

FEDERALLY SPONSORED RESEARCH OR DEVELOPMENT

This invention was made with government support under Grant No. HL131577 awarded by the National Institutes of Health and Grant No. W81XWH-14-1-0464 awarded by the Department of Defense. The government has certain rights in the invention.

BACKGROUND

The present disclosure generally relates to the field of biomedical devices. More particularly, the present disclosure relates to the synthesis of cilia targeting nanoparticle devices.

Autosomal dominant polycystic kidney disease (ADPKD) is the most common genetic kidney disease with the predominant form resulting from mutations in the genes Pkd1 and Pkd2. Although hypertension can be common in chronic kidney diseases, the pathogenesis of hypertension in ADPKD is unique. Hypertension in ADPKD is a ciliopathy with an average age onset of 30 years. As a result, many complications such as left ventricular hypertrophy occur earlier. In the age-matched controls from a general population, higher ambulatory blood pressure and left ventricular mass index were observed in ADPKD patients, indicating that treatment is actually required-even in normo-tensive patients.

The field of nanomedicine is a promising future in providing huge clinical impacts on advanced disease management and personalized medicine. Nanoparticles (NPs) have been used for targeted delivery at a desired site and a sustained release of a drug, which decreases the overall toxicity by delivering a smaller drug dosage. A possible approach to target primary cilia with nanoparticles with cilia specific antibody targeting. This technology allows researchers to cure several ciliopathies by changing therapeutic composition in this targeting system.

Ciliopathies are diseases caused by abnormal function or structure of primary cilia. Ciliopathies include the expanding spectrum of kidney, liver, and cardiovascular disorders. Ciliopathic patients are characterized with polycystic kidney disease (PKD) and associated with hypertension. Endothelial cilia are mechanical switches to initiate biosynthesis and release of nitric oxide (NO). Endothelial cilia therefore act as local regulators of blood pressure. Focal increases in blood pressure activates cilia and induces NO release, which in turn induces vasodilation. Abnormal endothelial cilia are therefore associated with vascular hypertension. Unfortunately, there is currently no cilia-targeted therapy available to treat hypertension in PKD patients. This is mainly a result of the lack of a specific drug that can target cilia.

SUMMARY

Disclosed herein are compositions comprising cilia-targeting nanoparticles, wherein the cilia-targeting nanoparticles comprise a core nanoparticle, oleic acid optionally coating the core, a polyethylene glycol (PEG), and a cilia-targeting molecule.

In some embodiments, the core nanoparticle is a polymeric nanoparticle or a metal nanoparticle. In some embodiments, the polymeric nanoparticle is a poly lactic-co-glycolic acid (PLGA) nanoparticle. In some embodiments, the metal nanoparticle is a gold (Au) nanoparticle. In some embodiments, the metal nanoparticle is a magnetic nanoparticle. In some embodiments, the metal nanoparticle is an iron oxide ($Fe_2O_3$) nanoparticle.

The composition according to claim 1, wherein the PEG is an activated PEG. In some embodiments, the activated PEG has a molecular weight from 3,000 to 10,000. In some embodiments, the activated PEG has a molecular weight from 4,000 to 8,000.

In some embodiments, the cilia-targeting molecule is an antibody. In some embodiments, the cilia-targeting molecule is an antibody specific for dopamine-receptor type-5.

In some embodiments, the cilia-targeting nanoparticle further comprises a pharmaceutical agent.

Also disclosed herein are methods of treating a ciliopathy in a subject in need thereof comprising administering a cilia-targeting nanoparticle disclosed herein. In some embodiments, the ciliopathy is a kidney disorder, a liver disorder, or a cardiovascular disorder. In some embodiments, the ciliopathy is Alstrom syndrome, Bardet-Biedl syndrome, Joubert syndrome, Meckel-Gruber syndrome, nephronophthisis, orofaciodigital syndrome, Senior-Loken syndrome, polycystic kidney disease (ADPKD and ARPKD), primary ciliary dyskinesia (Kartagener syndrome), asphyxiating thoracic dysplasia (Jeune syndrome), Marden-Walker syndrome, situs inversus/isomerism, cono-renal syndrome, Ellis-van Creveld syndrome, juvenile mycoclonic epilepsy, polycystic liver disease, and retinitis pigmentosa. In some embodiments, the ciliopathy is treated by reducing hypertension.

In some embodiments, wherein if the cilia-targeting nanoparticles are magnetic nanoparticles, the method further comprises application of a magnetic force to a treatment region in the subject.

BRIEF DESCRIPTION OF THE DRAWINGS

FIG. 2A depicts fluorescence microscopic imaging of DR-5 localization on primary cilia. FIGS. 2B-D depicts TEM images (FIG. 2B), hydrodynamic size distribution/DLS (FIG. 2C), and zeta-potential (FIG. 2D) of DAu and PLGA NPs before and after different surface functionalization. FIG. 2E depicts SDS-PAGE image showing the incorporation of DR-5 antibody to the DAu and PLGA NPs. The bar graph shows the DR-5 antibody concentrations in the pre- and post-conjugation solutions quantified by measuring the absorbance at 280 nm. FIGS. 2F-G depict fenoldopam-loading (FIG. 2F) and fenoldopam-releasing profiles (FIG. 2G) of CT-DAu-NPs and CT-PLGA-NPs. FIG. 2H presents photographs showing the synthesized powders of functional CT-DAu-NPs and CT-PLGA-NPs and their dispersion forms in distilled water. n=3 for all experiments; DR-5 localization was performed in 3 independent experiments from 3 separate coverslips. *$p<0.05$. Statistical analysis was performed using ANOVA followed by a Bonferroni post hoc test.

FIG. 3A depicts DIC and fluorescence microscopic imaging of live cells perfused with CT-DAu-NPs (upper panel) and CT-PLGA-NPs (lower panel) for 2 h of time at a constant flow speed. Representative line graphs showing the binding capacity of CT-DAu-NPs (left panel) and CT-PLGA-NPs (right panel) to the cilia and cell membrane. Fluorescence NPs were measured in intensity per area ($I/\mu m^2$). FIG. 3B depicts representative fluorescence imaging showing the cilia when treated with different treatments, and their length measurements were represented in the bar graph. n=3 for all experiments if not represented in dot plot. ****p<0.0001. Statistical analysis was performed using ANOVA followed by a Bonferroni post hoc test.

FIG. 4A depicts Fura-2AM ratiometric images showing the changes in the intracellular $Ca^{2+}$ concentrations when cells treated with different treatments under a fluid-shear force of 0.5 dyn/$cm^2$. The gradient bar indicates the levels of $Ca^{2+}$. FIG. 4B depicts DAF-AM radiometric images showing the changes in the intracellular NO productions when cells treated with different treatments under a fluid-shear force of 0.5 dyn/$cm^2$. The gradient bar indicates the levels of NO. FIG. 4C depicts single-live cell imaging showing the responses to different treatments. DIC imaging used for tracking a cilium. The induction of flow causes bending of cilium and a subsequent influx of $Ca^{2+}$. The GFP/mCherry ratio (pseudocolored) indicates normalized $Ca^{2+}$ levels. The rainbow color bar indicates the level of $Ca^{2+}$. n=3 for all experiments.

FIG. 5A depicts a scheme showing timeline for mutation induction and different treatment regimens. TX=tamoxifen. FIG. 5B depicts representative line graphs showing the changes in systolic (SBP) and mean arterial (MAP) blood pressures for 8 weeks. FIG. 5C depicts representative left ventricular pressure-volume (P-V) loops for control, fenoldopam, CT-DAu-NPs and CT-PLGA-NPs. FIG. 5D depicts P-V loops showing the stress response when treated with negative (diltiazem) or positive (epinephrine) chronotropic agents in different treatment groups. FIG. 5E depicts measurements of hearts from control and different treatments of mice were performed using electrocardiograms (ECG). Arrows indicate abnormal spacing. n=3 for all experiments. *p<0.05, p<0.01, *p<0.001, ****p<0.0001 compared to wild-type vehicle. #p<0.05, ##p<0.01, ###p<0.001, ####p<0.0001 compared to Pkd2 vehicle. Statistical analysis was performed using a second order quadratic polynomial Goodness of Fit followed with ANOVA using a Tukey's multiple comparisons test.

FIG. 6A depicts measurement of nitrate/nitrite (NOx) and blood urea nitrogen (BUN) concentrations. FIG. 6B assesses the heart hypertrophic effect, the thickness of the left ventricle was compared in whole-heart-cross sections using H&E staining. Representative microscopic images of H&E-stained sections of the left ventricle (LV), showing disparate pathological changes with different treatments. Representative microscopic images of Masson-trichrome-stained sections of LV; myocytes; collagenous tissue. FIG. 6C presents representative zoomed microscopic images of Masson-trichrome-stained sections of LV showing the amount of fibrosis. Representative line graphs showing the % of fibrosis in different treatment hearts. n=3 for all experiments if not represented in dot plot. *p<0.05, p<0.01, *p<0.001, ****p<0.0001 compared to wild-type vehicle. #p<0.05, ##p<0.01, ###p<0.001, ####p<0.0001 compared to Pkd2 vehicle. Statistical analysis was performed using ANOVA followed by a Bonferroni post hoc test.

FIG. 7E depicts a FTIR-spectra representing the functional groups associated with the functionalized nanoparticles. FIG. 7F depicts the HPLC spectra of known fenoldopam (reference compound) concentrations to obtain a standard approach and fenoldopam retention time (top). An HPLC calibration curve of fenoldopam is also shown (bottom). FIG. 7G depicts the fluorescence spectra of CT-DAu-NPs and CT-PLGA-NPs. n=3 for all experiments.

FIG. 12A depicts representative line and bar graphs showing the intracellular $Ca^{2+}$ levels with different treatments. FIG. 12B depicts representative line and bar graphs showing the intracellular NO levels with different treatments. Arrows indicate the start of fluid-flow. n=5 for all experiments. *p<0.05, p<0.01, *p<0.001, ****p<0.0001. Statistical analysis was performed using ANOVA followed by a Bonferroni post hoc test.

FIG. 16A depicts mean cytosolic and cilioplasmic $Ca^{2+}$ levels in line graphs. FIG. 16B depicts kymograph analyses of $Ca^{2+}$ signalling in the cell body and cilia in response to 0.5 dyn/$cm^2$ flow were performed. FIG. 16C depicts representative traces of changes in $Ca^{2+}$ speed, acceleration, speed intensity and mean intensity within a single cilium are shown. n=3 for all experiments.

FIG. 19A depicts representative phase contrast images showing Pkd2 zebrafish at 48 hours post-fertilization. Fish were injected with vehicle (PBS), CT-DAu-NPs or CT-PLGA-NPs. Bar graphs showing the measurements of curly tail, which is an indication of disease phenotype. FIG. 19B depicts H&E sections showing the Pkd2 zebrafish treated with different treatments. Cystic kidneys are denoted by asterisks, and the bar graph shows the percentage of zebrafish with cystic kidneys. FIG. 19C depicts the quantitation of the artery diameters shown in the bar graph. FIG. 19D depicts representative line graphs showing single-blood-cell speed and acceleration within the main dorsal artery. FIG. 19E depicts quantitation of blood circulation characteristics and cardiac measurements shown in the bar graphs to examine cardiovascular functions. n=3 for all experiments if not represented in dot plot. *$p<0.05$, $p<0.01$, *$p<0.001$, ****$p<0.0001$ compared to wild-type vehicle. #$p<0.05$, ##$p<0.01$, ###$p<0.001$, ####$p<0.0001$ compared to Pkd2 vehicle. Statistical analysis was performed using ANOVA followed by a Bonferroni post hoc test.

FIG. 20A depicts representative immunofluorescence images of primary cilia in arteries (A; white box) and veins (V; black box) are shown when the zebrafish treated with vehicle (PBS), CT-DAu-NPs or CT-PLGA-NPs. Average cilia length of the blood vessels is shown in the bar graphs. FIG. 20B depicts representative immunofluorescence images of primary cilia in the heart is shown. The square boxes show one cilium for visualization purposes. Average cilia length in the heart is shown in the bar graphs in zebrafish treated with vehicle (PBS), CT-DAu-NPs or CT-PLGA-NPs. n=50 for all experiments. *$p<0.05$, $p<0.01$, *$p<0.001$, ****$p<0.0001$ compared to wild-type vehicle. #$p<0.05$, ##$p<0.01$, ###$p<0.001$, ####$p<0.0001$ compared to Pkd2 vehicle. Statistical analysis was performed using ANOVA followed by a Bonferroni post hoc test.

FIG. 21A depicts pharmacokinetics profile of fenoldopam showing bolus injection (CT-DAu-NPs and CT-PLGA-NPs) and 30-minute infusion (fenoldopam-alone). FIG. 21B depicts area under the curve calculated as an indication of total plasma concentration of fenoldopam in an hour. n=3 for each group. *$p<0.05$ compared to fenoldopam-alone. Statistical analysis was performed using ANOVA followed by a Bonferroni post hoc test.

FIG. 25A depicts parameters of heart function were analysed. FIG. 25B depicts NP fluorescence quantified in major visceral organs to determine the NP bio-distribution at 24 and 72 hours after the intravenous injection. FIG. 25C depicts H&E histopathological analysis of major visceral organs from different treatments, n=5 mice for all experiments. *$p<0.05$, $p<0.01$, *$p<0.001$, ****$p<0.0001$ compared to wild-type vehicle. #$p<0.05$, ##$p<0.01$, ###$p<0.001$, ####$p<0.0001$ compared to Pkd2 vehicle. Statistical analysis was performed using ANOVA followed by a Bonferroni post hoc test.

FIG. 26A depicts line graphs showing the changes in systolic (SBP) and mean arterial (MAP) blood pressures when IFT88 mice treated with different treatments for 8 weeks. FIG. 26B depicts representative left ventricular pressure-volume (P-V) loops from treatment with control (PBS), fenoldopam, CT-DAu-NPs or CT-PLGA-NPs. FIG. 26C depicts representative loop diagrams showing the LVV and LVP relationship without (vehicle; PBS) and with stressors. Stress was achieved with either epinephrine (Epi) or diltiazem (DIz). FIG. 26D depicts representative ECGs of the hearts over a 5-second duration. Arrows indicate uneven heart beats. ****$p<0.0001$ compared to wild-type vehicle. Statistical analysis was performed using a second order quadratic polynomial Goodness of Fit followed with ANOVA using a Tukey's multiple comparisons test.

FIG. 27A depicts reconstructed fluorescence images of cells showing DR5 localization to the primary cilium. FIG. 27B depicts an SDS-PAGE image showing a reduction in the amount of antibody in the supernatant before and after the conjugation reaction. The bar graph shows the antibody concentrations in the pre- and post-conjugation solutions quantified by measuring the A280. FIG. 27C depicts hysteresis loops of bare $Fe_2O_3$—NPs and the CT-M-$Fe_2O_3$—NPs showing the superparamagnetic characteristics of the CT-M-$Fe_2O_3$—NPs in the dispersed form. The inset photograph shows the particles dispersed in water with and without magnetic separation. FIG. 27D depicts TEM and selected area electron diffraction (SAED) micrographs showing bare $Fe_2O_3$-NPs and the CT-M-$Fe_2O_3$—NPs. FIG. 27E depicts a release profile of fenoldopam from the CT-M-$Fe_2O_3$—NPs in PBS was compared using a dialysis method and magnetic rotations. n=3 for all experiments; ****, $p<0.0001$ between groups.

FIG. 28A depicts a single-cell-single-cilium analysis performed in a live cell to quantify the targeting specificity of the CT-$Fe_2O_3$—NPs at different time points (0 to 120 min). The top panel shows DIC images to confirm the presence of a cilium and fluorescence images to verify the CT-$Fe_2O_3$—NP specificity. The bottom panel shows the fluorescence images of the CT-$Fe_2O_3$—NPs alone. The CT-$Fe_2O_3$—NP fluorescence intensity per area (I/μ$m^2$) was quantified in cilia vs. the cell body and the cell body vs. background fluorescence. FIG. 28B depicts Prussian blue staining confirming the direct and specific binding of the CT-$Fe_2O_3$—NPs to the primary cilia. FIG. 28C depicts fluorescence images showing that fenoldopam and the CT-$Fe_2O_3$—NPs increased the cilia length (16 h of treatment) compared with controls (PBS treatment or cCT-$Fe_2O_3$—NPs). The ciliary marker acetylated-α-tubulin and a nuclear marker, DAPI, were used. FIG. 28D depicts representative dot-plotted bar graph showing the ciliary lengths measured in cells receiving different treatments (acquired from 5 preparations in each group; a minimum of 10 cilia were randomly selected from each preparation). FIG. 28E depicts an external magnetic field acting on the CT-$Fe_2O_3$—NPs (CT-M-$Fe_2O_3$—NPs) induced passive cilia movements. The image was generated and compiled from 5 seconds of cilia movement. FIG. 28F depicts $5HT_6$-mCherry-G-GECO1.0 expressed in LLC-PK1 cells to measure cytosolic and intraciliary $Ca^{2+}$ signalling. GFP was used to measure changes in $Ca^{2+}$ signals, mCherry was used to normalize motion artefacts, and DIC was used to track cilia movement. The GFP/mCherry ratio (pseudocolored) indicates normalized $Ca^{2+}$ levels. Images of cells before and after challenge with either fluid flow (CT-$Fe_2O_3$—NPs) or the magnetic field (CT-M-$Fe_2O_3$—NPs) are shown (N=6, 30 fps). The gradient bar shows the $Ca^{2+}$ levels. FIG. 28G depicts an image of the cumulative intensity profile (achieved by ND acquisition, Nikon system) shows high cellular and ciliary $Ca^{2+}$ levels when cells were exposed to an external magnetic force.

FIG. 28H depicts average cytosolic and cilioplasmic $Ca^{2+}$ levels (in arbitrary units). FIG. 28I depicts kymograph analysis of $Ca^{2+}$ signalling in the cell body and cilia performed in cells treated with control (cCT-M-$Fe_2O_3$—NPs) and CT-M-$Fe_2O_3$—NPs. The gradient bar shows $Ca^{2+}$ levels. In all cases, vehicle (PBS) and superparamagnetic $Fe_2O_3$—NPs without loaded drug in the absence (cCT-$Fe_2O_3$—NPs) or presence (cCT-M-$Fe_2O_3$—NPs) of the magnetic field were used as controls. n=4 samples per group in each study. ****, p<0.0001 between groups.

FIGS. 29A-E depict measurements of cGMP and phosphorylated ERK levels. FIG. 29A depicts intracellular cGMP levels were quantified in cells treated with PBS (vehicle), fenoldopam and different types of CT-NPs. FIG. 29B depicts percent expression of NOS under static and flow conditions. FIG. 29C depicts representative immunoblots of cell lysates collected before (static) and after fluid-shear stress (flow) in the absence or presence of the PKG inhibitor Rp-8pCPT-cGMP. FIG. 29D depicts immunoblot data for p-ERK are shown in dot-plotted bar graphs. FIG. 29E depicts the proposed signalling pathway. n=4 samples per group in each study; *, p<0.05; , p<0.01; *, p<0.001; and ****, p<0.0001 compared with the control (static) group.

FIGS. 30A-E depict the use of CT-M-$Fe_2O_3$—NPs as therapeutic delivery agents in Pkd2 zebrafish. FIG. 30A) depicts photographs of zebrafish at 48 hours post-fertilization (hpf) for control (scrambled morpholino) and Pkd2 morphants exposed to PBS (vehicle), cCT-M-$Fe_2O_3$-NPs, CT-$Fe_2O_3$—NPs or CT-M-$Fe_2O_3$—NPs. FIG. 30B presents a bar graph showing the percentage of zebrafish with the curly tail phenotype. FIG. 30C depicts the quantitation of the artery diameters shown in the dot-plotted bar graph used as an arterial reactivity index. FIG. 30D depicts representative line graphs show single blood cell speed and acceleration parameters from the dorsal region of the main artery within the medial-posterior lateral trunk. FIG. 30E depicts quantitation of blood flow characteristics and cardiac parameters to examine cardiovascular functions. N=10-50 fish per group in each study; *, p<0.05; , p<0.01; *, p<0.001; and ****, p<0.0001 compared with the scrambled zebrafish. #, p<0.05; ##, p<0.01; ###, p<0.001; and ####, p<0.0001 compared with the Pkd2 morphants.

FIG. 31A depicts the timeline of the study using the endothelial-specific Pkd2 mutant. Cre recombination was activated at 1 week of age via daily intraperitoneal tamoxifen (TX) injections for five consecutive days. At 4 weeks of age, wild-type (Pkd2$^{flox}$ without Cre activation) and Pkd2 mice (Pkd2$^{flox}$ with Cre activation) were treated with the cCT-M-$Fe_2O_3$-NPs, CT-$Fe_2O_3$—NPs or CT-M-$Fe_2O_3$—NPs. Therapeutic delivery systems were administered intravenously, and mice were sacrificed 8 weeks later (at 12 weeks of age), unless indicated otherwise. FIG. 31B depicts plasma nitrate/nitrite and blood urea nitrogen (BUN) levels at the endpoint of the study. FIG. 31C depicts blood pressure measured at the end of each week for 8 consecutive weeks. Systolic blood pressure (SBP) and mean arterial pressure (MAP) are shown in the line graphs. FIG. 31D depicts representative immunofluorescence images of primary cilia from vascular endothelial cells showing red fluorescent NPs (arrows) and cilia lengths at 24 or 72 hours after the initial treatment. The insets show magnified views of cilia. FIG. 31E depicts cilia lengths (N=50; a minimum of 10 measurements were recorded for each mouse). FIG. 31F depicts representative loop diagrams showing the left ventricular volume (LVV) and pressure (LVP) relationship. FIG. 31G depicts LVV and LVP relationships in the absence (PBS or vehicle) and presence of stressors. Stress was achieved with either epinephrine (Epi; 4 μg/L for each mg of heart) or diltiazem (Dlz; 0.08 μg/L for each mg of heart). FIG. 31H presents representative electrocardiogram (ECG) traces of the hearts over a 5-second duration. Arrows indicate uneven heart rhythms. N=5 mice per group in each study, except for working heart studies (n=3 mice per group). *, p<0.05; , p<0.01; *, p<0.001; and ****, p<0.0001 compared with the wild-type mice. #, p<0.05; ##, p<0.01; ###, p<0.001; and ####, p<0.0001 compared with the Pkd2 mice.

FIG. 32A depicts sequential cross-sections of the same heart used for H&E (top panel) and Masson's trichrome (bottom panel) staining. With the exception of the muscle size, explicit differences in the morphology of the tissue were not observed using H&E staining. Fibrosis was evident in Masson's trichrome-stained sections. RV=right ventricle; LV=left ventricle. FIG. 32B depicts analyses of the sequential sections. The percent fibrosis was calculated from the fibrotic area per total cross-sectional area. FIG. 32C depicts Masson's trichrome staining of the left ventricle showing myocytes and collagenous fibrotic tissue. FIG. 32D depicts heart parameters calculated to determine changes in the physical characteristics of the hearts. FIG. 32E depicts localization of the NPs and length of cilia in myocytes. FIG. 32F depicts cilia length. N=5 mice per group in each study, except for working heart studies (n=3 mice per group); *, p<0.05; , p<0.01; *, p<0.001; and ****, p<0.0001 compared with the wild-type mice. #, p<0.05; ##, p<0.01; ###, p<0.001; and ####, p<0.0001 compared with the Pkd2 mice.

FIG. 33A depicts blood pressure measured for 60 minutes. SBP, MAP and heart rate (HR) are shown in the line graphs. FIG. 33B depicts survival curves for Pkd2 mice receiving different treatments for 8 weeks; mice that received repeated fenoldopam infusions only showed 40% mortality. FIG. 33C depicts an HPLC chromatogram of plasma spiked with an internal standard (SKF-38393; IS) and fenoldopam (FD). FIG. 33D depicts plasma concentration-time curves of the mean plasma fenoldopam concentrations measured in mice (N=3-5 animals) treated with the CT-M-$Fe_2O_3$—NPs or fenoldopam-alone. Fenoldopam was administered as a 1.0-μg/kg/min intravenous infusion for 30 minutes. FIG. 33E depicts blood pressure measured in mice that received different treatments at the end of each week for 8 consecutive weeks. SBP and MAP are shown in the line graphs. FIG. 33F depicts representative ECG traces of the hearts over a 5-second duration. Arrows indicate uneven heart rhythms. The corresponding loop diagrams show the LVV and LVP relationship without (PBS or vehicle) and with stressors. Stress was achieved with either epinephrine (Epi; 4 μg/L for each mg of heart tissue) or diltiazem (DIz; 0.08 μg/L for each mg of heart tissue). Unless indicated otherwise, n=4 mice per group in Pkd2 study, n=5 in IFT88 study; ****, $p<0.0001$ compared with the wild-type mice (without Cre activation).

FIG. 34A) presents a photograph of the synthesized CT-$Fe_2O_3$—NPs in powder and dispersed forms. FIG. 34B depicts the UV-visible spectra of different steps in the surface functionalization process for $Fe_2O_3$—NPs in dispersed form. FIG. 34C depicts hydrodynamic diameter measurements of bare $Fe_2O_3$—NPs with different surface modifications, as determined by DLS. FIG. 34D depicts Z-potentials showing the surface charges of bare $Fe_2O_3$—NPs with different surface modifications. FIG. 34E depicts XRD patterns of bare $Fe_2O_3$—NPs with different surface modifications. FIG. 34F depicts XPS patterns of bare $Fe_2O_3$—NPs with different surface modifications showing one complete and several more focused survey spectra, including the Fe 2p, C 1s, N 1 s and O 1s spectra. FIG. 34G depicts FTIR spectra showing the infrared signatures of bare $Fe_2O_3$—NPs with different surface modifications. FIG. 34H depicts fenoldopam retention time. An HPLC calibration curve of fenoldopam (reference standard) is also shown. FIG. 34I depicts Alexa Fluor 594 successfully conjugated to the antibody, as evidenced by the fluorescence excitation and emission spectra of the NPs. FIG. 34J depicts hydrodynamic size of NPs dispersed in PBS, DMEM/FBS and plasma. FIG. 34K depicts cellular toxicity visualized by DIC/fluorescence imaging. Annexin-V and propidium iodide (PI) were used as apoptotic and necrotic markers, respectively. FIG. 34L depicts toxicity quantified with flow cytometry. Data are tabulated for annexin-V, PI or annexin-V/PI positive cells for control (no staining), positive control (methanol permeabilization), negative control (no treatment) and NPs treated for 48 hours. N=3 samples for all experiments.

FIG. 35A depicts cytosolic $Ca^{2+}$ visualized with the $Ca^{2+}$-sensitive fluorescent dye Fura-2-AM. Radiometric images from 340 and 380 nm excitation wavelengths were captured at 50 fps. Numbers on the top of the representative images display the time in seconds(s). A subminimal fluid shear of 0.5 dyn/cm$^2$ was applied to the cells to induce $Ca^{2+}$ flux. The pseudocolor indicates $Ca^{2+}$ levels. FIG. 35B depicts average cytosolic $Ca^{2+}$ levels (in arbitrary units). Arrows indicate the commencement of flow or magnetic force. FIG. 35C depicts intracellular NO synthesis visualized with the NO-sensitive fluorescent dye DAF-AM. Effects of sub-minimal fluid shear stress showed greater NO production in treated cells than in control cells. The color intensity indicates NO levels. Numbers on the top of the representative images display the time in seconds(s). A sub-minimal fluid shear of 0.5 dyn/cm$^2$ was applied to the cells to induce NO flux. FIG. 35D depicts average NO levels. Arrows indicate the commencement of flow or magnetic force. In most cases, vehicle treatment (PBS treatment) and CT NPs without loaded drug (cCT-$Fe_2O_3$—NPs) were used as controls. n=5 samples per group in each study.

FIG. 39A depicts average cytosolic and cilioplasmic $Ca^{2+}$ levels. The presence of shear stress is represented by the background. FIG. 39B depicts Kymograph analyses of $Ca^{2+}$ signaling in the cell body and cilia were performed with controls or with the cCT-$Fe_2O_3$—NPs or CT-$Fe_2O_3$—NPs exposed to flow. FIG. 39C depicts representative traces of changes in $Ca^{2+}$ velocity, acceleration, speed intensity and mean intensity within a single cilium. The presence of shear stress is represented as the background. In all cases, vehicle (PBS) and the CT-$Fe_2O_3$—

NPs without loaded drug in the absence (cCTFe$_2$O$_3$—NPs) or presence (cCT-M-Fe$_2$O$_3$—NPs) of the magnetic field were used as controls; n=4 samples per group in each study.

Figure 40:
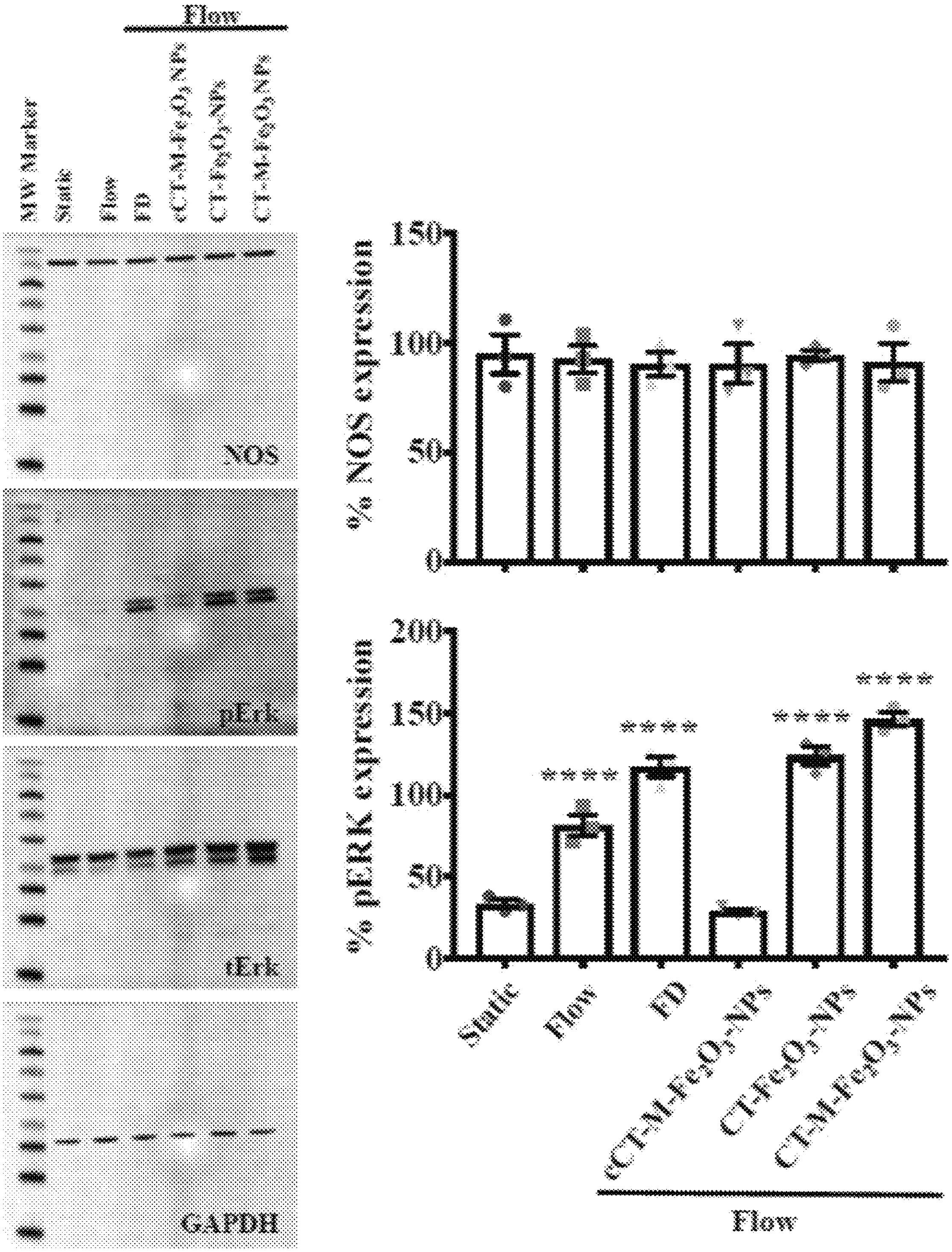

FIG. 40 depicts the effects of CT-Fe$_2$O$_3$—NPs on ERK phosphorylation in primary cultured cells. Representative immunoblots of endothelia show the % levels of NOS and phosphorylated ERK. *, p<0.05; , p<0.01; *, p<0.001; and ****, p<0.0001 compared with the control (static) group.

Figure 41A:
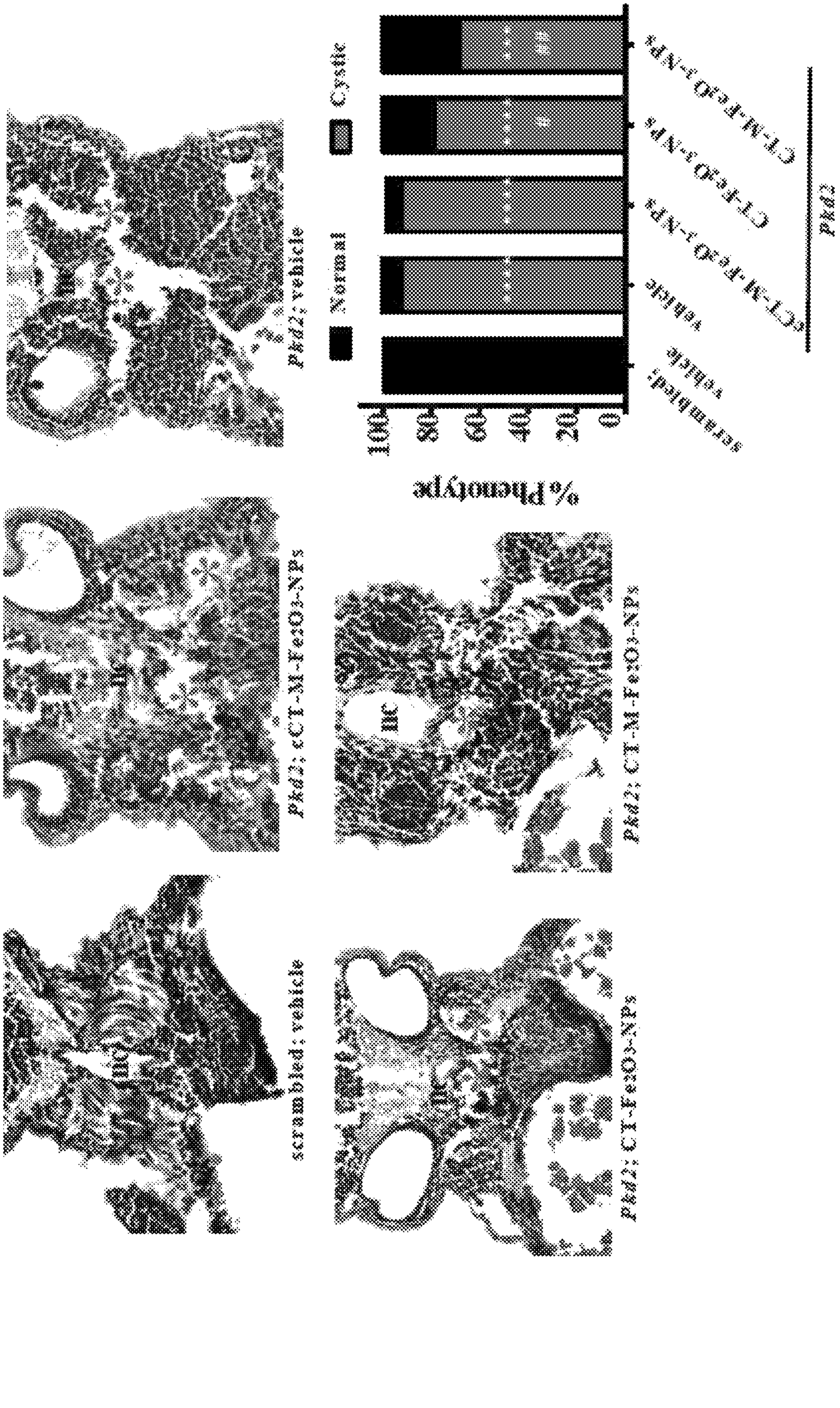
Figure 41B:
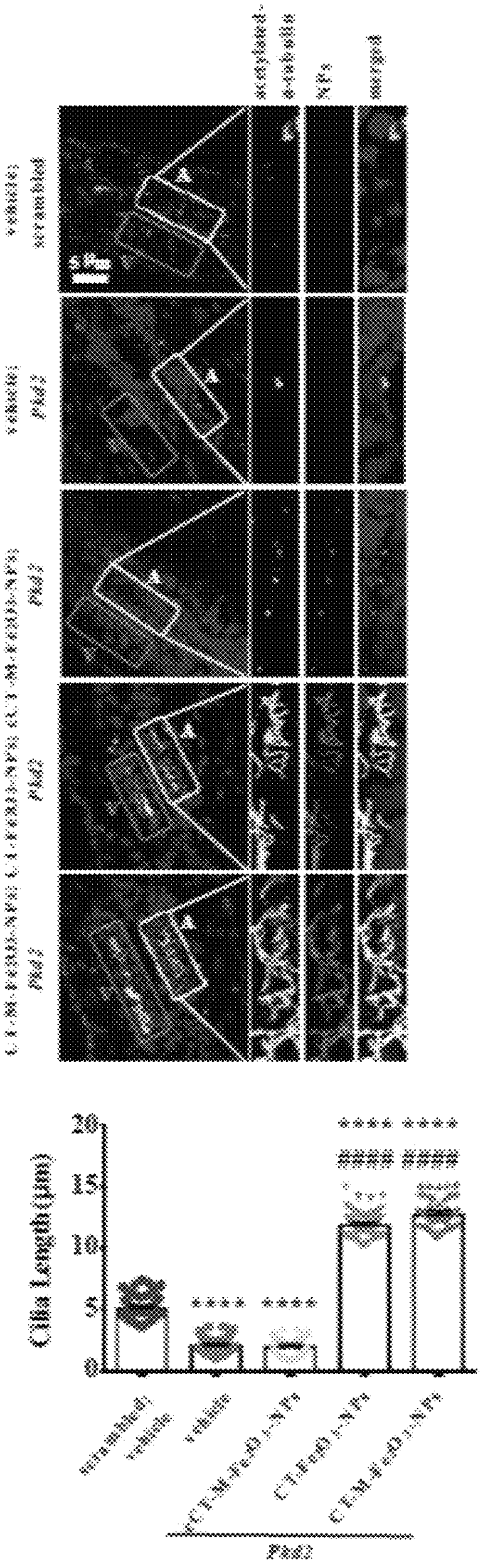
Figure 41C:
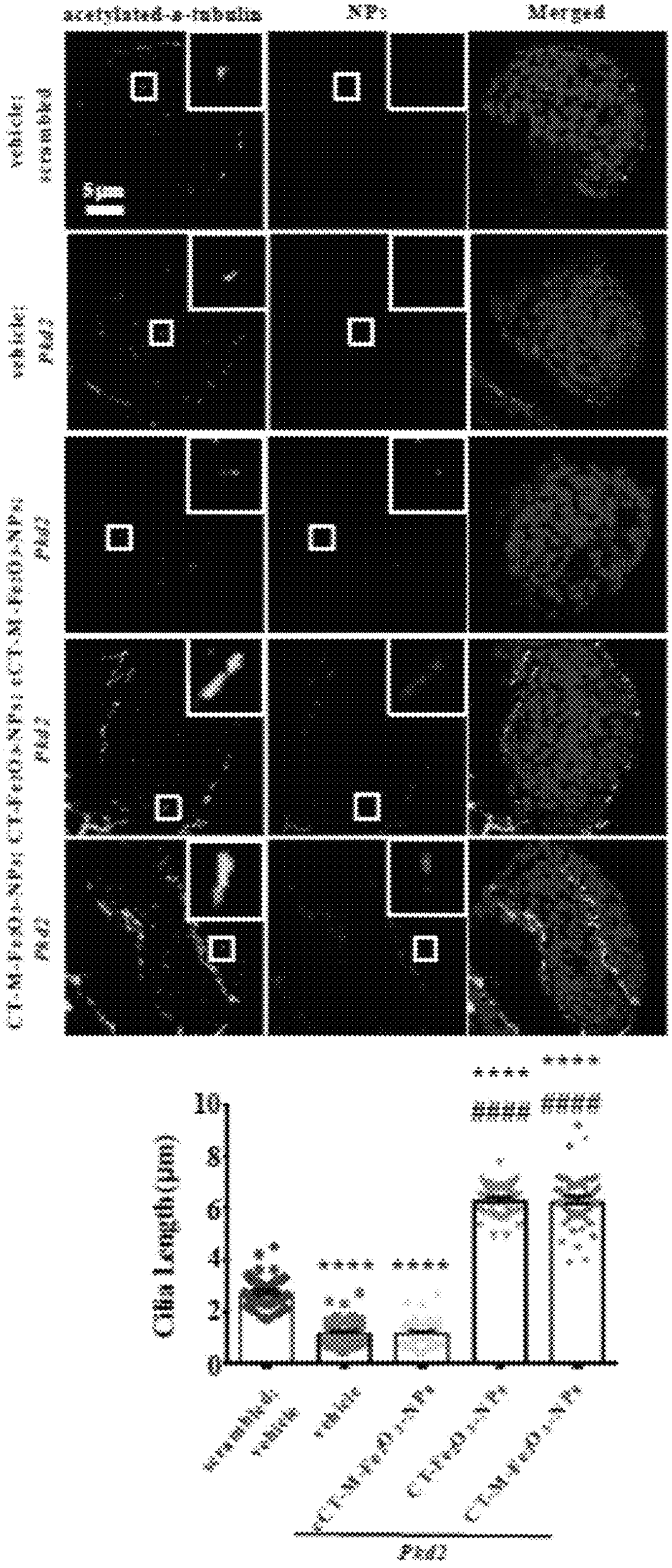

FIGS. 41A-C depicts CT-Fe$_2$O$_3$—NPs increasing the cilia length in Pkd2 zebrafish. FIG. 41A depicts H&E sections showing the notochord (nc) and renal nephron in scrambled and Pkd2 zebrafish treated with PBS, cCT-Fe$_2$O$_3$—NPs, CT-Fe$_2$O$_3$—NPs or CT-M-Fe$_2$O$_3$—NPs. Cystic kidneys are denoted by asterisks, and the bar graph shows the percentage of zebrafish with dilated or cystic nephrons. FIG. 41B depicts representative immunofluorescence images of primary cilia in arteries (A; white box) and veins (V; black box) of dorsal vessels are shown. The boxes were further magnified for better visualization. Average cilia length of the blood vessels is shown in the dot-plotted bar graphs. FIG. 41C depicts representative immunofluorescence images of primary cilia in myocytes throughout the heart. The boxes show one cilium for visualization purposes. Average cilia length in the heart is shown in the dot-plotted bar graphs. n=10-50 fish per group in each study; *, p<0.05; , p<0.01; *, p<0.001; and ****, p<0.0001 compared with the scrambled zebrafish. #, p<0.05; ##, p<0.01; ###, p<0.001; and ####, p<0.0001 compared with the Pkd2 morphants.

Figure 42A:
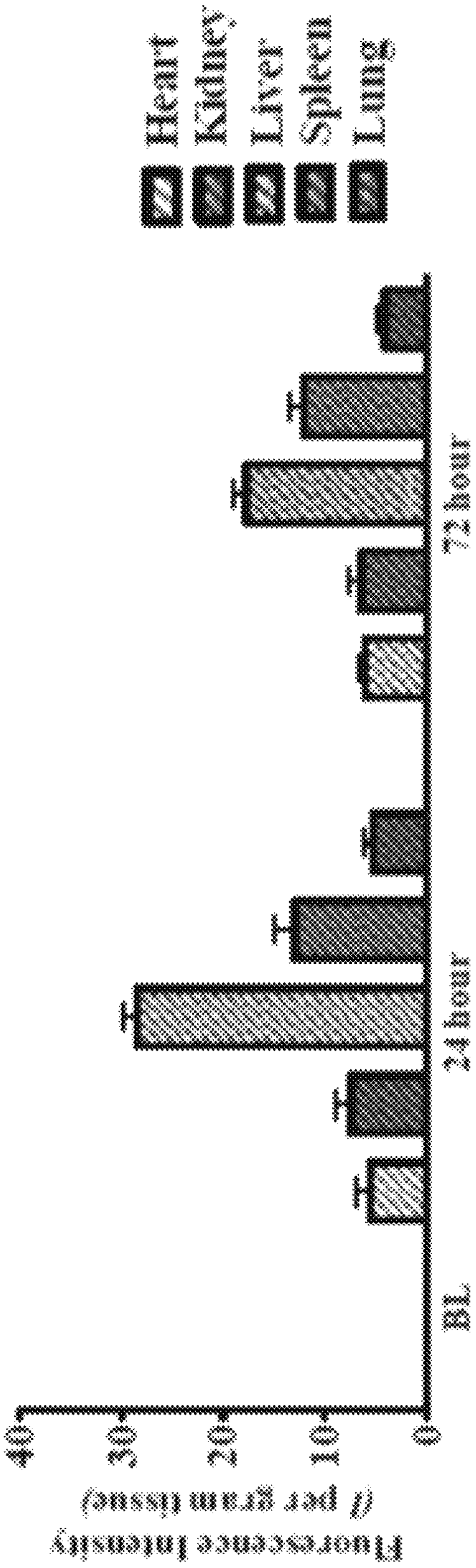
Figure 42B:
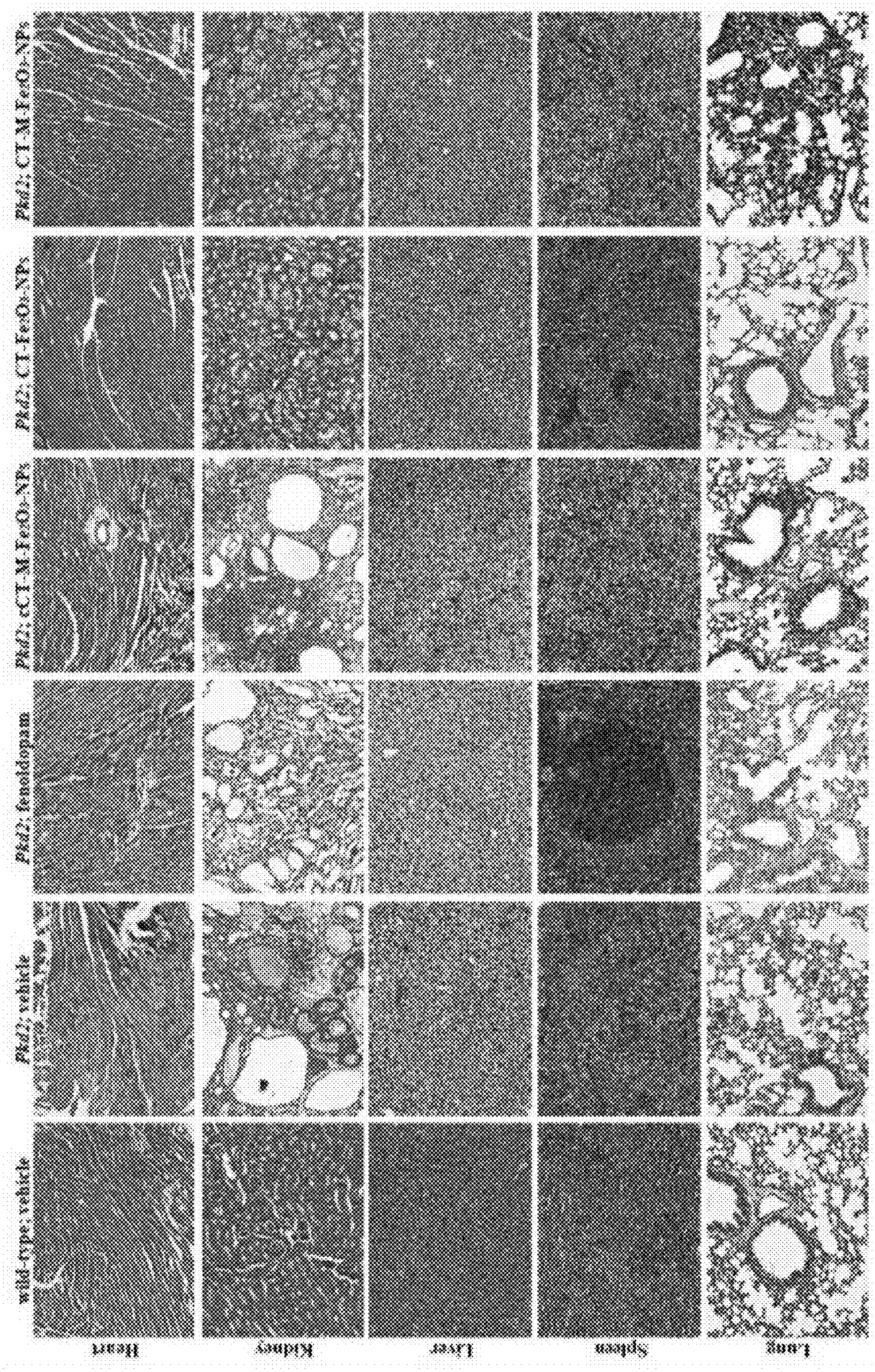

FIGS. 42A-B depict distribution and toxicology analyses of CT-Fe$_2$O$_3$—NPs. FIG. 42A depicts CT-Fe$_2$O$_3$—NPs fluorescence was quantified in major visceral organs to determine their biodistribution at 24 and 72 hours after the intravenous injection. Mice that did not receive an injection were used as a baseline (BL). FIG. 42B depicts a histopathological analysis of major visceral organs from Pkd2 mice performed using standard H&E staining did not reveal apparent signs of CT NP toxicity. n=5 mice per group in each study.

DETAILED DESCRIPTION

Disclosed herein are cilia-targeted (CT) nanoparticles (NPs) to serve as a precise therapeutic drug delivery system for pharmacological agents to treat ciliopathic vascular hypertension. Because primary cilia have a diameter of about 250 nm, NPs are a very promising vehicle for delivering drugs to the cilia. In one embodiment, magnetic nanoparticles (CT-Fe$_2$O$_3$-NPs) specifically target primary cilia in order to control movement, length, and function of cilia. Existing drugs can be specifically targeted to cilia for achieving maximum therapeutic outcome and reducing overall side effect via NPs deliveries.

The main differences between hypertension in general population and ciliopathic patients are as follows: First, the median age of hypertension is 32 years old in a ciliopathic patient compared to 50 years old in general population. Second, some ciliopathic patients show resistance to anti-hypertensive therapy. Third, serum nitrate/nitrite as an indicator for endothelial function is significantly lower in ciliopathic patients than that in the general hypertensive population. Fourth, focal vascular injuries, including death associated with aneurysm rupture, become very common in ciliopathic patients, probably because of the lack of the "local" blood-pressure regulation. In addition, secondary abnormalities in the heart and kidney are more apparent in ciliopathic hypertensive patients than in the general hypertensive population. Perhaps the most important clinical data that are commonly overlooked are that children with ciliopathy kidney disorder have hypertension as young as 18 months old.

Dopamine and its derivative fenoldopam have been used as experimental drugs in hypertensive patients with a ciliopathy. However, the use of dopamine and fenoldopam is limited due to their broad spectrum of physiological functions in the body. A very slow perfusion rate is required during the administration of fenoldopam to achieve a peripheral effect on primary cilia in mice, making it less ideal for use in humans. In these studies, fenoldopam was selected as the drug of choice due to its milder ciliary response compared with that of dopamine. Furthermore, as shown in the previous study, activation of dopamine receptors had very little or no effect on cells with very short cilia (Tg737), confirming the specificity of fenoldopam toward cilia function. Of note is that fenoldopam is a nonselective agent that we intended to delivery specifically to the cilia. In addition to its nonspecific effects to the adrenergic receptors, fenoldopam is a partial agonist that activates different subtypes of dopamine receptors. In general, the dopamine receptors (DR) are classified into D1 (increasing intracellular cAMP) and D2 (decreasing intracellular cAMP). The D1 family includes DR1 and DR5, whereas the D2 family consists of DR2, DR3, and DR4. Only DR5 is shown to be localized to cilia and involved in cilia length increase. Besides dopamine and fenoldopam, there are many other agents that can also increase cilia length. Unfortunately, the mechanisms by which these agents increase cilia length are neither known nor tested in ciliopathy models.

Primary cilia are involved in chemo and mechanosensing that transmit the extracellular signals into intracellular biochemical signaling. The chemosensory and mechanosensory functions of cilia are interconnected; chemicals that lengthen primary cilia enhances the mechanosensitivity of single cells. A cilium is a cell organelle that exposes itself to the extracellular lumen. This characteristic provides important access to target a cilium in cultured cells in vitro or in organ systems in vivo.

Figure 1:
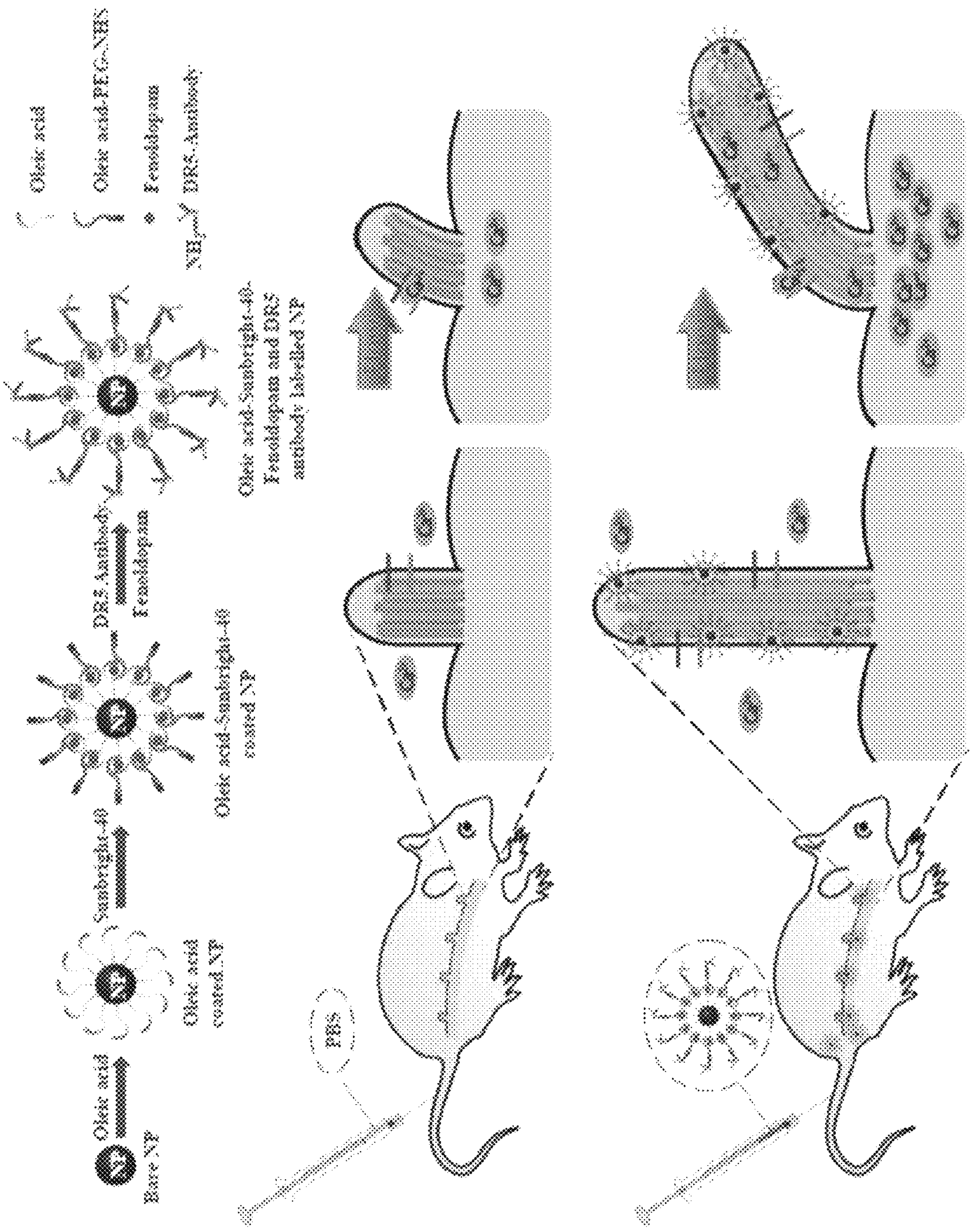
FIG. 1 depicts a schematic illustration of the design and functional applications of the cilia-targeted nanoparticle drug delivery systems (CTNDDS).

ACilia targeted nanoparticles (CTNPs) are synthesized following the scheme in FIG. 1, resulting in successful cilia-targeted NPs. The CTNPs comprise a core nanoparticle, oleic acid optionally coating the core, a polyethylene glycol coating, and a cilia-targeting molecule.

In some embodiments, the core nanoparticle is a polymeric nanoparticle, a metal nanoparticle, or a magnetic nanoparticle.

In some embodiments, the polymeric nanoparticle is formed of a biocompatible polymer. Biocompatible polymers include but are not limited to polystyrenes, poly (hydroxy acid), poly(lactic acid), poly(glycolic acid), poly (lactic acid-co-glycolic acid), poly(lactic-co-glycolic acid), poly(lactide), poly(glycolide), poly(lactide-co-glycolide), polyanhydrides, polyorthoesters, polyamides, polycarbonates, polyalkylenes, polyethylenes, polypropylene, polyalkylene glycols, poly(ethylene glycol), polyalkylene oxides, poly(ethylene oxides), polyalkylene terephthalates, poly (ethylene terephthalate), polyvinyl alcohols, polyvinyl ethers, polyvinyl esters, polyvinyl halides, poly(vinyl chloride), polyvinylpyrrolidone, polysiloxanes, poly(vinyl alcohols), poly(vinyl acetate), polyurethanes, co-polymers of polyurethanes, derivativized celluloses, alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulfate sodium salt, polymers of acrylic acid or methacrylic acid, copolymers of methacrylic acid, derivatives of methacrylic acid; poly(methyl methacrylate), poly(ethyl methacrylate), poly(butylmethacrylate), poly(isobutyl methacrylate), poly (hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(butyric acid), poly(valeric acid), poly(lactide-co-caprolactone), copolymers of poly (lactide-co-caprolactone), blends of poly(lactide-co-caprolactone), hydroxyethyl methacrylate (HEMA), copolymers of HEMA with acrylate, copolymers of HEMA with polymethylmethacrylate (PMMA), polyvinylpyrrolidone/vinyl acetate copolymer (PVP/VA), acrylate polymers/copolymers, acrylate/carboxyl polymers, acrylate hydroxyl and/or carboxyl copolymers, urethane polymers, silicone-urethane polymers, epoxy polymers, cellulose nitrates, polytetramethylene ether glycol urethane, polymethylmethacrylate-2-hydroxyethylmethacrylate copolymer, polyethylmethacrylate-2-hydroxyethylmethacrylate copolymer; polypropylmethacrylate-2-hydroxyethylmethacrylate copolymer, polybutylmethacrylate-2-hydroxyethyl-methacrylate copolymer, polymethylacrylate-2-hydroxyethylmethacrylate copolymer, polyethyl-acrylate-2-hydroxyethylmethacrylate copolymer, polypropylacrylate-2-hydroxymethacrylate copolymer, polybutylacrylate-2-hydroxyethylmethacrylate copolymer, copolymermethylvinylether maleicanhydride copolymer, poly(2-hydroxyethyl methacrylate) acrylate polymer/copolymer, acrylate carboxyl and/or hydroxyl copolymer, olefin acrylic acid copolymer, ethylene acrylic acid copolymer, polyamide polymers/copolymers, polyimide polymers/copolymers, ethylene vinylacetate copolymer, polycarbonate urethane, silicone urethane, polyvinylpyridine copolymers, polyether sulfones, polygalactin, poly-(isobutyl cyanoacrylate), poly(2-hydroxyethyl-L-glutamine); polydimethyl siloxane, poly(caprolactones), poly (ortho esters), polyamines, polyethers, polyesters, polycarbamates, polyureas, polyimides, polysulfones, polyacetylenes, polyethyeneimines, polyisocyanates, polyacrylates, polymethacrylates, polyacrylonitriles, polyarylates, and combinations, copolymers and/or mixtures of two or more of any of the foregoing.

In some embodiments, the polymeric nanoparticle is a poly lactic-co-glycolic acid (PLGA) nanoparticle.

In some embodiments, the metal nanoparticle is a gold nanoparticle.

In some embodiments, the metal nanoparticle is a magnetic nanoparticle. In some embodiments, the magnetic particle includes, but is not limited to, magnetite nanoparticles, superparamagnetic nanoparticles, and ferrimagnetic particles. In some embodiments, the magnetic nanoparticle is an iron-containing nanoparticle. In some embodiments, the nanoparticle is a $Fe_2O_3$ nanoparticle.

In some embodiments, the targeting molecule is an antibody. In some embodiments, the targeting molecule is an antibody specific for dopamine-receptor type-5 (DR-5).

In some embodiments, the CTNP further comprises one or more pharmaceutical agents. As used herein "pharmaceutical agent" is used interchangeably with "drug" or "active agent", and refers to pharmaceutical substances, including small molecule pharmaceuticals, biologicals and bioactive agents. Pharmaceutical agents can be naturally occurring, recombinant or of synthetic origin, including proteins, polypeptides, peptides, nucleic acids, organic macromolecules, synthetic organic compounds, polysaccharides and other sugars, fatty acids, and lipids. The pharmaceutical agents can fall under a variety of biological activity and classes, such as vasoactive agents, neuroactive agents, hormones, anticoagulants, immunomodulating agents, cytotoxic agents, antibiotics, antiviral agents, antigens, infectious agents, inflammatory mediators, hormones, and cell surface antigens.

In some embodiments, the pharmaceutical agent is an anti-hypertensive agent. In some embodiments, the pharmaceutical agent is a dopamine agonist including, but not limited to an adamantane (i.e., amantadine, memantine, rimantadine), an aminotetralin (i.e., 7-OH-DPAT, 8-OH-PBZI, rotigotine, UH-232), a benzazepine (i.e., 6-Br-APB, fenoldopam, SKF-38,393, SKF-77,434, SKF-81,297, SKF-82,958, SKF-83,959), an ergoline (i.e., bromocriptine, cabergoline, dihydroergocryptine, lisuride, lysergic acid diethylamide (LSD), pergolide), a dihydrexidine derivative (i.e., 2-OH-NPA, A-86,929, ciladopa, dihydrexidine, dinapsoline, dinoxyline, doxanthrine), A-68,930, A-77,636, A-412,997, ABT-670, ABT-724, aplindore, apomorphine, aripiprazole, bifeprunox, BP-897, CY-208,243, dizocilpine, etilevodopa, flibanserin, ketamine, melevodopa, modafinil, pardoprunox, phencyclidine, PD-128,907, PD-168,077, PF-219,061, piribedil, pramipexole, propylnorapomorphine, pukateine, quinagolide, quinelorane, quinpirole, RDS-127, Ro10-5824, ropinirole, rotigotine, roxindole, salvinorin A, SKF-89,145, sumanirole, terguride, umespirone, and WAY-100,635.

In some embodiments, the pharmaceutical agent is a D1-receptor agonist. In some embodiments, the D1-receptor agonist is fenoldopam, ibopamine, or stepholidine.

In some embodiments, the nanoparticles comprise a fatty acid coating coating between the core particle and the PEG coating. In some embodiments, the fatty acid coating is an oleic acid coating.

In some embodiments, the PEG coating comprises an activated PEG has a molecular weigh between 3,000 and 10,000. In another embodiment, the PEG has a molecular weight of between 4,000 and 8,000. In some embodiments, the PEG contains an NHS group. In some embodiments, the PEG is SUNBRIGHT® OE-040 CS (oleyl-O$(CH_2CH_2)_n$CO—$CH_2CH_2$—COO—NHS, PEG Mw 4,000) or SUNBRIGHT® OE-80 CS (oleyl-O$(CH_2CH_2)_n$CO—$CH_2CH_2$—COO—NHS, PEG Mw 8,000) (NOR Corporation).

In some embodiments, the cilia-targeting nanoparticles have a diameter, determined by dynamic light scattering, of less that 1 μm. In some embodiments, the cilia-targeting nanoparticles have a diameter of about 10-500 nm, about 10-400 nm, about 10-300 nm, about 10-200 nm, about 15-500 nm, about 15-400 nm, about 15-300 nm, about 15-200 nm, 20-500 nm, about 20-400 nm, about 20-300 nm, about 20-200 nm, about 25-150 nm, about 40-110 nm, or any range bound by these values.

Figure 3A:
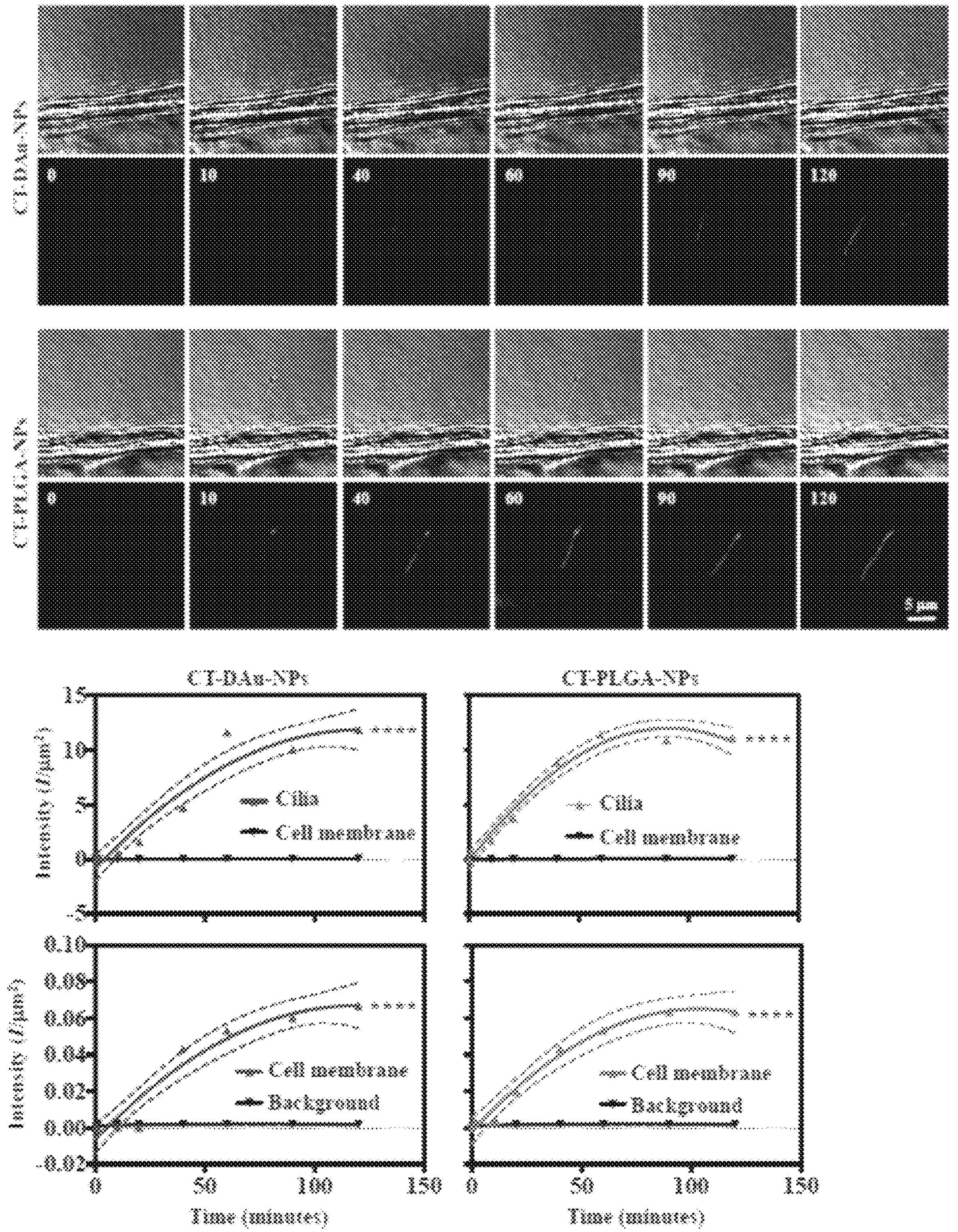
FIGS. 3A-B depicts in vitro fluorescence imaging of cilia targeted nanoparticles.
Figure 3B:
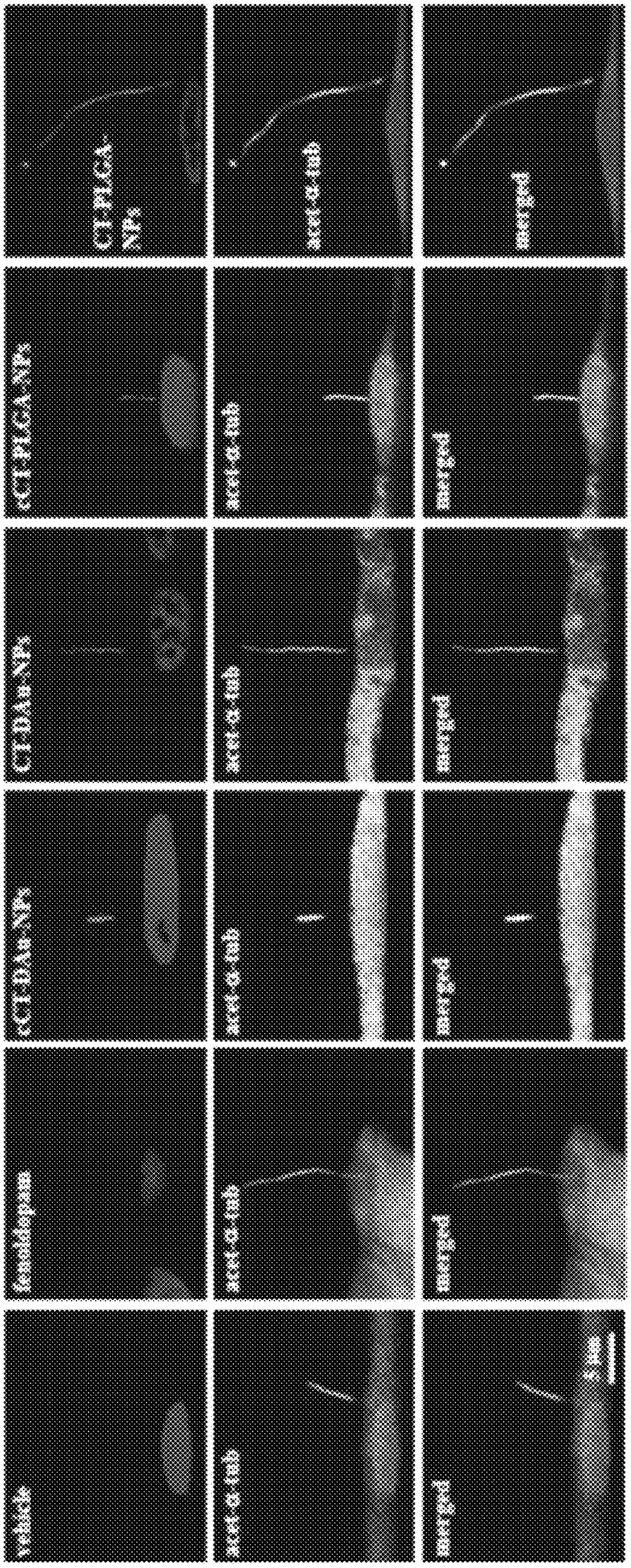
Figure 3B:
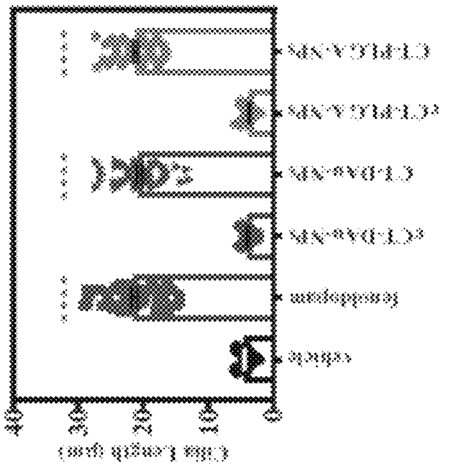
Figure 4A:
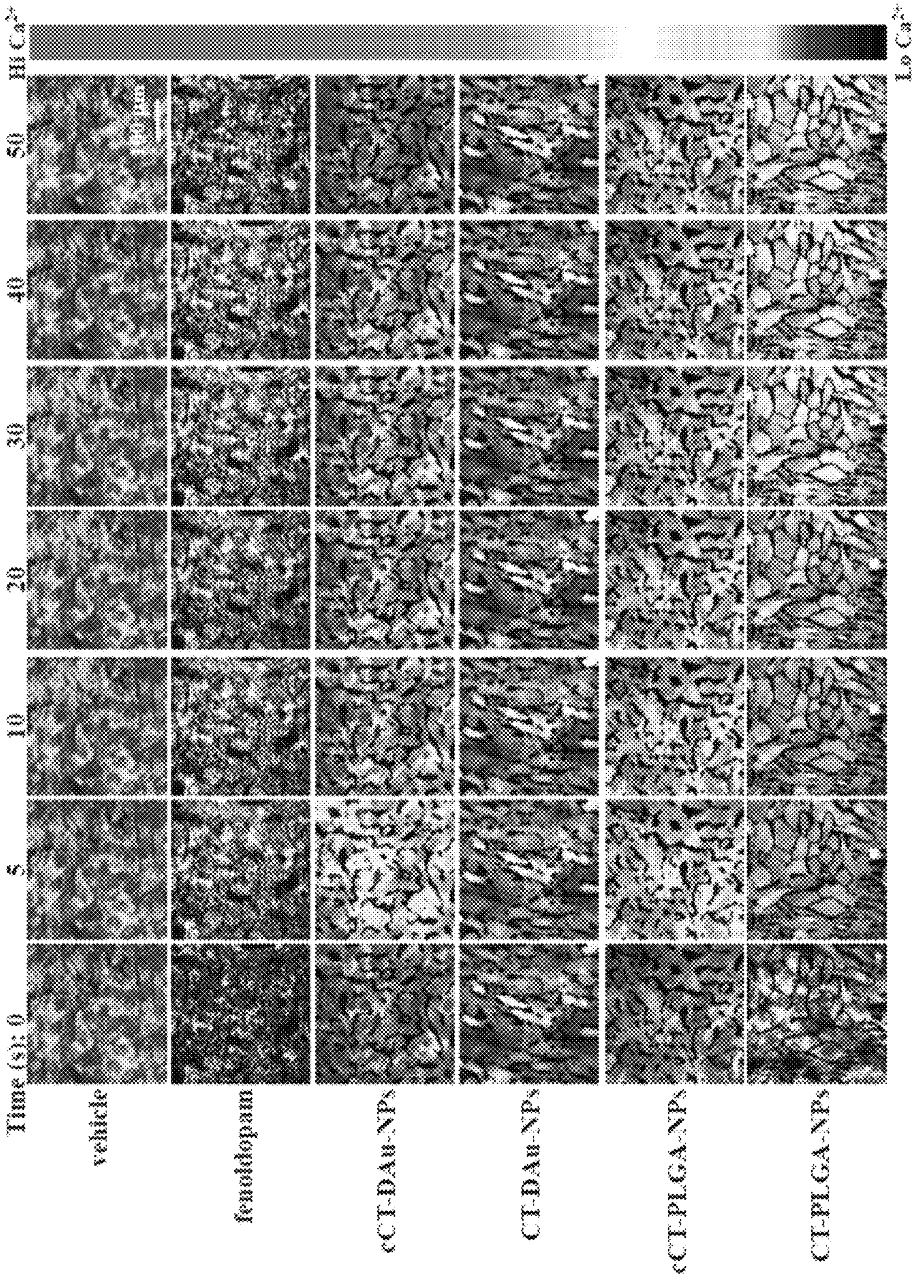
FIGS. 4A-C depicts cellular calcium ($Ca^{2+}$) and nitric oxide (NO) measurements.
Figure 4B:
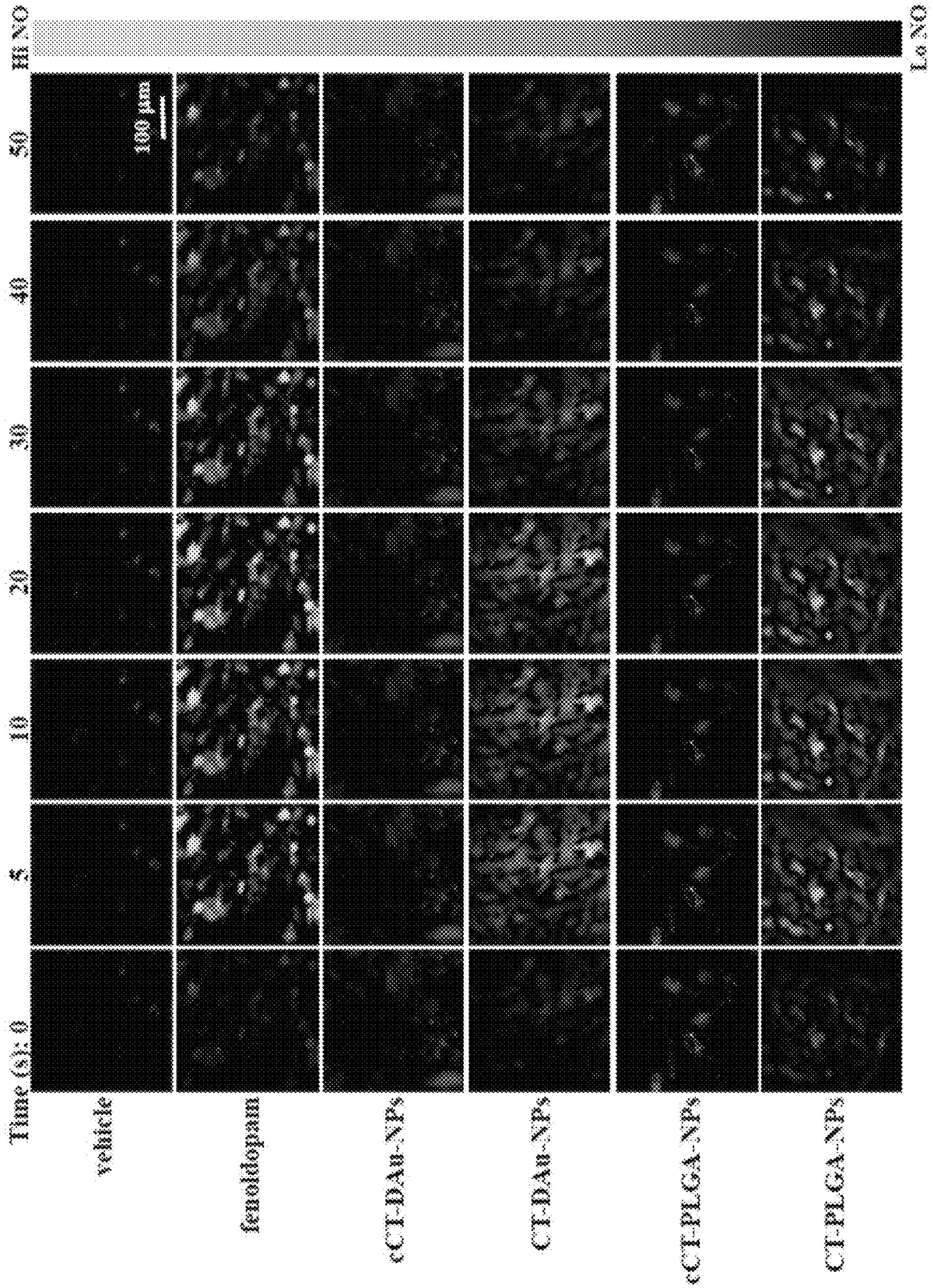

The synthesized native and surface functionalized nanoparticles disclosed herein have been compared and characterized with transmission electron microscopy (TEM) to reveal the scale and shape of nanoparticles before and after surface functionalization. As showed, the bare PLGA-NPs show spherical-shaped structures with a size of about ~125 nm (FIG. 3). After surface functionalization (CTNPs), the size is increased to ~145 nm. The DLS analysis shows the size distributions of individual synthesis steps of NPs (FIG. 4). A slightly increased in particle size following surface functionalization is seen, confirming the TEM results. The surface charge characteristics of the synthesized NPs were shown in FIG. 5 and these results explains that the high negative charge (−30 mV) of the particles could have added advantage in in vivo due to their high stability. The high-performance liquid chromatography approach to obtain an accurate dopamine profile has been generated and standardized (data not shown). The loading efficiency of dopamine is about 55% (data not shown). Importantly, the slow-sustained release of the drug reaches between 50-60% of maximum release over 60 hours (FIG. 6). There is no apparent cellular toxicity of CTNPs as analyzed with flow cytometry and imaging. The selectivity and specificity of synthesized fluorescent-CTNPs to the primary cilia has been evaluated in Pkd2 mice. After 24 hours IV injection of CTNPs, the mice were sacrificed and different organs (heart, kidney and femoral arteries) were collected and fixed for the immunohistochemistry study. FIG. 27 shows the cross section of femoral arteries and magnified images for the location of cilia. The fluorescence from CTNPs indicate the successful binding of NPs to the primary cilia in vivo.

Cilia targeted drug delivery using nanoparticles is a promising therapeutic approach for treating hypertension/ciliopathies. Cilia-specific drug delivery opens the opportunity to revisit known therapeutics that control hypertension/ciliopathies without systemic side effects.

In some embodiments, the cilia-specific drug delivery nanoparticles are formulated for systemic delivery. In some embodiments, the cilia-specific drug delivery nanoparticles are formulated for local delivery. In some embodiments, the cilia-specific drug delivery nanoparticles are formulated for targeted delivery. In some embodiments, the nanoparticles are formulated for administered by injection. In some embodiments, the formulation includes one or more pharmaceutically acceptable excipients or carriers.

Thus, disclosed herein is an approach to remotely control primary cilia. The cilia-targeted magnetic nanoparticles are used to control non-motile primary cilia movement, cilia length and function. Compared to a short-acting drug-alone, the use of nanoparticle drug delivery is superior in providing a more specific cellular target and provides a slow-release mechanism to avoid non-specific reflexes or other systemic adverse effects. This formulation is thus be a useful approach for nanotherapy in ciliopathy treatment.

EXAMPLES

Example 1. Specifically Targeting Cell Organelles to Improve Vascular Hypertension

Materials and Methods

DAu-NP Synthesis and Functionalization. The DAu-NPs were prepared according to a previous protocol with some modifications (Liu et al. ACS Nano 7:9384-9395, 2013). Briefly, 20 mL of 0.1 M HAuCl4 was placed in a 100-mL conical flask, and 1 mL of 4 mM dopamine hydrochloride was added and kept for 5 minutes at room temperature (r.t.). Then, 2 mL of 1 mM trisodium citrate dihydrate ($Na_3C_6H_5O_7 \cdot 2H_2O$) was added to the flask, and the reaction mixture was heated at 45° C. for 1 hour under stirring. After cooling to r.t., the product was briefly centrifuged; the pellet was collected and washed with deionized water three times to washout any unbound dopamine. The purified DAu-NPs (100 mg) were re-dispersed in Milli-Q water. Oleic acid (OA) was conjugated to the free amine on DAu-NPs through an amide bond linkage between carboxylates and amines. Then, 20 mg of OA was activated with DCC and NHS (OA:DCC:NHS=1:1:1) in 4 mL of dimethylformamide containing 1% triethylamine (DMF-TEA) for 30 minutes. A dispersion of 100 mg of DAu-NPs in 10 mL of DMF-TEA was added to the above mixture such that the activated OA could react with the free amine on DAu-NPs. The reaction mixture was stirred (500 rpm) for 2 hours at r.t. The resulting product was then briefly centrifuged, and the pellet was first washed with DMF and later with distilled water five times. Sunbright-40 (OA-PEG-NHS)-functionalized OA-DAu-NPs were prepared by adding an aqueous solution of Sunbright-40 (100 mg/5 ml distilled $H_2O$) and undergoing stirring for another 24 hours at r.t. All the bare DAu-NPs and Sunbright-40-OA-DAu-NPs were separated by centrifugation process. The particles were washed with 50 mL of nitrogen-purged sterile water three times using centrifugation at low speed (1,000 rpm) to remove large aggregated particles.

PLGA-NP Synthesis and Functionalization. PLGA-NPs were prepared by the solvent evaporation method. Briefly, 100 mg of PLGA (50:50, lactide:glycolide) solubilized in 2 ml of acetone was added dropwise into 15 mL of an aqueous phase containing 0.77 g of Tween-20 (as emulsifier) under magnetic stirring at 2,500 rpm for one hour to generate a nanoemulsion. Subsequently, 4.5% (w/v) OA was added to the above crude emulsion, which was then sonicated for 20 minutes with a probe sonicator (Fisher Scientific) at an optimal amplitude of 55% and a frequency of 20 KHz. The resulting solution was stirred at 1,200 rpm for 1 week to evaporate the organic solvent. Then, the OA-PLGA-NPs were collected, centrifuged and washed. For the Sunbright-40 functionalization, OA-PLGA-NPs were prepared by adding an aqueous solution of Sunbright-40 (100 mg/5 ml distilled $H_2O$) and stirred for 24 hours at r.t. The particles were then washed and dialyzed with 12-kD MWCO dialysis membrane (Spectrum Labs).

Antibody Conjugation and Drug Loading. We first conjugated DR-5 antibody (EMD Millipore; cat #324408) with AF594 maleimide using an AF594 Antibody Labeling Kit to target thiol groups, according to manufacturer's instructions (Thermo Fisher Scientific). The pre-conjugated DR-5-AF594 binding and fenoldopam loading to the synthesized Sunbright-40-OA-DAu-NPs and Sunbright-40-OA-PLGA-NPs was performed. Briefly, Sunbright-40-OA-DAu-NPs or Sunbright-40-OA-PLGA-NPs were cooled to 4° C. Each of these materials was mixed with DR-5-AF594 to a final volume of 25 mL in PBS and shaken overnight at 4° C. A DMSO solution of fenoldopam (400 µL, 15 mg/ml in each reaction) was then added, and the reaction was allowed to occur under continuous stirring (400 rpm) for another 16 hours at cold conditions. The antibody- and fenoldopam-loaded Sunbright-40-OA-DAu-NPs and Sunbright-40-OA-PLGA-NPs were separated from free antibody and free fenoldopam. CT-DAu-NPs and CT-PLGA-NPs were then washed with PBS several times, lyophilized and stored in the dark.

A set of control groups was also prepared in a same way but without fenoldopam (cCT-DAu-NPs and cCT-PLGA-NPs). In a separate reaction, fluorescent unconjugated DR-5 antibody loading was also carried out accordingly. The DR-5 antibody binding to all synthesized CT-NPs was analyzed by fluorescence spectrometer at $\lambda_{ex}$=590 nm and $\lambda_{em}$=617 nm with a fluorescence plate reader (Molecular Devices). Conjugation efficiency of the DR-5 to the different NPs was further assessed with SDS-PAGE and protein concentration measurements indicated by optical density at 280 nm with a NanoDrop.2000 spectrophotometer (Thermo Scientific). The fenoldopam loading efficiency was quantified by HPLC (SHIMADZU). Fenoldopam release was measured by dialyzing 1 mL of each NP solution at a concentration of 5 mg/mL in PBS using 3.5 k MWCO dialysis tubing and subjected to HPLC. A standard plot was prepared under standard conditions with a fenoldopam concentration range from 5-200 μg/mL.

Characterizations. The initial synthesis of the DAu-NPs and PLGA-NPs was confirmed with UV-visible spectroscopy using a SpectraMax system. NP stability was determined by preserving them in an 8% sucrose solution. For the measurements of size and shape, all synthesized nanomaterials were examined by TEM using a FEI/Philips 200 kV CM-20 electron microscope. The size and surface zeta-potential of all synthesized NPs were obtained by DLS measurements using a Malvern ZETASIZER (Nano-ZS; ZEN3600). All samples of lyophilized NPs were subjected to XRD using a Rigaku SmartLab X-ray diffractometer and Cu-Kα (Cu target) radiation at a scanning rate of 1° per min in the region of 2θ=10−90°. X-ray photoelectron spectra of the samples were recorded on a Kratos Analytical AXIS Supra system with a monochromated Al/Ag X-ray source (Al target). Total survey spectra were recorded in a range from 1200 to −5 eV binding energy (dwell time 200 ms, step size 1 eV, 2 sweeps), and all the region scans were conducted with suitable ranges (dwell time 500 ms, step size 0.05 eV and 5 sweeps). The FTIR spectra were recorded using a Bruker ALPHA (Platinum-ATR) spectrometer in the diffuse reflectance mode at a resolution of 4 $cm^{-1}$.

Cell Culture. Porcine kidney epithelial cells (ATCCR CL-101™) were cultured in Dulbecco's Modified Eagle Medium (Corning Cellgro), 10% fetal bovine serum (HyClone) and 1% penicillin/streptomycin (Corning Cellgro) at 37° C. in a 5% $CO_2$ incubator. For endothelial cell lines, we used previously generated mouse endothelial cells. Prior to all experiments, cells at 75-85% confluence were differentiated for 24-48 hours in serum-free media so we could accurately quantify and study the effects of CT-NPs in each experiment.

Live Imaging of a Single Cilium from a Single Cell. To determine the selective targeting efficiency of NPs for targeting cilia, CT-DAu-NPs and CT-PLGA-NPs were evaluated via the side view of both a cell and cilium to avoid bias in the data analysis. Cells were grown on Formvar® polymer (Electron Microscopy Science). Formvar® was dissolved in ethylene dichloride to make a 2% Formvar® solution. Cells were then grown on this collagen-coated Formvar® flexible substratum (FFS). The FFS was placed on a custom-made glass-bottomed plate. A thin pipette tip was connected to the inlet and outlet clear plastic PVC tubes with a 0.031-inch inside diameter. The tubes were inserted into the in-flow and out-flow pumps (InsTech P720), and the pipette tips were inserted between the bottom glass plate and held with a cover glass slide on top. Different concentrations (0.1-1 μg/mL) of cCT-DAu-NPs, cCT-PLGA-NPs, CT-DAu-NPs or CT-PLGA-NPs were perfused through the cells and imaged for 2 hours. Different NP targeting capacities to cilia were observed with a Nikon Eclipse Ti microscope. The microscope is also equipped with an incubator to control $CO_2$, humidity, temperature and light to provide a suitable environment for the cells during the experiment.

Immunocytochemistry. For the in vitro cilia length measurements, cells were grown on the Formvar® polymer, as mentioned above. Primary cilia consisting of acetylated microtubule structures were measured by direct immunofluorescence with acetylated-α-tubulin staining with 0, 2, 4, 8, 16, 24 and 32 hours of incubation with different concentrations (0.1-5 μg/mL) of CT-DAu-NPs or CT-PLGA-NPs. Likewise, materials without fenoldopam loading were used as corresponding controls for the CTNDDSs (cCT-DAu-NPs and cCT-PLGA-NPs) and also fenoldopam alone used. The cells were rinsed with sodium cacodylate buffer, fixed with 3% glutaraldehyde in 0.2 M sodium cacodylate buffer for 10 minutes, and permeabilized with 1% Triton-X in sodium cacodylate for 5 min. Acetylated-α-tubulin (1:10,000 dilution, Sigma) and the secondary antibodies were also diluted in 10% FBS to decrease the background florescence; FITC fluorescence secondary antibody (1:1000; Pierce, Inc.) was used. The cells were then washed three times for 5 minutes each with cacodylate buffer and mounted with DAPI (Vector laboratories). Confocal microscopic images were obtained using an inverted Nikon Eclipse Ti confocal microscope.

$Ca^{2+}$ and NO Imaging. For monolayer cell populations, intracellular measurements were obtained. After incubation for 16 hours without or with different concentrations (0.1-5 μg/mL) of fenoldopam, cCT-DAu-NPs, cCT-PLGA-NPs, CT-DAu-NPs or CT-PLGA-NPs, cells were incubated with 5 μM Fura2-AM (TEFLabs) for 45 minutes at 37° C. in a 5% $CO_2$ incubator. After washed to remove excess Fura-2 AM, cytosolic $Ca^{2+}$ images were captured every second by recording $Ca^{2+}$-bound Fura-2 AM excitation fluorescence at 340/380 nm and emission at 510 nm. For intracellular nitric oxide (NO) measurements, the cells were incubated for 30 minutes at 37° C. with 20 μM DAF-FM (Cayman Chemicals). NO was then measured every second at the excitation and emission wavelengths of 495 and 515 nm, respectively. The cells were placed in PBS during the experiments and observed with a Nikon Eclipse Ti microscope. Fluid shear stress was then applied to cells through InsTech P720 peristaltic pumps with an inlet and outlet setup. The fluid was perfused through cell monolayers at a sub-minimal shear stress of 0.5 $dyn/cm^2$.

In single-cell studies, cells were grown on 2% Formvar® and transfected with the $Ca^{2+}$ fluorescence reporter $5HT_6$-mCherry-G-GECO1.0 (Addgene) using the JetPrime transfection reagent (Polyplus transfection). The shear stress ranged from 0.01-1.0 $dyn/cm^2$ and was accurately measured and controlled at all times. After transfection, the cells were treated with different concentrations of fenoldopam, cCT-DAu-NPs, cCT-PLGA-NPs, CT-DAu-NPs or CT-PLGA-NPs, and $5HT_6$-mCherry-G-GECO1.0-expressing cilia were observed under an inverted Nikon Eclipse Ti confocal microscope. For these experiments, none of the CT-NPs contained AF594 dye to avoid interference with the mCherry signal. Confocal laser scanning microscopy in fast-scan mode was used to avoid potential excessive photo bleaching. All videos were processed using NIS-Elements High Content AR 4.30.02 (Nikon) used for the live tracking and kymograph analysis of both the cell and cilia. $Ca^{2+}$ tracking was very efficiently achieved by using binary spotting tracks. The GFP/mCherry ratio calculations were also done using Nikon tracking software.

In Vitro Cytotoxicity. The in vitro toxicity of CT-DAu-NPs or CT-PLGA-NPs were performed in renal epithelial cells using Annexin V-FITC/propidium iodide apoptosis assay (Molecular Probes and Life Technologies). Cells were treated with different concentrations of 1 to 10 μg/mL of each CTNDDS for 48 hours. Normal, apoptotic, and necrotic cells were distinguished by flow cytometry analysis (BD Facsverse). Representative images of cells were captured using a standard fluorescence and DIC microscopy.

CGMP Study. To quantify the cGMP content, cells were pre-treated with either PBS or different concentrations (0.1-5 μg/mL) of fenoldopam, CT-DAu-NPs or CT-PLGA-NPs. The cGMP levels were measured using a cGMP ELISA Kit (Cayman Chemical Company). The results were converted to pmol/mL via standard curves.

Animal Studies. All animal procedures were performed according to the University of California Irvine or Chapman University Animal Care and Use Committee Guidelines. To eliminate biases and subjective analyses, all animal studies were performed by double-blinded operators. Wild-type zebrafish AB strains were obtained from the Zebrafish International Resource Center. Embryos were injected with 1 mM morpholino oligos (GeneTools) at the 1-2 cell stage and cultured at 28.5° C. in sterile egg water. The following morpholino sequences were used: control scrambled MO: 5'-CCT CTT ACC TCA GTT ACA ATT TAT A-3' (SEQ ID NO:1), Pkd2: 5'-AGG ACG AAC GCG ACT GGG CTC ATC-3' (SEQ ID NO:2). The cardiac function was assessed by placing zebrafish on their dorsal axis to examine the relative locations of the ventricle and bulbus arteriosus, blood circulation and the heartbeat. Measurements of blood flow characteristics and heart parameters were performed using a Nikon Eclipse Ti microscope. NIS-Elements High Content AR 4.30.02 (Nikon) was used for the live tracking of the speed and acceleration of a single blood cell.

One-week-old Tie2Cre•Pkd2$^{WT/WT}$ (with cre activation; control group) or Tie2Cre•Pkd2$^{flox/flox}$ (without cre activation; control group), and Tie2Cre•Pkd2$^{flox/flox}$ (with cre activation; experimental group) mice were injected intra-peritoneally with 5 μg/μL tamoxifen every day for five consecutive days. A limited number of IFT88 mice were also used as no cilia model. The overall process for the preparation of the final nano-formulation for the animal studies included the following steps. The lyophilized antibody conjugated and drug-loaded CT-DAu-NPs or CT-PLGA-NP powders were first brought to the room temperature from a storage at −50° C. Then, the required amounts (0.5, 1.0, 1.5 and 2.0 mg) of CT-DAu-NPs or CT-PLGA-NPs were weighed carefully in the dark room using a highly sensitive weighing balance (Sartorius). The final formulations for the injections were prepared by individually dispersing them in 150 μL of PBS. The formulations were mixed by vortex for 2 minutes followed by filtration of 0.2 μm. The mice were next injected with PBS (control), CT-DAu-NPs or CT-PLGA-NPs (0.5 to 2.0 mg/kg body weight) via intravenous (IV) injections. Fenoldopam alone (1 μg/kg/min) was perfused for 30 minutes every 72 hours for 8 weeks. The mice were treated every 72 hours with different NPs for 8 weeks. Blood pressure from four-week-old mice was taken with the non-invasive tail-cuff method using the CODA system (Kent Scientific). Blood pressure was measured twice daily for the duration of the study after the initial three days of acclimating each mouse to the cuff. At the end of the 12 weeks of treatment, the hematology parameters, including the blood urea nitrogen (BUN) and plasma nitrate/nitrite measurements, were examined. BUN assays were conducted using a calorimetric kit (Arbor Assays). Plasma nitrate/nitrite concentrations were quantified using a nitrate/nitrite assay kit (Cayman). All steps were followed according to the manufacturer's instructions.

Sections of the zebrafish and mouse major organs, including the heart, kidneys, liver, spleen and lungs, were collected and subjected to H&E staining for zebrafish cysts and histopathology by starting with fixation in 10% paraformaldehyde overnight at 4° C. Then, the tissues were dehydrated using buffered ethanol, and xylene. Finally, the tissues were embedded in wax, sectioned (4 μm, Microtome, HM-355S, Thermo Scientific) and were subsequently stained with standard hematoxylin and eosin (H&E). The pathology slices were observed and imaged using a KEYENCE-BZ-X710 microscope. Mouse heart sections were stained with Masson's Trichrome to detect fibrosis using a Masson's Trichrome Stain Kit (Polysciences, Inc.).

The pharmacokinetics of different NPs treated mice were studied. Blood samples of 50 μL were collected prior to drug injections and 5-60 minutes during the duration of injections (for NPs) or perfusions (for fenoldopam). Blood samples were collected into heparin-coated tubes and centrifuged for 10,000 g for 8 minutes to obtain plasma. All drugs were extracted from plasma samples and HPLC analysis performed. In the biodistribution studies, whole organs from the fluorescent-labelled NPs treated mice (heart, kidney, liver, spleen and lung) were collected, homogenized and measured for fluorescence intensity to assess the amount of NP distribution in different organs at 24- and 72-hours after treatments. For the in vivo toxicity studies, 200 μL of blood samples were collected from different treatments (PBS, CT-DAu-NPs or CT-PLGA-NPs). Biochemistry was performed using biochemical analyzer (VetScan VS2).

Working Heart Perfusion System. To study heart function independently from neuronal innervation or humoral effect, ex vivo heart parameters were collected using a mouse working heart system from Emka Technologies. This system collected data of the cardiac contractile strength, electrical heart propagation (ECG; electrocardiogram) and other cardiac functions, including the heart rate (HR), left ventricle pressure (LVP), left ventricular volume (LVV), left atrial pressure (LAP), aortic out flow (AOF), stroke volume (SV), cardiac output (CO), end diastolic/systolic volume (Edv-Esv), rate of left atrial pressure raise (+dp/dt) and fall (−dt/dt), preload, afterload, and main aortic pressure. Heparin (100 units, IP), xylazine (10-15 mg/kg, IP), and ketamine (200-350 mg/kg, IP) were used to prevent blood coagulation in the coronary arteries and to anesthetize the mice. After cannulation, the heart was perfused with Krebs-Ringer superfusion solution (in mM: 125 NaCl, 2.5 KCl, 1.25 $NaH_2PO_4$, 2 $CaCl_2$), 1 $MgCl_2$, 25 $NHCO_3$ and 25 glucose). Throughout the experiment, the solution was continuously bubbled with carbogen (95% $O_2$ and 5% $CO_2$) to reach 7.4 pH at 38° C. Stress tests were performed in the heart by perfusing epinephrine (4 μg/L) or diltiazem (0.08 μg/L). The cardiac function was plotted in a loop diagram showing the LVV-LVP relationship (volume-pressure loop).

Statistical Analysis. All quantifiable data are reported as the mean±standard error of the mean (SEM). The homogeneity of variance (homoscedasticity) was verified within each data set. When a data set was not normally distributed or heterogeneous variance was detected, the distributions were normalized via log transformation. This approach produced normally distributed data sets. Statistical analysis was performed using ANOVA (analysis of variance) followed by a Bonferroni or Tukey post hoc test. Power analysis was determined from the coefficient variant. When the coefficient variant was above 15%, the number of experimental and corresponding control groups was increased. Both the control and experimental groups were run in parallel therefore, control and experimental values represent matched observations. In some cases, all the experimental groups (including the corresponding controls) were analyzed with the post hoc test. In other cases, only the selected pairs (vehicle vs. experimental groups) were tested. Whenever possible, paired-experimental analysis was used to design the studies to allow for a more powerful statistical analyses and to reduce the number of mice used in each study group. Most of the statistical analyses were performed with GraphPad Prism (version 7.0). Linear regression was performed to obtain a standard calibration curve and linear equation. In this case, the analysis was done with the ordinary least squares regression of y on x. A non-linear logarithmic regression was used to fit the sigmoidal trend curve to show the dose-response relationship. Sample sizes are included in figures/legends. * and # symbols represent statistically significant differences at various probability levels (P).

Results

Figure 2A:
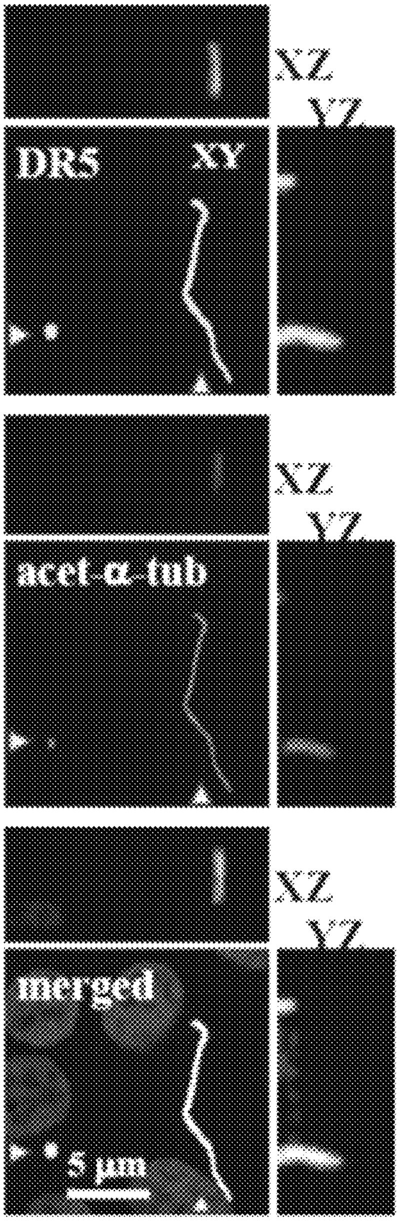
FIGS. 2A-H depicts the synthesis and characterization of CTNDDS.
Figure 7A:
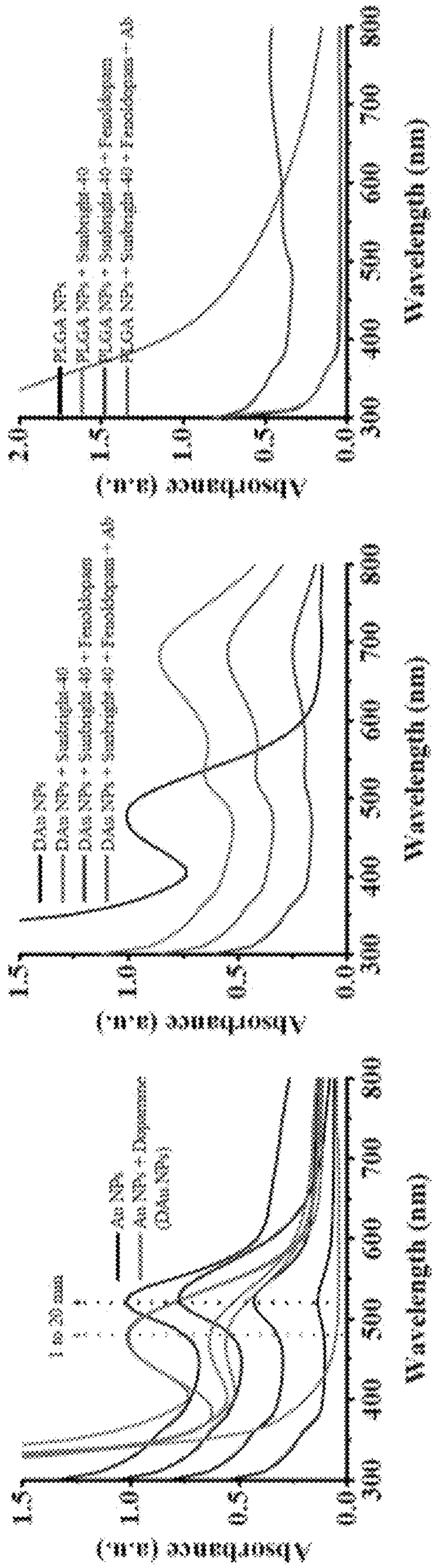
FIGS. 7A-G depict UV-visible (FIG. 7A), XRD (FIG. 7B), and XPS spectral patterns (FIG. 7C, D) of both DAu and PLGA nanoparticles. Each spectrum represents the progression of native nanoparticles to active cilia-targeted nanoparticles.
Figure 7B:
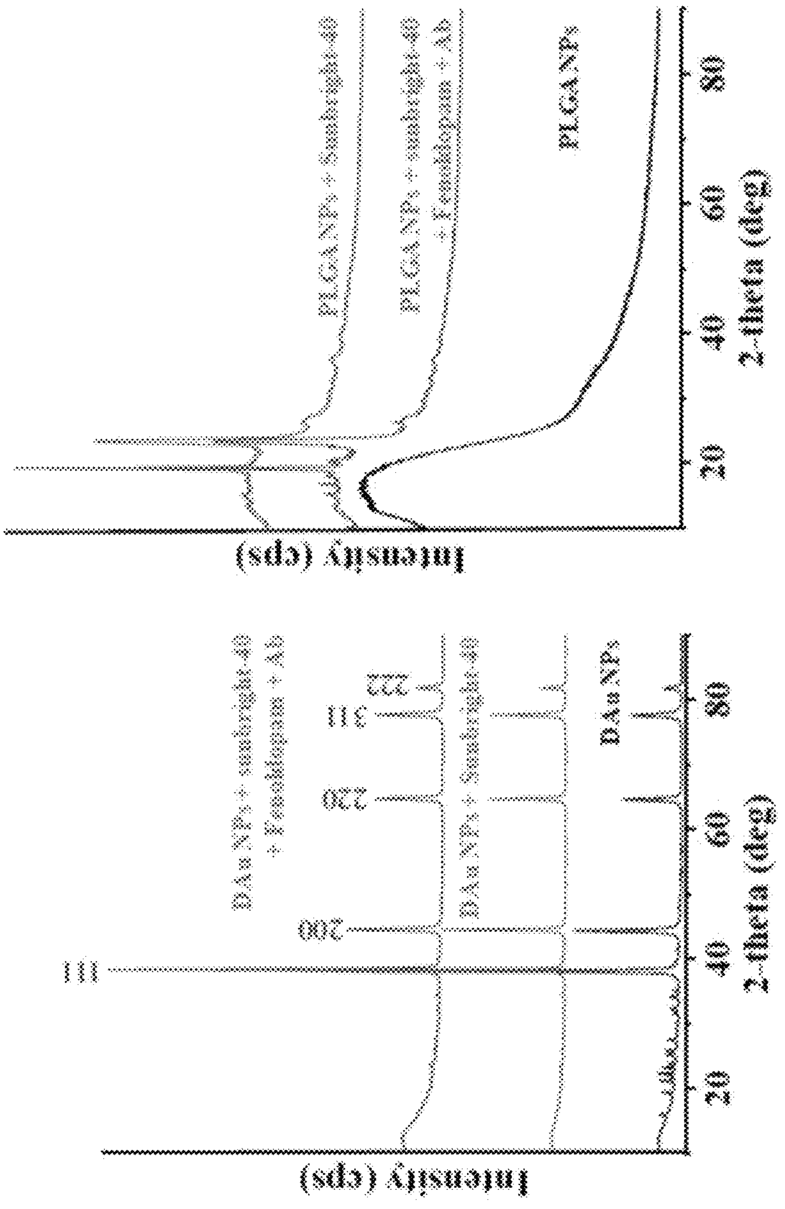
Figure 7C:
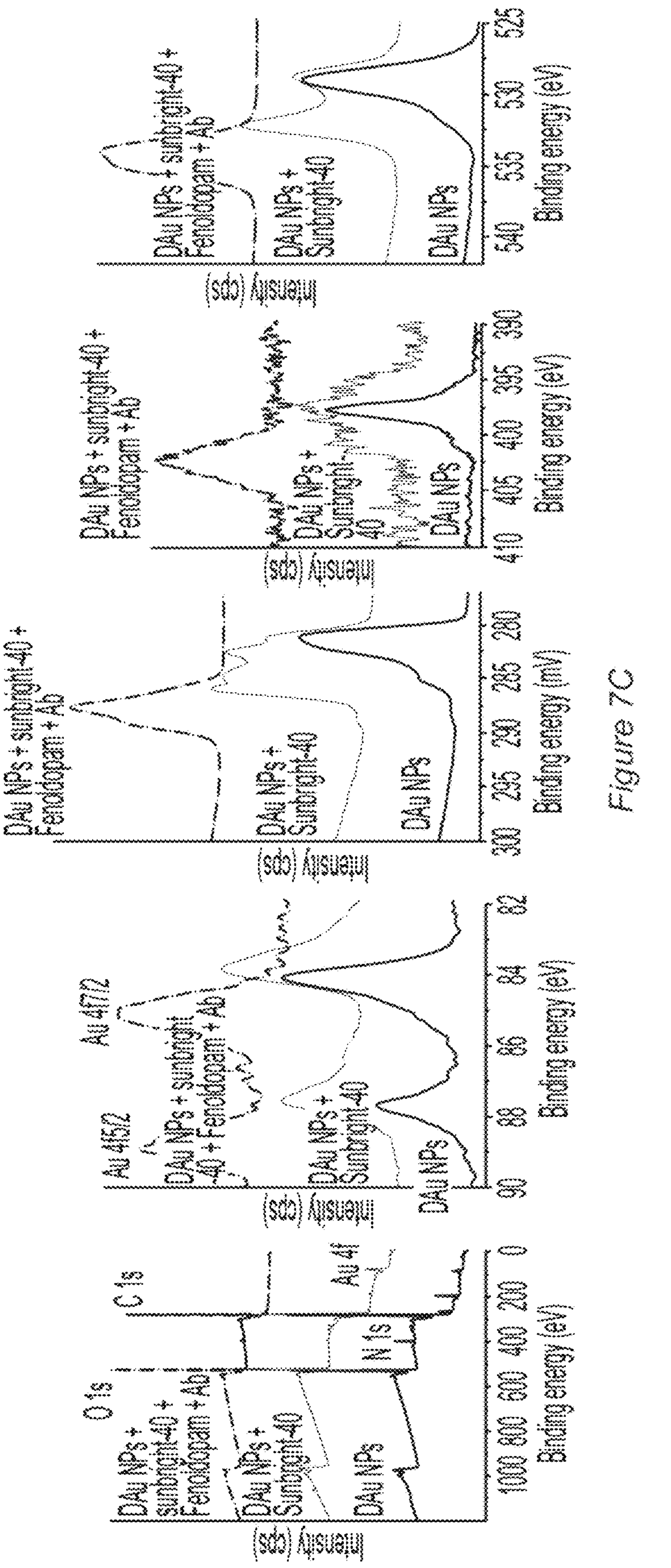
Figure 7D:
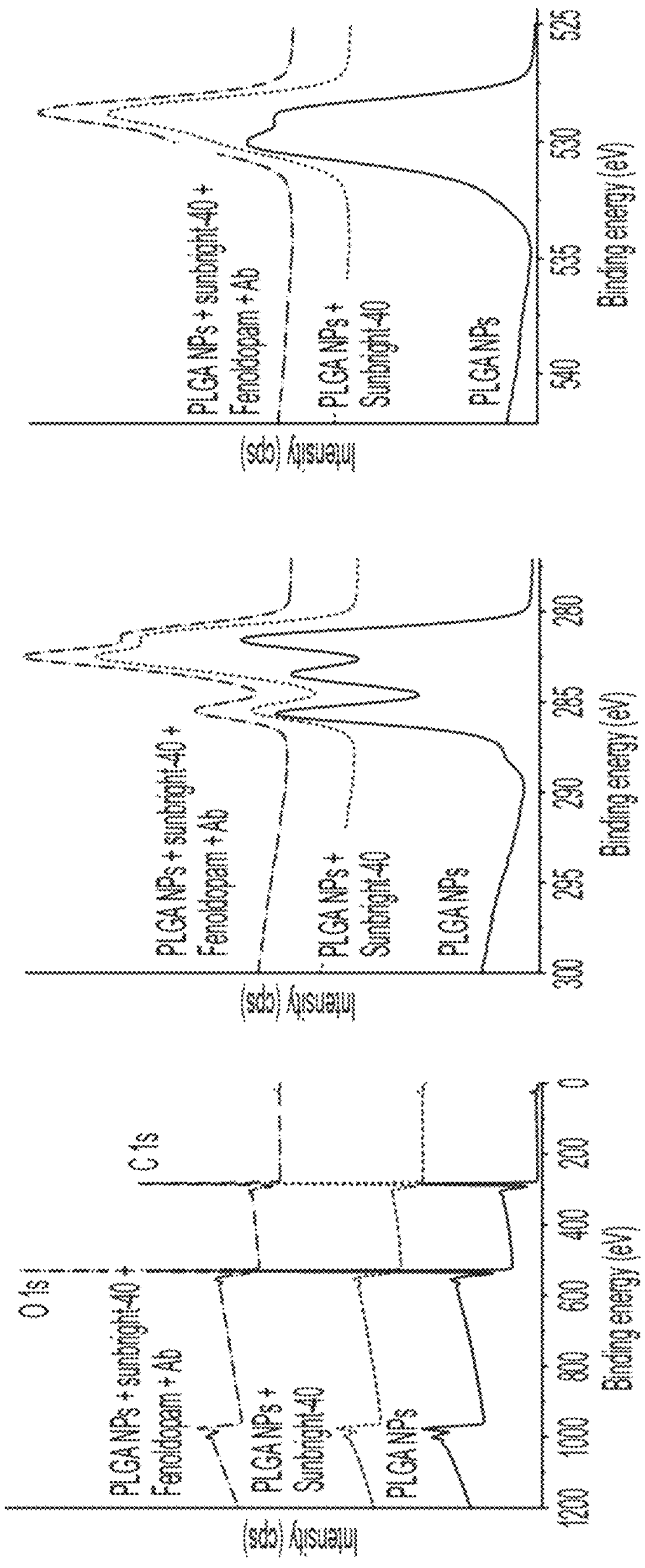
Figure 7E:
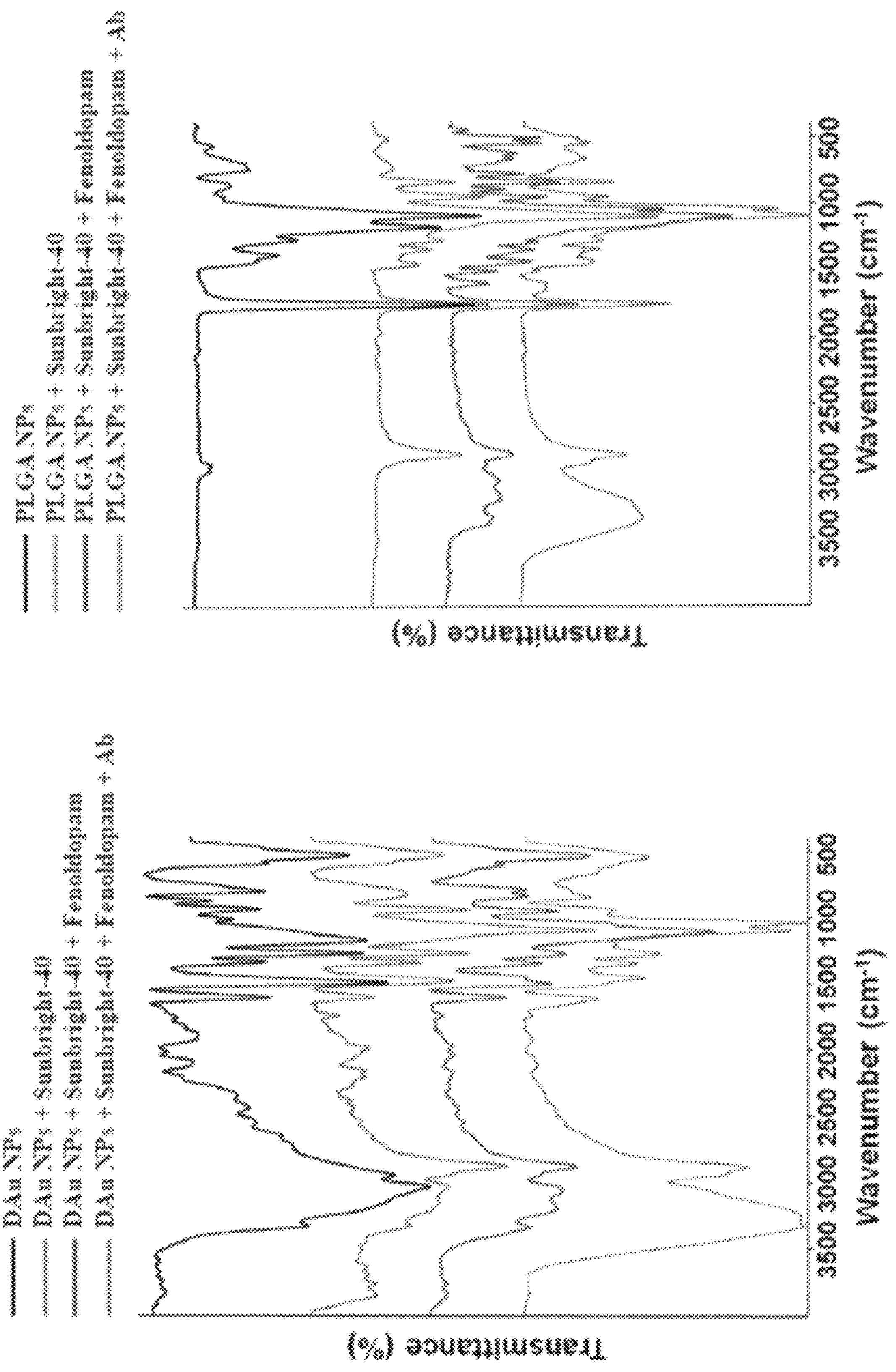

Dopamine-receptor type-5 (DR-5) is largely expressed in cilia (FIG. 2A). We therefore generated NPs to target ciliary DR-5. We devised two cilia-targeted (CT) NPs to evaluate and compare their efficiencies, efficacies, potencies and safety profiles. CT-DAu-NPs and CT-PLGA-NPs were loaded with the experimental drug fenoldopam. Fenoldopam was selected based on prior screening, showing that it could improve mechanosensory function of cilia by increasing cilia length. These cilia-targeted nanoparticle drug delivery systems (CTNDDS) were also conjugated with AF594 dye to enable us to visualize and study the particle profiles. The UV-visible absorbance (FIG. 7A), X-ray diffraction (FIG. 7B), X-ray photoelectron spectroscopy (FIG. 7C, D), and Fourier transform infrared (FIG. 7E) spectra of CTNDDS were closely monitored to validate surface functionalization steps.

Figure 2B:
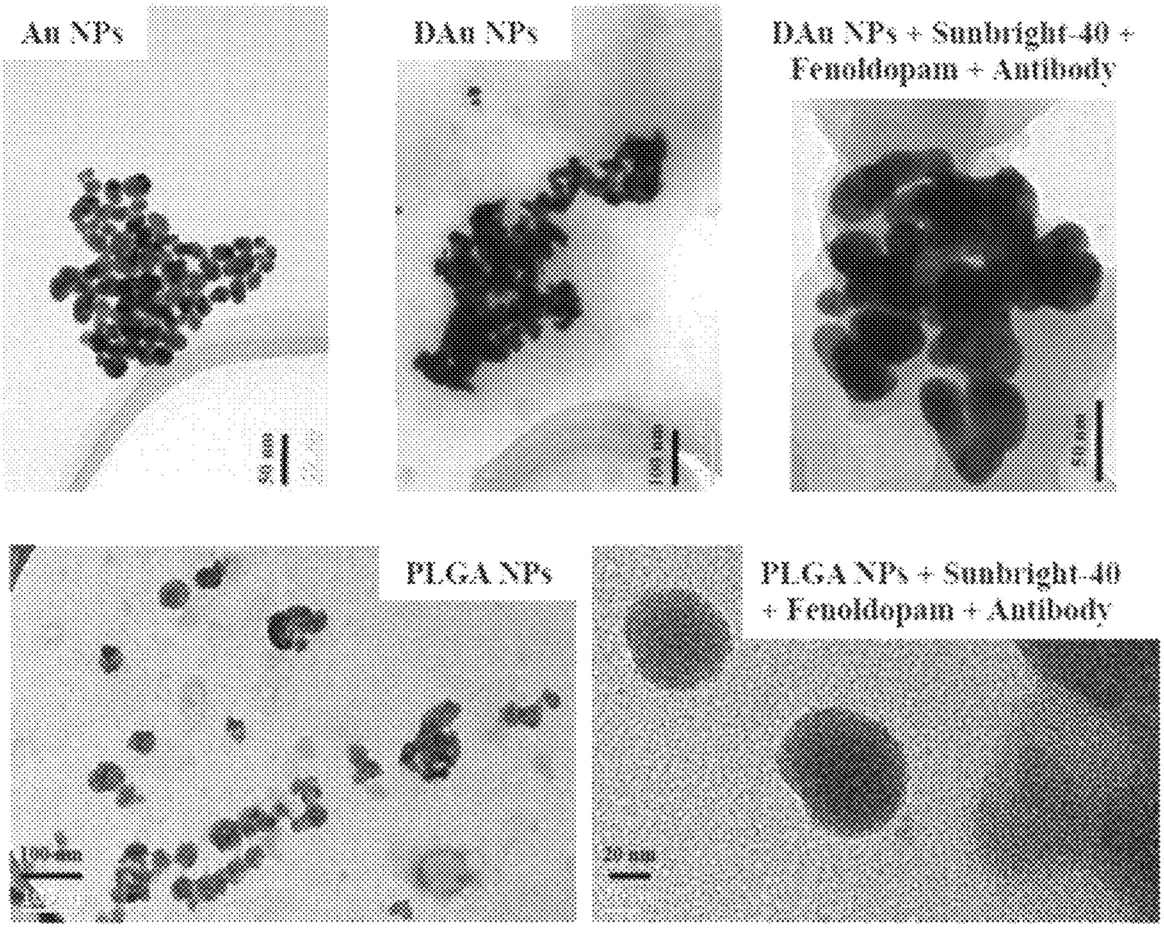
Figure 2C:
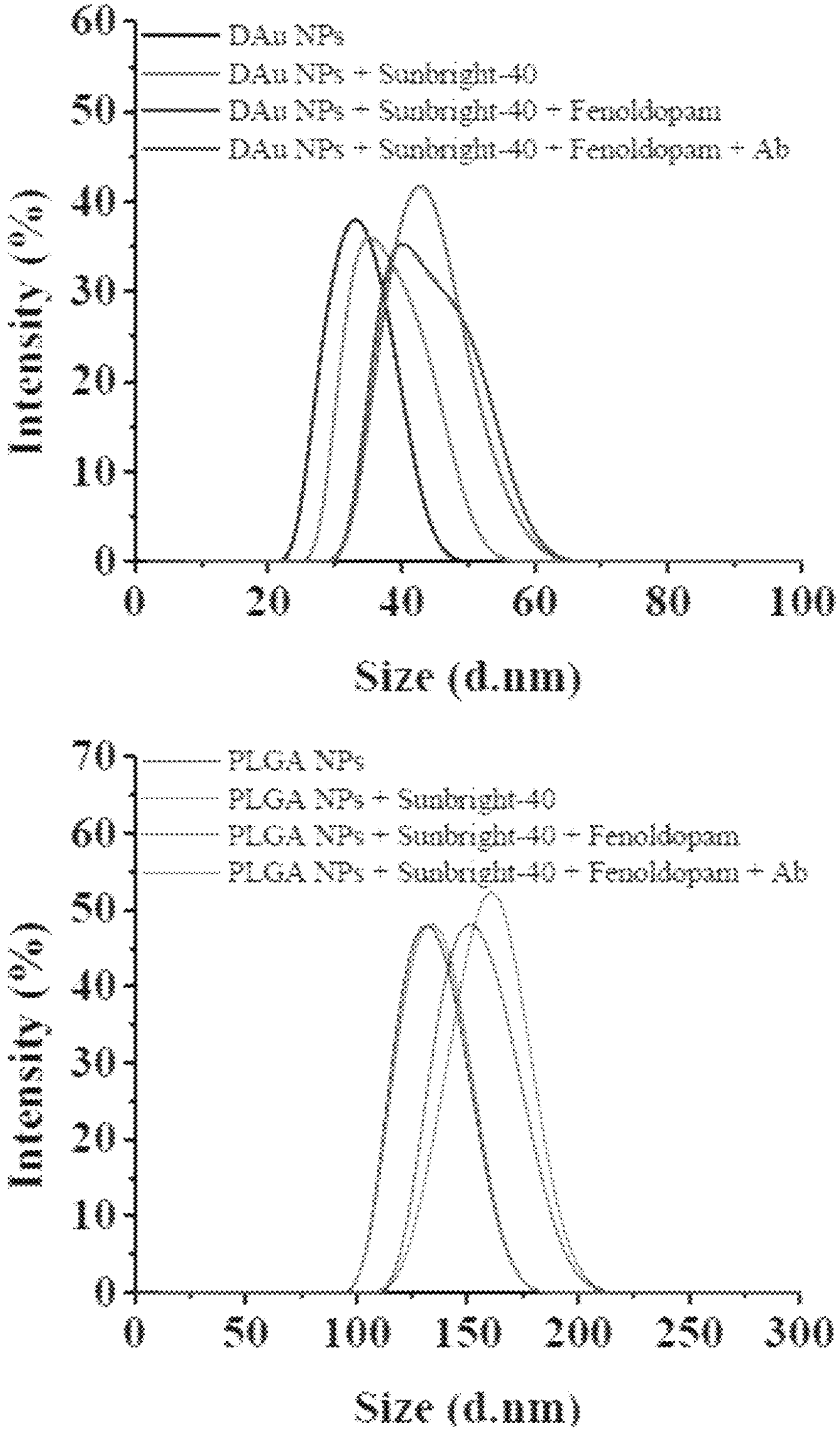
Figure 2D:
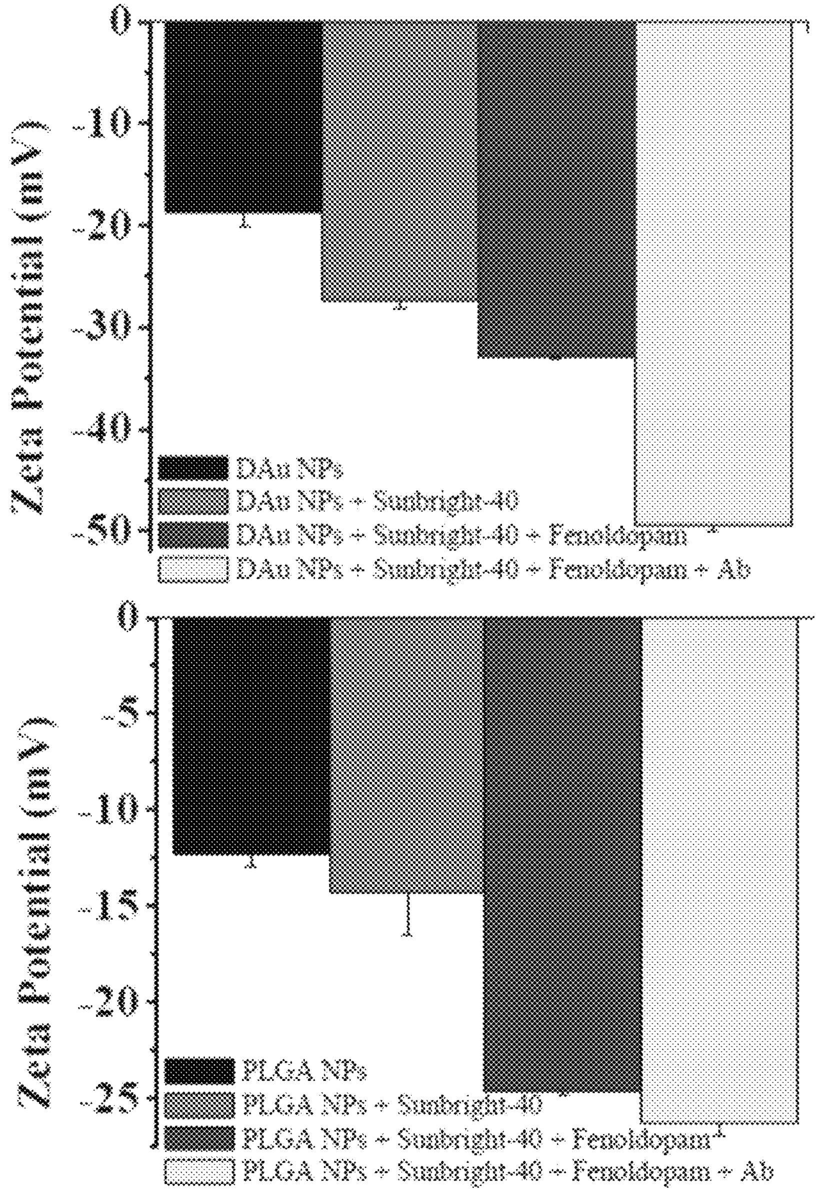
Figure 2E:
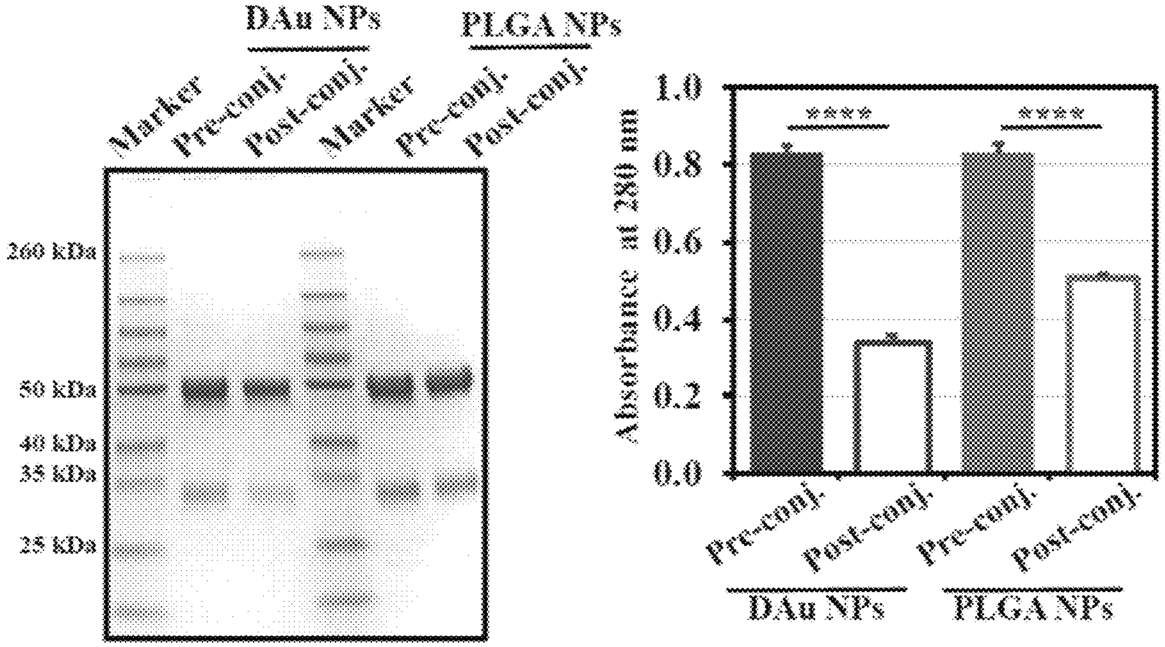
Figure 2F:
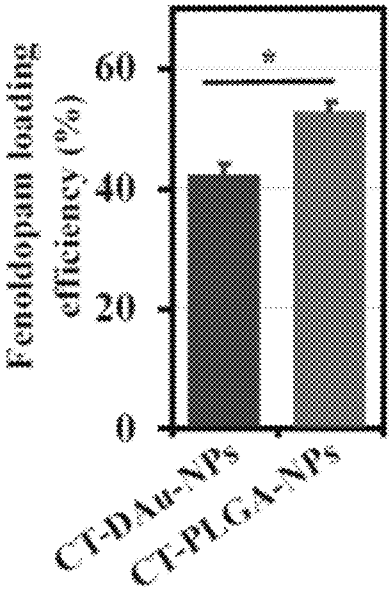
Figure 2G:
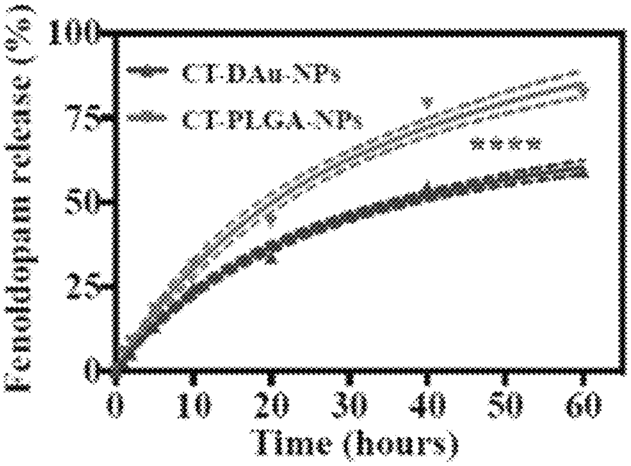
Figure 2H:
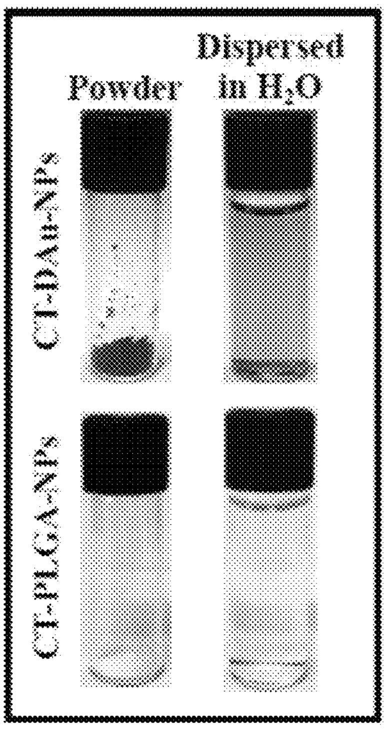
Figure 7F:
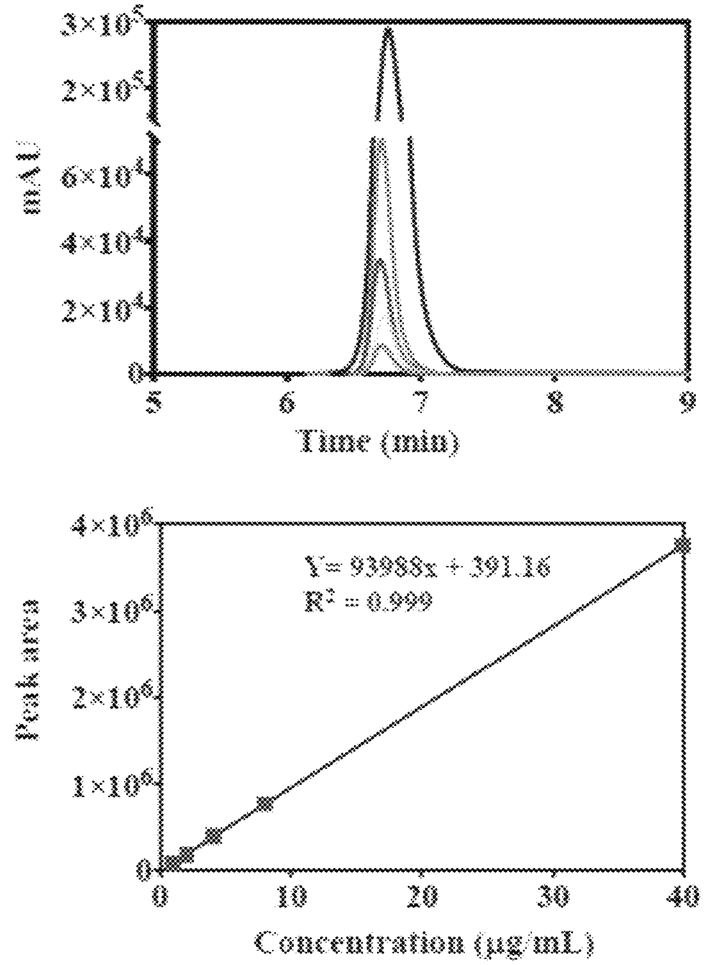
Figure 7G:
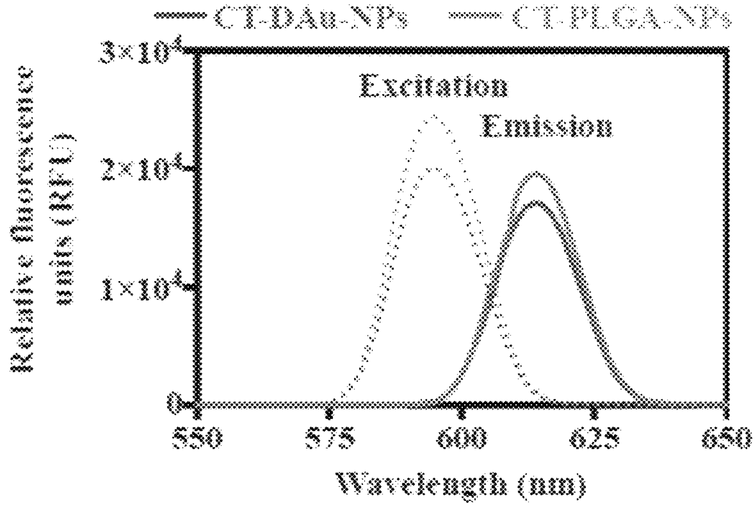
Figure 8A:
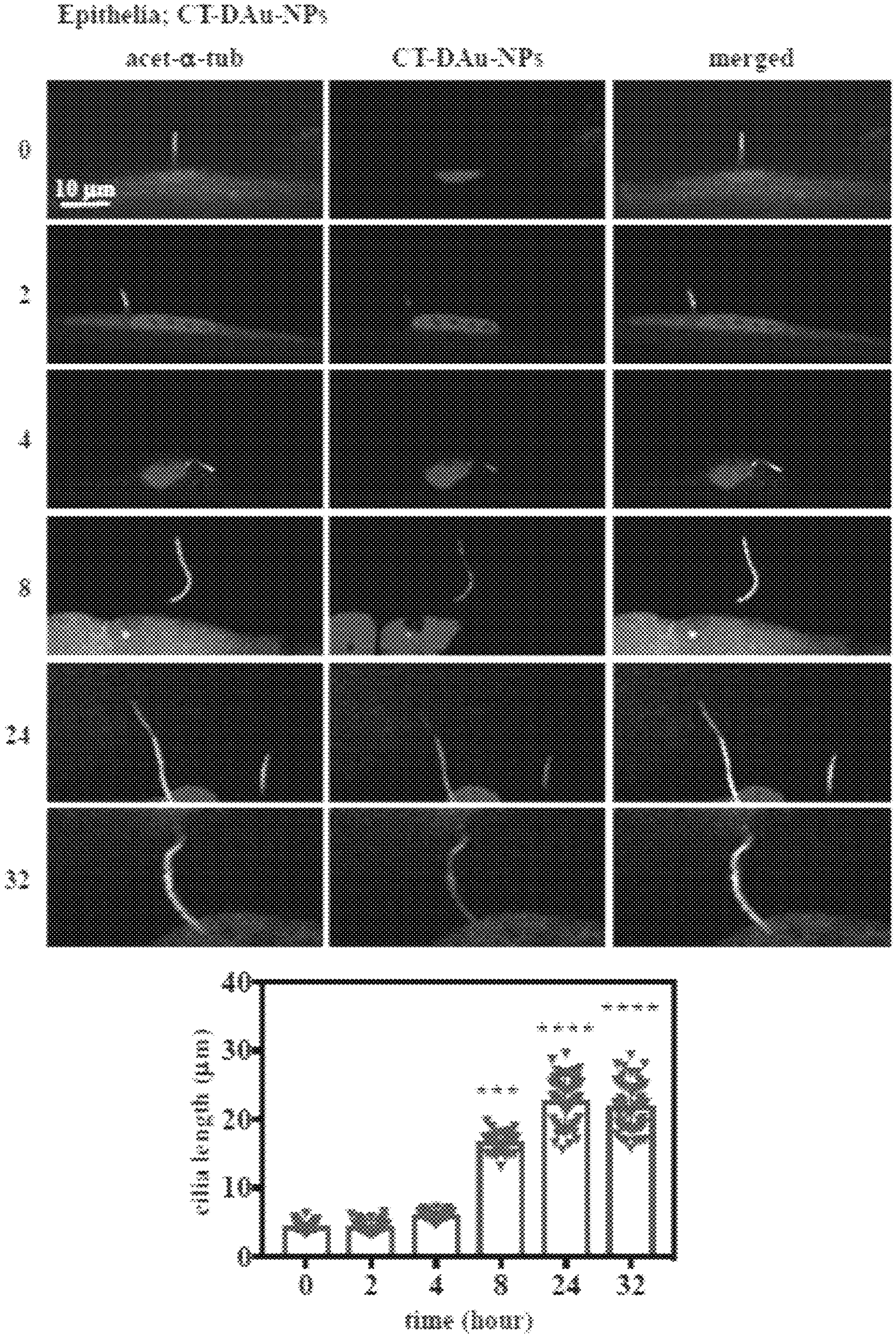
FIGS. 8A-B depict representative images on the effects of CT-DAu-NPs (FIG. 8A) and CT-PLGA-NPs (FIG. 8B) on primary cilia of renal epithelia. Numbers indicate time in hour. *p<0.001, **p<0.0001 compared to time 0, prior to the treatment with CTNDDS. Statistical analysis was performed using ANOVA followed by a Bonferroni post hoc test.
Figure 8B:
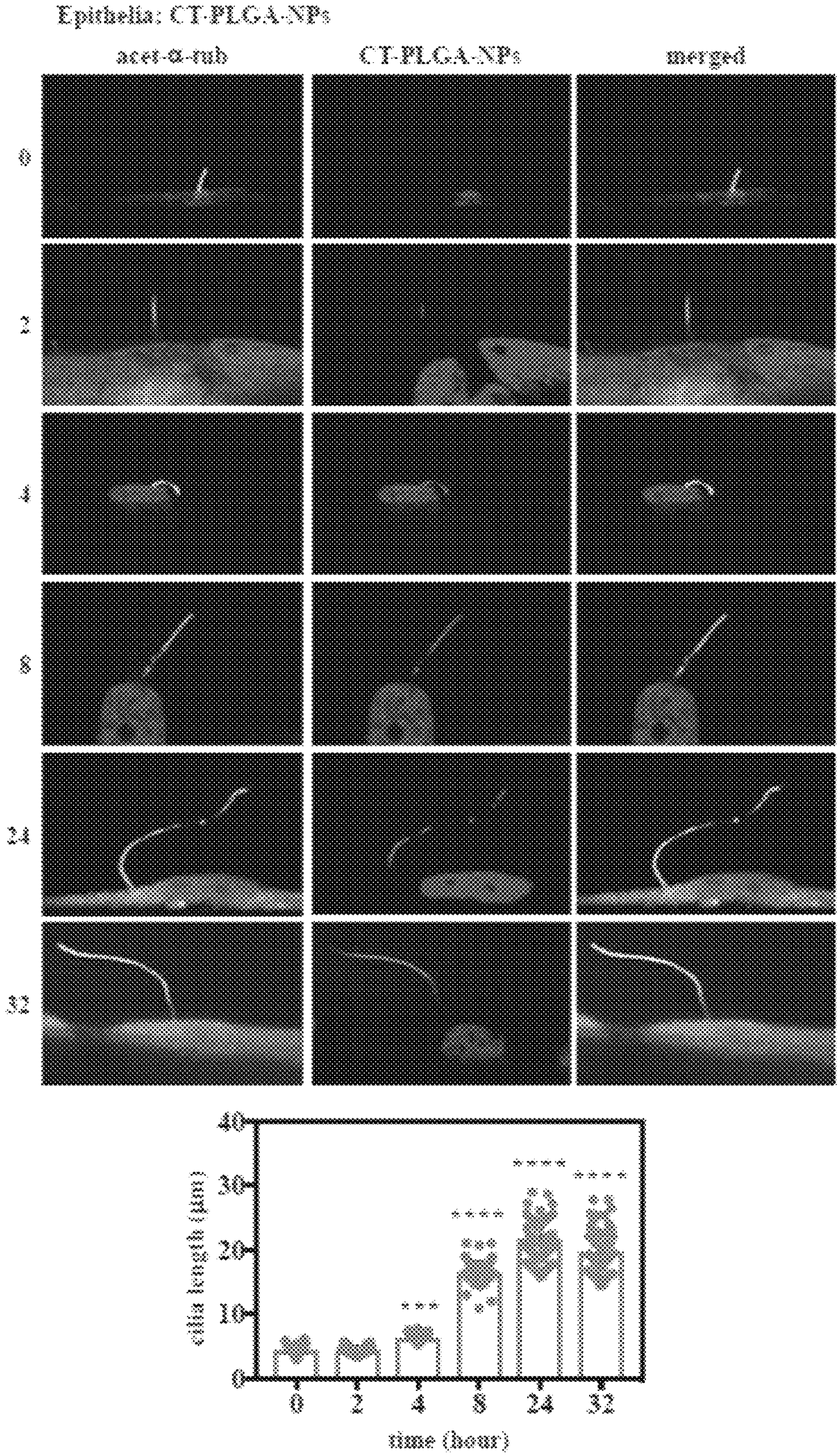
Figure 9A:
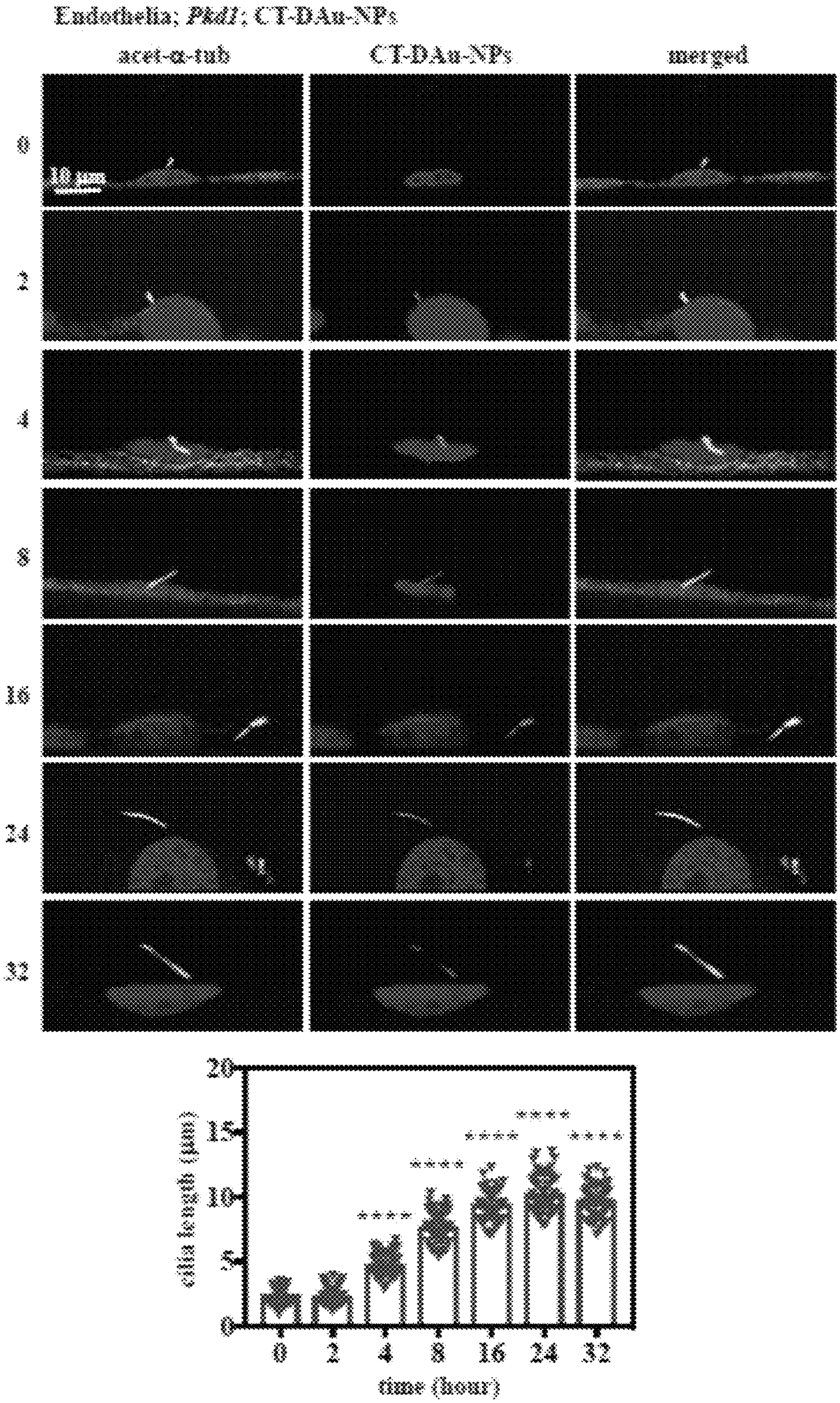
FIGS. 9A-B depict representative images on the effects of CT-DAu-NPs (FIG. 9A) and CT-PLGA-NPs (FIG. 9B) on primary cilia of vascular endothelia from Pkd1 mice. Numbers indicate time in hour. ****p<0.0001 compared to time 0, prior to the treatment with CTNDDS. Statistical analysis was performed using ANOVA followed by a Bonferroni post hoc test.
Figure 9B:
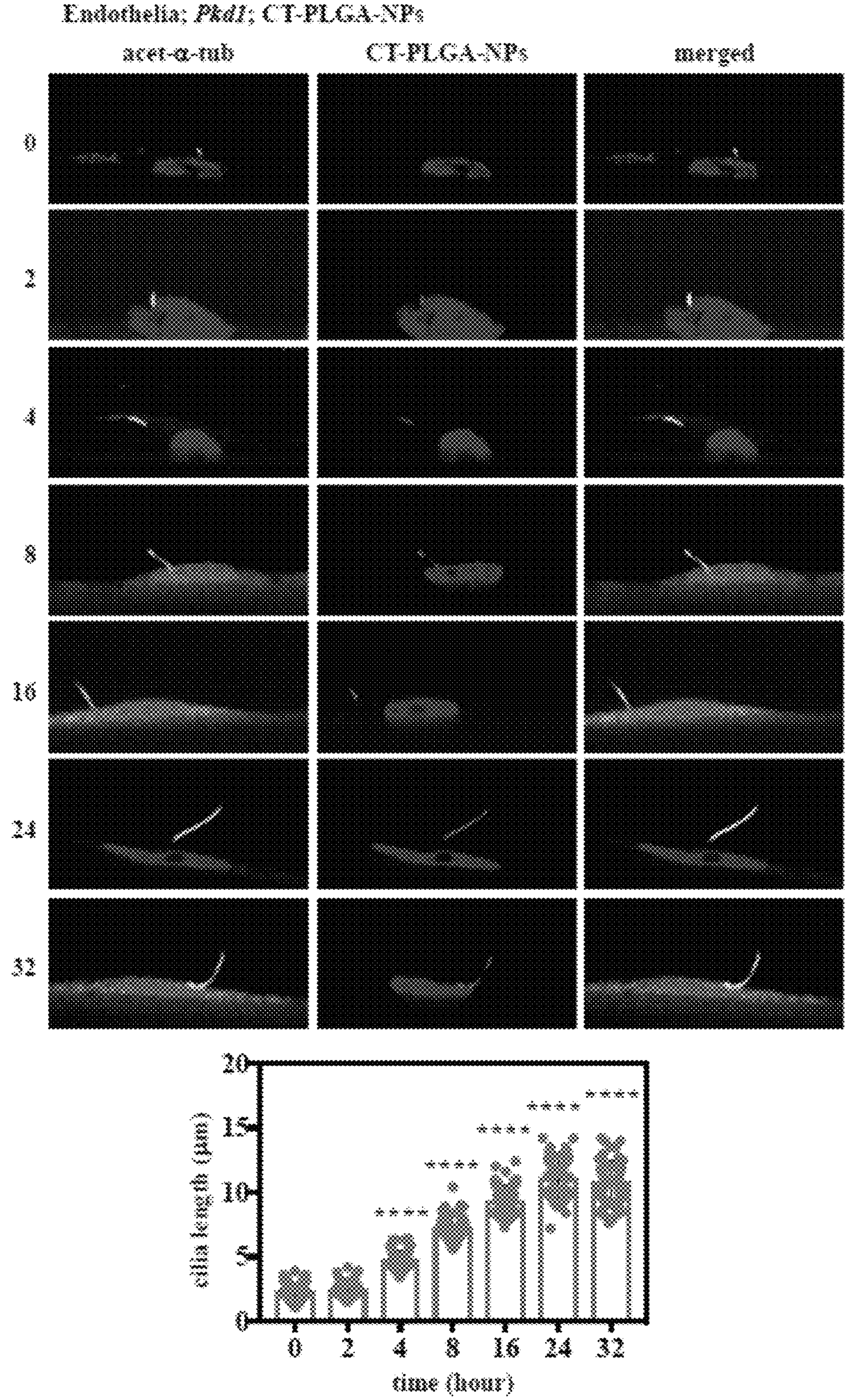
Figure 10A:
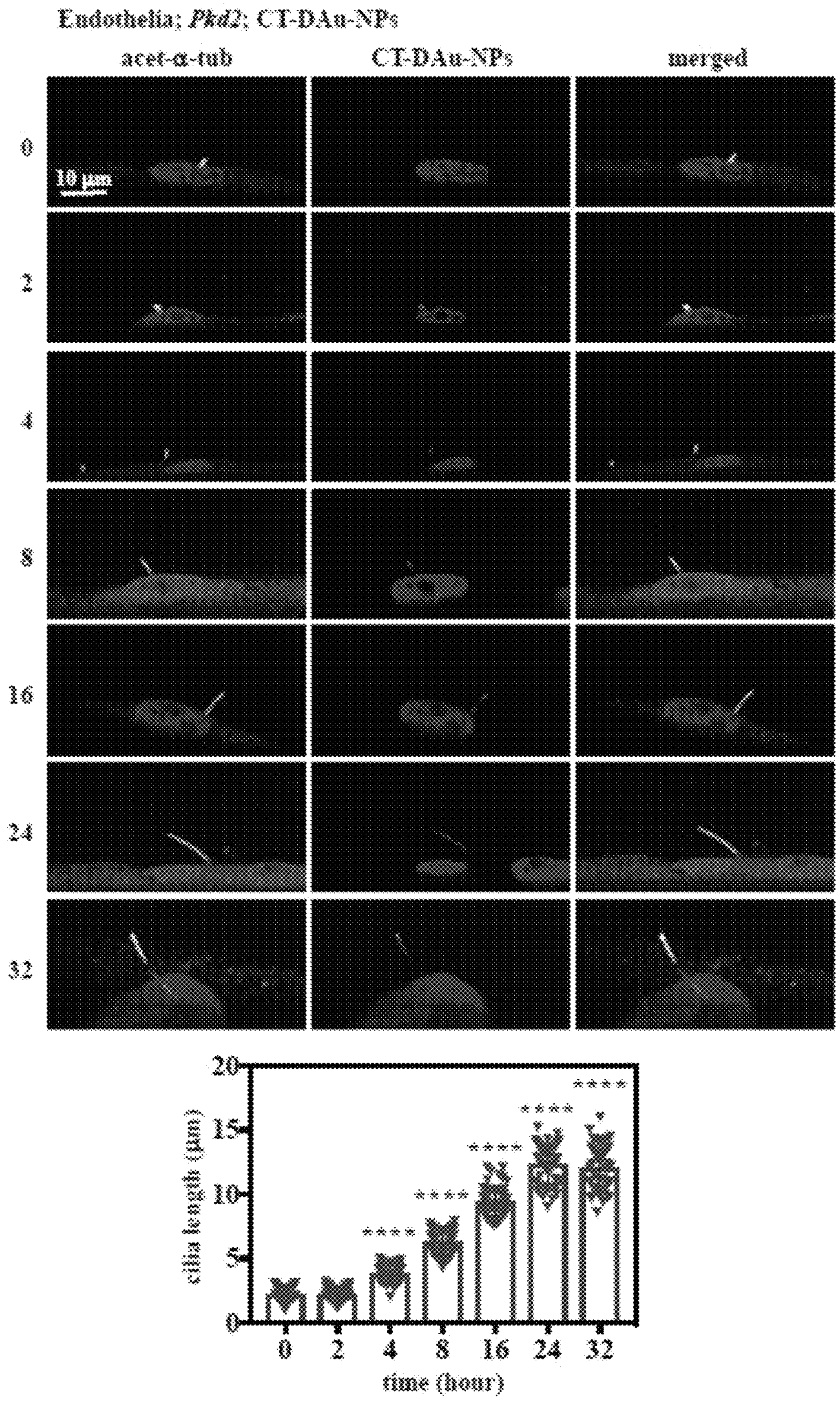
FIGS. 10A-B depict representative images on the effects of CT-DAu-NPs (FIG. 10A) and CT-PLGA-NPs (FIG. 10B) on primary cilia of vascular endothelia from Pkd2 mice. Numbers indicate time in hour. ****p<0.0001 compared to time 0, prior to the treatment with CTNDDS. Statistical analysis was performed using ANOVA followed by a Bonferroni post hoc test.
Figure 10B:
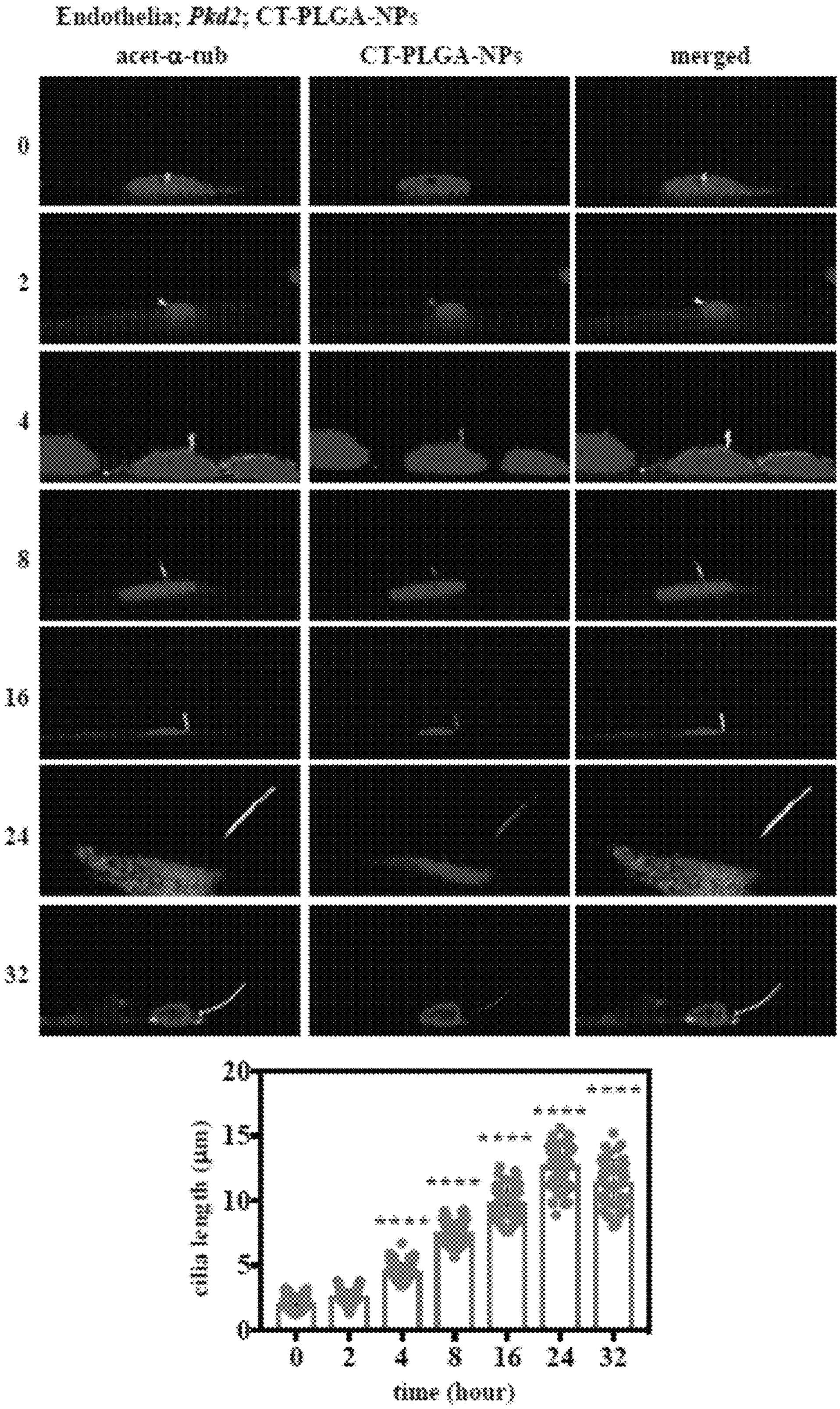
Figure 11A:
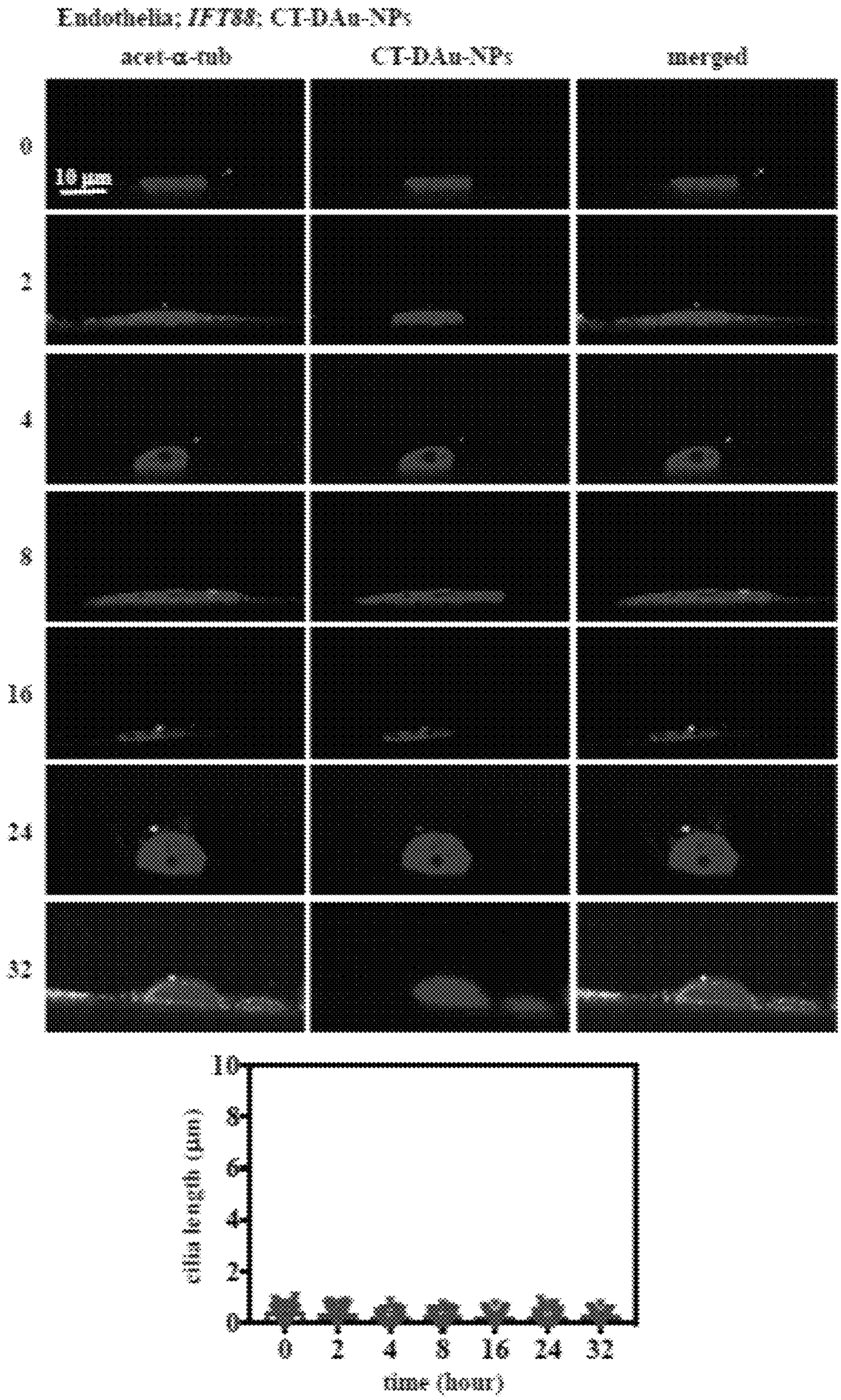
FIGS. 11A-B depict representative images on the effects of CT-DAu-NPs (FIG. 11A) and CT-PLGA-NPs (FIG. 11B) on primary cilia of vascular endothelia from IFT88 mice. Numbers indicate time in hour. Statistical analysis was performed using ANOVA followed by a Bonferroni post hoc test, and there was no statistical significance within groups.
Figure 11B:
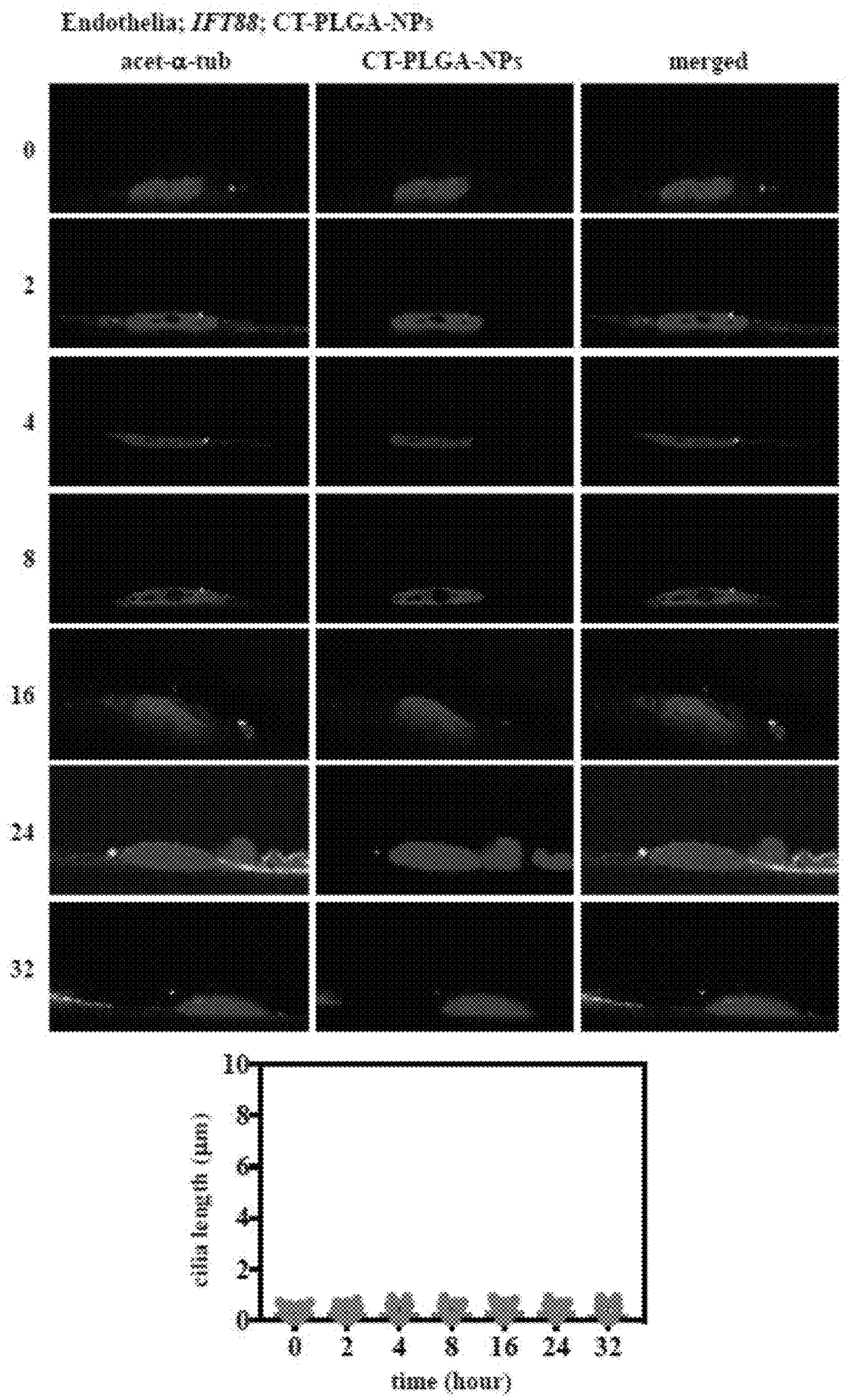

The structures and sizes of CTNDDS were visualized with electron micrographs (FIG. 2B). The size of the CTNDDS was also confirmed with the dynamic light scattering (DLS; FIG. 2C). The diameters of CT-DAu-NPs and CT-PLGA-NPs were approximately 40±2.5 and 102±4.8 nm, respectively. The surface charge of CT-DAu-NPs (−47.3±1.2 mV) was significantly more negative than CT-PLGA-NPs (—25.9±1.0 mV; FIG. 2D). This is consistent with the Corrected Debye-Hückel theory of surface charging, where a smaller particle size tends have a lower zeta-potential. Unlike CT-PLGA-NPs, CT-DAu-NPs were also dopaminergized resulting in a more negative charge surface. Fourier transform infrared spectroscopy (FTIR) also confirmed the conjugation of DR-5 antibody with both CTNDDS (FIG. 2E); the DR-5 antibody was to target dopamine receptor type-5 in the primary cilia. A standard HPLC curve for fenoldopam was prepared to standardize fenoldopam quantitation (FIG. 7F). Fenoldopam was significantly more efficient to be loaded (FIG. 2F) and released (FIG. 2G) into/from CT-PLGA-NPs than CT-DAu-NPs. CT-PLGA-NPs could function as better cargos than CT-DAu-NPs at least for fenoldopam. Of note was that the functional CTNDDS were generated (FIG. 2H), and they retained their fluorescence characteristics for microscopy imaging (FIG. 7G).

Figure 12A:
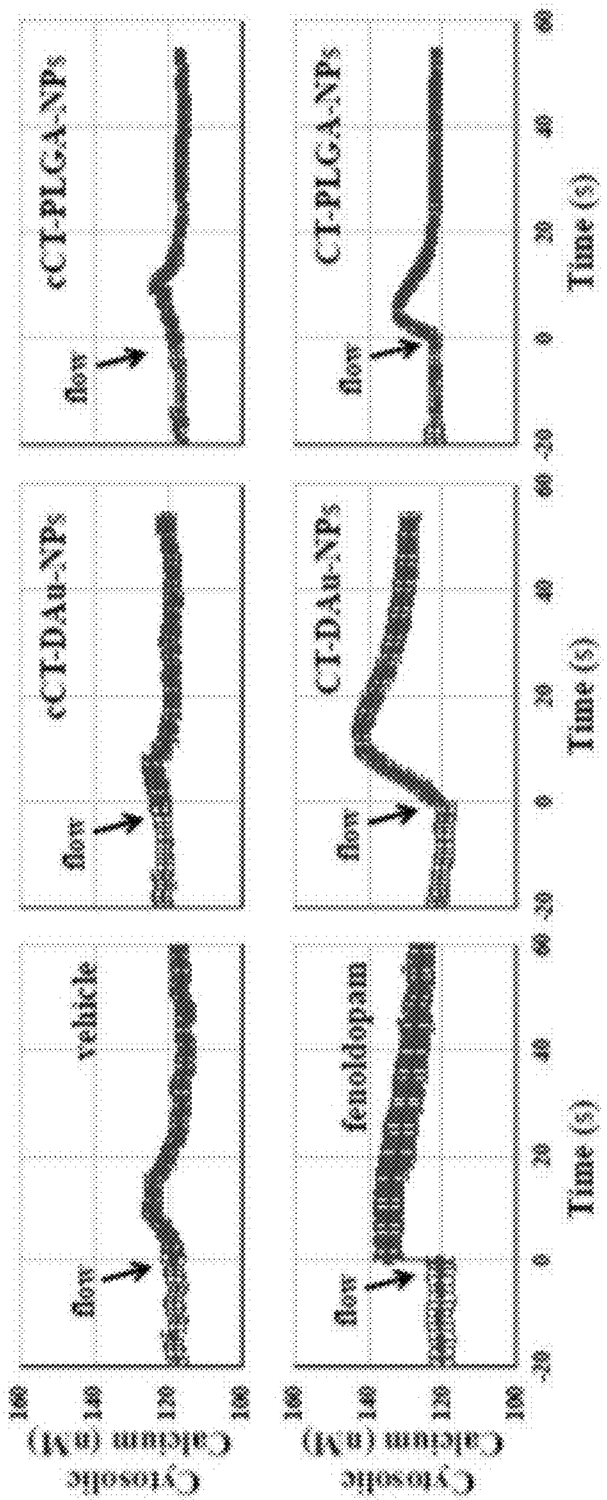
FIG. 12A-B.
Figure 12A:
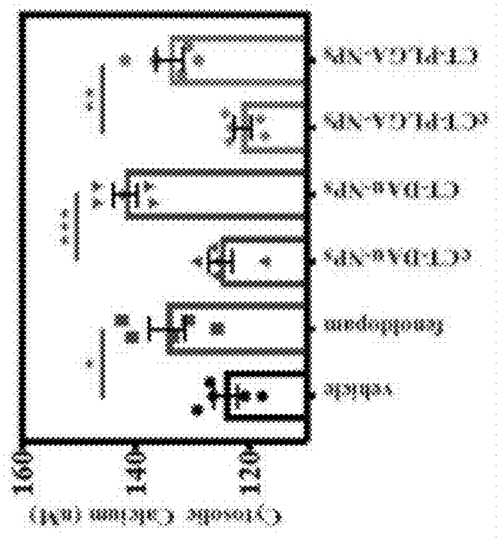
Figure 12B:
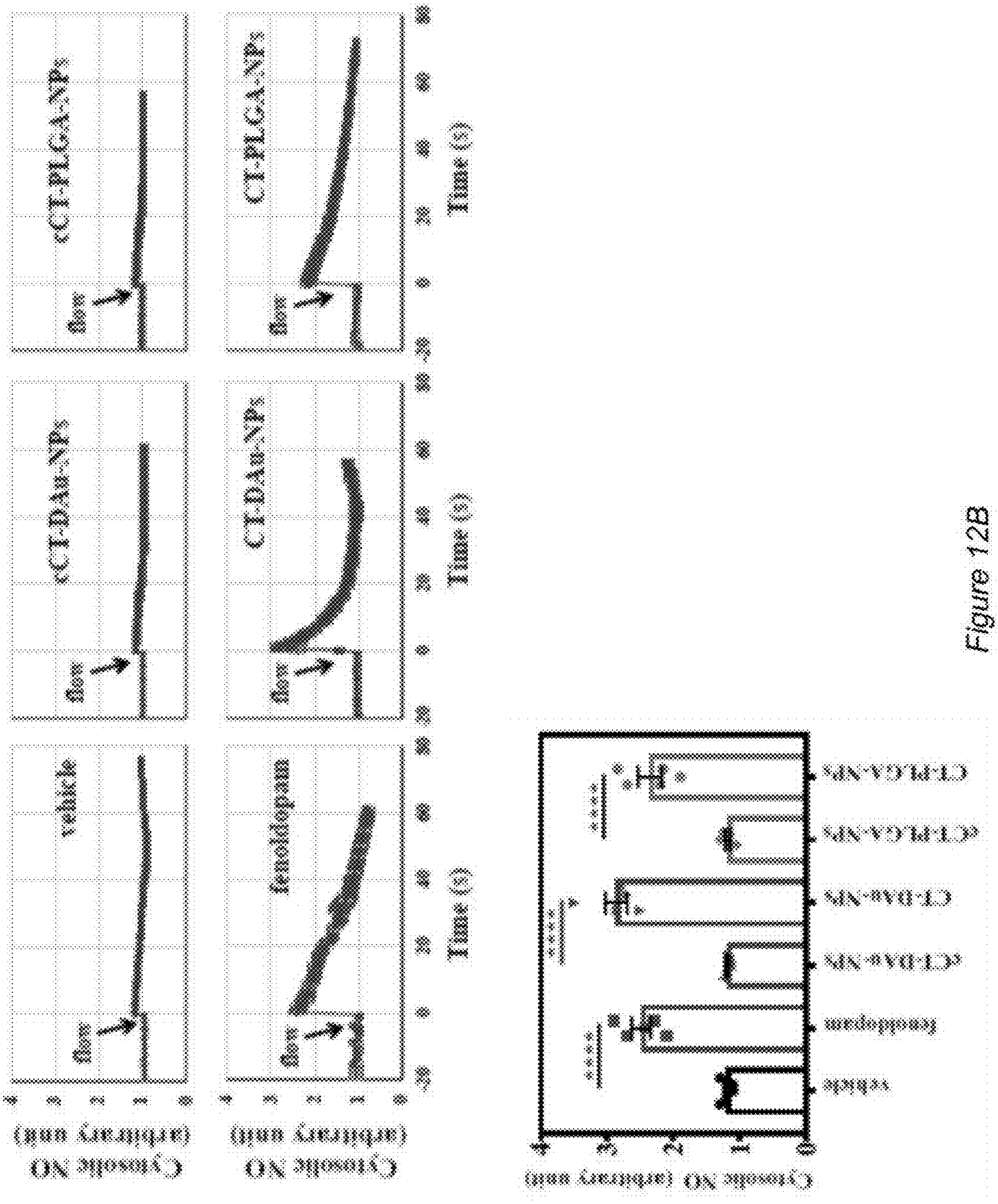

A single cell was randomly selected to calculate the binding specificities of fluorescence CTNDDS to the cilium and cell membrane. While the binding kinetics of CT-DAu-NPs (0.21±0.06 $min^{-1}$) and CT-PLGA-NPs (0.26±0.04 $min^{-1}$) to cilia were not significantly different, both CTNDDS showed very minimal binding to the cell membrane (0.0012±0.0004 $min^{-1}$ and 0.0013±0.0004 $min^{-1}$, respectively; FIG. 3A). Importantly, both CTNDDS showed maximum binding to cilia in less than 2 hours. The time-dependent cilia length increase by CTNDDS was separately analyzed in various cell types, including IFT88 cilia-less cells used as a negative control (FIGS. 8-11). In these studies, we consistently observed that 16-hour of treatment was an optimal effect of CTNDDS on primary cilia. After 16 hours, the efficacies of CTNDDS were thus examined and compared to their respective negative fenoldopam-free controls (cCT-DAu-NPs and cCT-PLGA-NPs; FIG. 3B). Fenoldopam-alone was also used as a positive control. Fenoldopam-loaded CTNDDS and fenoldopam-alone significantly increased cilia length compared to their corresponding controls, and there was no significant difference in cilia length between fenoldopam-alone and fenoldopam-loaded CTNDDS. Fluid flow-induced cilia bending can activate intracellular calcium ($Ca^{2+}$) followed with nitric oxide (NO) biosynthesis, which are used as indices to measure cilia function. While fenoldopam-alone and fenoldopam-loaded CTNDDS significantly increased cytosolic $Ca^{2+}$ (FIG. 4A; FIG. 12A) and NO biosynthesis (FIG. 4B; FIG. 12B) compared to their corresponding controls, there was no difference in cilia function among cell populations treated with fenoldopam-alone and fenoldopam-loaded CTNDDS.

Figure 4C:
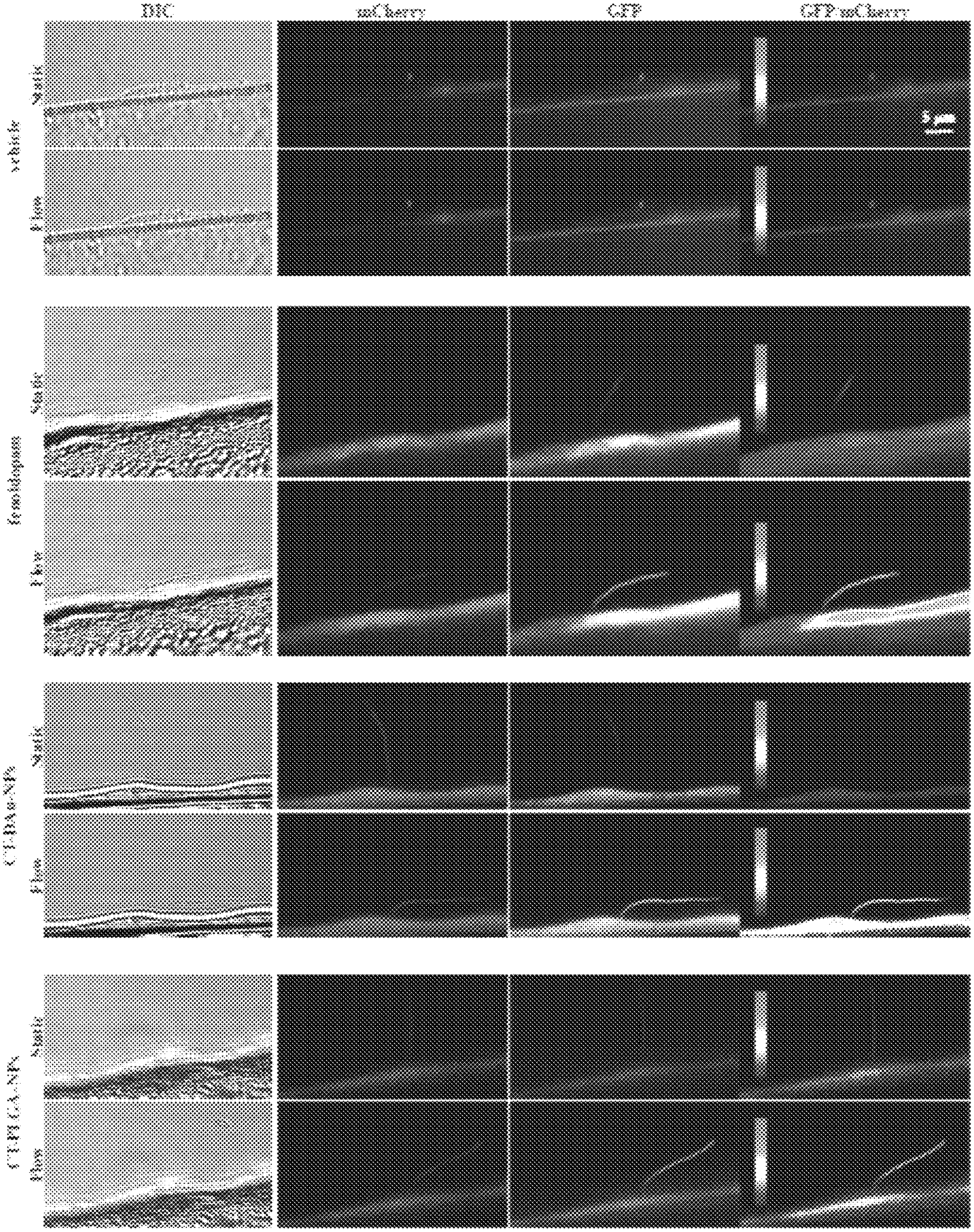
Figure 13A:
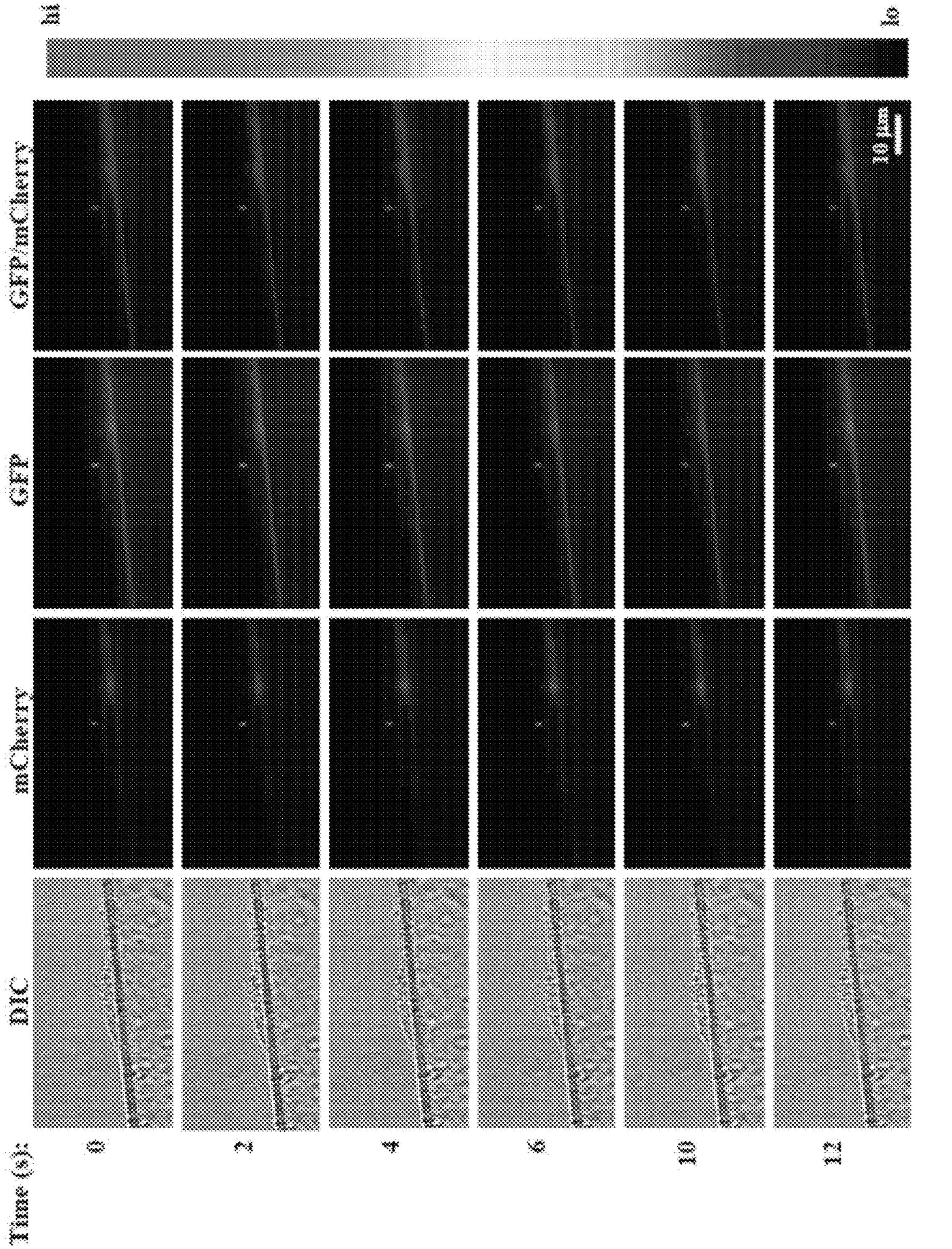
FIGS. 13A-B depict the cytosolic and ciliary calcium, the DIC, mCherry and GFP after cells were treated with PBS (FIG. 13A) or fenoldopam (FIG. 13B) under sub-minimal shear stress (0.5 dyn/$cm^2$). The gradient bar indicates $Ca^{2+}$ levels. n=3 for all experiments.
Figure 13B:
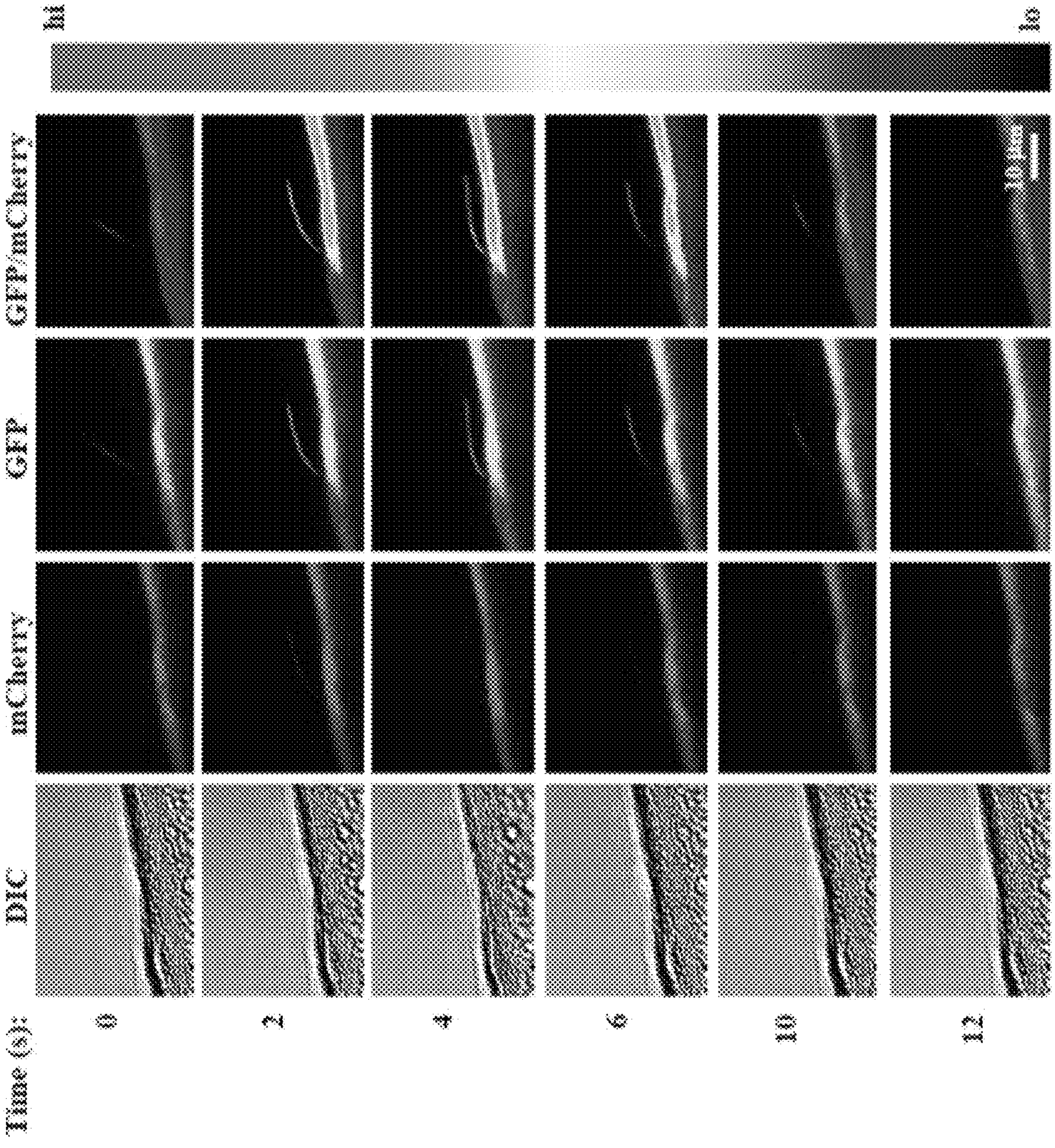
Figure 14A:
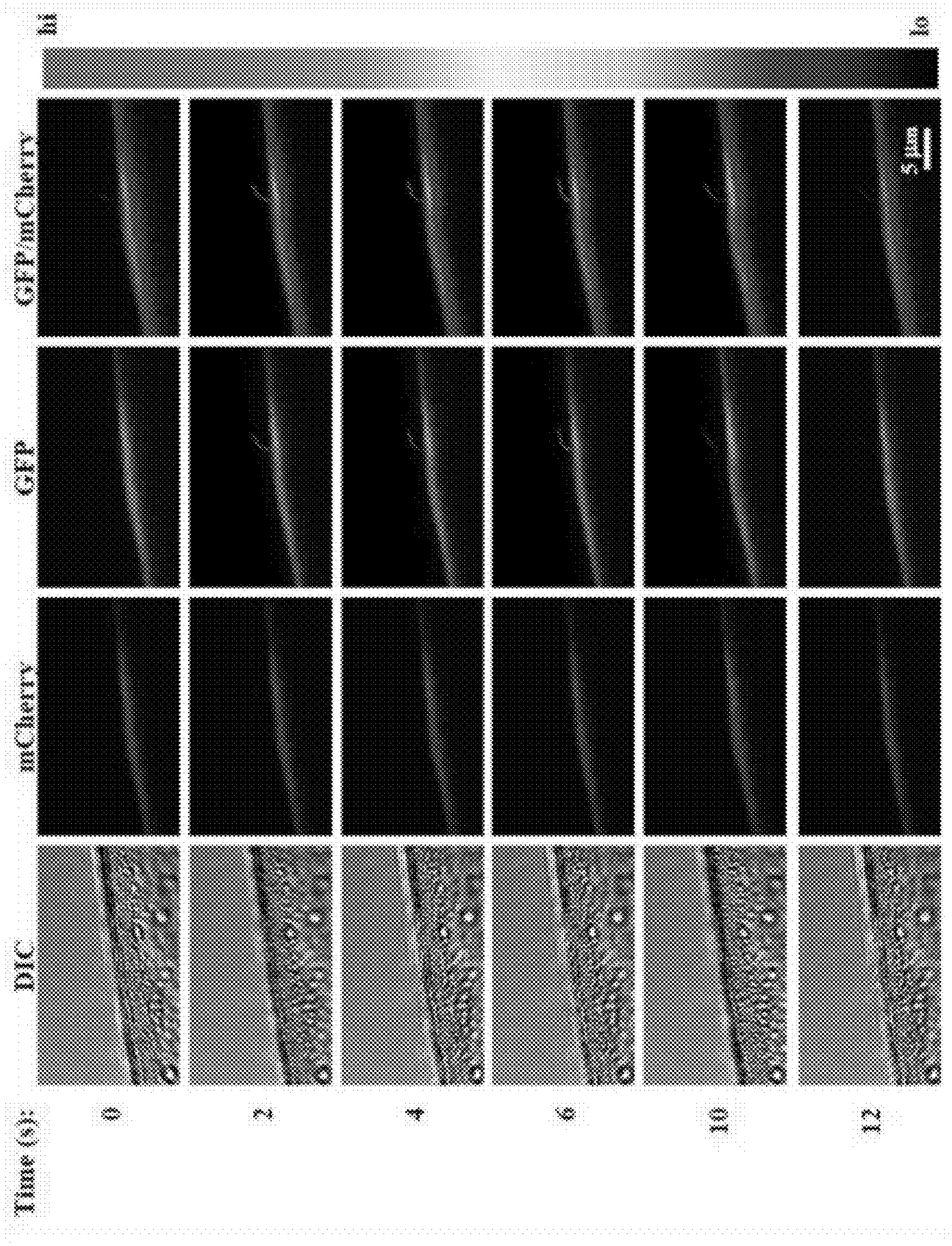
FIGS. 14A-B depict the cellular and ciliary calcium, the DIC, mCherry and GFP after cells were treated with cCT-DAu-NPs (FIG. 14A) or CT-DAu-NPs (FIG. 14B) under sub-minimal shear stress (0.5 dyn/$cm^2$). The gradient bar indicates $Ca^{2+}$ levels. n=3 for all experiments.
Figure 14B:
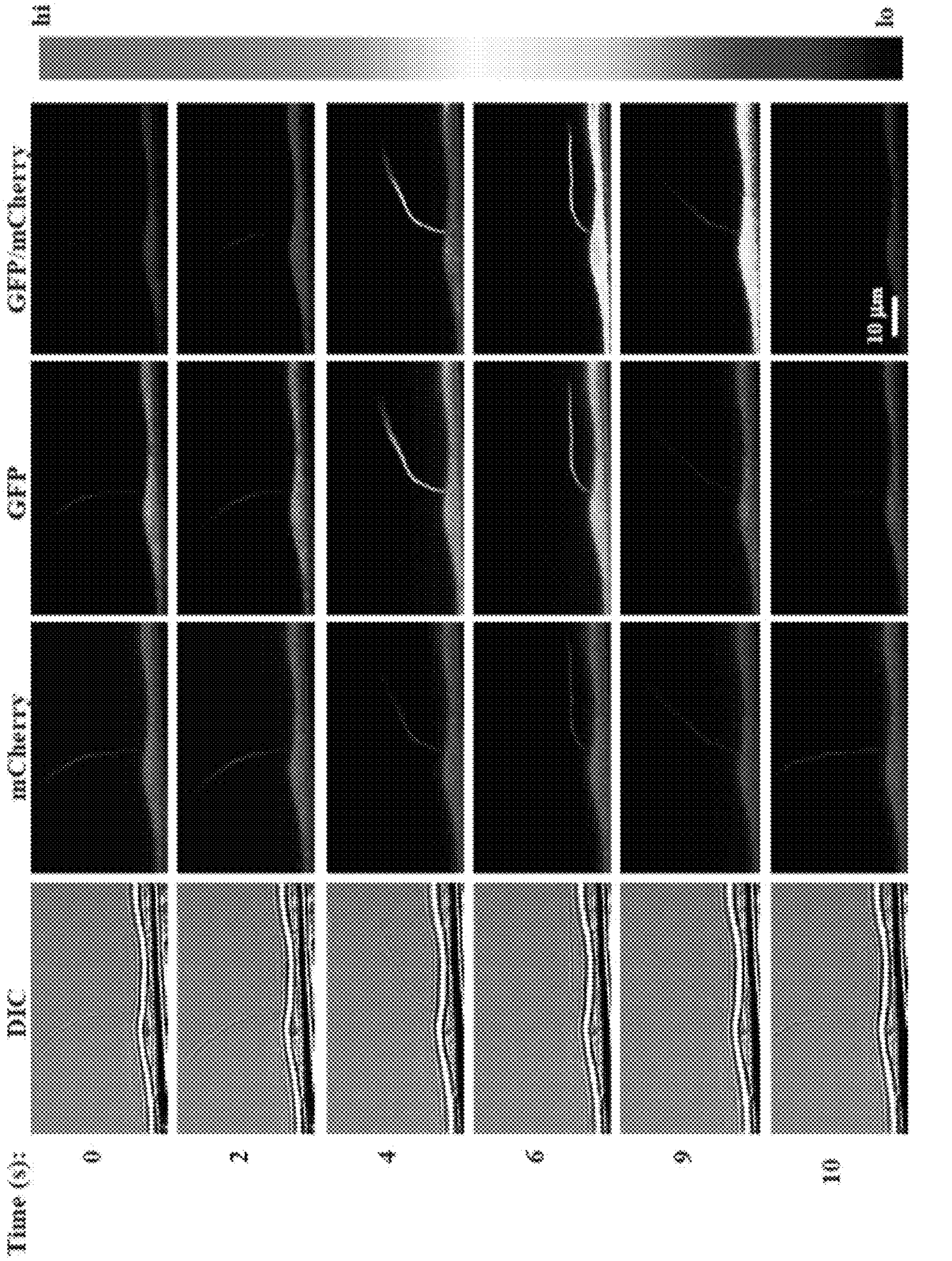
Figure 15A:
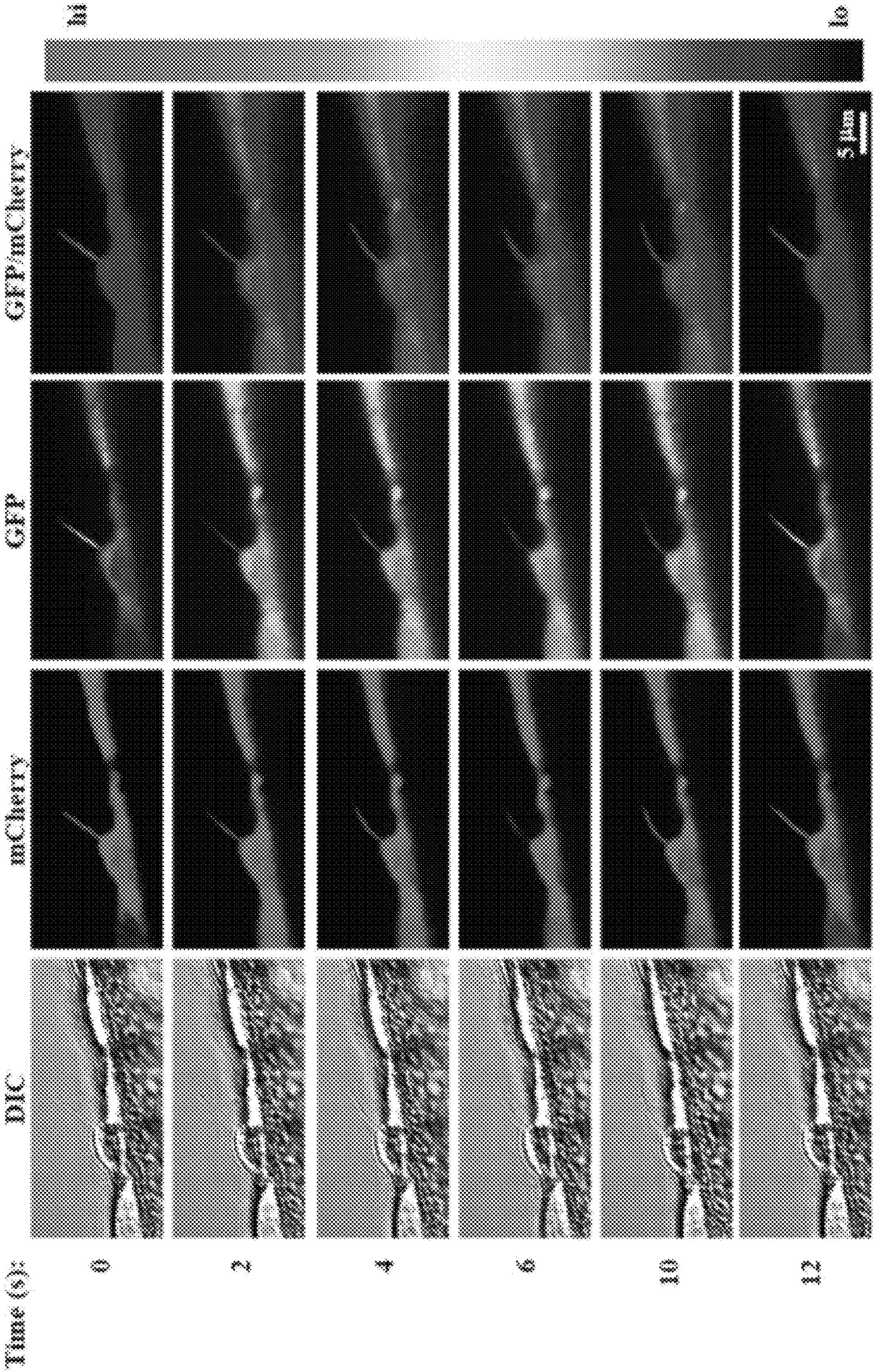
FIGS. 15A-B depict the cellular and ciliary calcium, the DIC, mCherry and GFP after cells were treated with cCT-PLGA-NPs (FIG. 15A) and CT-PLGA-NPs (FIG. 15B) under sub-minimal shear stress (0.5 dyn/$cm^2$). The gradient bar indicates $Ca^{2+}$ levels. n=3 for all experiments.
Figure 15B:
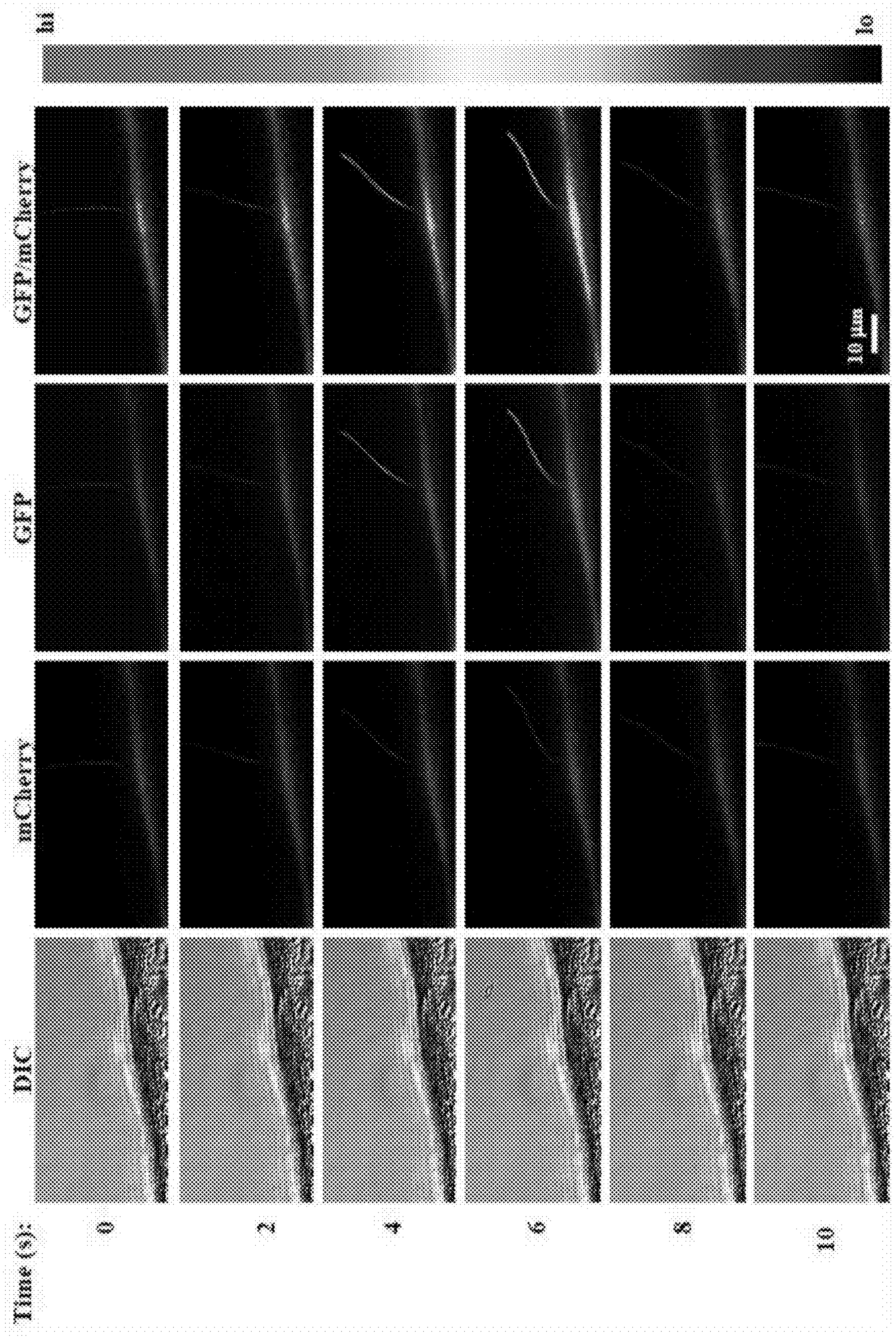
Figure 16A:
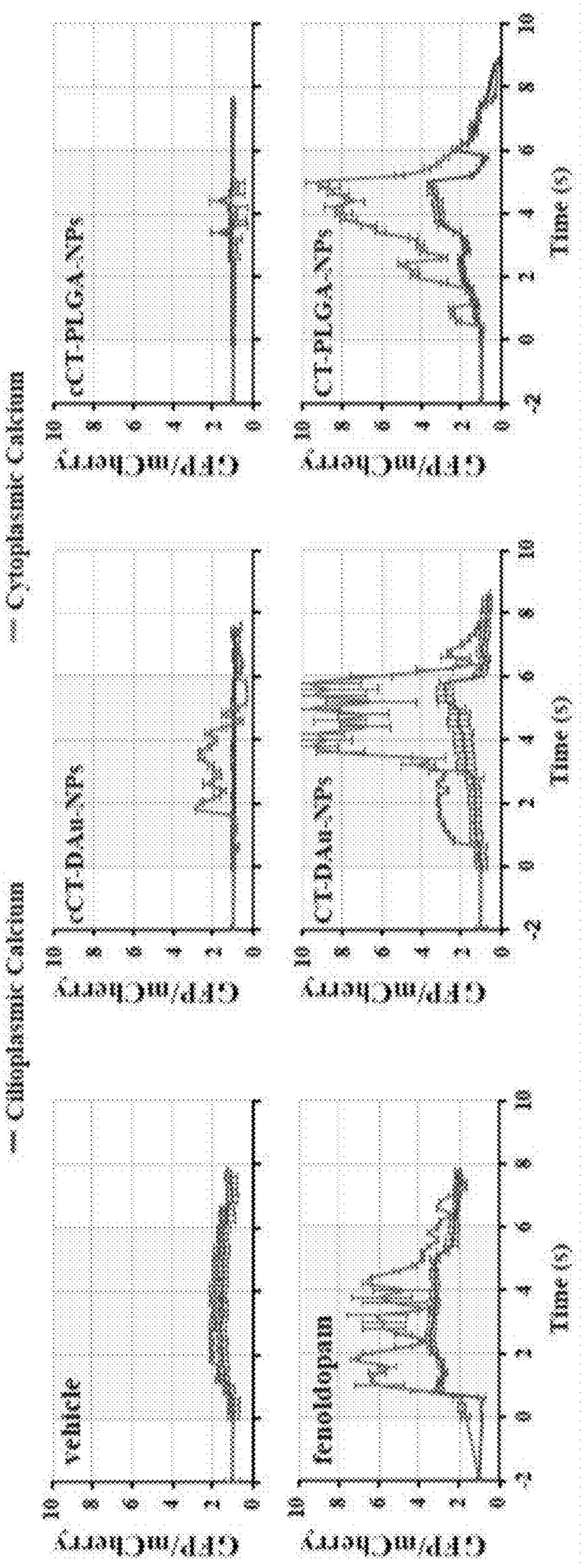
FIGS. 16A-C.
Figure 16B:
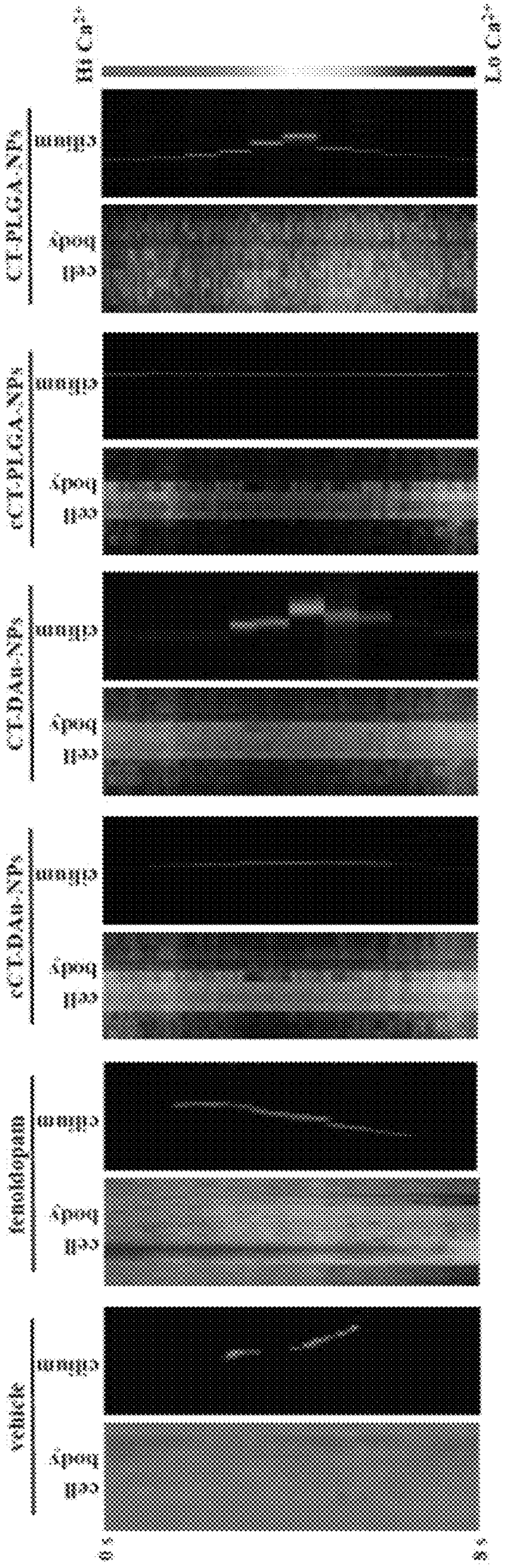
Figure 16C:
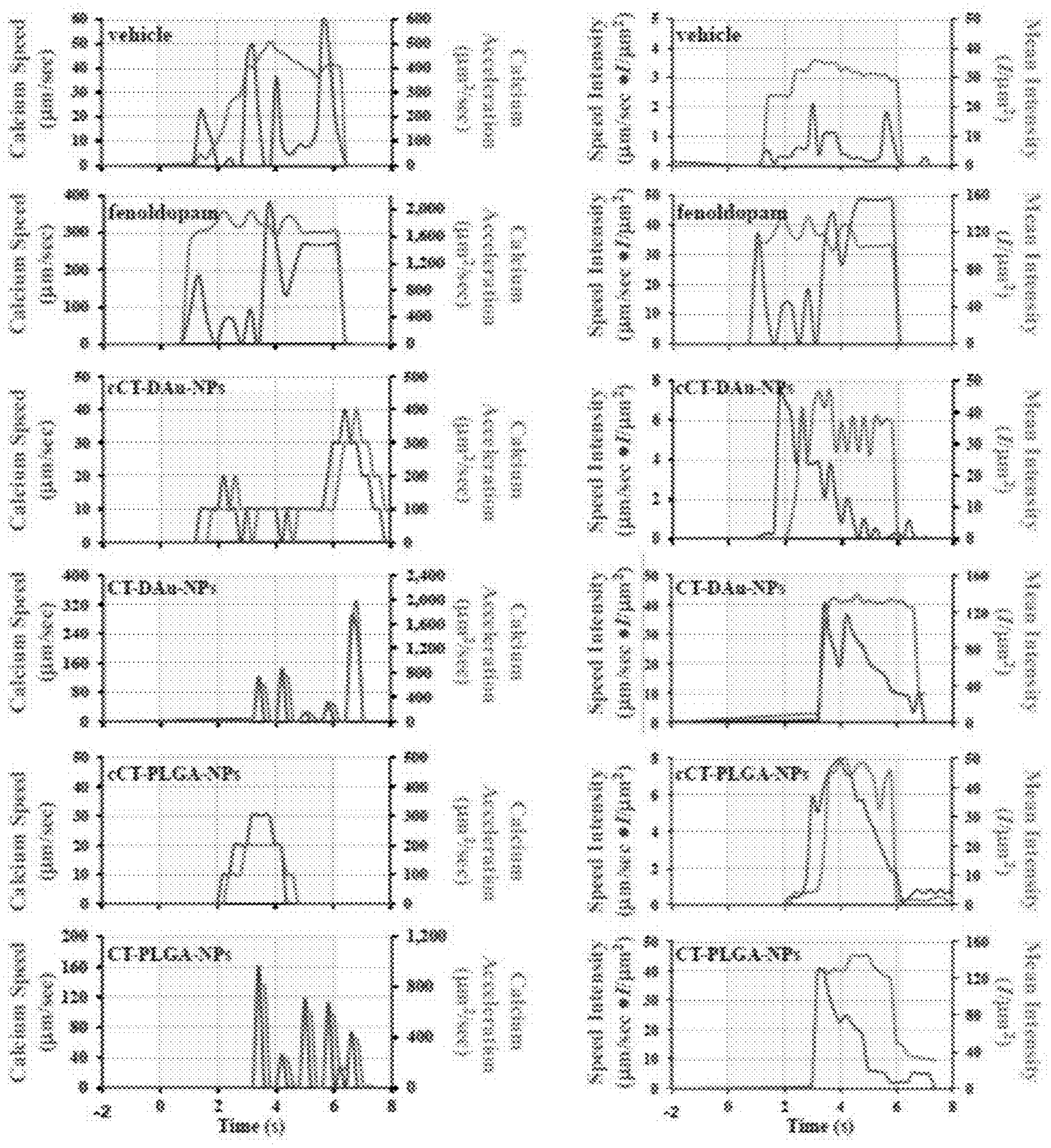
Figure 17A:
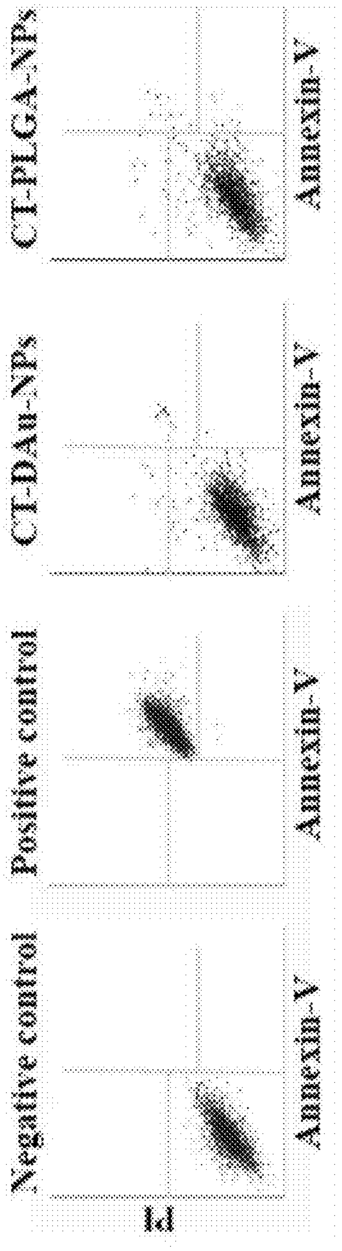
FIGS. 17A-B depict the cytotoxicity of CTNDDS (10 μg/mL for 48 hours) analyzed with apoptotic (Annexin-V) and necrotic (propidium iodide, PI) markers by FACS (FIG. 17A) and microscopy (FIG. 17B). DIC=differential interference contrast; negative control=phosphate saline treatment; positive control=30 minutes of methanol treatment.
Figure 17B:
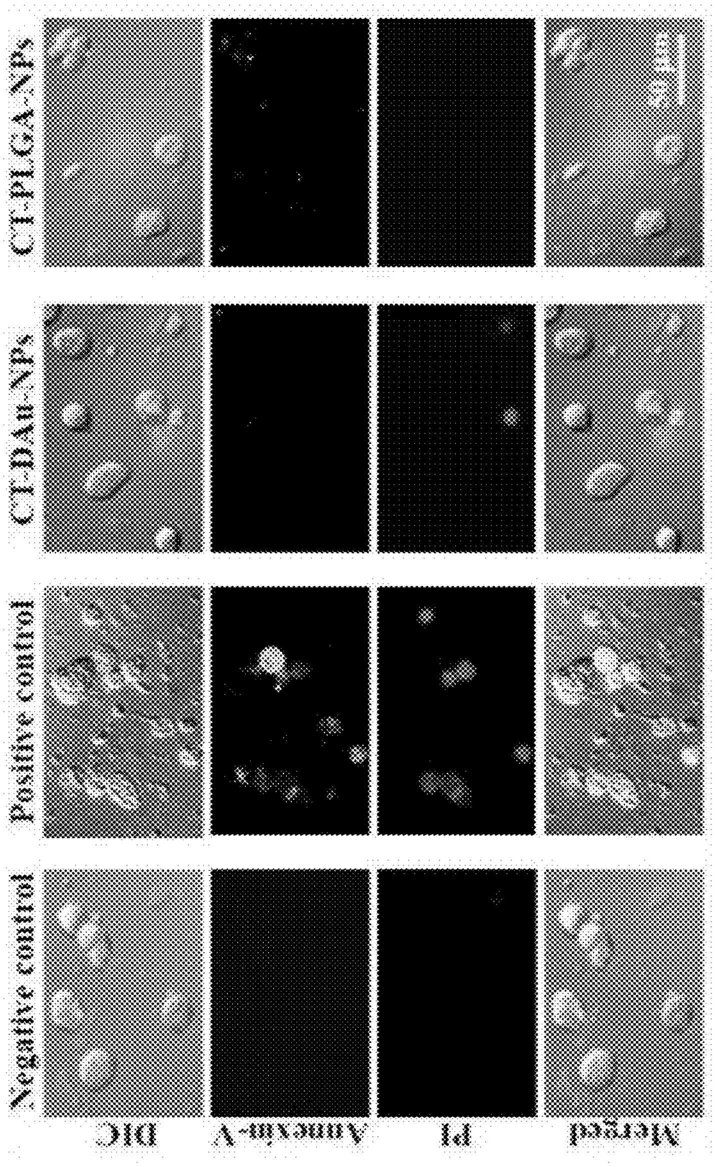
Figure 18:
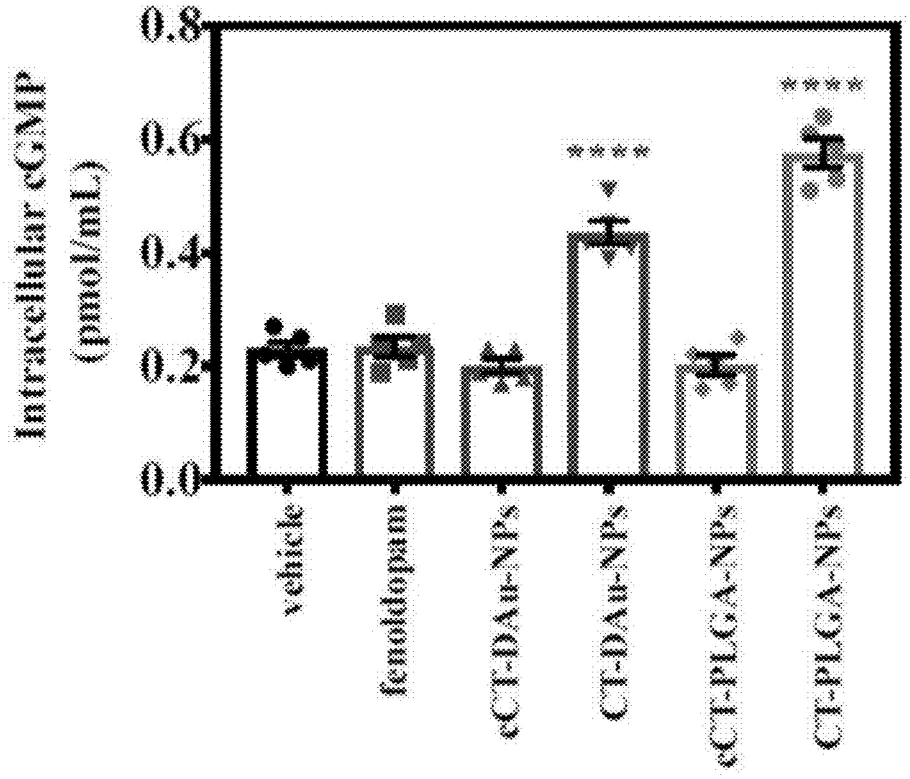
FIG. 18 depicts intracellular cGMP levels quantified in cells treated with vehicle (PBS; control) or other treatments. Statistical analysis was performed using ANOVA followed by a Bonferroni post hoc test.
Figure 19A:
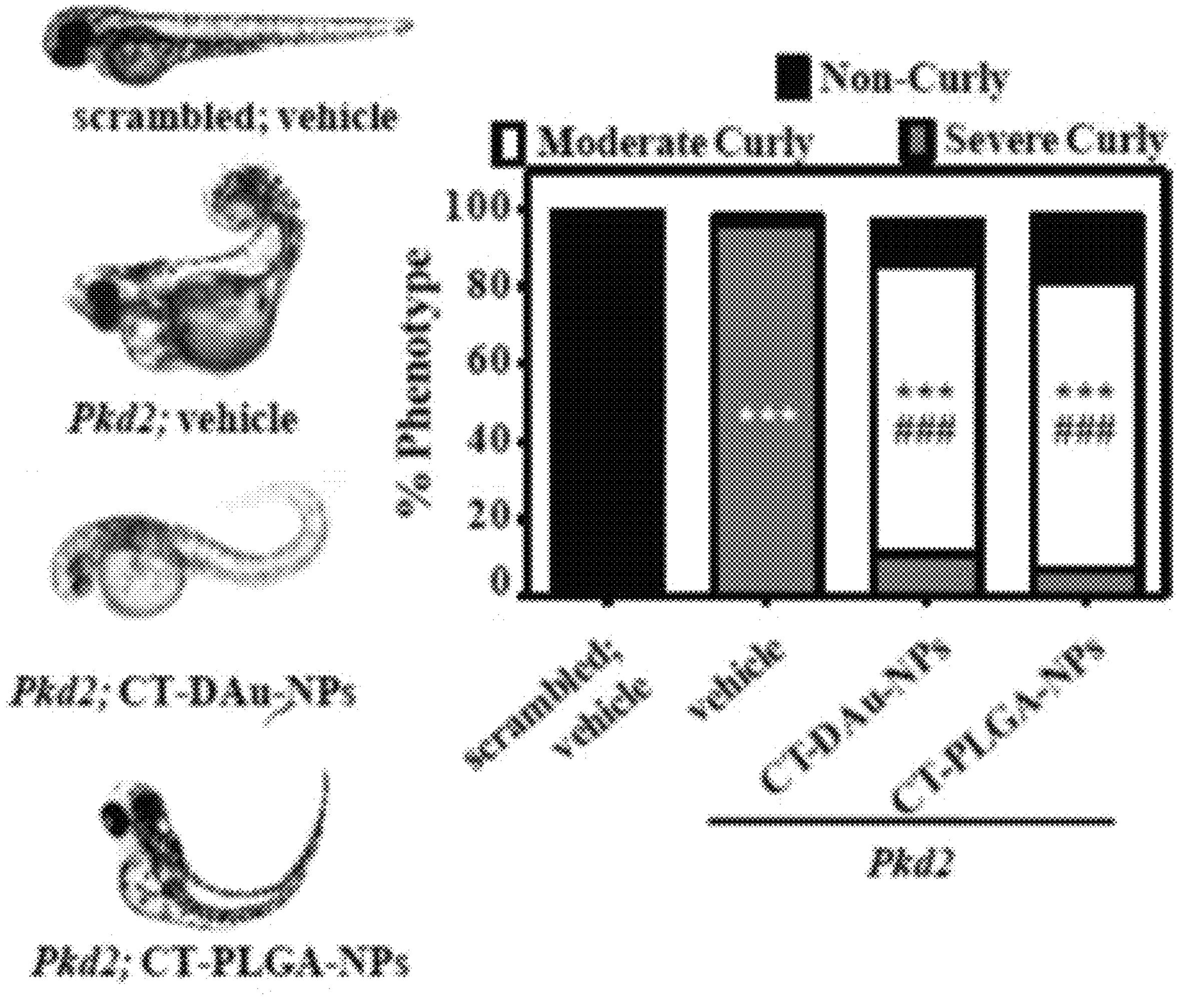
FIGS. 19A-E.
Figure 19B:
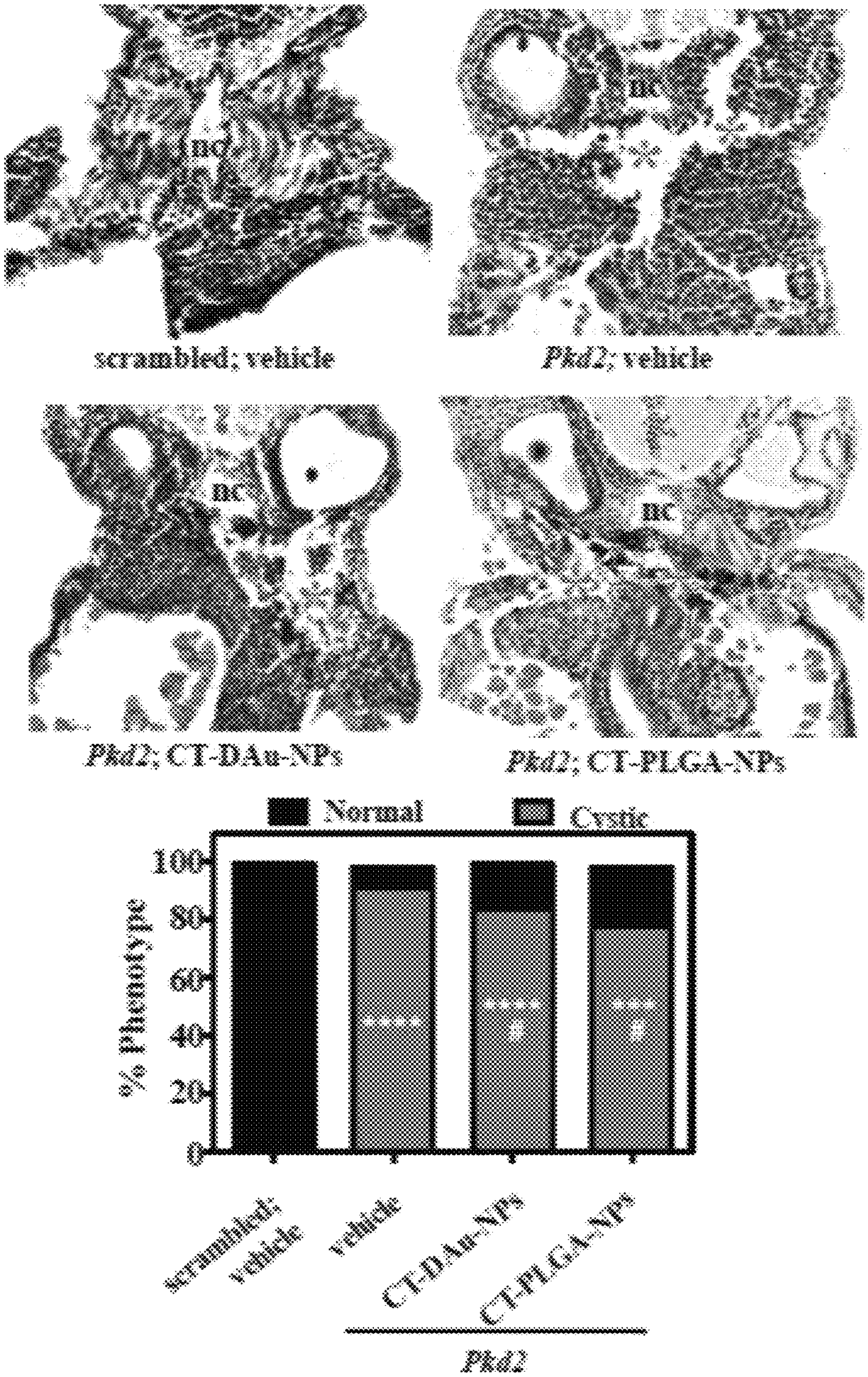
Figure 19C:
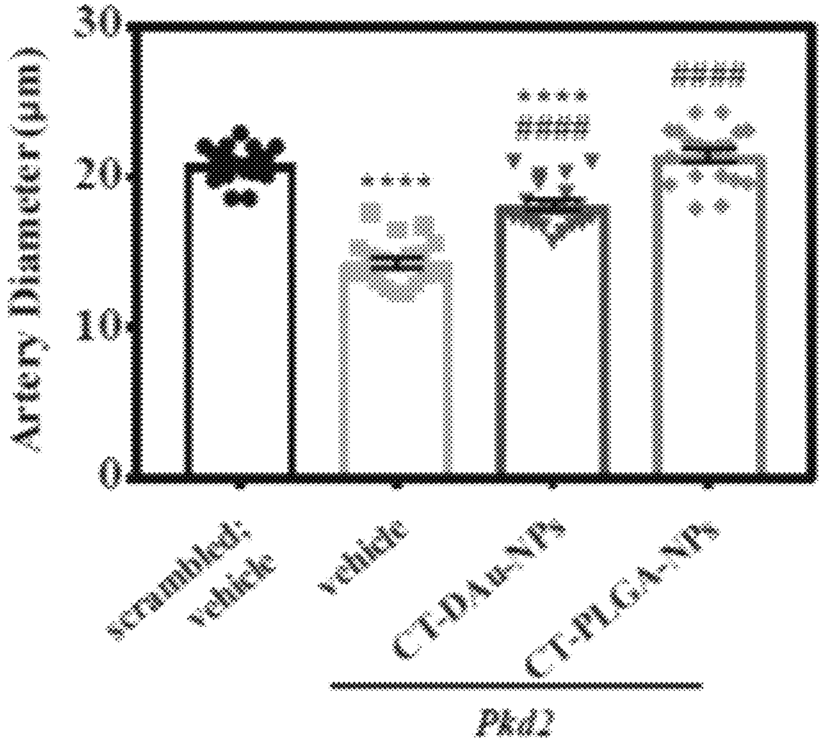
Figure 19D:
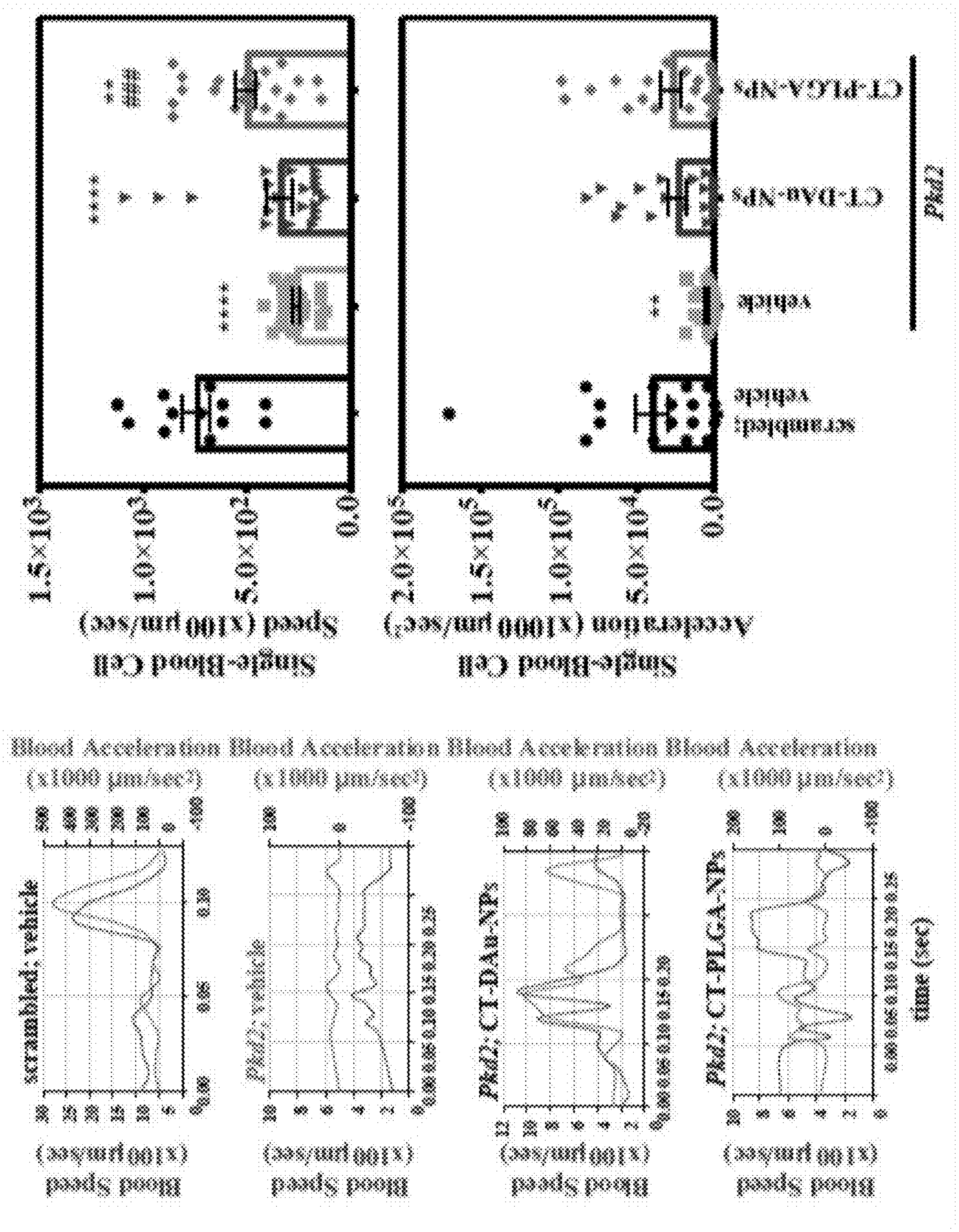
Figure 19E:
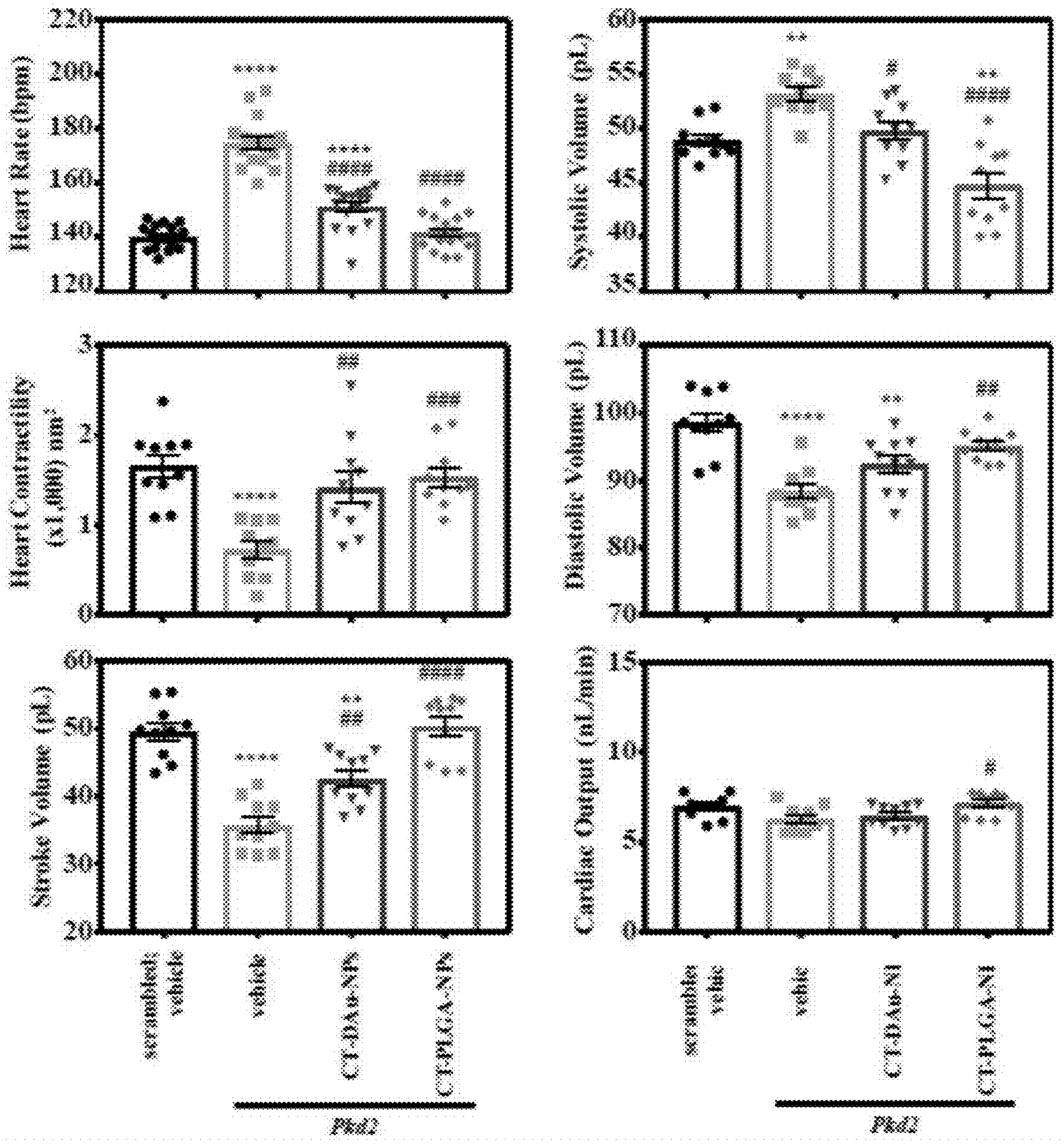

We next performed single-cell mechanosensory functional studies to tease out potential noises in cell population experiments (FIG. 4C). The $5HT_6$-mCherry-G-GECO1.0 construct was used to measure both cilioplasmic and cytoplasmic $Ca^{2+}$. Vehicle (PBS) and fenoldopam-alone (FIG. 13A, B) were compared to fenoldopam-free and fenoldopam-loaded CTNDDS (FIGS. 14 and 15). Despite using single-cell analyses, no difference in functional cilia was observed with regard to cilioplasmic and cytoplasmic $Ca^{2+}$ signaling between fenoldopam-alone and fenoldopam-loaded CTNDDS (FIG. 16A). To ensure that no signal artifact was recorded in the studies, we plotted $Ca^{2+}$ signaling in kymographs (FIG. 16B). Changes in the patterns of $Ca^{2+}$ speed and acceleration were corresponded to the changes in speed and mean signal intensity, indicating no signal artifact was recorded (FIG. 16C). We next screened for potential toxicity of CTNDDS, showing no cytotoxicity (FIG. 17). We also screened for cyclic guanosine monophosphate (cGMP) level as a potential marker of downstream NO signaling. Fenoldopam-loaded CTNDDS showed significantly higher intracellular cGMP levels compared to the control groups (FIG. 18), indicating that CTNDDS were potentially different from fenoldopam-alone. This might be due to improved specificity of CTNDDS action on primary cilia.

Figure 20A:
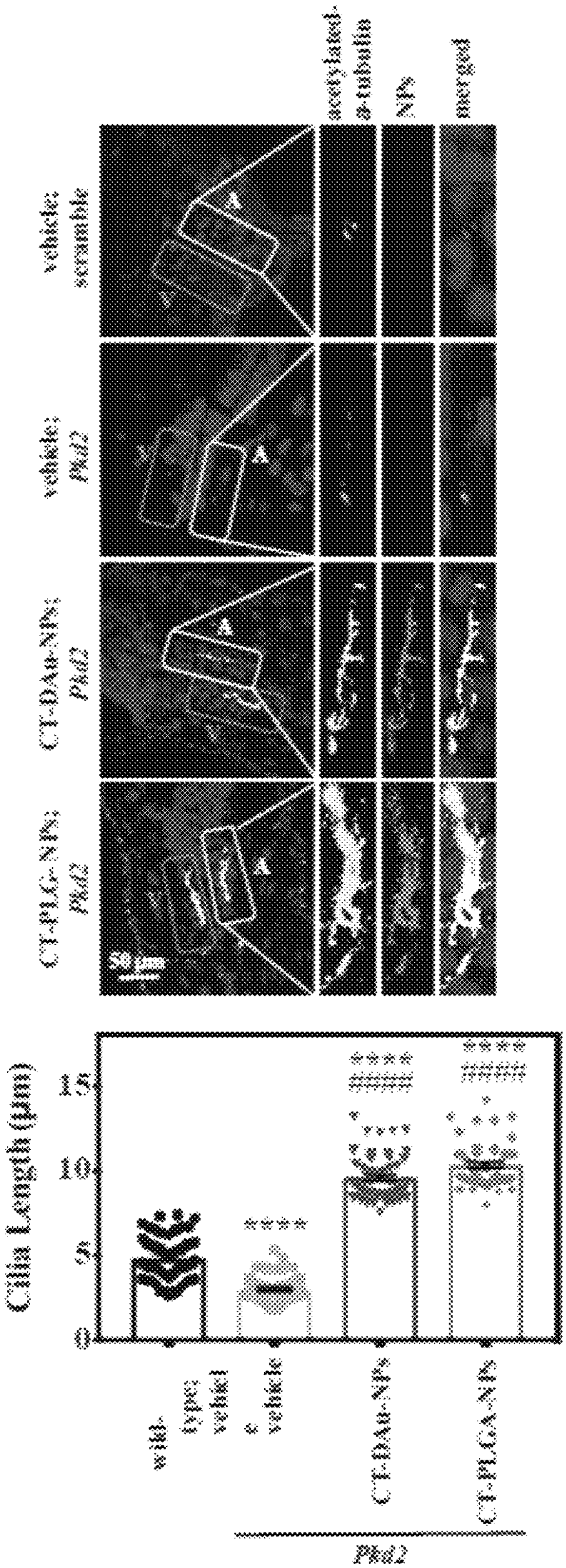
FIGS. 20A-B.
Figure 20B:
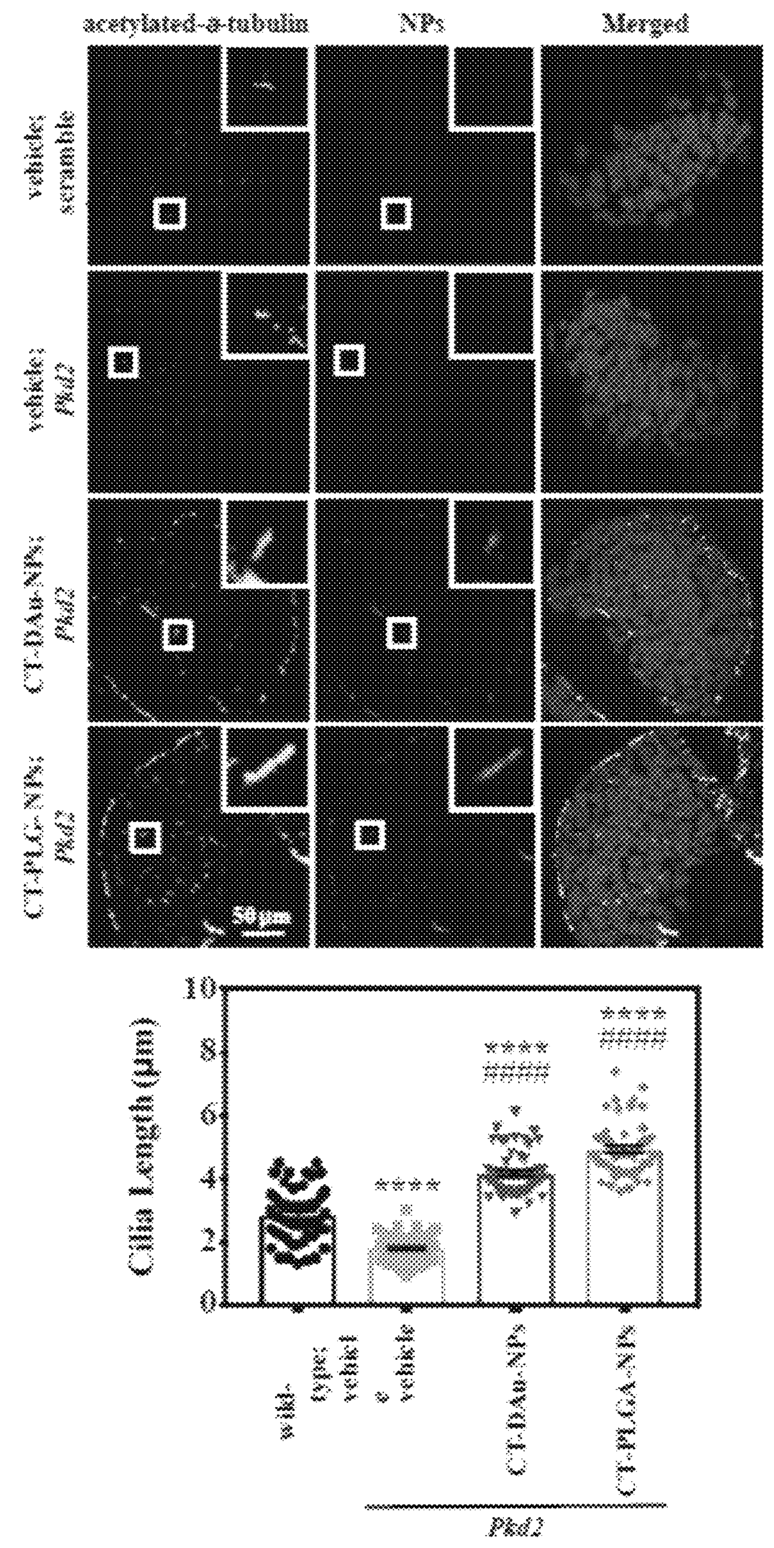
Figure 21A:
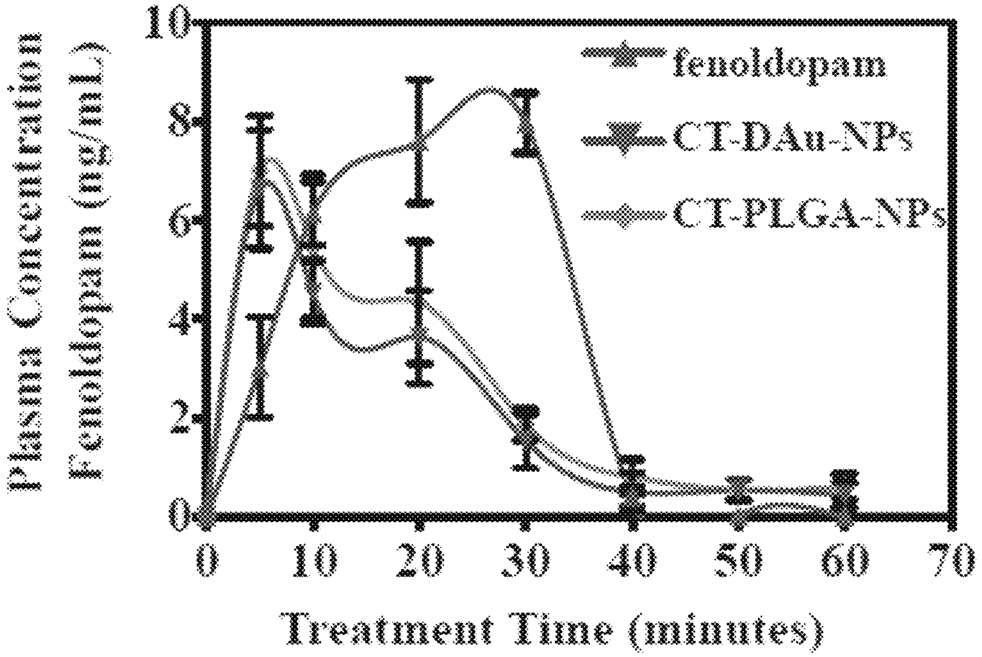
FIGS. 21A-B.
Figure 21B:
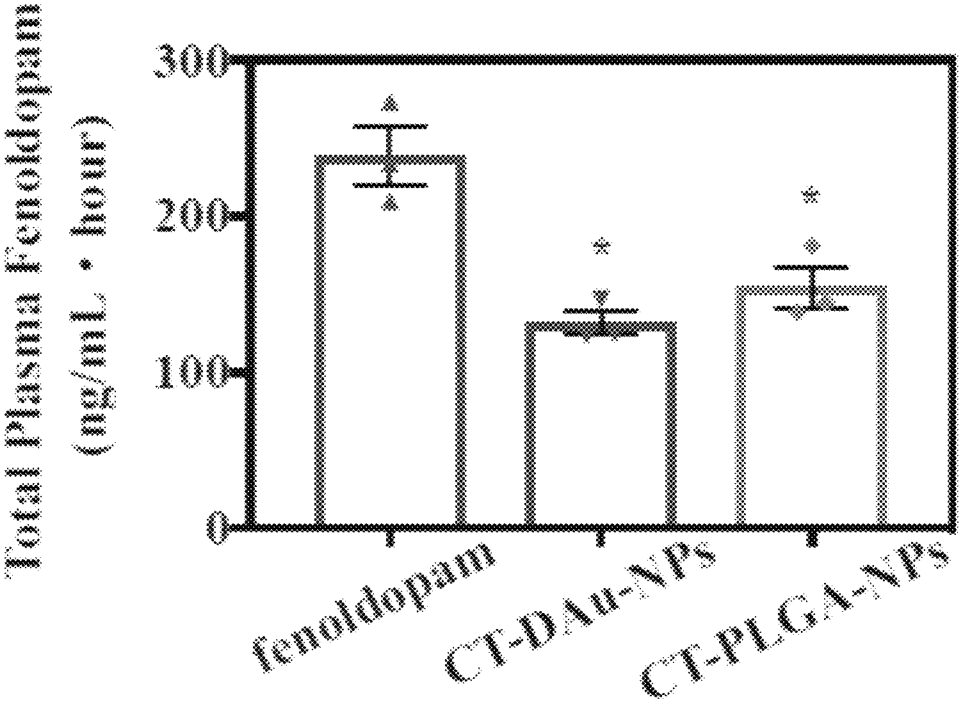
Figure 22:
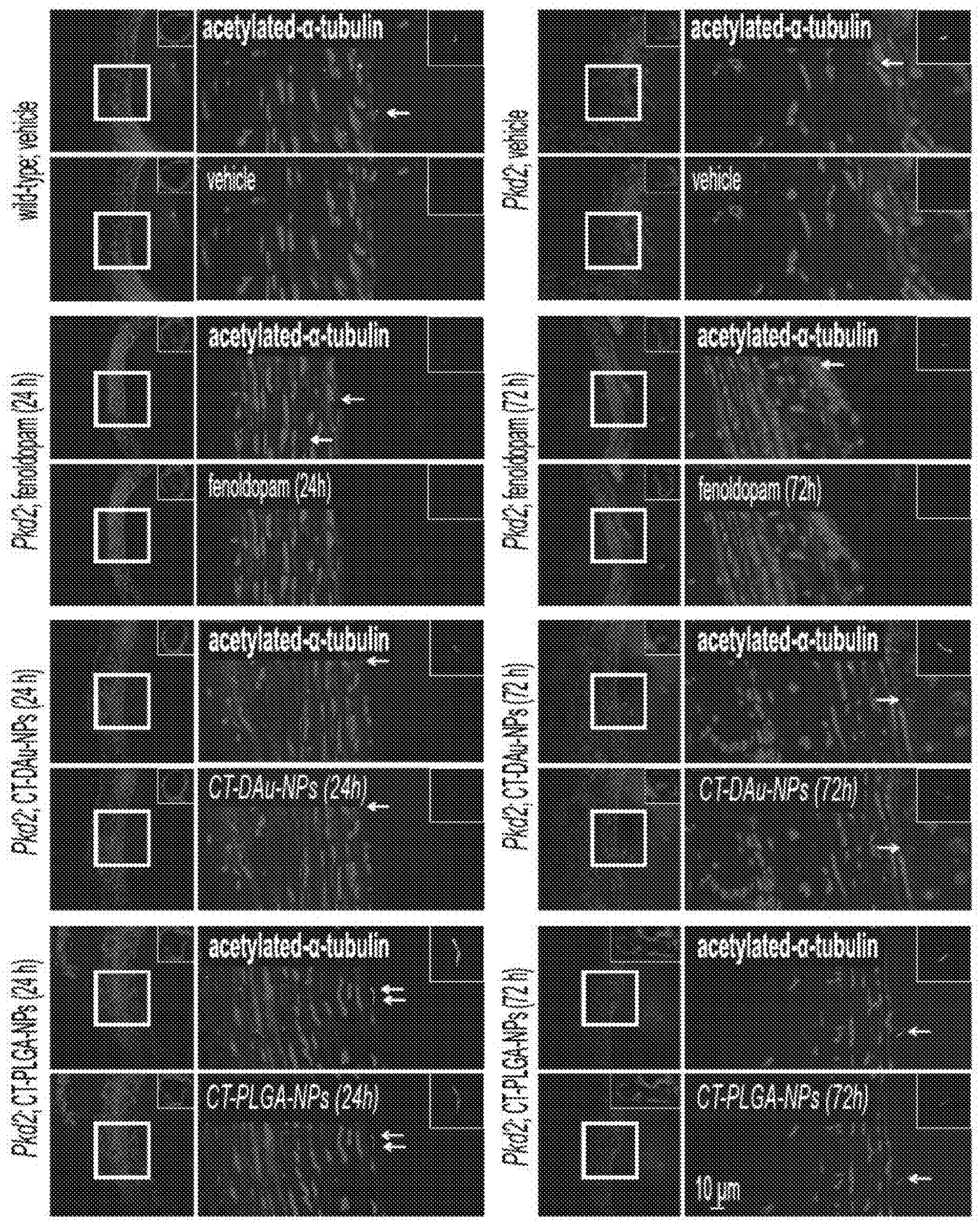
FIG. 22 depicts representative immunofluorescence images of primary cilia from aortic endothelial cells showing fluorescent CTNDDS (arrows) and cilia (arrows) at 24 or 72 hours after treatment. The insets show reduced views of the whole aorta and magnified views of cilia. White boxes indicated the magnified areas. Cilia length is shown in the bar graph. n=50 for all experiments. ****$p<0.0001$ and ####$p<0.0001$, compared to vehicle-treated wild-type and Pkd2 mice, respectively. Statistical analysis was performed using ANOVA followed by a Bonferroni post hoc test.
Figure 22:
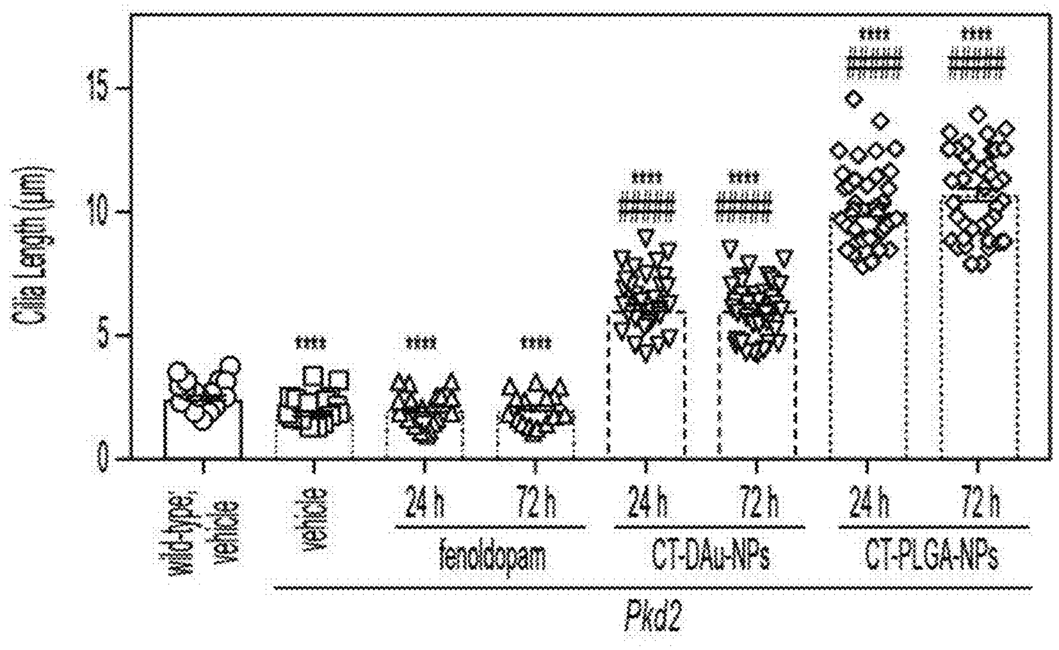
Figure 23:
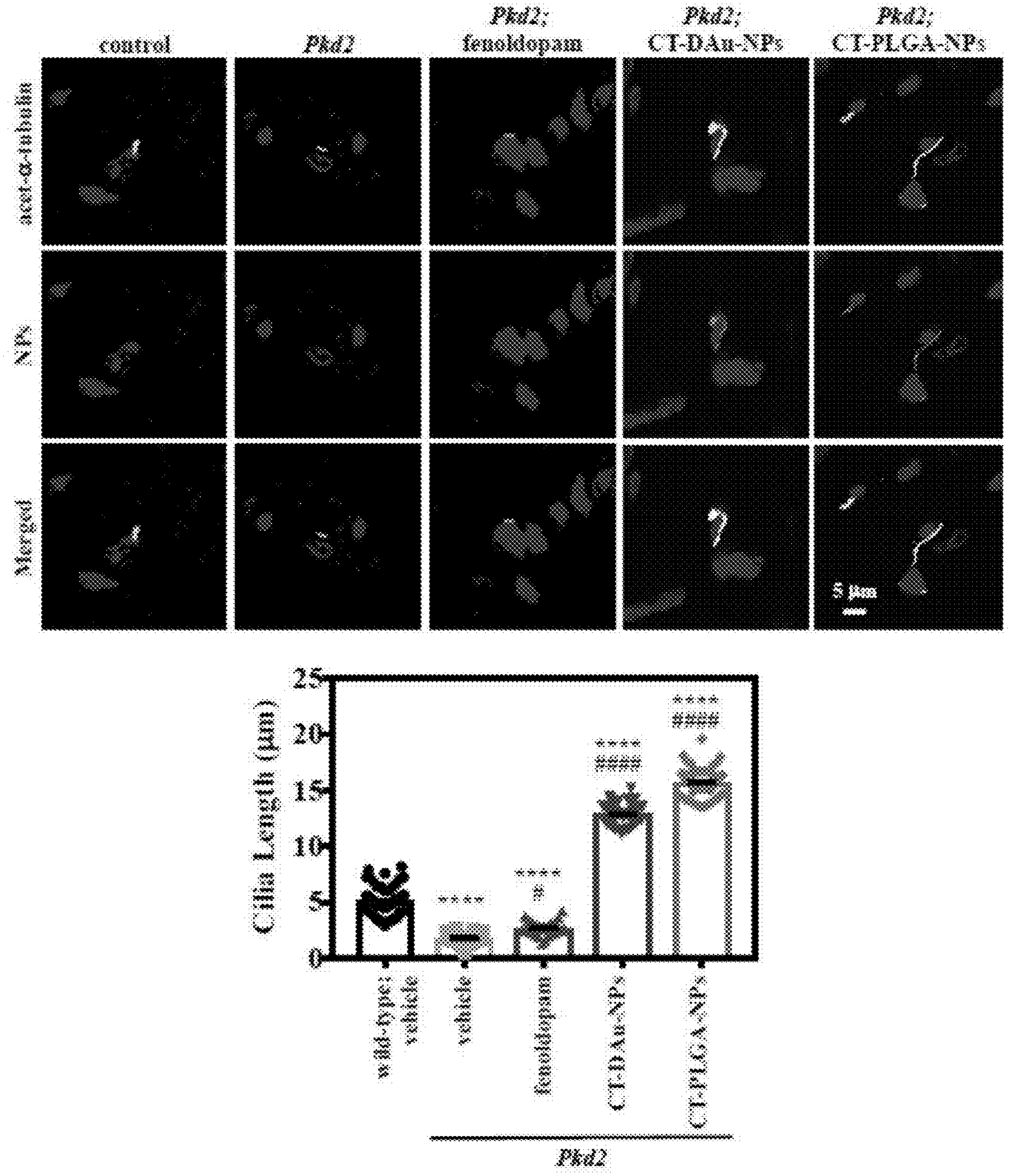
FIG. 23 depicts representative immunofluorescence images show the localization of CTNDDS and length of cilia in cardiac myocytes. Cilia length is presented in the bar graphs. n=50 for all experiments. ****$p<0.0001$ and ####$p<0.0001$, compared to vehicle-treated wild-type and Pkd2 mice, respectively. Statistical analysis was performed using ANOVA followed by a Bonferroni post hoc test.

We next compared fenoldopam alone and CTNDDS in zebrafish as the in vivo ciliopathy model. Unfortunately, we could not perform neither bolus injection nor infusion of fenoldopam in the fish. While bolus injection caused tachycardia-associated death, a slow fenoldopam perfusion into the fish remained a technical challenge with a high likelihood to injure young, 48 hours-post fertilization fish. Regardless, we were encouraged that CTNDDS could significantly rescue the ciliopathic phenotypes, including improving tail curvature defects, preventing cystic kidney formation, vasodilating the blood vessels and therefore improving blood flow and overall cardiac functions (FIG. 19). Importantly, CTNDDS increased length of primary cilia in the fish artery and heart (FIG. 20). This supported the idea that CTNDDS were functionally viable for use in in vivo without triggering reflex tachycardia as seen in fenoldopam-alone, suggesting the slow-sustained release nature of CTNDDS was suitable for further investigation in a larger animal model. The pharmacokinetics profiles of CTNDDS on fenoldopam release was first compared with fenoldopam alone by collecting blood plasma from the mice (FIG. 21A). Total plasma concentration of fenoldopam was significantly higher in fenoldopam-alone than fenoldopam-loaded CTNDDS mice (FIG. 21B). The plasma level of fenoldopam in CTNDDS in the first 20 minutes could be due to circulating NPs in the blood, perhaps prior to binding to the primary cilia. To investigate this possibility, we examined localization of CTNDDS to primary cilia in aorta (FIG. 22) and heart (FIG. 23). After 24- or 72-hours of bolus injection of CTNDDS, we could detect CTNDDS fluorescence in the primary cilia. Importantly, cilia length was increased by CTNDDS but not fenoldopam. Of note is that continuous fenoldopam for 5 days is needed to increase cilia length.

Figure 5A:
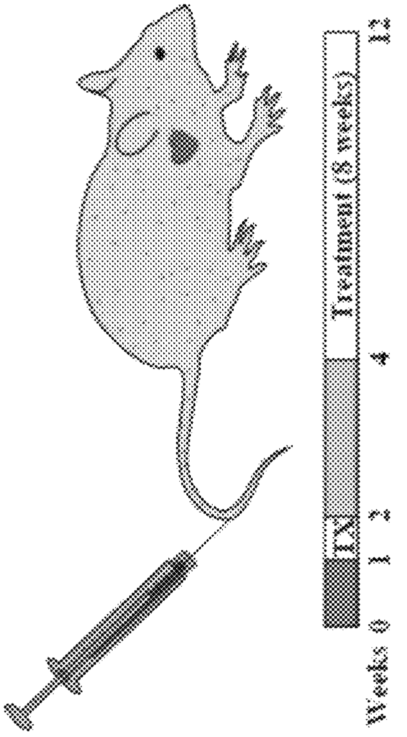
FIGS. 5A-E depict treatment in a hypertensive Pkd2 mouse model.
Figure 5B:
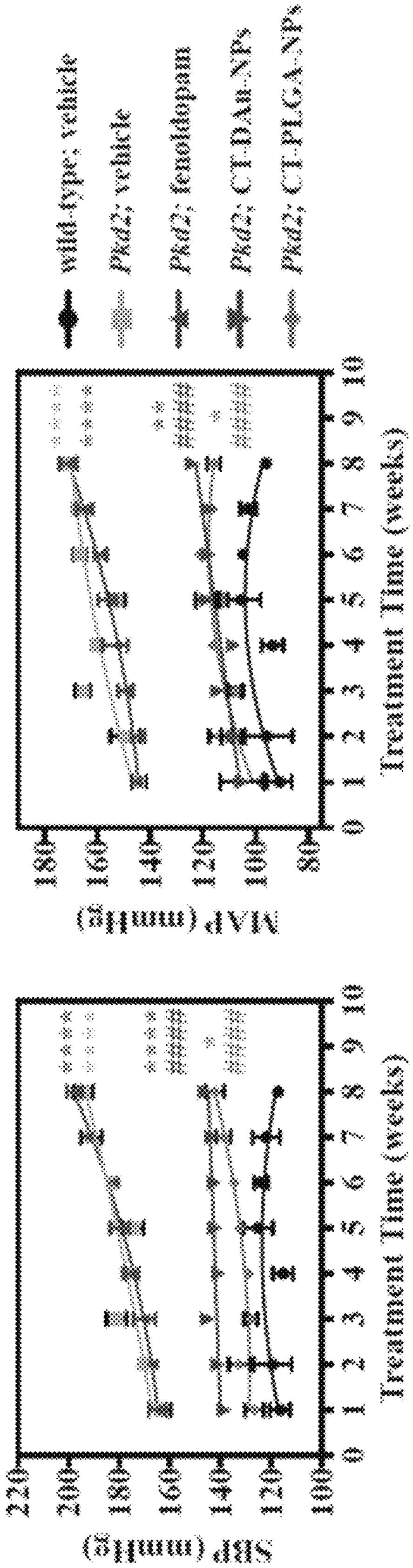
Figure 5C:
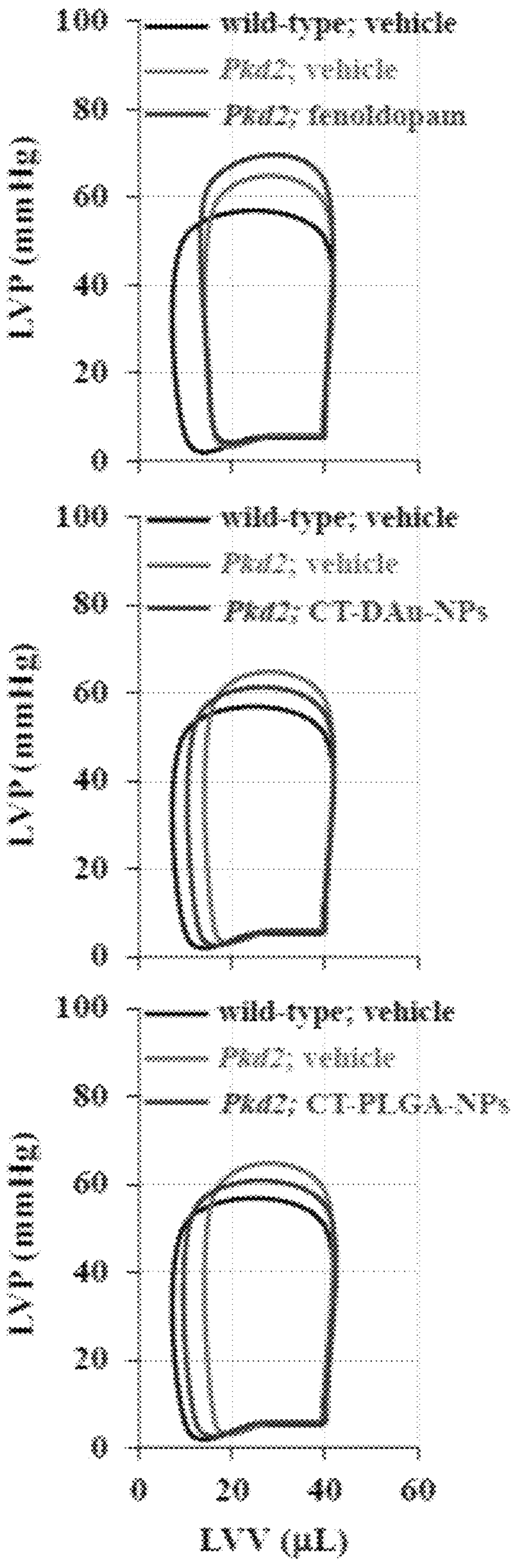
Figure 5D:
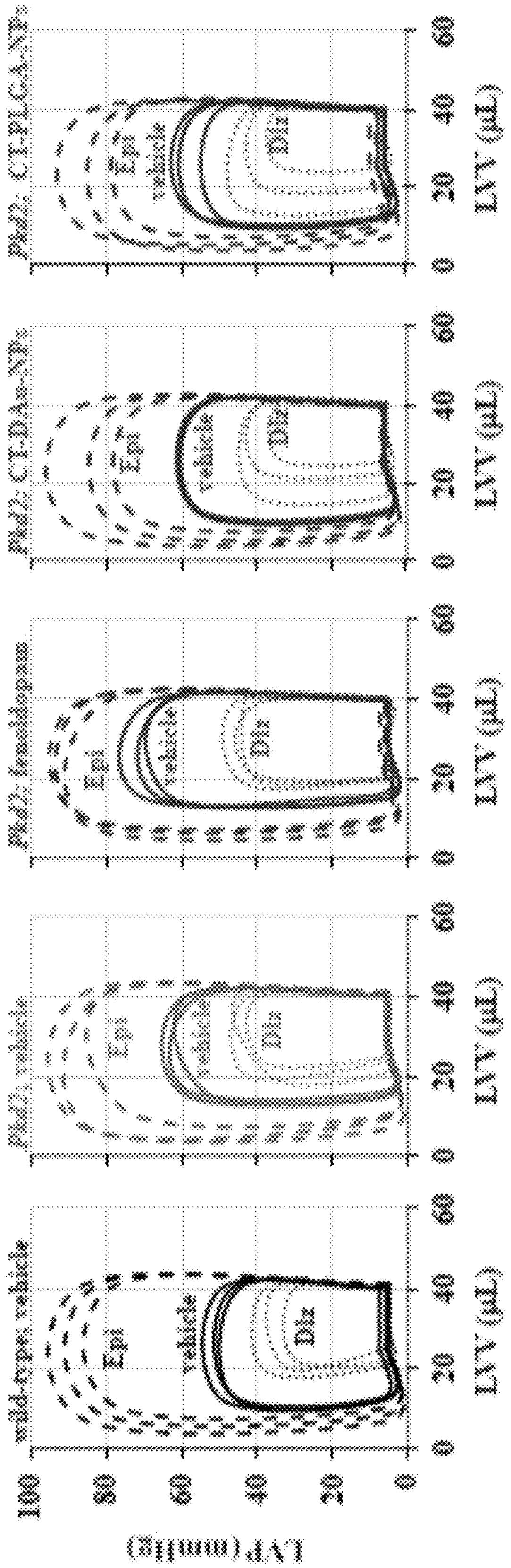
Figure 5E:
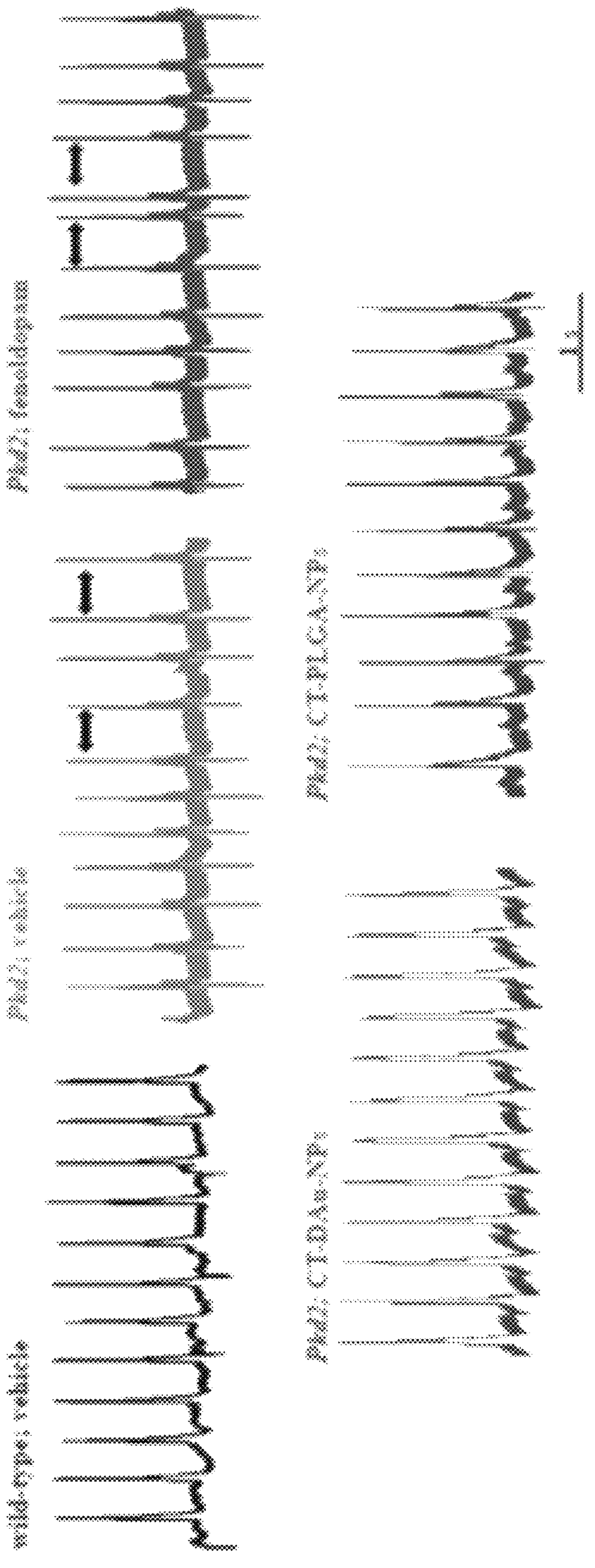

Defective polycystin-2 gene (Pkd2) in mouse and human is associated with aberrant cellular mechanosensory resulting in abnormal $Ca^{2+}$ signaling and biosynthesis NO, a clinical consequence in hypertension. To compare the efficacies among CTNDDS and fenoldopam-alone, we therefore used an endothelia-specific Pkd2 knockout mouse model. Knockout was induced in 1-week-old mice followed by every 3 days injection/infusion of fenoldopam-alone or CTNDDS for an 8-week treatment period (FIG. 5A). While CT-DAu-NPs significantly reduced blood pressure in hypertensive Pkd2 mice, CT-PLGA-NPs further decreased blood pressure toward the wild-type's level. Short 30-min infusions of fenoldopam showed no long-term effect, indicating an advantage of sustained-release of CTNDDS (FIG. 5B). Because long-term hypertension can influence heart function, comprehensive heart parameters was analyzed using a working heart system (Tables 1-3). These parameters were summarized in the left ventricle volume (LVV) and pressure (LVP) graphs, showing that compared to wild-type, Pkd2 hearts had a significantly higher LVP with narrower LVV (smaller ejection fraction; FIG. 5C). Both CTNDDS but not fenoldopam-alone corrected these abnormalities. To further analyze if the heart functions could be further deteriorated with positive (epinephrine) and negative (diltiazem) heart stressors, hearts were challenged with these stressors (FIG. 5D). No additional abnormality was observed in Pkd2 hearts without or with fenoldopam-alone/CTNDDS treatment (Tables 1-3). Surprisingly, Pkd2 hearts were characterized with arrhythmogenic, which could be corrected with 8-week treatment of CTNDDS but not fenoldopam-alone (FIG. 5E). This indicated that CTNDDS was a more superior approach than fenoldopam-alone in a long-term treatment. No obvious difference was observed between the CT-PLGA-NPs and CT-DAu-NPs on the blood pressure, cardiac functions and arrhythmogenic effects. However, it was important to note that CT-PLGA-NPs tended to correct the abnormalities in Pkd2 to the normal wild-type's levels more effectively than the CT-DAu-NPs.

Figure 24:
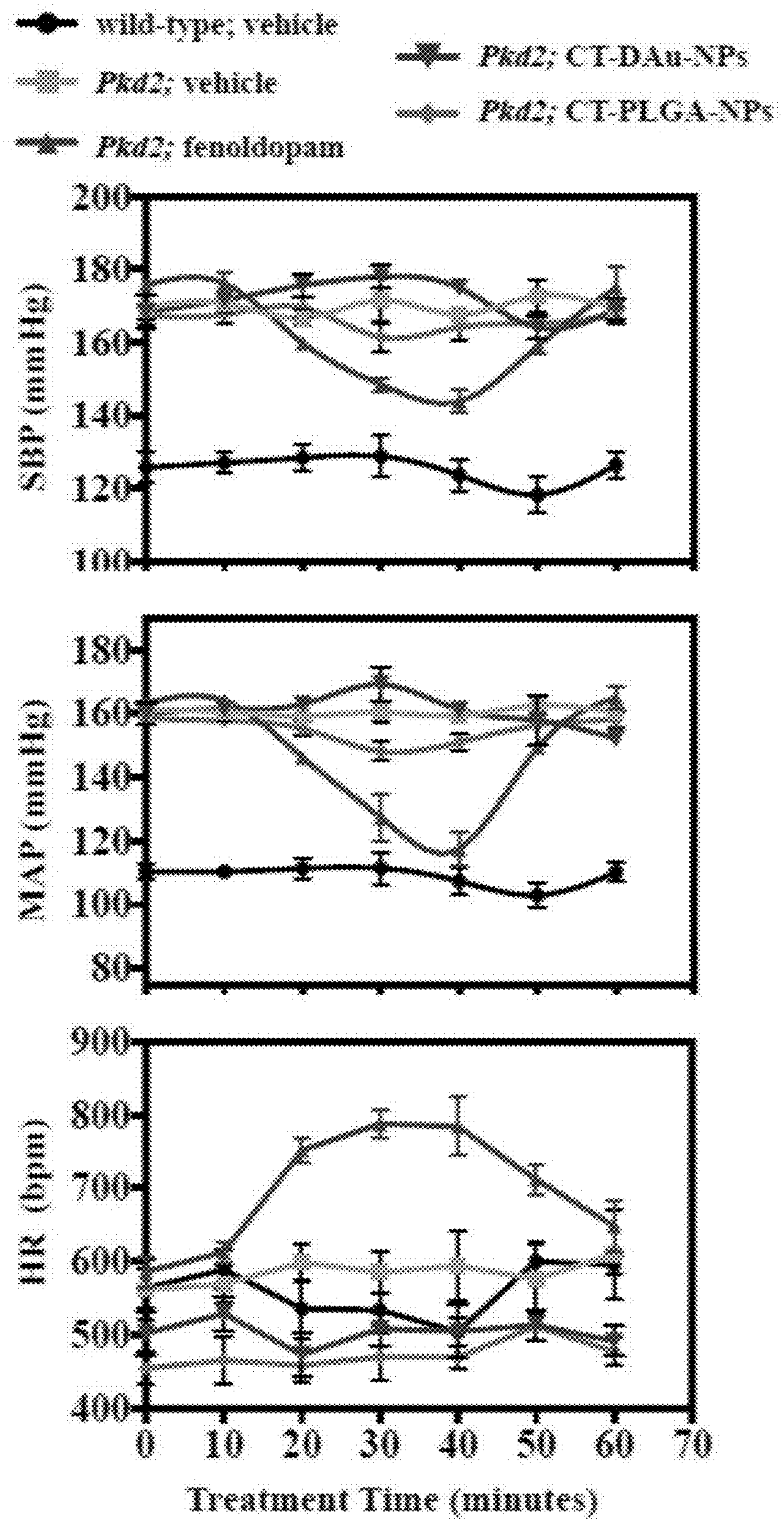
FIG. 24 depicts systolic blood pressure (SBP), mean arterial pressure (MAP) and heart rate (HR) measurement.

While fenoldopam-alone seemed to have no effect on Pkd2 mice (FIG. 24). A 10-minute infusion of fenoldopam significantly decreased blood pressure followed by reflex tachycardia. Fenoldopam is an agonist for dopamine receptors by activating D1 receptor family, including DR-1 and DR-5. Activation of D1 receptors in blood vessels results in vasodilation. Fenoldopam has also been shown to inhibit $\alpha$1- and $\alpha$2-adrenergic receptors.24-25 Blocking of $\alpha$1-adrenergic receptors result in a side effects of tachycardia, among others. Blocking of $\alpha$2-adrenergic receptors in the nervous system will also result in tachycardia. These non-specific effects of fenoldopam-alone infusion may contribute to the tachycardia in addition to the physiological reflex from a rapid drop of blood pressure by fenoldopam.

Figure 6A:
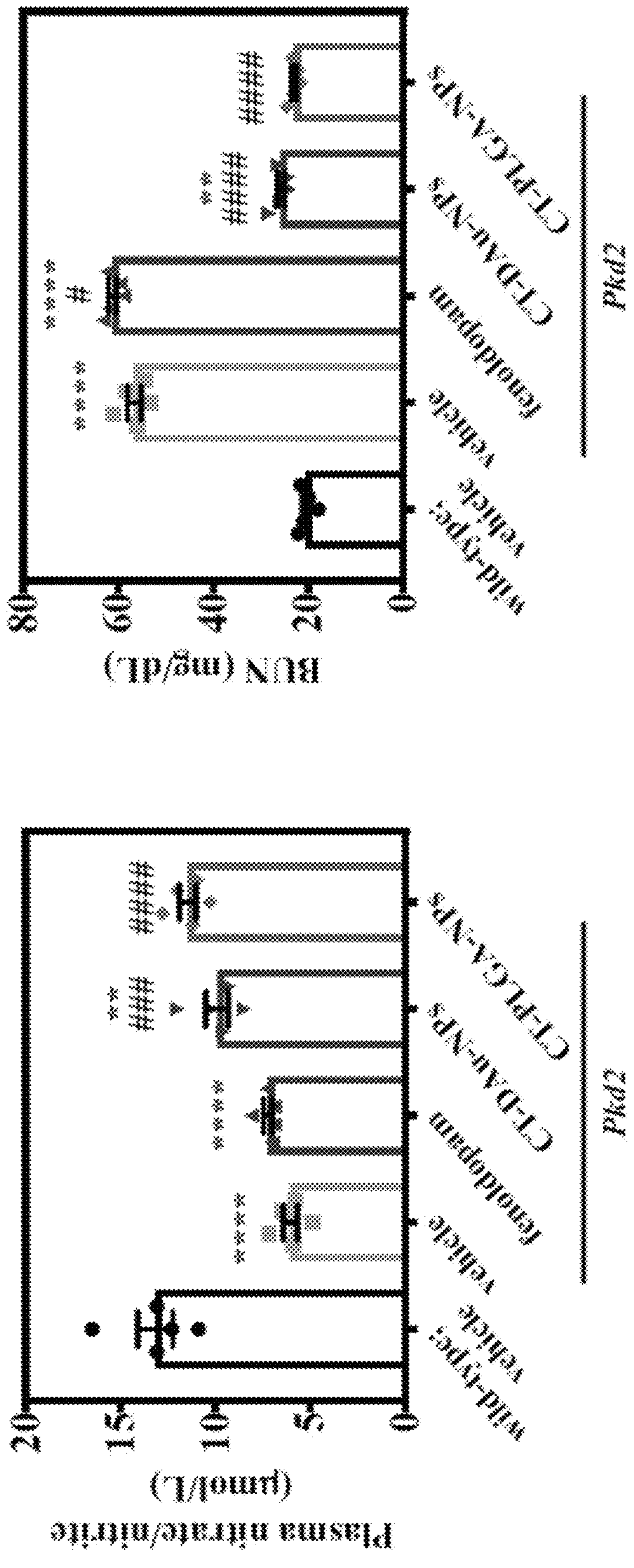
FIGS. 6A-C depicts the improvement of biochemistry and heart phenotypes in Pkd2 mice model.
Figure 6B:
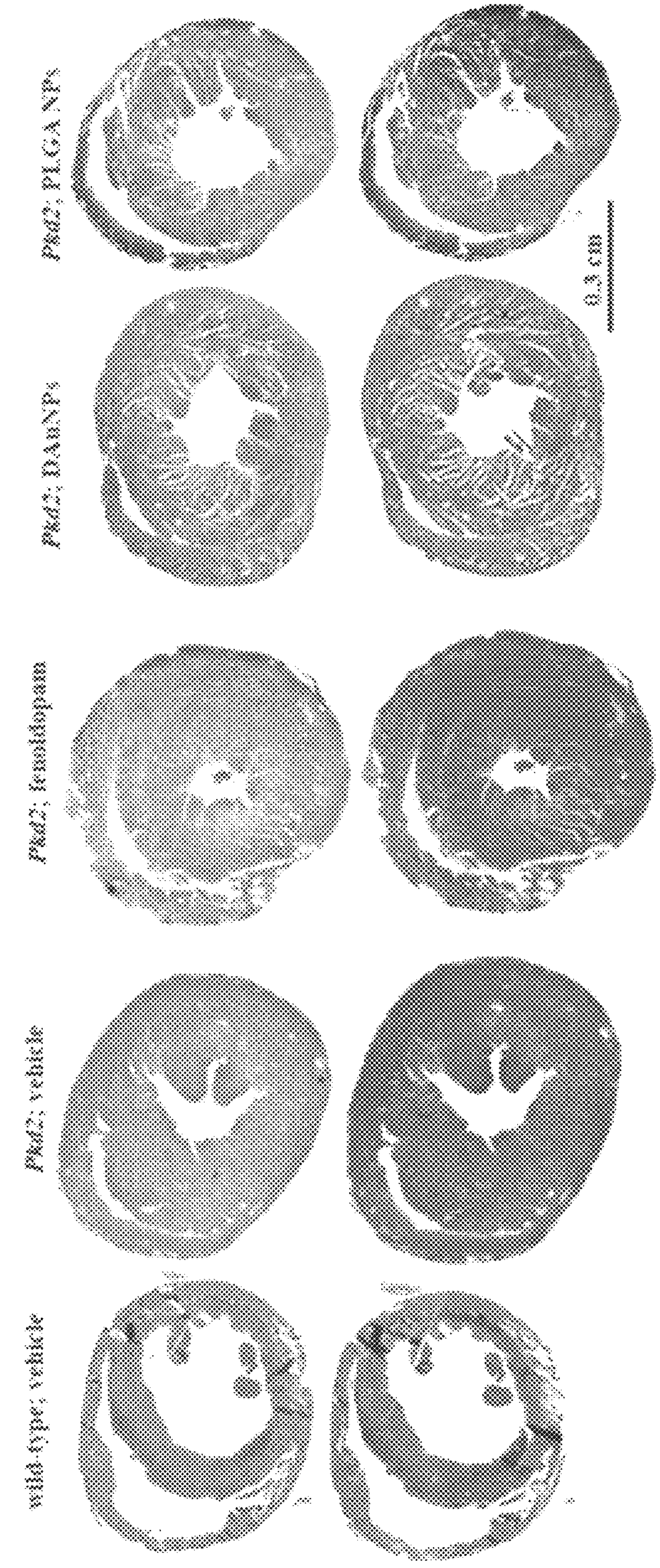
Figure 6C:
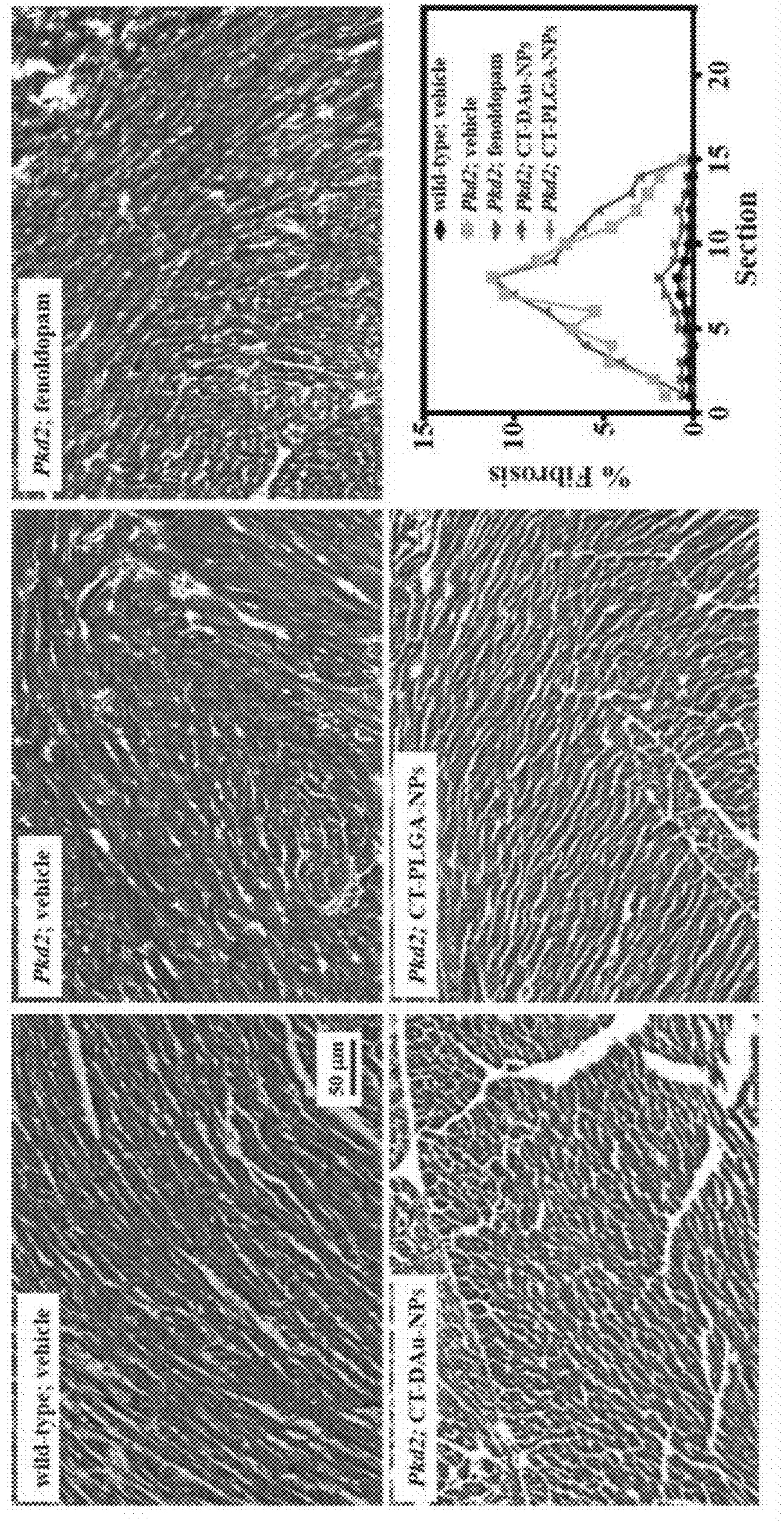
Figure 25A:
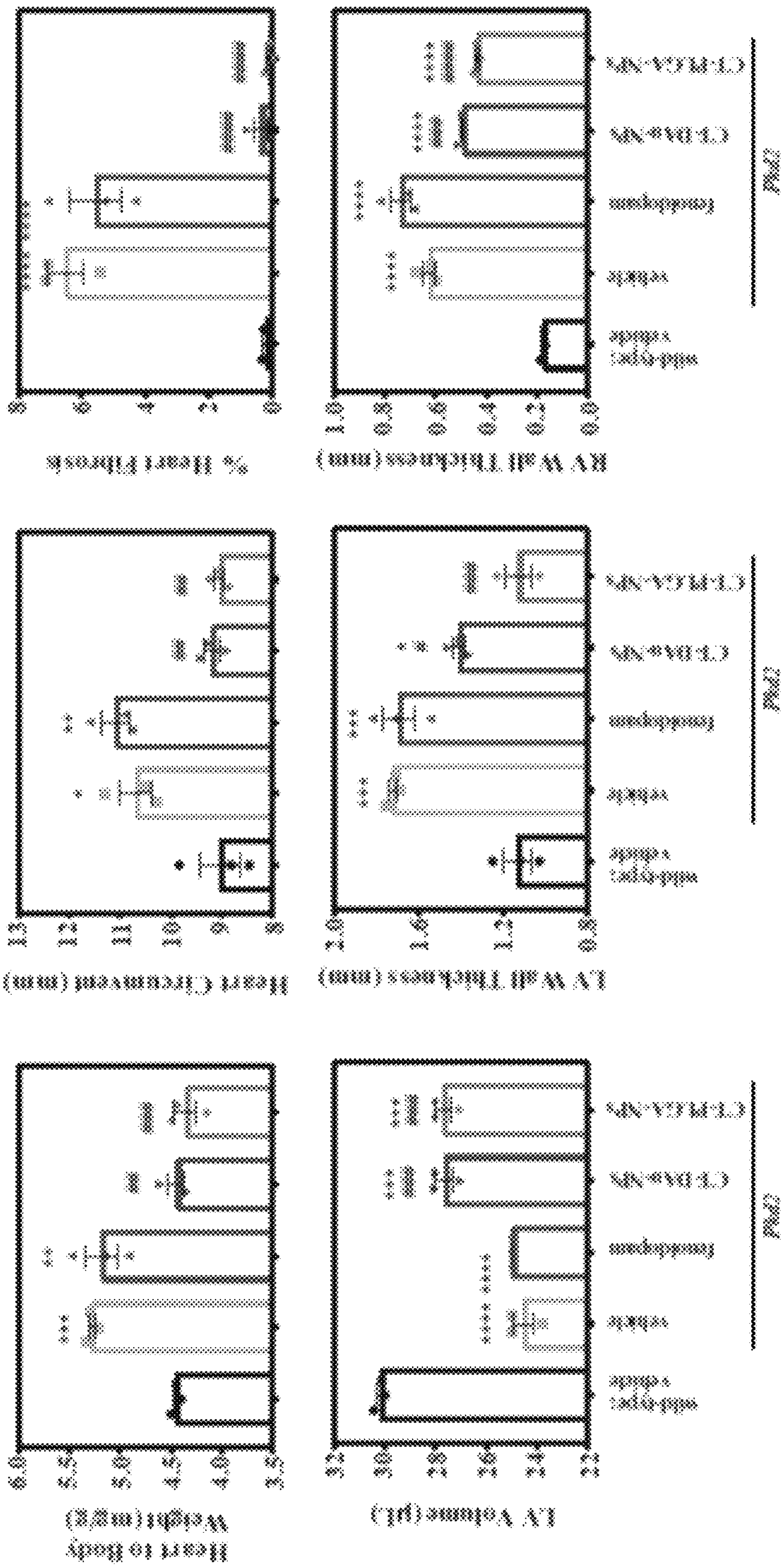
FIGS. 25A-C.
Figure 25B:
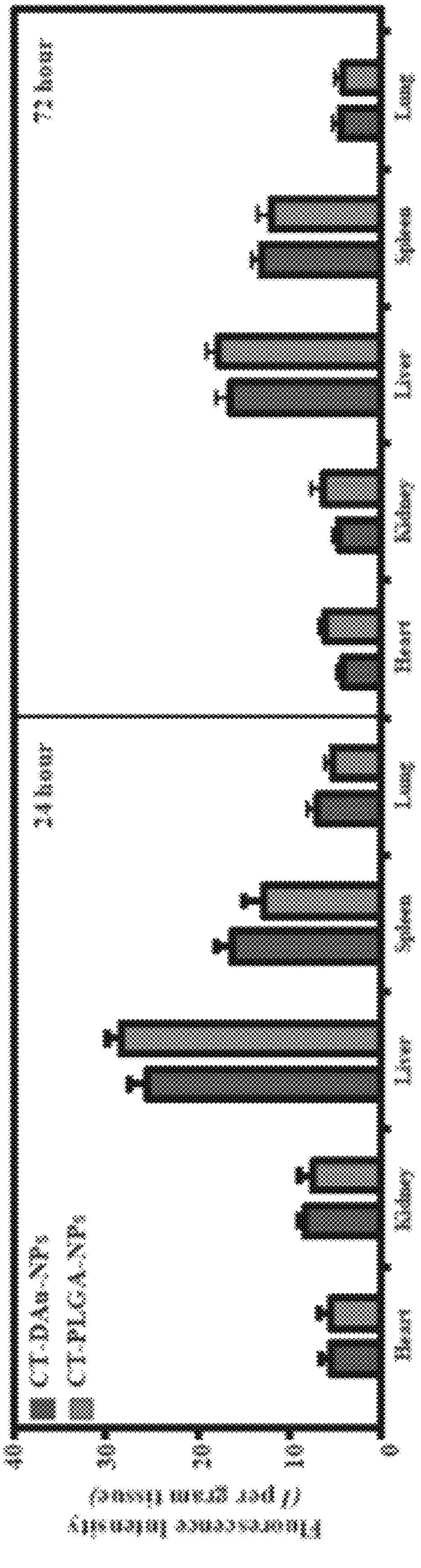
Figure 25C:
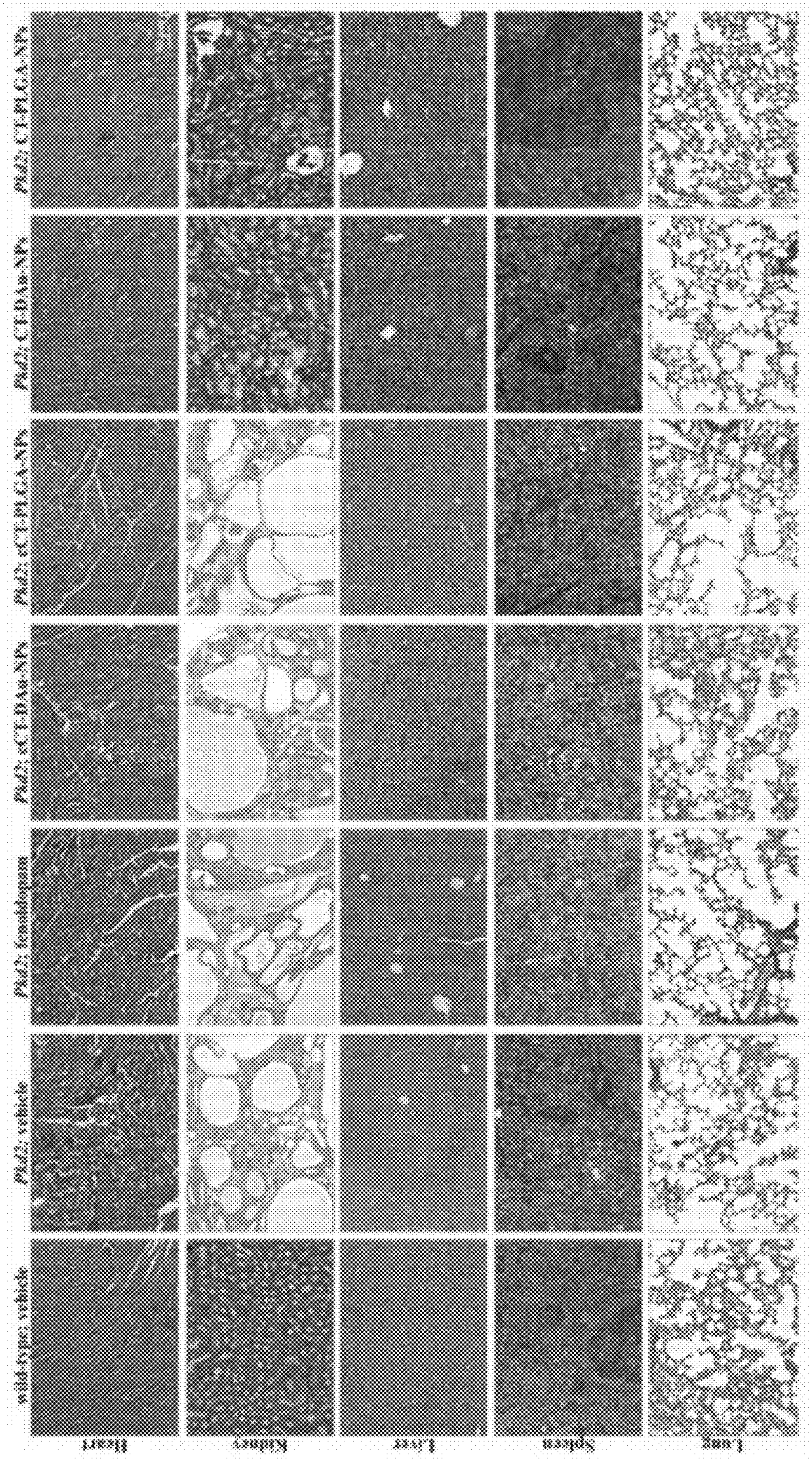

To investigate if reduction of blood pressure by CTNDDS involved NO, we measured nitrate/nitrite in the plasma because NO is readily converted to nitrite which can be further converted to nitrate. Blood urea nitrogen (BUN) was also measured due to a potential cystic kidney formation that could alter kidney function. The abnormal levels of nitrate/nitrite (as an indication of vascular function) and BUN (as an indication of renal function) in Pkd2 mice could not be corrected with fenoldopam-alone (FIG. 6A). While CT-DAu-NPs significantly corrected nitrate/nitrite and BUN levels in Pkd2 mice, CT-PLGA-NPs further brought the nitrate/nitrite and BUN to comparable levels of wild-type. When heart morphology was closely evaluated, it was apparent that PKd2 hearts were characterized by hypertrophy (FIG. 6B) and fibrosis (FIG. 6C) which could be mitigated with CTNDDS (FIG. 25A). Fluorescence intensity was also analyzed to examine CTNDDS bio-distribution in different organs (FIG. 25B). Among other organs, CTNDDS were concentrated in the liver the most. Organ toxicity of CTNDDS was also examined with H&E histology imaging (FIG. 25C). There was no apparent indication of CTNDDS toxicity in vivo, and this was validated independently from a different set of mice (Table 8).

Figure 26A:
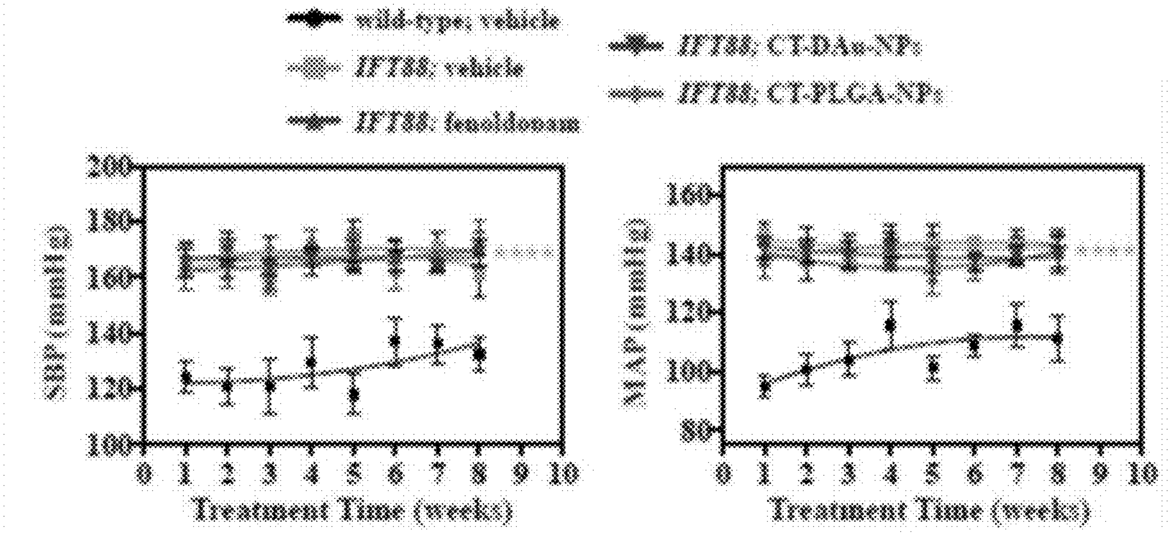
FIGS. 26A-D.
Figure 26B:
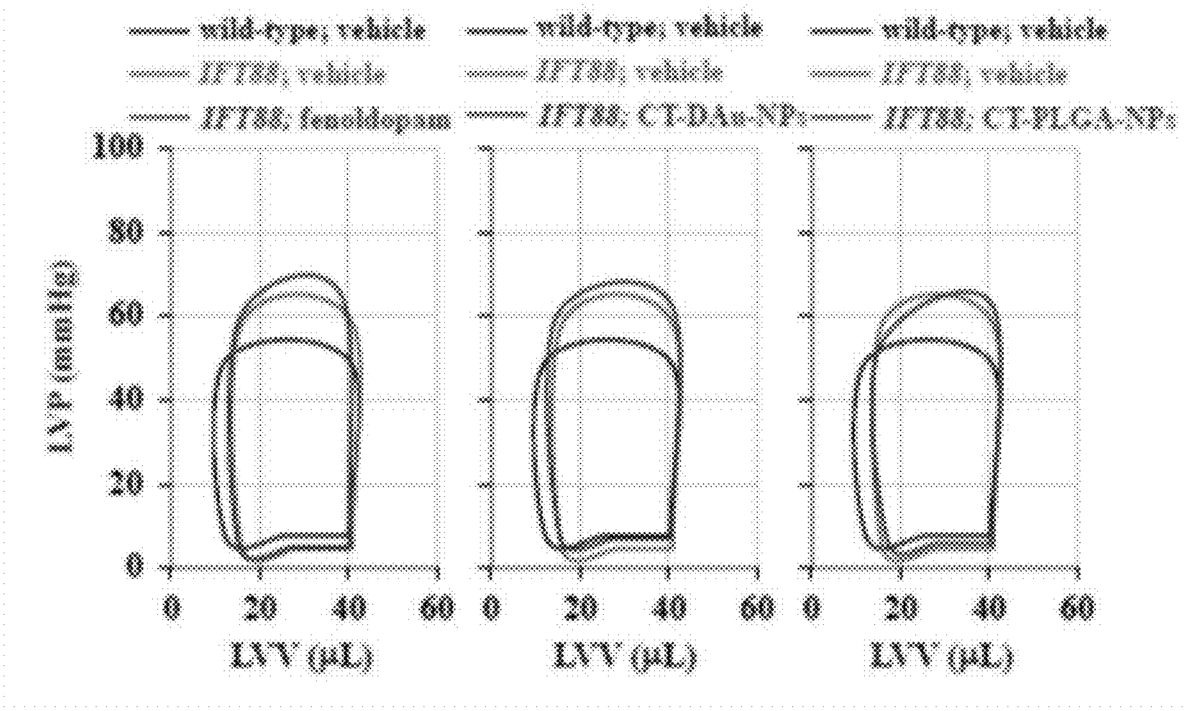
Figure 26C:
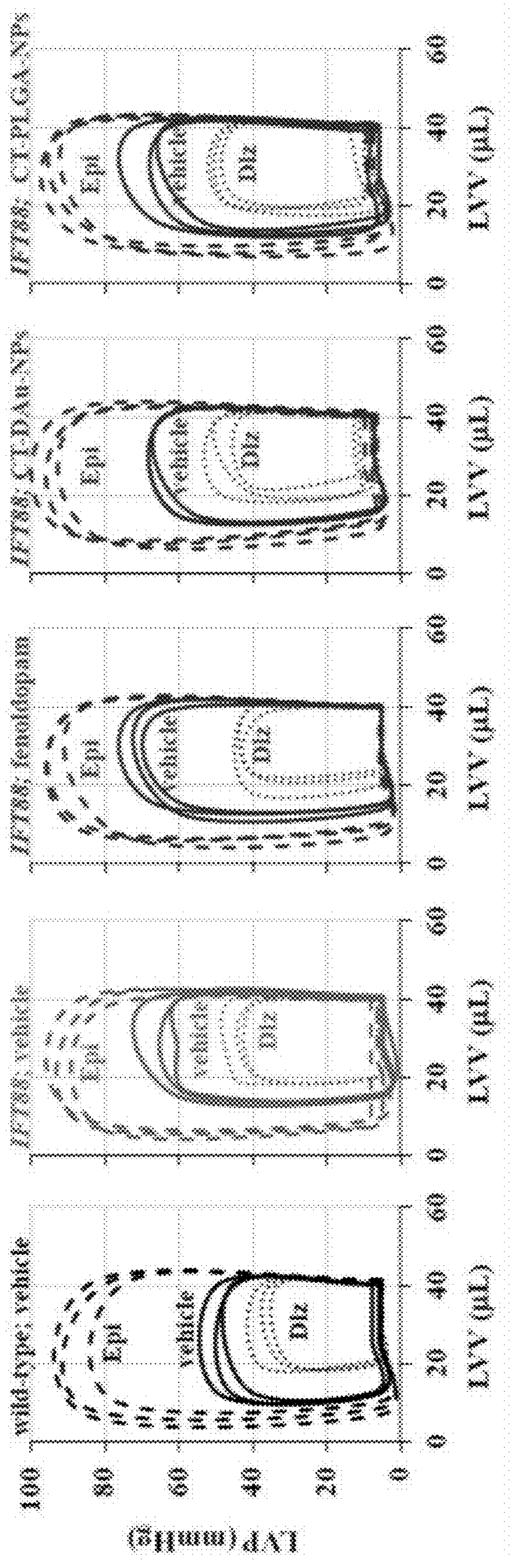
Figure 26D:
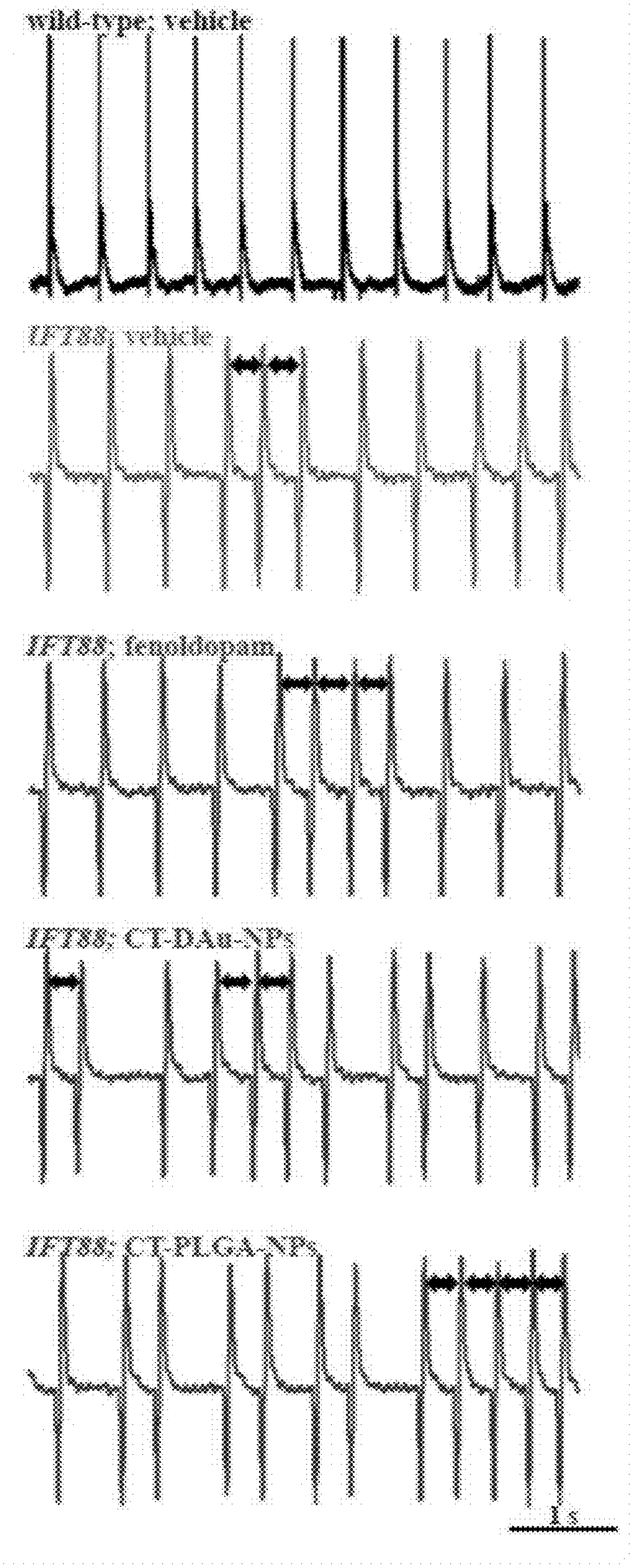

To validate if the mechanism of action of CTNDDS required primary cilia, similar experiments were performed in endothelia-specific IFT88 knockout mouse model. Like Pkd2 mice, IFT88 mice were also characterized with high blood pressure (FIG. 26A) and high LVP with narrow LVV (FIG. 26B). The hearts from the IFT88 mice also responded well to epinephrine and diltiazem stressors (FIG. 26C). Although IFT88 hearts were also arrhythmogenic, the arrhythmia was characterized by inverted P wave denoting atrial arrhythmia (FIG. 26D). Importantly, CTNDDS did not show any effect in IFT88 mice suggesting that the mechanism of CTNDDS required the presence of cilia. This confirmed that the pharmacology action of CTNDDS depended on the presence of primary cilia, while fenoldopam still could exert its non-specific effect independently from primary cilia.

In summary, we have successfully generated two cilia-targeted biomaterials that were capable of delivering fenoldopam to primary cilia. We reported that although there were no obvious advantages of the CTNDDS compared to drug-alone in cultured cells in vitro, CTNDDS were far superior in providing a more specific target to primary cilia and more efficacious therapy in vivo. Compared to fenoldopam, CTNDDS did not induce non-specific reflex tachycardia. CTNDDS also allowed a bolus injection that was not possible with fenoldopam. Fenoldopam was significantly more efficient to be loaded into and released from CT-PLGA-NPs than CT-DAu-NPs, although both types of particles were effective. While we did not find therapeutic differences between CT-DAu-NPs and CT-PLGA-NPs, CT-PLGA-NPs tended to improve the physiological parameters closer to those of healthy wild-type levels. The results showed the slow-sustained release of fenoldopam from CTNDDS was more advantageous than the short-infusion of fenoldopam in vivo. These studies opened a paradigm of harnessing a novel mechanism for future strategies in nano-medicine toward more personalized medicine for ciliopathy.

Example 2. Remote Control of Primary Cilia Movement and Function by Magnetic Nanoparticles Methods $Fe_2O_3$—NP synthesis and surface functionalization. For the synthesis of $Fe_2O_3$—NPs, ferric Tris (dodecyl sulphate) [$Fe(DS)_3$] was first prepared by completely dissolving 8.64 g (0.12 M) of SDS in 200 mL of distilled water (Solution A). In another preparation, 4.04 g (0.04 M) of $Fe(NO_3)$ $3\cdot9H_2O$ was dissolved in 50 ml of distilled water (Solution B). Solutions A and B were then mixed at room temperature (r.t.), stirred and allowed to reach equilibrium for 1 hour. The resulting yellow precipitate of Fe(DS) 3 was filtered, washed with distilled water several times and dried under vacuum at r.t. for 24 hours. For the synthesis of bare $Fe_2O_3$—NPs, 100 mg of Fe(DS) 3 was dissolved in 20 mL of distilled water in a 500-mL conical flask, and a 25% ammonia solution was immediately added to achieve a pH of 11.0. Next, the flask was placed in an autoclave and processed at 150° C. and 15 psi for 3 hours. After cooling to r.t., the material was washed, followed by brief centrifugation (5,000 rpm, 5 minutes) and calcination at 300° C.; a dark-red fine powder of bare $Fe_2O_3$—NPs was collected.

Oleic acid (OA) surface functionalization of the synthesized $Fe_2O_3$—NPs was performed using a previously described method (Yallapu et al. Pharm. Res. 27:2283-2295, 2020; Jain et al. Biomaterials 29:4012-4021, 2008). After autoclaving (150° C. and 15 psi for 3 hours), the reaction mixture was cooled to r.t. and stirred under a nitrogen-gas atmosphere for 1 hour. Then, 100 mg of OA was added to the above mixture, heated to 80° C. and stirred for 30 minutes. The resulting reaction mixture was cooled to r.t. and stirred for another 24 hours. Sunbright-40 (OA-PEG-NHS)-functionalized OA-$Fe_2O_3$—NPs were prepared by adding an aqueous solution of Sunbright-40 (100 mg/5 ml of distilled $H_2O$) to the mixture and stirring it for another 24 hours at r.t. All bare $Fe_2O_3$-NPs and Sunbright-40-OA-$Fe_2O_3$—NPs were separated by placing a magnet (100 T; VWR International) below the beaker, and the solution was allowed to clear. The particles were washed with 50 mL of nitrogen-purged sterile water three times using magnetic separation and centrifuged at low speed (1,000 rpm) to remove large aggregated particles.

Antibody conjugation and drug loading of $Fe_2O_3$—NPs. The DR5 antibody (EMD Millipore) was generated from a synthetic peptide corresponding to amino acids 2-10 of the DR5 N-terminus, and did not cross-react with other dopamine receptors. Initially, we conjugated DR5 to Alexa Fluor 594 maleimide using an Alexa Fluor 594 antibody labelling kit to target thiol groups, according to manufacturer's instructions (Thermo Fisher Scientific). The pre-conjugated DR5-Alexa Fluor 594 antibody and fenoldopam were bound to the synthesized Sunbright-40-OA-$Fe_2O_3$—NPs using a previously reported method, with some modifications (Yallapu et al.). Briefly, Sunbright-40-OA-$Fe_2O_3$—NPs (100 mg) were cooled to 4° C., mixed with 500 μg of DR5-Alexa Fluor 594 antibodies to a final volume of 25 mL in PBS and shaken overnight at 4° C. A DMSO solution of fenoldopam (400 μL, 15 mg/mL in each reaction) was added to the NP solution, and the reaction was allowed to proceed under stirring (400 rpm) for another 16 hours at 4° C. The antibody- and fenoldopam-loaded Sunbright-40-OA-$Fe_2O_3$—NPs (now designated the CT-$Fe_2O_3$—NPs) were separated from the free antibody and free fenoldopam. The CT-$Fe_2O_3$—NPs were then washed with PBS several times, lyophilized and stored in the dark.

A set of control groups was also prepared in the same way, but without fenoldopam (designated as the cCT-$Fe_2O_3$—NPs). Fluorescent unconjugated DR5 antibody loading was also conducted in a separate reaction. The binding of the DR5 antibody to synthesized CT-NPs was analysed by fluorescence spectrofluorometry at $\lambda_{ex}$=590 nm and $\lambda_{em}$=617 nm with a FLUOstar omega filter-based multi-mode microplate reader (BMG LABTECH). The conjugation efficiency of the antibody to the NPs was further assessed with SDS-PAGE, and protein concentrations were measured by recording the optical density at 280 nm with a NanoDrop 2000 spectrophotometer (Thermo Scientific). The fenoldopam loading efficiency was quantified by HPLC (SHIMADZU Prominence-I, LC-20302 3D). Fenoldopam release was measured by dialyzing 1 mL of each NP solution at a concentration of 5 mg/mL in PBS using 3.5 k MWCO dialysis tubing (Spectrum Labs), and the dialysate was subjected to HPLC. A standard plot was prepared under standard conditions with fenoldopam concentrations ranging from 5-200 μg/mL.

Chemical and physical characterization of $Fe_2O_3$—NPs. The initial synthesis of $Fe_2O_3$-NPs was confirmed by UV-visible spectroscopy using a SpectraMax-M5 system (Molecular Devices). Stability studies of the synthesized NPs were conducted by dissolving them in PBS (0.25, 0.5 and 1 mg/mL). NP stability was determined by preserving them in a 10% sucrose solution. For measurements of size and shape, the synthesized nanomaterials were examined by TEM using an FEI/Philips 200 kV CM-20 electron microscope. The particle size in the TEM images was measured using SIS imaging software (Munster, Germany). TEM was also used to study the SAED patterns. The size and surface Z-potential of synthesized NPs were obtained by DLS measurements using a Malvern ZETASIZER (Nano-ZS; ZEN3600, UK). Samples of lyophilized NPs were subjected to XRD using a Rigaku SmartLab X-ray diffractometer and Cu-Kα (Cu target) radiation at a scanning rate of 1° per min in the region of 2θ=10-90°. X-ray photoelectron spectra of the samples were recorded on a Kratos Analytical AXIS Supra system with a monochromatic Al/Ag X-ray source (Al target). Survey spectra were recorded in a range from 1200 to −5 eV binding energy (dwell time 200 ms, step size 1 eV, and 2 sweeps), and scans of all regions were conducted with suitable ranges (dwell time 500 ms, step size 0.05 eV and 5 sweeps). The FTIR spectra were recorded using a Bruker ALPHA (Platinum-ATR) spectrometer in the diffuse reflectance mode at a resolution of 4 cm-1. The magnetization capacity of the bare magnetic $Fe_2O_3$—NPs and CT-$Fe_2O_3$—NPs was measured at r.t. using a vibrating sample magnetometer (VSM, LKSM-7410).

The colloidal stability of the CT-$Fe_2O_3$—NPs was investigated in PBS, Dulbecco's Modified Eagle's Medium (DMEM) containing 10% fetal bovine serum (FBS) and extracted blood plasma at 37° C. using DLS. Samples were prepared by the addition of 50 μL of the CT-$Fe_2O_3$-NPs to 1 mL of each sample (with a final concentration of 0.5 mg/mL) and were incubated at 37° C. to imitate biological conditions. The sizes of the CT-$Fe_2O_3$—NPs were measured at different time points (0-48 h).

Cell culture. LLC-PK1 cells were purchased from the ATCC (CL-101) and cultured in DMEM (Corning Cellgro) supplemented with 10% FBS (HyClone), and 1% penicillin/streptomycin (Corning Cellgro) at 37° C. in a humidified, 5% $CO_2$ atmosphere. The cell line was confirmed to be mycoplasma free with repeated testing, using a mycoplasma detection kit (MycoAlert, Lonza). Prior to the experiments, antibiotics were withdrawn, and cells were serum starved for 24 hours to induce differentiation. In some experiments, primary culture endothelial cells were generated from Tie2Cre•Pkd2$^{WT/WT}$ mouse aortas. Prior to the experiments, these cells were cultured in DMEM (Corning Cellgro) containing 10% FBS (HyClone) at 39° C. in a humidified, 5% $CO_2$ atmosphere.

Toxicity studies. The cytotoxicity of the CT-$Fe_2O_3$—NPs was assessed in LLC-PK1 cells in vitro using a FITC-Annexin-V/Propidium Iodide Apoptosis kit (Molecular Probes & Life Technologies). Furthermore, a FACS analysis was used to assess the percentages of apoptotic and necrotic cells with a BD Facsverse flow cytometer and BD FACsuite software. Representative images of cells were captured using standard fluorescence and DIC microscopes (Nikon Eclipse Ti microscope). For the in vivo toxicity studies, 100 μL of blood samples were collected from different treatments (PBS and CT-M-$Fe_2O_3$—NPs). Hemanalysis and biochemistry were performed using a blood cell analyzer (VetScan HM5 v2.2, Abaxis) and a biochemical analyzer (VetScan VS2, Abaxis), respectively.

Live imaging of a single cilium from a single cell under flow conditions. The CT-$Fe_2O_3$-NPs were evaluated by capturing images of the lateral view of both the cell body and cilium to determine the specificity of cilia targeting by NPs and to avoid biases in the data analysis. LLC-PK1 cells were grown on Formvar® (Electron Microscopy Science). The Formvar® polymer was dissolved in ethylene dichloride to produce a 2% Formvar® solution. Cells were then grown on this collagen-coated Formvar® polymer thin film (FPTF). The FPTF was placed on a custom-made glass-bottomed plate. A thin pipette tip (Fisher Scientific) was connected to the inlet and outlet clear plastic PVC tubes with a 0.031-inch inner diameter (Nalgene). The tubes were inserted into the in-flow and out-flow pumps (InsTech P720), and the pipette tips were inserted between the bottom glass plate and held with a cover glass slide on top. Different concentrations (0.1-1 μg/mL) of the cCT-$Fe_2O_3$—NPs and CT-$Fe_2O_3$—NPs were perfused (1.0 dyn/$cm^2$) through the cells, and images were captured for 2 hours. Different NP targeting capacities to the same cilia were observed with a Nikon Eclipse Ti microscope (×100 1.40 numerical aperture oil-immersion objective lens). The microscope is also equipped with an incubator (Okolab) to control $CO_2$, humidity, temperature and light to provide a suitable environment for the cells during the experiment. All the environmental controls were monitored by an Oko touch screen.

Prussian blue staining. The CT-$Fe_2O_3$—NPs were evaluated using Prussian blue staining to determine the presence of NPs on cilia and the specificity of cilia targeting by NPs. First, LLC-PK1 cells were grown on Formvar® for 16 h and treated with 0.1 to 1 μg/mL of the CT-$Fe_2O_3$—NPs with a very slow perfusion. After 48 h, cells were washed with PBS and fixed with 4% glutaraldehyde in PBS for 10 min. Subsequently, the cells were washed with distilled $H_2O$ and stained using an Iron Staining Kit (BioPAL). Cells were then washed again with distilled $H_2O$, and photographs were taken using a light microscope (Nikon Eclipse Ti, ×100 1.40 numerical aperture oil-immersion objective lens).

Immunocytochemistry and confocal microscopy. For the in vitro cilia length measurements, cells were grown on the Formvar® polymer, as mentioned above. Primary cilia consisting of acetylated microtubule structures were measured by direct immunofluorescence staining with an acetylated-α-tubulin antibody following a 16-h incubation with different concentrations (0.1-5 μg/mL) of the CT-$Fe_2O_3$—NPs. Likewise, the CT-$Fe_2O_3$—NPs without loaded fenoldopam were used as the corresponding control (cCT-$Fe_2O_3$—NPs). Fenoldopam-alone was also used as another control. Cells were rinsed with sodium cacodylate buffer, fixed with 2.5% glutaraldehyde in 0.2 M sodium cacodylate buffer for 10 min, and permeabilized with 1% Triton X-100 in sodium cacodylate buffer for 5 minutes. An antibody against acetylated-α-tubulin (1:10,000 dilution, Sigma-Aldrich) and the secondary antibodies were also diluted in 10% FBS to decrease the background florescence; a FITC-conjugated secondary antibody (1:1000; Pierce) was used. Cells were then washed three times for 5 minutes each with cacodylate buffer and sealed with mounting media containing DAPI (Vector Laboratories). Confocal images were obtained using an inverted Nikon Eclipse Ti confocal microscope (×60 1.40 numerical aperture oil-immersion objective lens). Images were processed using NIS-Elements High Content AR 4.30.02 (Nikon). Automated image acquisition (ND acquisition) was conducted under the same ×60 magnification (selected area capturing option) field and Z-stack (0.1 μm slices) settings to create a 3D video. All imaging and video acquisition times and the microscope stage were automatically controlled (XY, XZ and YZ) by an automated perfect focusing system (PFS). The in vivo cilia length measurements and NP localizations in the zebrafish and mouse tissues were performed using the same method.

Intracellular $Ca^{2+}$ and NO imaging. Cells were grown as monolayer on glass-bottomed plates to enable live microscopy imaging. After a 16-h incubation without or with different concentrations (0.1-5 μg/mL) of fenoldopam, cCT-$Fe_2O_3$—NPs or CT-$Fe_2O_3$—NPs, cells were loaded with 5 μM Fura-2 (AM) (TEFLabs) at 37° C. for 30 minutes. After washing to remove excess Fura-2 (AM), cytosolic $Ca^{2+}$ images were captured every second by recording the fluorescence of $Ca^{2+}$-bound Fura-2 (AM) at an excitation wavelength of 340/380 nm and an emission wavelength of 510 nm. For intracellular NO measurements, cells were loaded with 20 UM DAF-FM (Cayman Chemical) for 30 minutes at 37° C. NO was then measured every second at excitation and emission wavelengths of 495 and 515 nm, respectively. Cells were placed in Dulbecco's PBS during the experiments and observed under a Nikon Eclipse Ti microscope using a ×40 1.40 numerical aperture oil-immersion objective lens. Baseline $Ca^{2+}$ and NO levels were measured for 2 minutes prior to data acquisition. Fluid shear stress was then applied to cells through InsTech P720 peristaltic pumps with an inlet and outlet setup. The fluid was perfused through cell monolayers at a sub-minimal shear stress of 0.5 dyn/$cm^2$. An oscillating magnetic field (1.35 T) was applied to cells treated with the CT-$Fe_2O_3$—NPs (CT-M-$Fe_2O_3$—NPs) or fenoldopam-free CT-$Fe_2O_3$—NPs (cCT-M-$Fe_2O_3$—NPs). An alnico cylindrical magnet (VWR International, PA) was used to oscillate a primary cilium. This 100-gram AlNiCo magnet produced a permanent magnetic field of 1.35 T. Once a cilium was placed on the specimen holder and in the plane of view, the magnet was mounted on the top of an inverted Nikon Ti-E microscope. The magnet was then mechanically moved with an oscillation frequency of 1.6 Hz. The movement of cilia by the magnetic field was continuously recorded for the duration of the experiment. To examine how much force the magnetic field generated onto a cilium, we calculated the movement of cilia in response to the oscillating magnetic field (Supplement). Based on the flexural stiffness of cilia of $3\times10^{-23}$ $Nm^2$, a constant magnetic field of a alnico magnet produced a force of 0.1 pN on a cilium. Of note is that a magnitude of 10 pN of magnetic force was needed to move a fixed cell expressing ferritin.

$Ca^{2+}$ imaging in primary cilia. In single-cell-single-cilium studies, LLC-PK1 cells were first grown on 2% Formvar® and later transfected with the $Ca^{2+}$ fluorescence reporter $5HT_6$-mCherry-G-GECO1.0 (Addgene) using JetPrime transfection reagent (Polyplus transfection). The single-cell-single-cilium studies were performed as mentioned above. The shear stress ranged from 0.01 to 1.0 dyn/$cm^2$ and was accurately measured and controlled at all times. An oscillating magnetic field (1.35 T) was applied to cells treated with the CT-$Fe_2O_3$—NPs (CT-M-$Fe_2O_3$—NPs). After successful transfection, cells were treated with different concentrations of fenoldopam, cCT-$Fe_2O_3$—NPs or CT-$Fe_2O_3$—NPs, and 5HT6-mCherry-G-GECO1.0-expressing cilia were observed under an inverted Nikon Eclipse Ti confocal microscope by focusing fluorescence lasers only on a single cell or single cilium. For these experiments, none of the CT-NPs contained Alexa Fluor 594 to avoid interference with the mCherry signal. Confocal laser scanning microscopy in fast-scan mode was used to avoid potential excessive photo bleaching. Approximately 15-20 cilia were analysed for each treatment using different fluorescence filters. With this specific experimental setup, we observed the cell body and cilia in an unbiased way. Moreover, we were able to capture DIC images of the cilia. All videos were processed using NIS-Elements High Content AR 4.30.02 (Nikon) used for the live tracking and kymograph analysis of both the cell and cilia. The $Ca^{2+}$ tracking was very efficiently achieved using binary spotting tracks. The GFP/mCherry ratios were also calculated using Nikon tracking software.

Immunoblotting. Untreated cells (control) or cells treated with the CT-$Fe_2O_3$—NPs were rinsed with PBS and scraped from the culture plates in the presence of RIPA buffer supplemented with Complete Protease Inhibitor (MedChemExpress). Cells were lysed using probe sonication (Fisher Scientific) for 10 minutes at 20 kHz using a pulse of 1 $s^{-1}$ and 40% acoustic power. Samples were kept on ice during sonication to prevent overheating. Samples were then centrifuged at 15,000 rpm for 20 min, and the supernatants were collected and subjected to protein quantification. The PAGE (polyacrylamide gel electrophoresis) on 6-10% SDS gels was performed followed by semi-dry transfer to PVDF membranes using a Bio-Rad Trans-Blot Turbo Transfer System and detection using antibodies against t-ERK (1:1,000), p-ERK (1:1,000), NOS (1:200), and GAPDH (1:2,000) (Cell Signaling Technology). Blots were scanned with both calorimetry to image molecular markers and chemiluminescence to capture the protein signal intensity using a Bio-Rad imager.

Intracellular cyclic nucleotide measurements. LLC-PK1 cells were pre-treated with either PBS or different concentrations (0.1-5 μg/mL) of fenoldopam and CT-$Fe_2O_3$—NPs to quantify the cGMP content. The cGMP levels were measured using a cGMP ELISA Kit (Cayman Chemical, MI). The results were converted to pmol/mL using standard curves.

Zebrafish experiments. Zebrafish experiments were performed by two operators who were blinded to the experimental conditions. Adult wild-type AB zebrafish were obtained from the Zebrafish International Resource Center (Eugene, OR) and used for breeding. Embryos were injected with 1 mM antisense translation blocking morpholino oligonucleotides (GeneTools) at the 1- to 2-cell stage. Zebrafish embryos were then cultured at 28° C. in sterile egg water. The following morpholino sequences were used: control scrambled MO: 5'-CCT CTT ACC TCA GTT ACA ATT TAT A-3' (SEQ ID NO: 1) and Pkd2: 5'-AGG ACG AAC GCG ACT GGG CTC ATC-3' (SEQ ID NO: 2). The zebrafish were then injected with PBS (control), CT-$Fe_2O_3$—NPs or control NPs via the caudal vein at 24 hpf. Measurements of blood flow characteristics and heart parameters were performed using a Nikon Eclipse Ti microscope at 48 hpf. NIS-Elements High Content AR 4.30.02 software (Nikon) was used for the live tracking of the speed and acceleration of a single blood cell. Videos were recorded at a high speed of 100-120 fps to study the vascular and cardiac functions of the fish. The contractility rate of the heart was measured using the image segmentation method in NIS-Elements High Content AR 4.30.02 software. The ventricular stroke volume was measured from the perpendicular long axis ($r_l$) and short axis ($r_s$) of ventricular diameters. Ventricular volumes were calculated by measuring the end of systole ($V_{end_s}$) (when the ventricle is most contracted) and diastole (Venda) (when the ventricle is most relaxed). A minimum of 15 $V_{end_s}$ and $V_{end_d}$ were averaged for each animal. The ventricular volume was calculated based on the formula: volume$=0.5\times r_l \times r_s^2$. The stroke volume was calculated by subtracting Venda from Vends (stroke volume=Vends-Venda) and cardiac output was calculated by multiplying the stroke volume by the heart rate (cardiac output=stroke volume×heart rate).

Mouse models. All mouse experiments were performed by two operators who were blinded to the experimental conditions. All animal procedures were performed according to the University of California Irvine and Chapman University Animal Care and Use Committee Guidelines. One-week-old Tie2Cre•Pkd2$^{WT/WT}$ (with Cre activation; control group), Tie2Cre•Pkd2$^{flox/flox}$ (without Cre activation; control group) or Tie2Cre•Pkd2$^{flox/flox}$ (with Cre activation; experimental group) mice were intraperitoneally injected with 250 μg of tamoxifen in a 50-μL volume daily for five consecutive days. A limited number of IFT88 mice was also used as a cilia-less model in this study. The mice were then injected with PBS (control), CT-$Fe_2O_3$—NPs or control NPs (0.5 to 2.0 mg/kg body weight in 150 μL of PBS) via the tail vein. Mice were treated with the CT-$Fe_2O_3$—NPs every 72 hours for 8 weeks. On the other hand, fenoldopam-alone (1 μg/kg/min) was perfused for 30 minutes every 72 hours for 8 weeks. In separate experiments, magnetic stimulation was applied every 72 hours to mice treated with the CT-$Fe_2O_3$—NPs (designated as the CT-M-$Fe_2O_3$—NPs). Five minutes after the CT-$Fe_2O_3$—NP injection, a 1.35-T AlNiCo cylindrical magnet (VWR International) was placed at the posterior and anterior regions of the mouse for 10 minutes daily.

Mouse blood pressure measurements. Four-week-old Tie2Cre•Pkd2$^{WT/WT}$ Tie2Cre•Pkd2$^{flox/flox}$ and Tie2Cre•IFT88$^{flox/flox}$ mice (injected with either 0.5-2.0 mg/kg NPs or 1 μg/kg/min infusion of fenoldopam for 30 minutes) were subjected to blood pressure monitoring by the non-invasive tail-cuff method using a CODA high-throughput system (Kent Scientific). Blood pressure was measured twice daily for the duration of the study after the initial three days of acclimating each mouse to the cuff. All measurements were performed by operators in a double-blind. At the end of the 12-week treatment, the haematology results including the BUN and plasma nitrate/nitrite measurements were examined. BUN assays were conducted using an Arbor Assays calorimetric Detection Kit. Plasma nitrate/nitrite concentrations were quantified using a Cayman nitrate/nitrite assay kit. All steps were performed according to the manufacturers' instructions.

Working heart perfusion system. The ex vivo measurements of heart parameters were recorded using a mouse working heart system from Emka Technologies to study heart function independently of neuronal innervation or humoural effects. This system collected data regarding the cardiac contractile strength, electrical heart propagation or ECG and other cardiac functions, including the HR, LVP, LVV, left atrial pressure (LAP), aortic out flow (AOF), stroke volume (SV), cardiac output (CO), end diastolic/systolic volume (Edv-Esv), rate of left atrial pressure raise (+dp/dt) and fall (−dt/dt), and the preload, afterload, and main aortic pressure. Heparin (100 units, IP), xylazine (10-15 mg/kg, IP), and ketamine (200-350 mg/kg, IP) were used to prevent blood coagulation in the coronary arteries and to anaesthetize the mice. After cannulation, the heart was perfused with Krebs-Ringer superfusion solution (in mM: 125 NaCl, 2.5 KCl, 1.25 $NaH_2PO_4$, 2 $CaCl_2$), 1 $MgCl_2$, 25 $NaHCO_3$ and 25 glucose). Throughout the experiment, the solution was continuously bubbled with carbogen (95% $O_2$ and 5% $CO_2$) to reach pH 7.4 at 38.0° C. Stress tests were performed on the heart by perfusing epinephrine (4 μg/L) or diltiazem (0.08 µg/L). Cardiac function was plotted in a loop diagram showing the LVV-LVP relationship (volume-pressure loop).

Pharmacokinetics in mice. Tie2Cre•Pkd2$^{WT/WT}$ mice (5 mice for each compound, 2515 g body weight) were treated with PBS (control), NPs (0.5 to 2.0 mg/kg body weight in 150 µL of PBS), or fenoldopam-alone (1 µg/kg/min; 30 minutes) via tail vein. Blood samples of 50 µL were collected prior to drug injections and 5, 10, 20, 30, 40, 50 and 60 minutes during the duration of injections (for NPs) or perfusions (for fenoldopam). Blood samples were collected into heparin-coated tubes and centrifuged for 8,000 g for 10 minutes to obtain plasma. All the standard stock solutions (fenoldopam and SKF-38393 hydrochloride (IS; Enzo Life Sciences)) were prepared at 50 ng/ml concentrations. All drugs were extracted from plasma samples. Plasma calibration standards were prepared by adding a suitable amount of working solutions to blank plasma. The HPLC analysis was performed using a Shimadzu Prominence-I separation system. Separation was achieved on a LaChrom-C18 (5 µm) column (4.6 mm I.D.×150 mm L). The column temperature was set to 28° C. The mobile phase was composed of 0.5% formic acid in distilled $H_2O$ with 10% acetonitrile, which was increased linearly to 90% from 1 to 8 minutes of the run. The flow rate was maintained at 0.3 mL/minute and the total run time was 12 min.

H&E and Masson's trichrome staining. Sections of the zebrafish (whole body) and major mouse organs, including the hearts, kidneys, livers, spleens and lungs, were collected and subjected to H&E staining for zebrafish cysts and histopathology by fixation in 10% formalin. Then, the tissues were dehydrated in buffered formalin, ethanol, and xylene. Finally, the tissues were embedded in liquid paraffin, sectioned (4 µm), and stained with H&E for histological examinations. The pathology slices were observed and imaged using a KEYENCE-BZ-X710 microscope. Mouse heart sections were stained with Masson's trichrome to detect fibrosis using a Masson's Trichrome Stain Kit (Polysciences).

Quantification and statistical analysis. Representative images are shown whenever possible to verify the extraction of information from the digital images. Nikon NIS-Element for Advanced Research software was used for image capture and analysis, including 3D object reconstruction, image scanning and segmentation, optical flow, single-particle tracking, and automatic object recognition. We did not enlarge the image during information extraction to avoid unnecessary magnification. Thus, all images were captured at the highest resolving power allowed by the imaging system. A Photometric Coolsnap EZ CCD Monochrome Digital Camera connected to a Nikon Ti-E microscope with a 1392×1040 imaging array was used to resolve fine details of the images. In other cases, both resonant and galvano scanners were used with a Nikon A1R confocal microscope for the high-speed scanning of 30 fps (frame per second) and 420 fps at a resolution of 4096×4096 and 512×512 pixels$^2$, respectively. All images were finalized on a 6-core Mac Pro, 3.9 GHZ, to facilitate complete data extraction. Scale bars are provided in all figures to indicate the actual image size.

All quantifiable data are reported as the mean±SEM. Distribution analyses were performed on all datasets before any statistical comparisons to confirm a normal data distribution. Homogeneity of variance (homoscedasticity) was also verified within each dataset. When a dataset did not display a normally distribution or heterogeneous variance was detected, the distributions were normalized by log transformation. This approach produced normally distributed datasets. After the distribution and variance analyses, data from more than two groups were compared using an ANOVA followed by the Tukey post hoc test. The Bonferroni post hoc test was used to compare data between specific groups in ANOVA analysis. Comparisons between two groups were performed using Student's t-test. Whenever possible, a paired-experimental design was used in the studies to enable a more powerful statistical analysis and to reduce the number of mice used in each study group. For all comparisons, power analyses were performed routinely to enable reliable conclusions, and comparisons with negative results had a statistical power of ≥0.8. Unless indicated otherwise, the difference between groups was considered significant at $p<0.05$. Statistical significance is indicated with the asterisk (*) or hashtag (#) sign at various probability levels (p). The p values of the significant differences are indicated in each figure and legend. The comparison with the wild-type control, non-treated or non-induced group is indicated with *, whereas comparisons with the mutant or non-treated group are shown using #. Comparisons with additional control groups without drug loading (cCT-$Fe_2O_3$—NPs and cCT-M-$Fe_2O_3$—NPs) are also shown using #. The p value of the significant differences at various probability levels, the number of experimental replicates and sample sizes are indicated in the figure legends. Most of the statistical analyses were performed using GraphPad Prism software, version 7.0. In some cases, Microsoft Excel v. 15.4 software was used for regression analyses. Linear regression analyses were performed to obtain a standard calibration curve and linear equation. In this case, the analysis was conducted with the ordinary least squares (OLS) regression of y on x. A non-linear logarithmic regression analysis was used to fit the sigmoidal trend curve to show the dose-response relationship. While data analyses were conducted using statistical software, they were verified by a mathematician/statistician.

Results

Characterization of $Fe_2O_3$-Nanoparticles

Figure 34A:
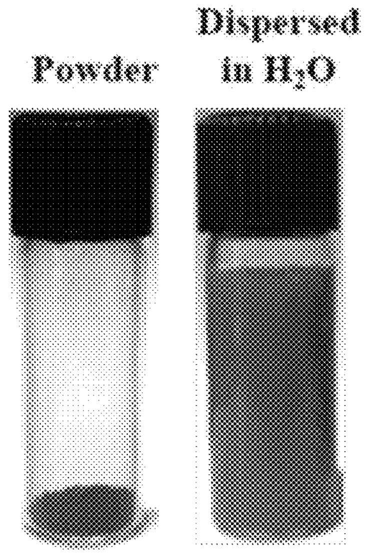
FIGS. 34A-L depict physical and chemical characterization of functionalized CTNDDSs.
Figure 34B:
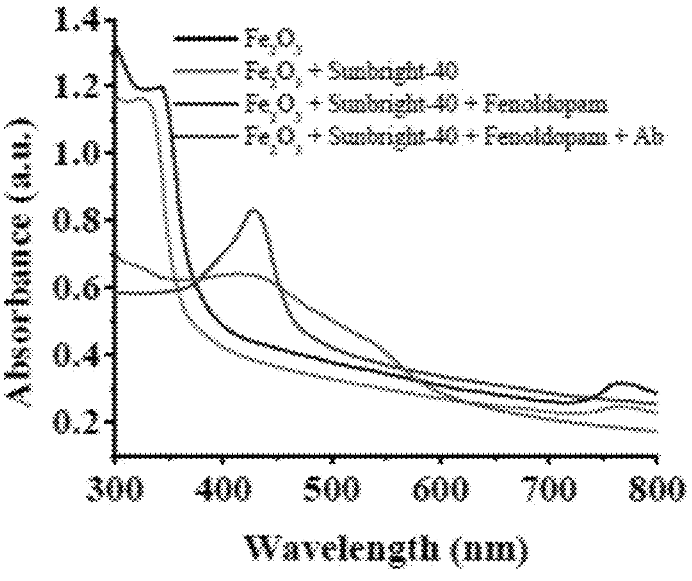
Figure 34C:
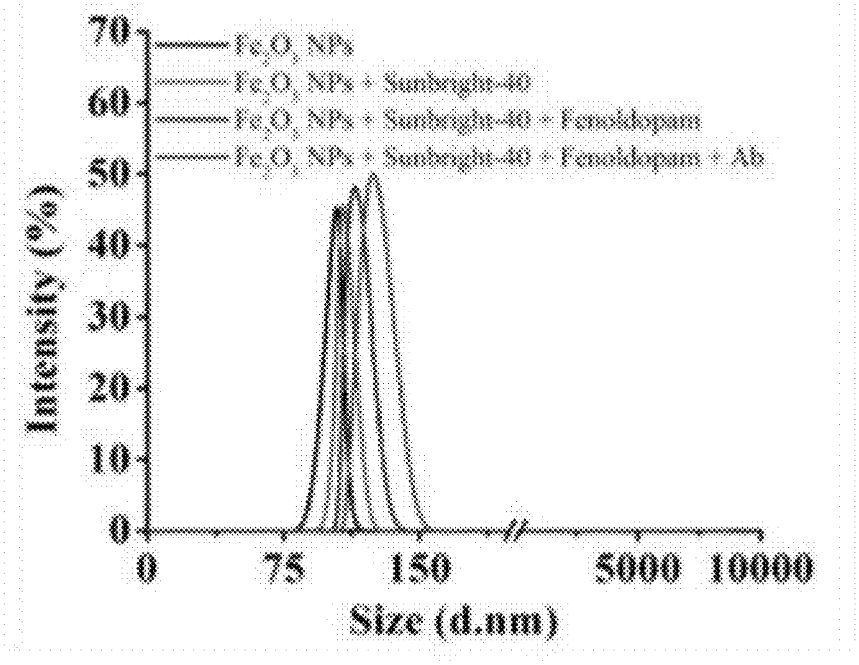
Figure 34D:
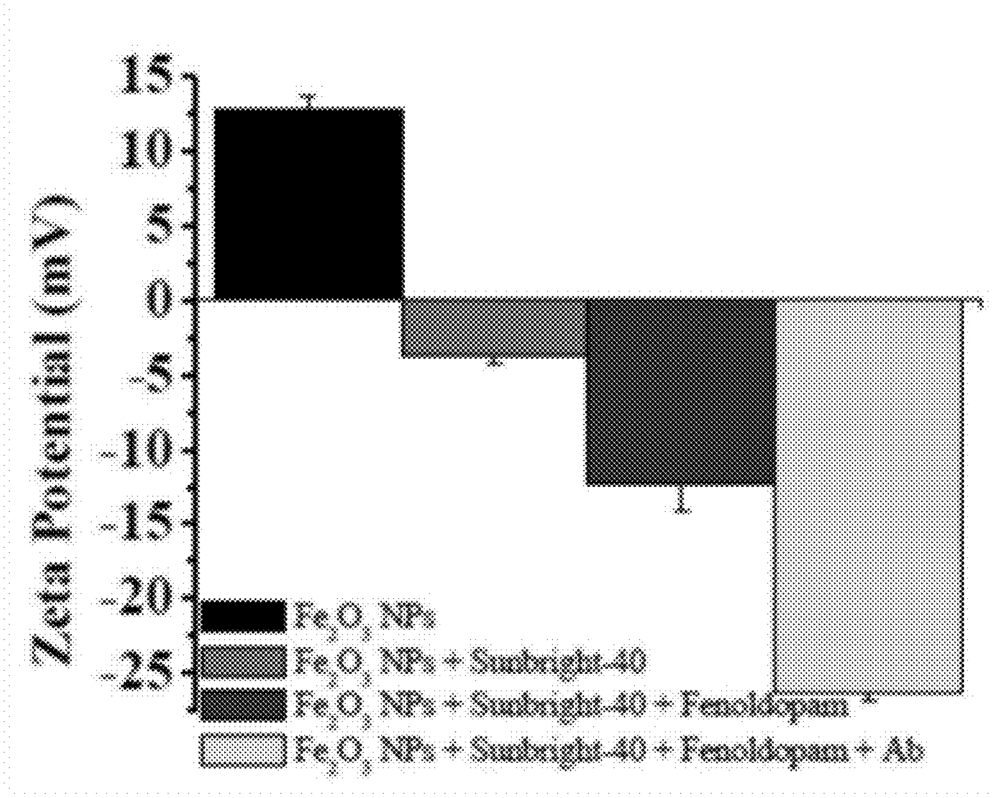
Figure 34E:
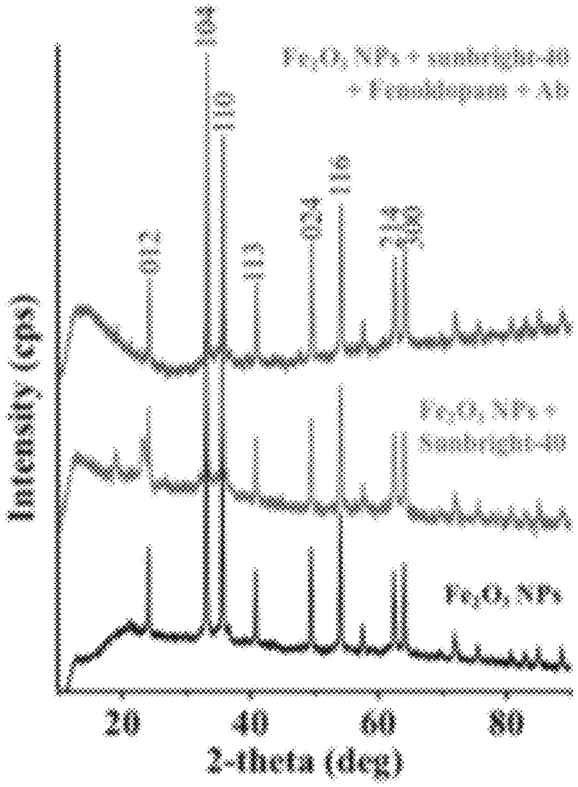
Figure 34G:
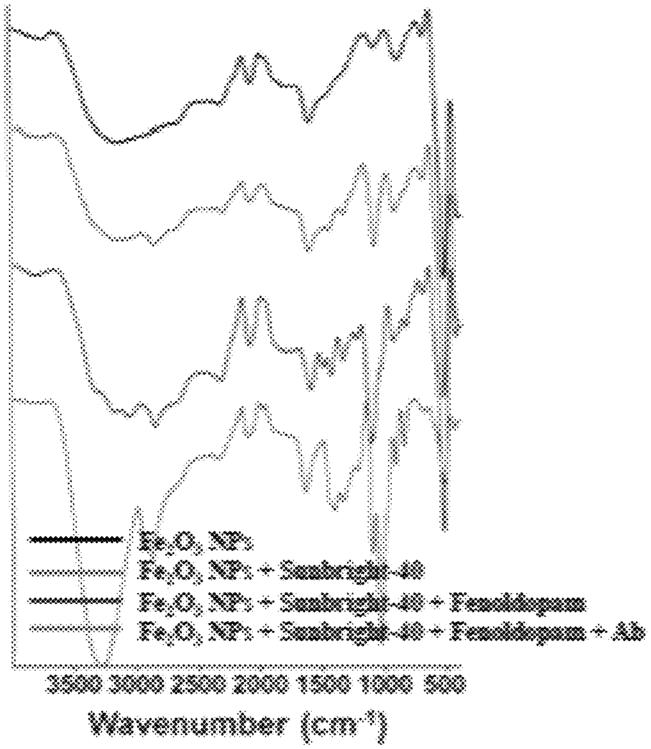
Figures 1, 34F:
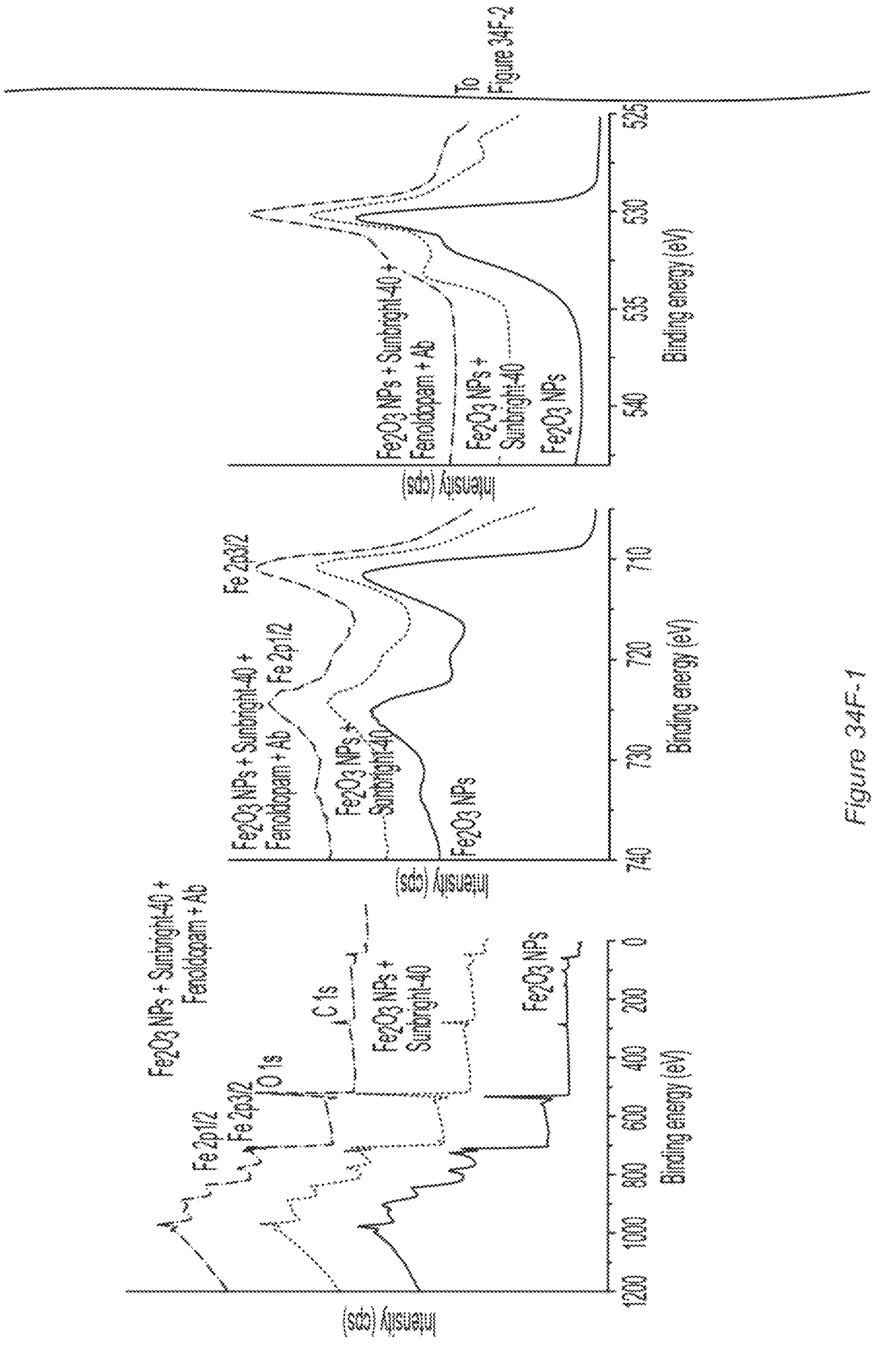
Figures 2, 34F:
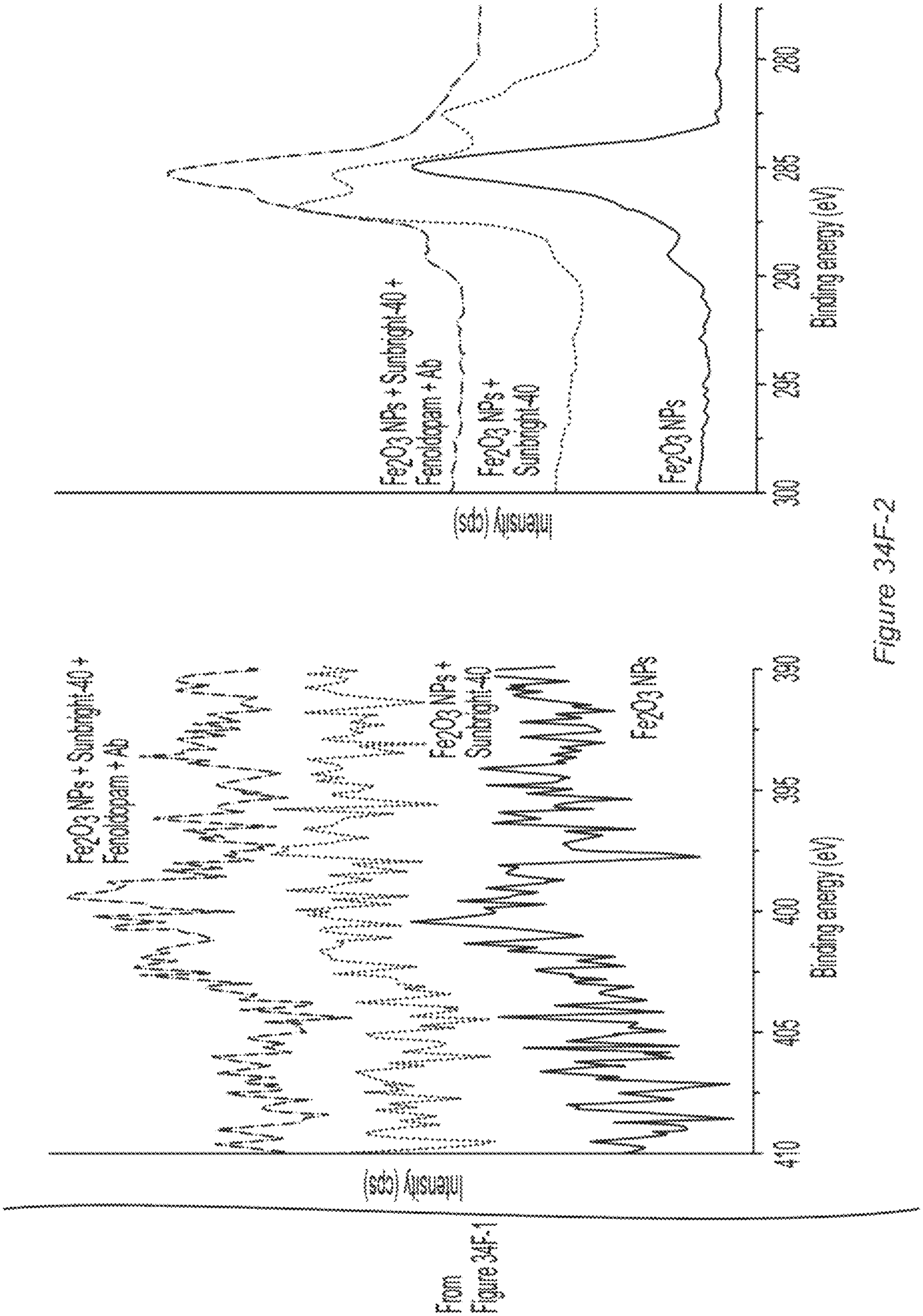

For these studies selected haematite metal oxide ($\alpha$-$Fe_2O_3$) as the nanomaterial due to its excellent biocompatibility, magnetic properties and applicability for use in vivo to target primary cilia. We prepared stable $Fe_2O_3$-nanoparticles (NPs) using several synthesis steps. We analysed and characterized the products from each synthesis and surface functionalization step: bare NPs to functional cilia-targeted (CT)-$Fe_2O_3$—NPs (FIG. 34A). The typical UV-visible absorbance spectra were recorded at different steps in $Fe_2O_3$—NP synthesis in dispersed form (FIG. 34B). Dynamic light scattering (DLS) measurements showed that upon surface functionalization, the size distributions were increased from 102±3.8 to 126±4.6 nm (FIG. 34C). When the surface charge of the particles was analysed, the charge repulsion increased after every functionalization step from ±12.9±2.8 to −27.9±3.4 (FIG. 34D). The Z-potential of the CT-$Fe_2O_3$—NPs decreased to −25 mV, indicating the excellent surface stability of the CT-$Fe_2O_3$—NPs in suspension and their suitability for intravenous applications. The successful formation of bare NPs and their surface functionalization were also examined by collecting X-ray diffraction (XRD) and X-ray photoelectron spectroscopy (XPS) spectra (FIGS. 34E and 34F). Fourier transform infrared spectroscopy (FTIR) was also used to obtain spectral signatures of each synthesis and surface functionalization step (FIG. 34G).

Figure 27A:
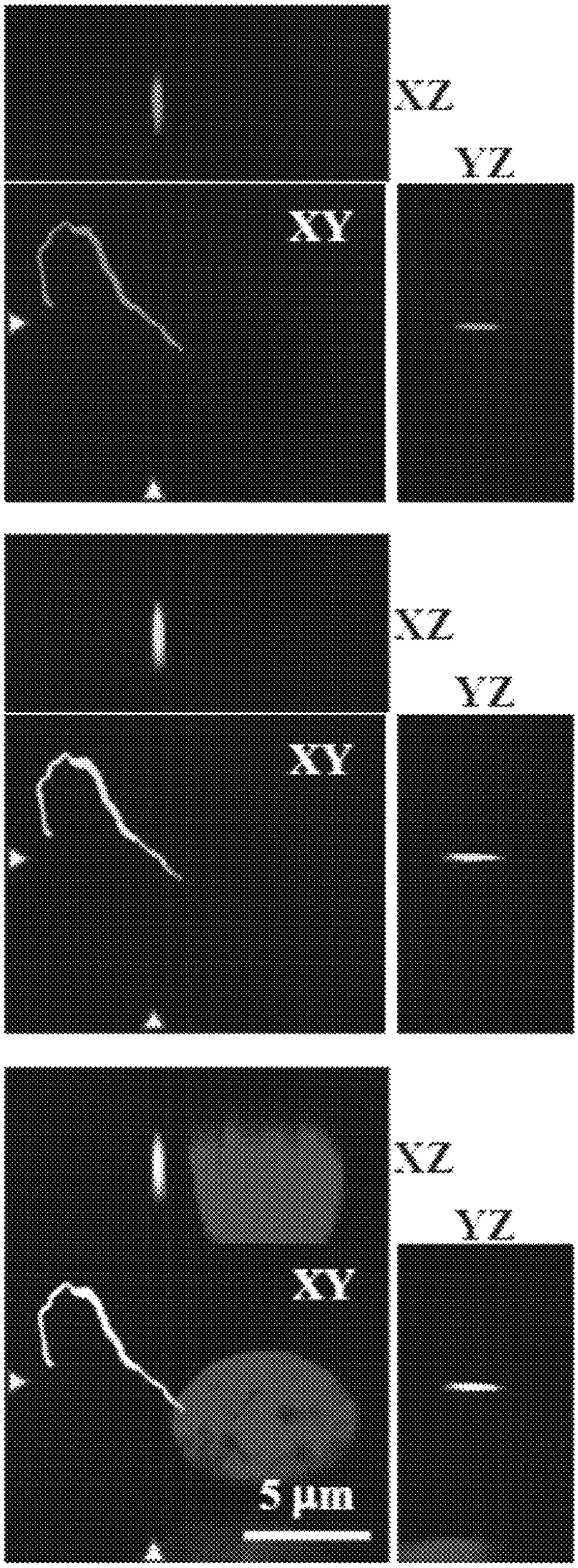
FIGS. 27A-E depict the preparation and characterization of the CT-$Fe_2O_3$—NPs.
Figure 28A:
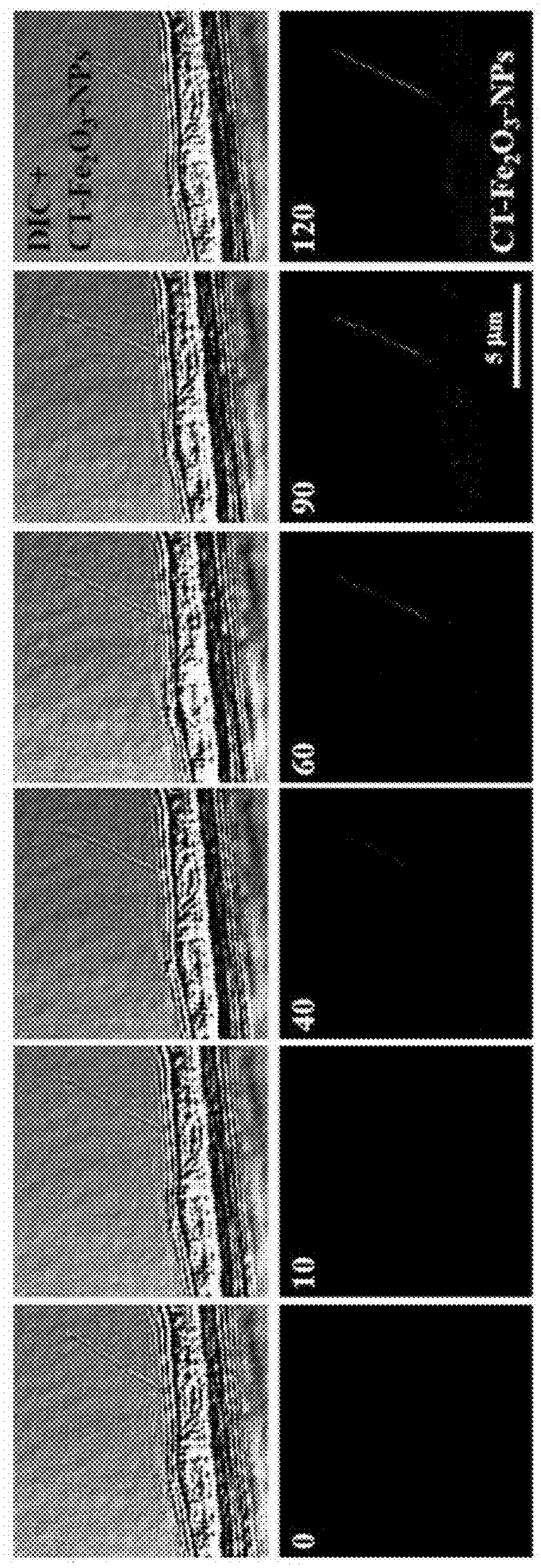
FIGS. 28A-I depict CT-$Fe_2O_3$—NPs specifically targeting primary cilia under flow conditions and improve cilia structure and function.

The CT-$Fe_2O_3$—NPs were tagged with DR5-specific antibodies because DR5 has primarily been shown to be concentrated in the primary cilia of fibroblasts, endothelial cells, and epithelial cells. The agonist binding pocket of the dopamine receptor is located between transmembrane helices 3, 4, 5, and 6. The DR5 antibody selectively recognizes the extracellular N-terminus between amino acids 2 and 10. In addition to the localization of DR5 antibodies on the cilia surface for epitope accessibility, we validated that the DR5 antibody was approximately 95±12 times more selective for cilia than the cell body by recording relative intensity measurements in permeabilized, fixed cells (FIG. 27A). Once tagged with the CT-$Fe_2O_3$—NPs, the ratio of cilia-to-cell body specificity of DR5 antibody was 158±19 in non-permeabilized live cells. The specificity of DR5 antibody in cilia, relative to cell body, was increased in non-permeablized compared to permeablized cells, indicating the antibody could penetrate more readily into the cell body through the permeabilized cell membrane. Further, the proportion of specific binding of the CT-$Fe_2O_3$—NPs to cilium:cell:background was about 17,000:500:1 (FIG. 28A).

Figure 27B:
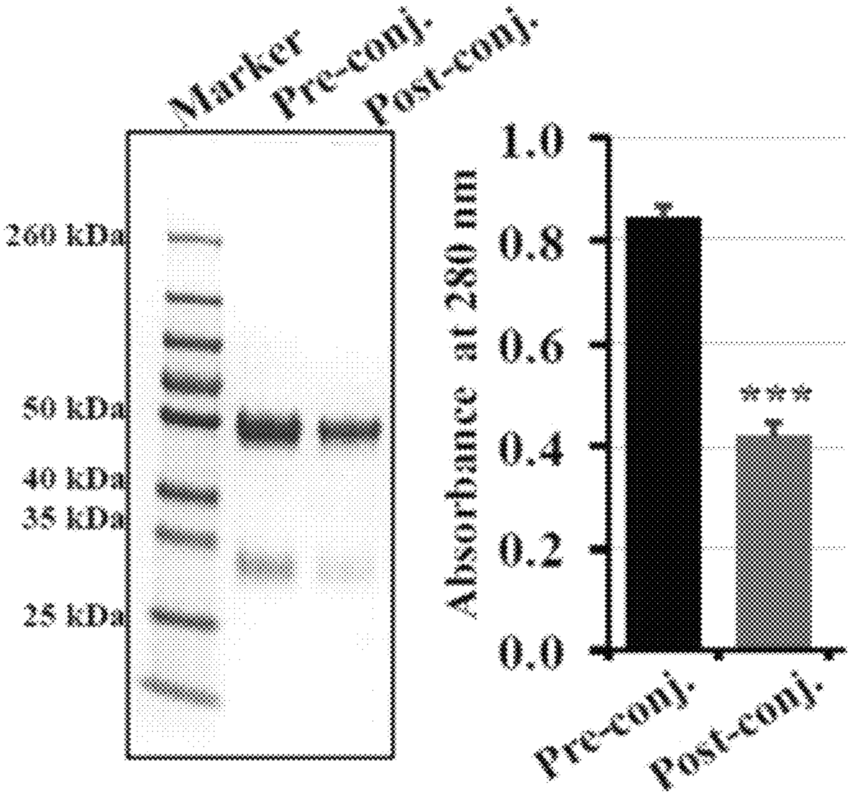
Figure 27C:
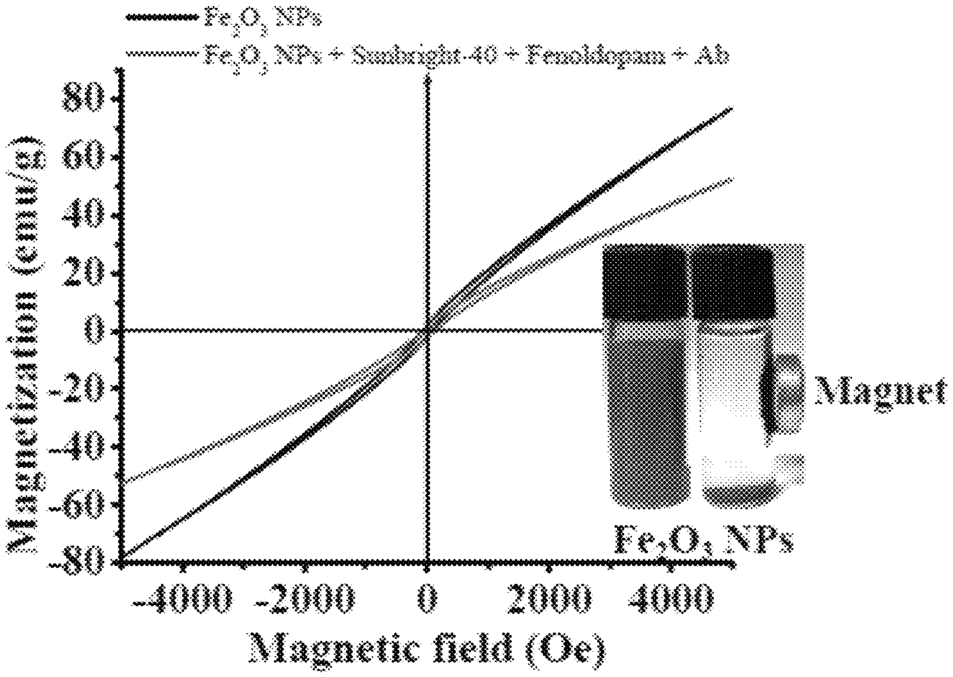
Figure 27D:
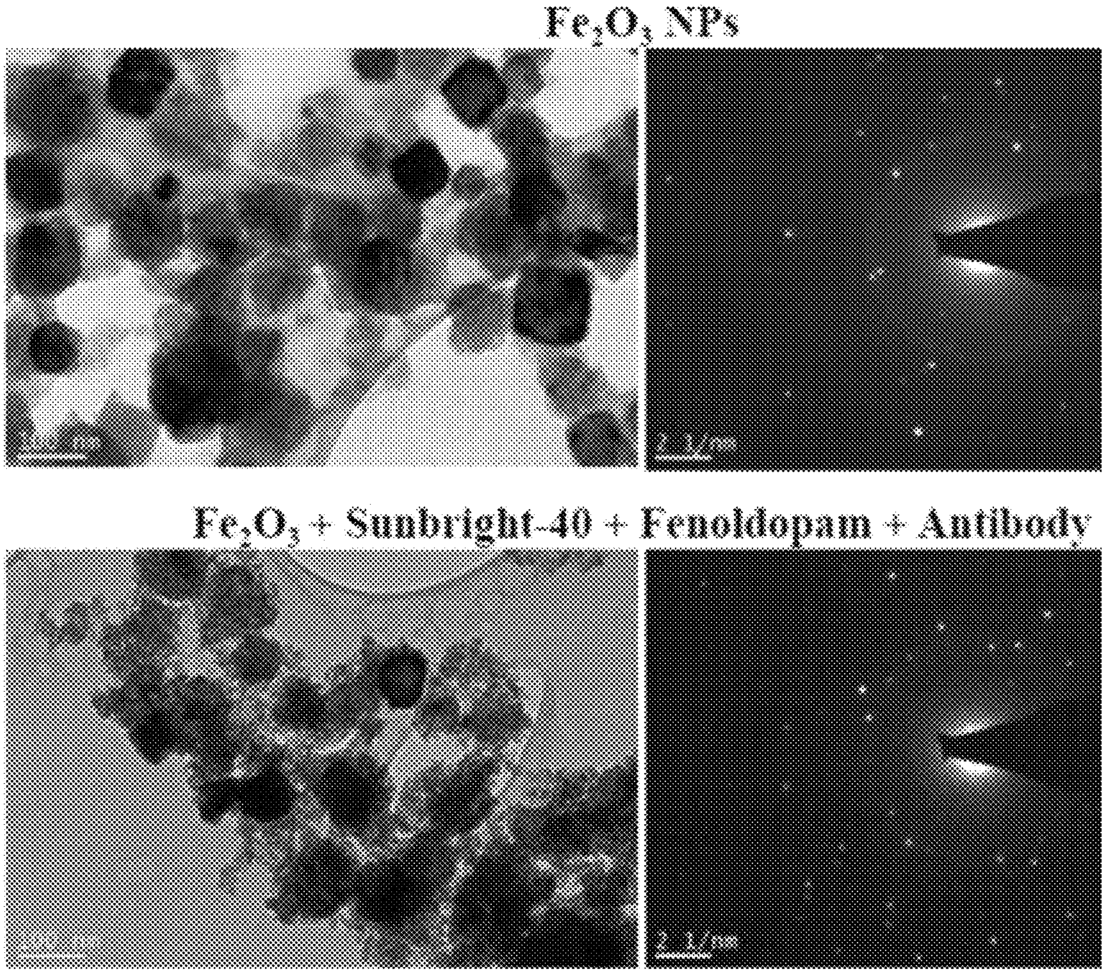

The NPs were coated with Sunbright-40 (oleyl-O $(CH_2CH_2)_nCO$—$CH_2CH_2$—COO—N-hydroxysuccinimide; PEG MW=4000) to enable covalent conjugation of the Alexa Fluor 594-labelled DR5 antibody via amide bonds (NHS ester reaction chemistry). The efficiency of DR5 antibody conjugation to the NPs was confirmed by a decrease in the antibody concentration in solution after conjugation as examined by SDS-PAGE and quantified by spectrophotometry (FIG. 27B). The CT-$Fe_2O_3$—NPs showed low magnetic coercivity, indicating that the NPs responded to the magnetic field in a superparamagnetic manner (FIG. 27C). When examined under transmission electron microscopy (TEM), the resulting CT-$Fe_2O_3$—NPs showed a typical core-shell structure depicting the surface functionalization around the cubic shaped core (FIG. 27D).

Figure 27E:
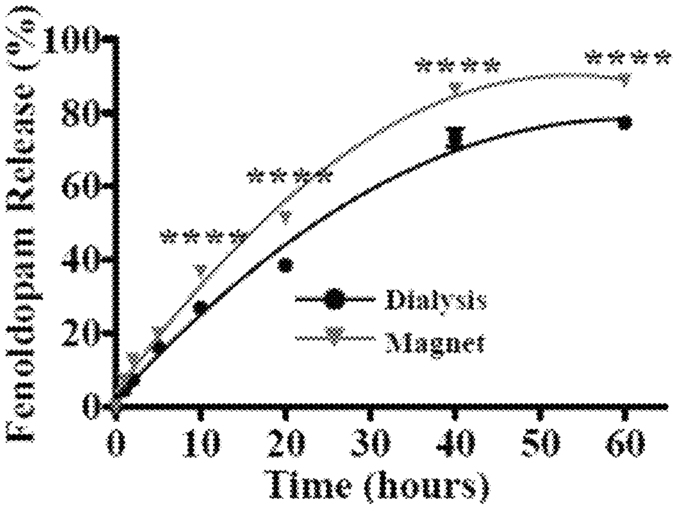
Figure 34H:
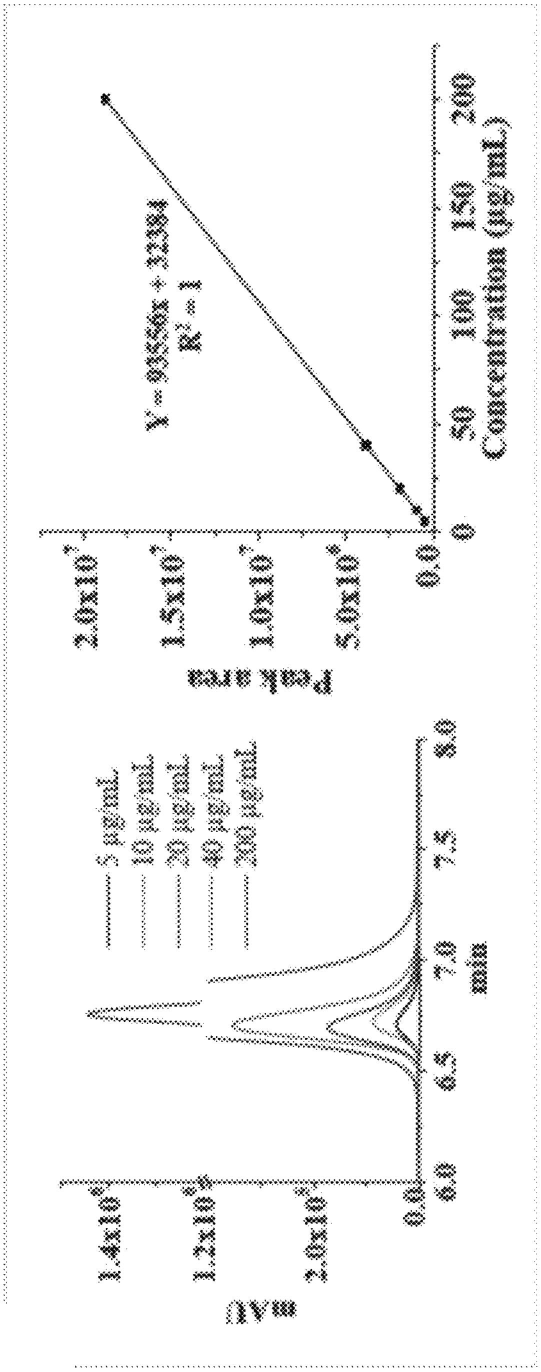
Figure 34I:
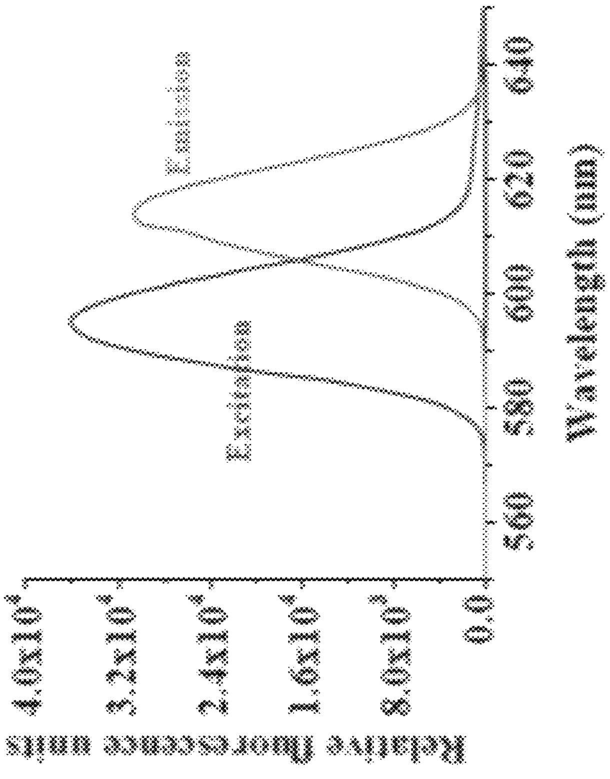
Figure 34J:
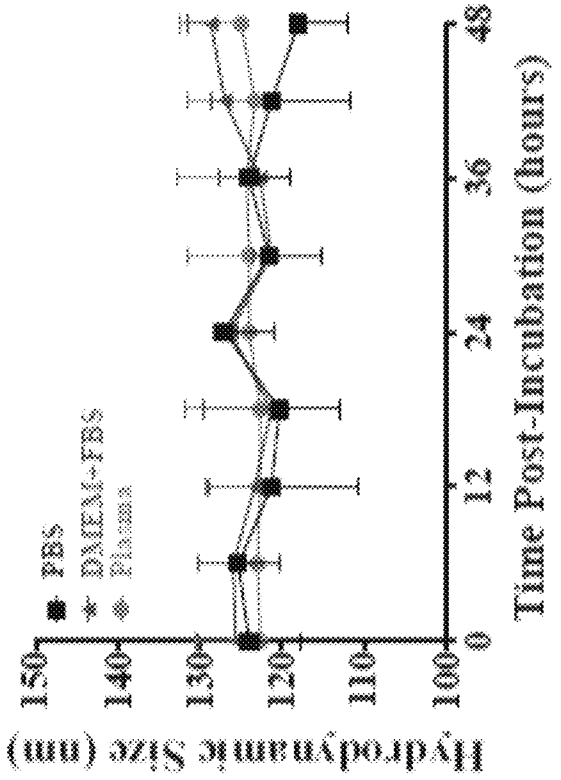
Figure 34K:
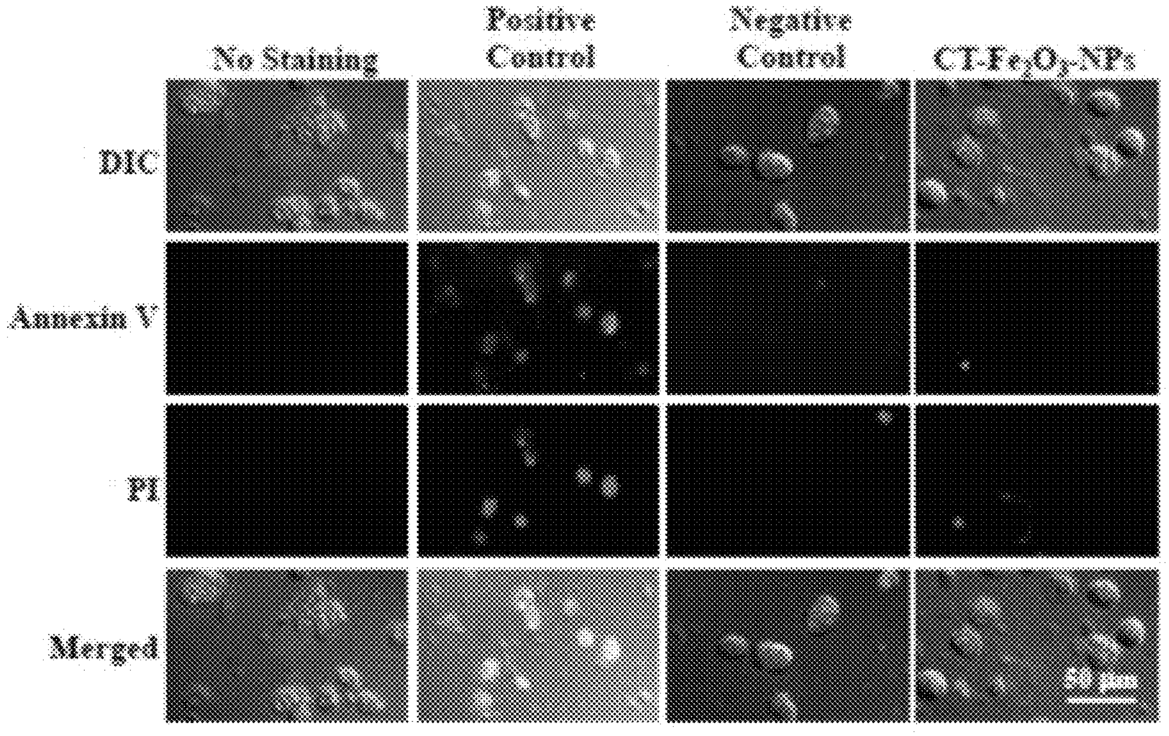
Figure 34L:
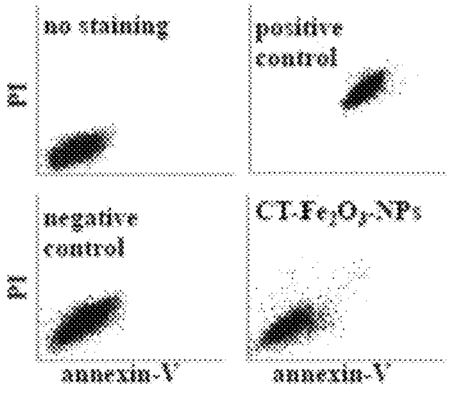

Fenoldopam was loaded in the oleyl-chains surrounding the NP surface. The loading efficiency of fenoldopam and its release rate from the CT-$Fe_2O_3$—NPs were quantified independently using a standardized high-performance liquid chromatography (HPLC) approach to obtain an accurate fenoldopam profile (FIG. 34H). The loading efficiency of fenoldopam was approximately 50%. Importantly, the slow, sustained release of fenoldopam reached 60-85% of the maximum release over 60 hours (FIG. 27E). Compared with standard dialysis (or the passive diffusion of the CT-$Fe_2O_3$—NPs), the magnetic field (CT-M-$Fe_2O_3$—NPs) significantly increased the release of fenoldopam. The Alexa Fluor 594 fluorescent dye that was pre-conjugated to the DR5 antibody was confirmed to retain its excitation and emission spectra, indicating the incorporation of the antibody and potential utility of the CT-$Fe_2O_3$—NPs in imaging studies (FIG. 34I). We thus examined the CT-$Fe_2O_3$—NP stability in control saline, culture media, and blood plasma, monitored with DLS for 48 hours prior to the in vitro and in vivo studies (FIG. 34J). Under all conditions, the CT-M-$Fe_2O_3$—NPs maintained stable sizes, indicating a high colloidal stability attributable to surface functionalization (FIG. 34J). Further, the biocompatibility of the CT-$Fe_2O_3$—NPs was confirmed in vitro, and no cellular apoptosis was observed (FIGS. 34K and 34L).

In these studies, DR5 was selected as a molecular target for cilia, because of the specificity of DR5 antibody to primary cilia of vascular endothelial cells in vivo.

Selectivity and Specificity of the CT-$Fe_2O_3$—NPs

The selectivity and specificity of the CT-$Fe_2O_3$—NPs for primary cilia were evaluated in live cells under flow conditions (FIG. 28A). Prior to introducing the CT-$Fe_2O_3$—NPs to live cells, high-resolution differential interference contrast (DIC) images were used to randomly locate a cilium. The fluorescence of the CT-$Fe_2O_3$—NPs was measured in the cilium and cell body for two hours. After approximately one hour, the cilia surface was saturated with the fluorescent CT-$Fe_2O_3$—NPs, while the cell body showed very minimal fluorescence. The selectivity of the CT-$Fe_2O_3$—NPs for the cilia was further confirmed by iron-specific Prussian blue staining (FIG. 28B) and was observed in a time-dependent manner.

NPs were applied to cells for 16 hours to further confirm the cellular effects of the CT-$Fe_2O_3$—NPs. When NPs, including all control NPs, were applied to the cells, the NPs were slowly perfused with the media. The fluid shear from the media helped eliminate non-specific binding of the NPs. In addition to a phosphate-buffered saline (PBS)-treated control group (vehicle), we used the CT-$Fe_2O_3$—NPs without fenoldopam (cCT-$Fe_2O_3$—NPs) and fenoldopam-alone as two independent sets of controls. Both cCT-$Fe_2O_3$—NPs and CT-$Fe_2O_3$—NPs showed specific CT delivery, but only the presence of fenoldopam significantly increased the cilia length (FIGS. 28C and 28D). Thus, fenoldopam was successfully released from the CT-$Fe_2O_3$—NPs and activated DR5 receptors. These results supported the hypothesis that the activation of dopaminergic receptors increases cilia length in embryonic fibroblasts, vascular endothelial cells and renal epithelial cells. In addition to the fluorescence from the CT-$Fe_2O_3$—NPs, analyses of the ciliary marker acetylated-α-tubulin and three-dimensional images were used to obtain more precise cilia length measurements.

Figure 28E:
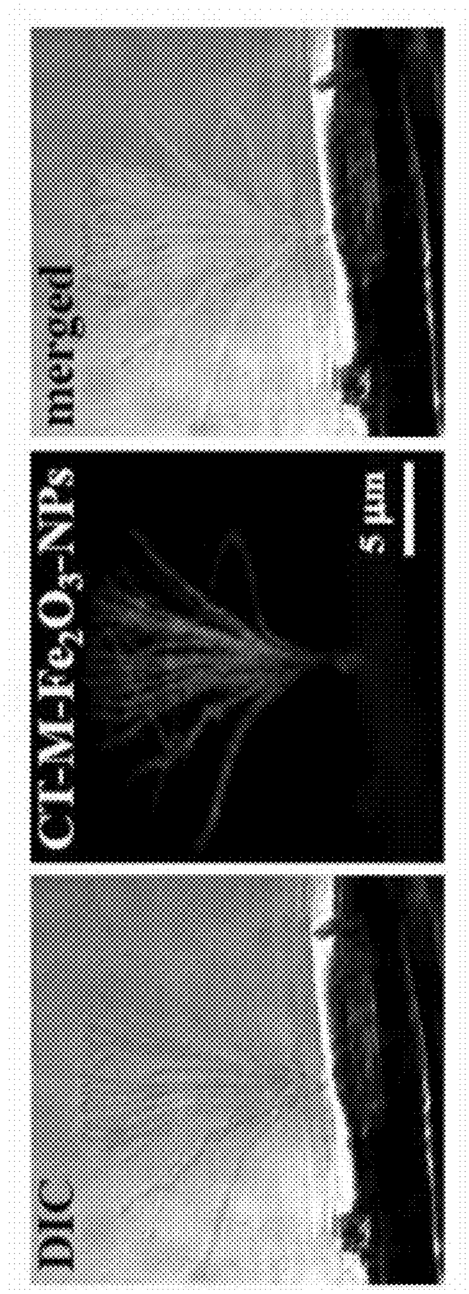
Figure 28B:
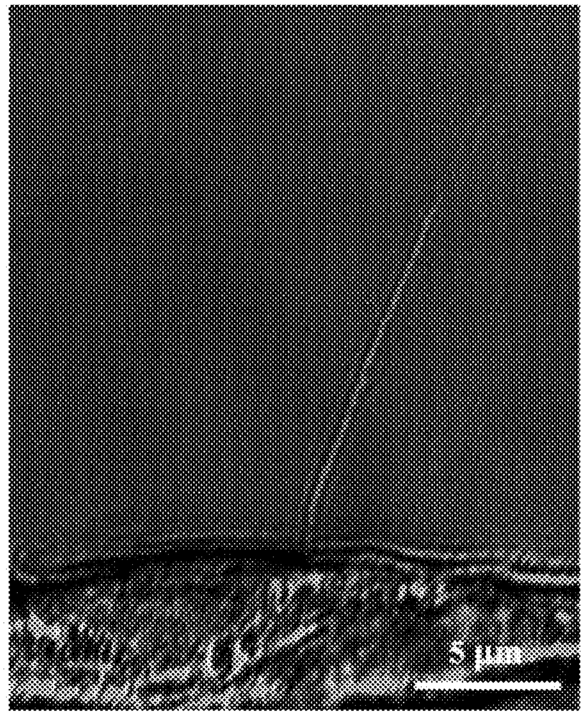
Figure 28D:
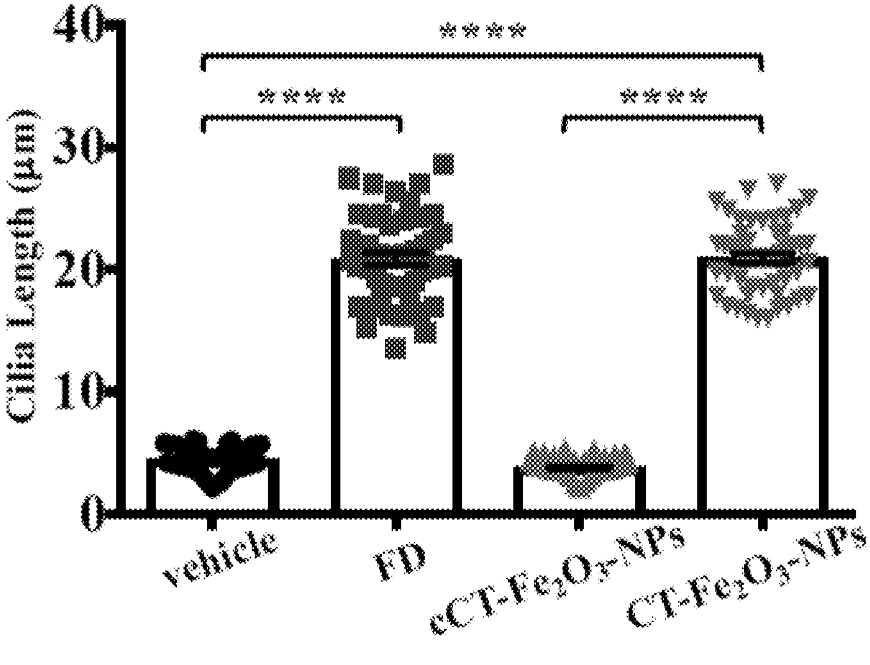
Figure 28C:
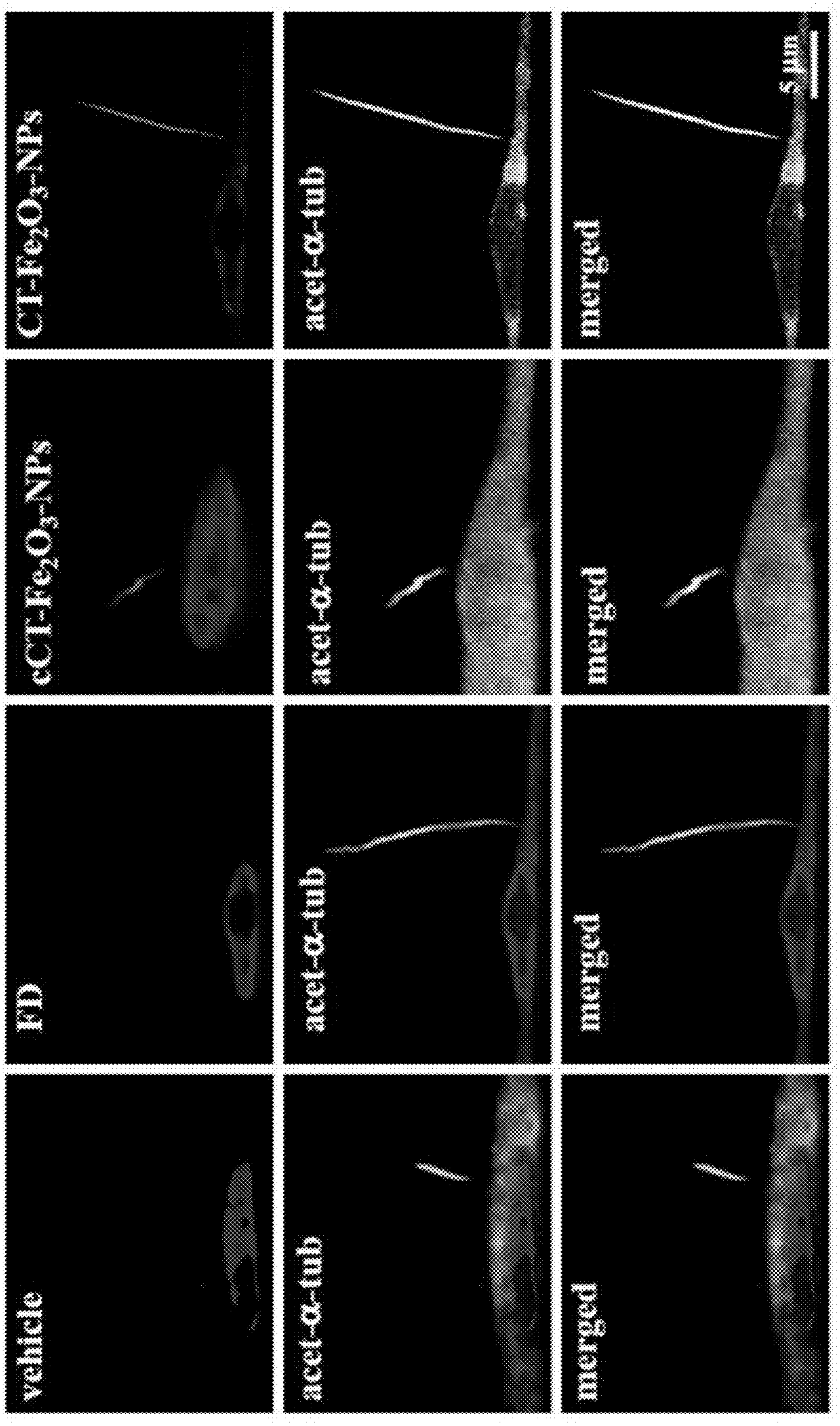

In live cells, the specificity of the CT-$Fe_2O_3$—NPs for cilia allowed application of an external magnetic field to control non-motile cilia movement (CT-M-$Fe_2O_3$—NPs, FIG. 28E). The significance of this approach was that non-motile primary cilia with a "9+0" structure are able to be converted to motile-like cilia using nanotechnology to mimic nodal cells, the only known cells displaying a "9+0" ciliary structure and motility. According to the mathematical model, approximately 780 CT-$Fe_2O_3$—NPs attached to a single cilium, where the total energy of the cilium consists of the elastic and magnetic energy of cilium-α-$Fe_2O_3$—NPs; therefore, the magnetic field imposed on the cilium was sufficiently sensitive to generate magnetic forces due to the rotation of the magnetic moment of α-$Fe_2O_3$—NPs (field alignment effect) and the attraction of the magnetic moment towards the increasing magnetic field (field gradient effect) to overcome cilia bending rigidity and bend the cilia at 45°. Because the angular displacement of the magnetic field changes as a result of the motion of the external magnet, the magnetic forces along the cilia length were altered, resulting in a wave-like movement throughout the ciliary shaft. The wave-like motion generated by the oscillating magnetic field of 1.35 T on the cilium was comparable to the force of 0.1 pN needed to bend a cilium, providing a theoretical basis for a strong interaction between the CT-$Fe_2O_3$—NPs and cilia. Thus, a magnetic force of 0.1 pN could facilitate fenoldopam release upon magnetic stimulation through the field alignment and gradient effects.

Figure 35A:
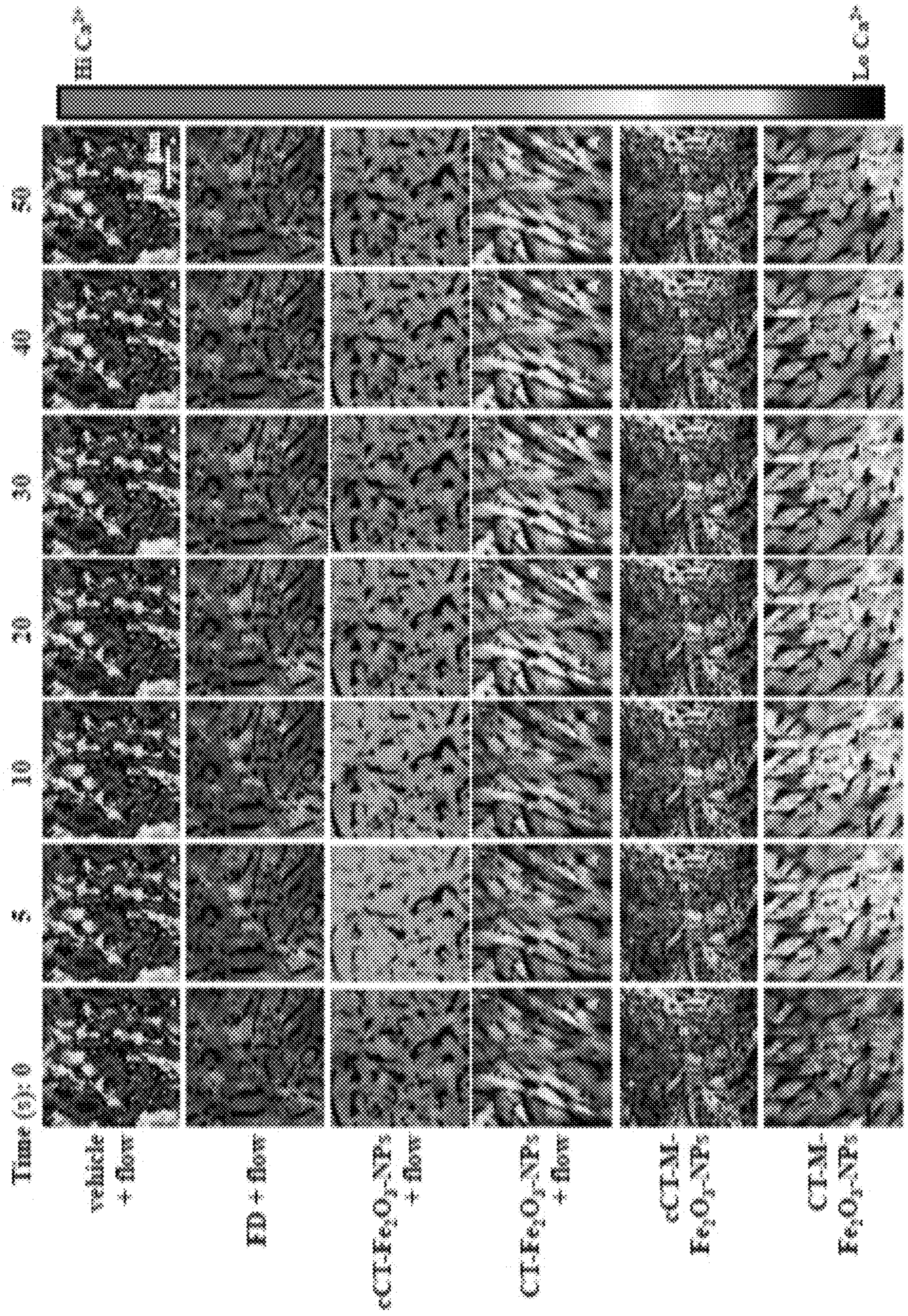
FIGS. 35A-D depict intracellular $Ca^{2+}$ and NO measurements.
Figure 35B:
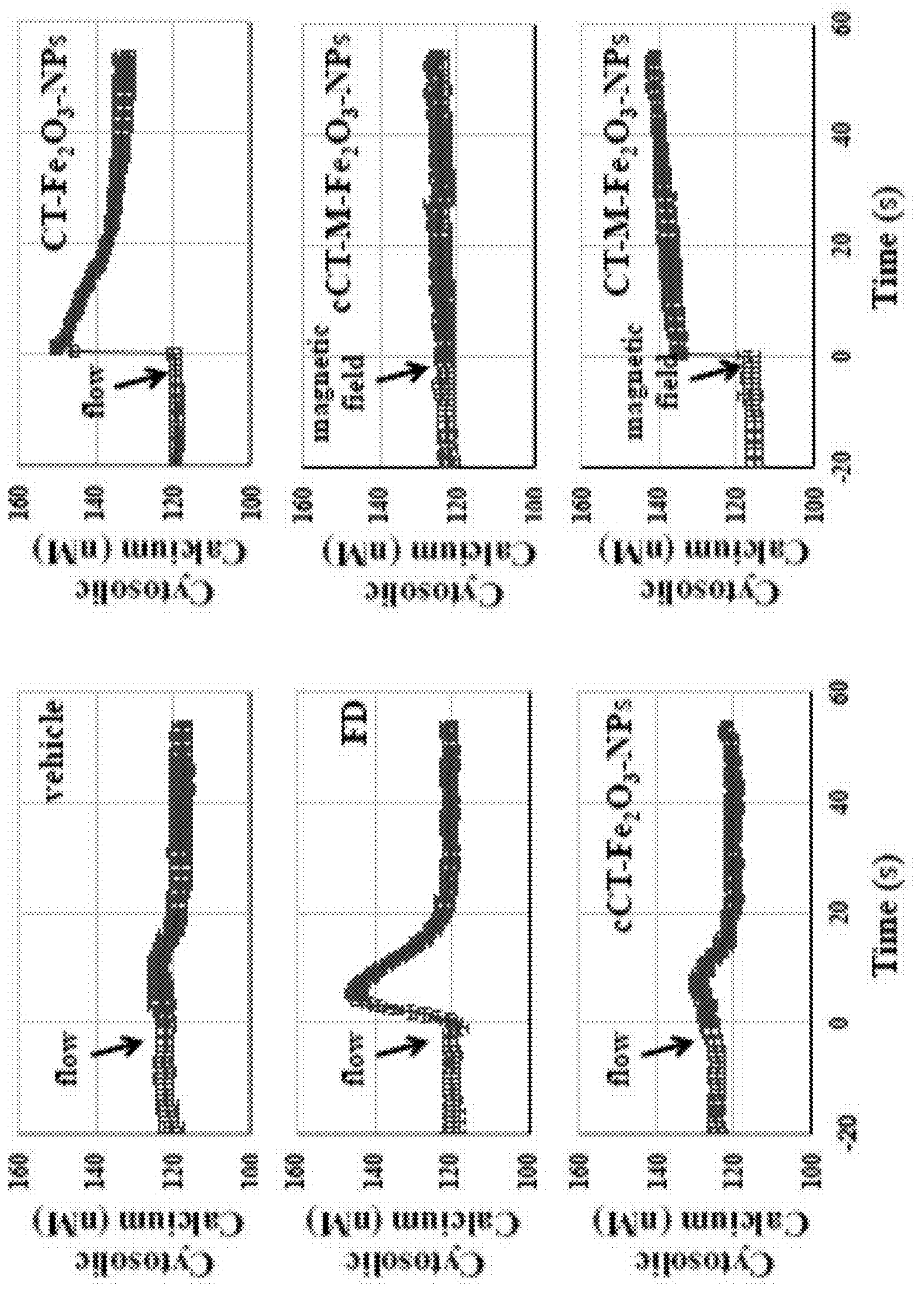

Effects of the CT-$Fe_2O_3$—NPs in Magnetic- and Flow-Induced Cilia Bending on Intracellular $Ca^{2+}$ Signalling Primary cilia function has been primarily examined by monitoring fluxes in cytosolic $Ca^{2+}$ concentrations. Therefore, the cytosolic $Ca^{2+}$ indicator Fura-2AM was used to differentiate cilia function by fluid-flow perfusion and magnetic-field induction. Cilia activity as sensory antennae in the cells depends of its length; as the length of a cilium (antenna) increases, the cell becomes more sensitive for cellular sensing. Shear stress was thus reduced from 1.0 to 0.5 dyn/$cm^2$ to magnify changes in sensitivity in terms of $Ca^{2+}$ signalling in control cells compared with that in the CT-$Fe_2O_3$—NP-treated cells. As expected, fluid-flow shear stress induced an increase in the cytosolic $Ca^{2+}$ concentration (FIGS. 35A and 35B). The application of a magnetic field also increased the cytosolic $Ca^{2+}$ concentration. While the fluid flow (CT-$Fe_2O_3$—NPs) and magnetic field (CT-M-$Fe_2O_3$—NPs) resulted in increased cytosolic $Ca^{2+}$ concentrations, their cytosolic $Ca^{2+}$ profiles were not the same. Sustained increases in cytosolic $Ca^{2+}$ concentrations were observed in magnet-treated cells, while a brief increase in the cytosolic $Ca^{2+}$ concentration was observed in flow-treated cells.

Figure 35C:
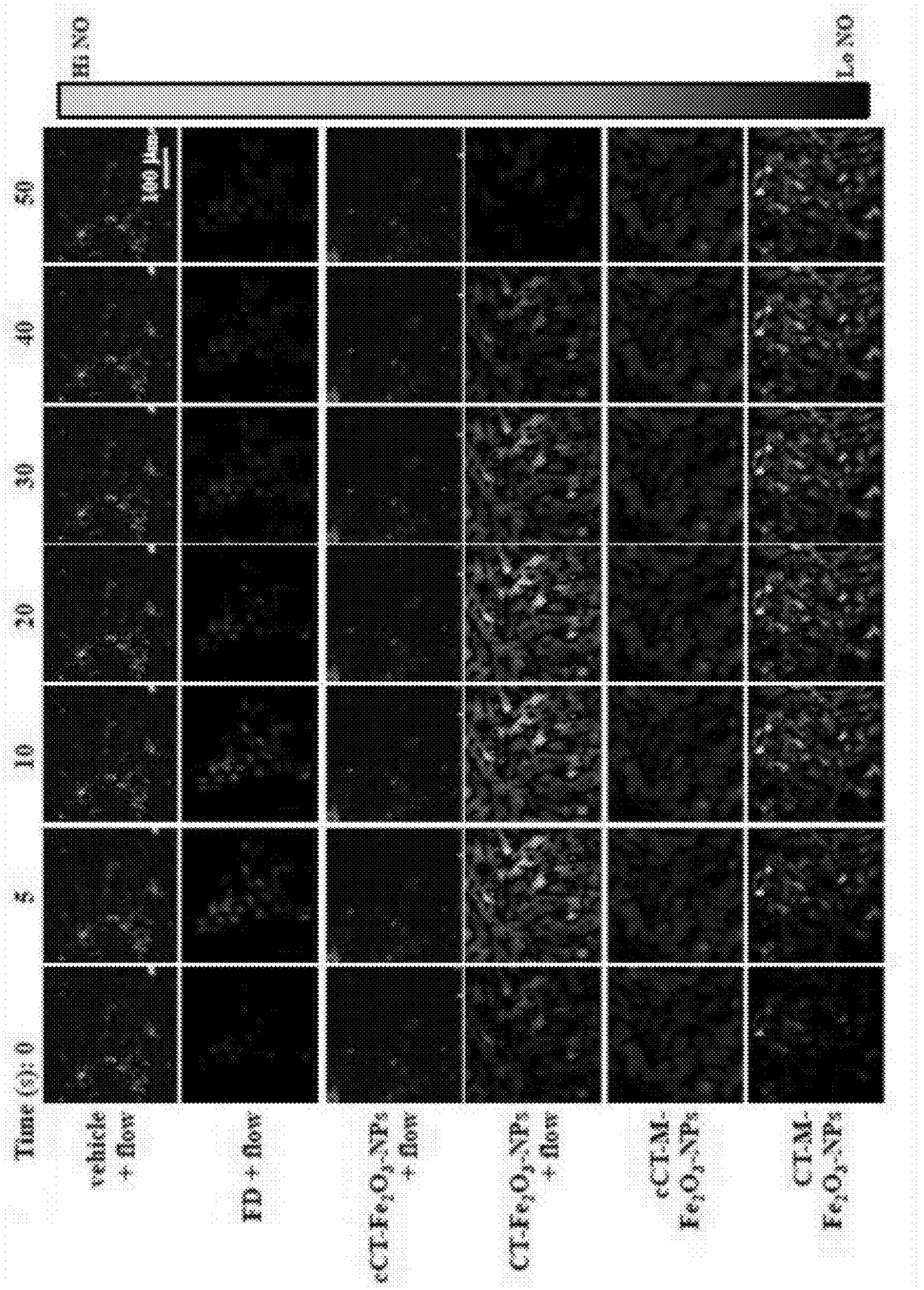
Figure 35D:
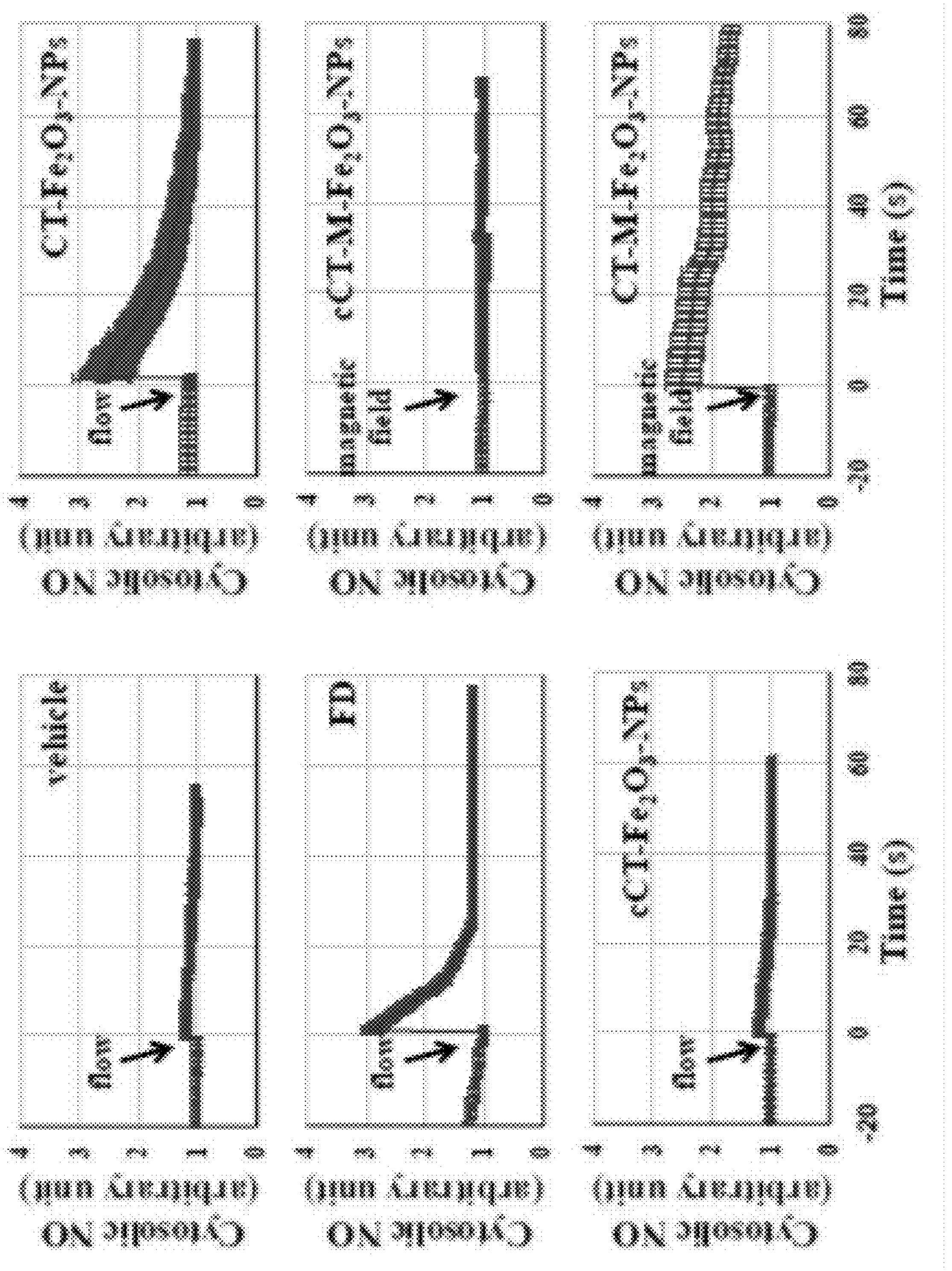
Figure 36A:
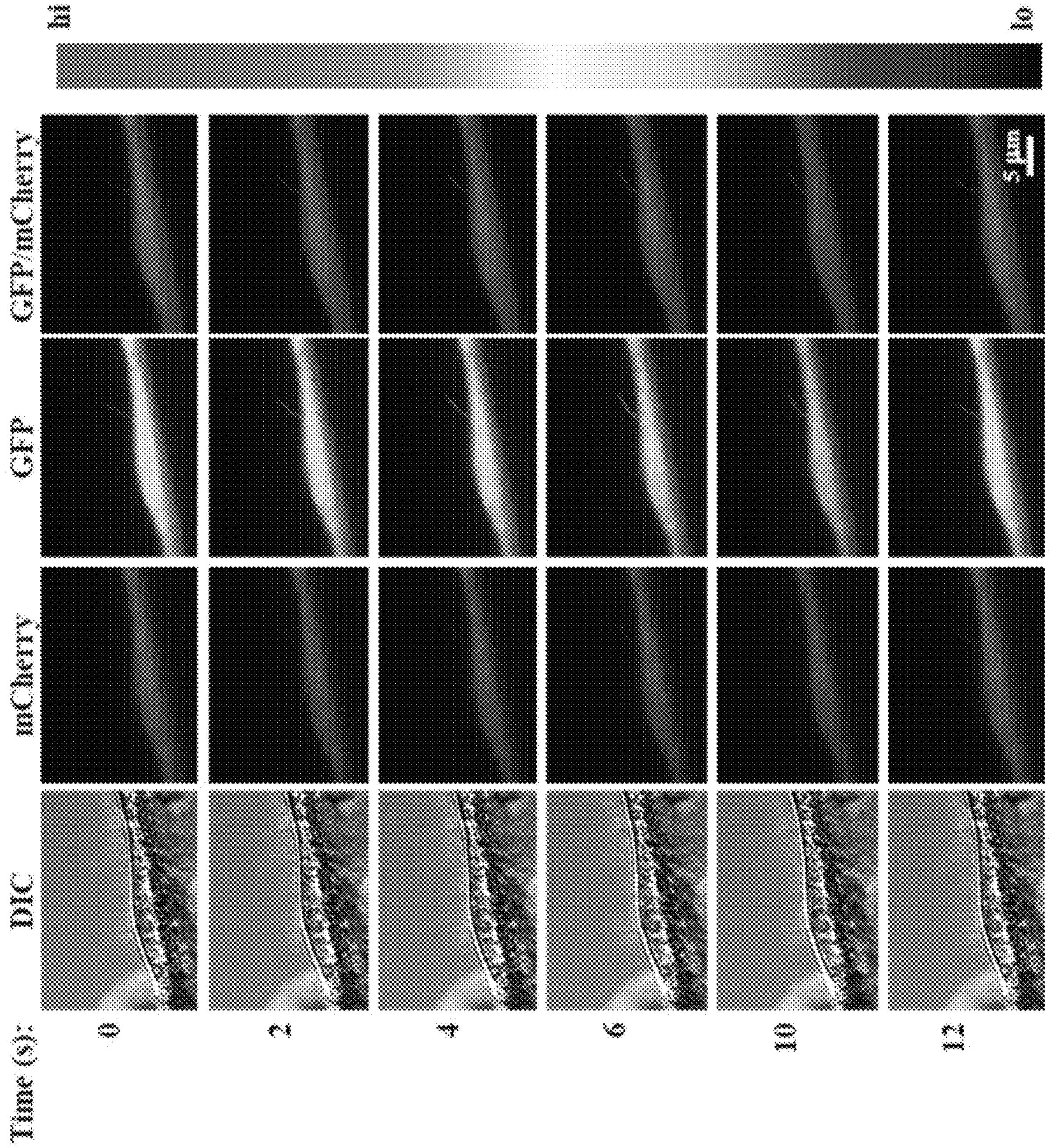
FIGS. 36A-B depict single-cell-single-cilium imaging for detecting intraciliary and cytosolic $Ca^{2+}$ levels in control- (FIG. 36A) and fenoldopam (FD) (FIG. 36B)-treated cells challenged with flow. Three sets of images (DIC, mCherry and GFP) were captured at 30 fps. DIC was used to track cilia movement, mCherry was used to normalize motion artefacts, GFP was used to measure changes in $Ca^{2+}$ signals, and the GFP/mCherry ratio (pseudocolored) indicates the normalized $Ca^{2+}$ level to avoid potential artefacts. The gradient bar indicates $Ca^{2+}$ levels. After treatment with PBS (vehicle) or fenoldopam, the cell was challenged with sub-minimal shear stress (0.5 dyn/cm$^2$). n=4 samples per group in each study.
Figure 36B:
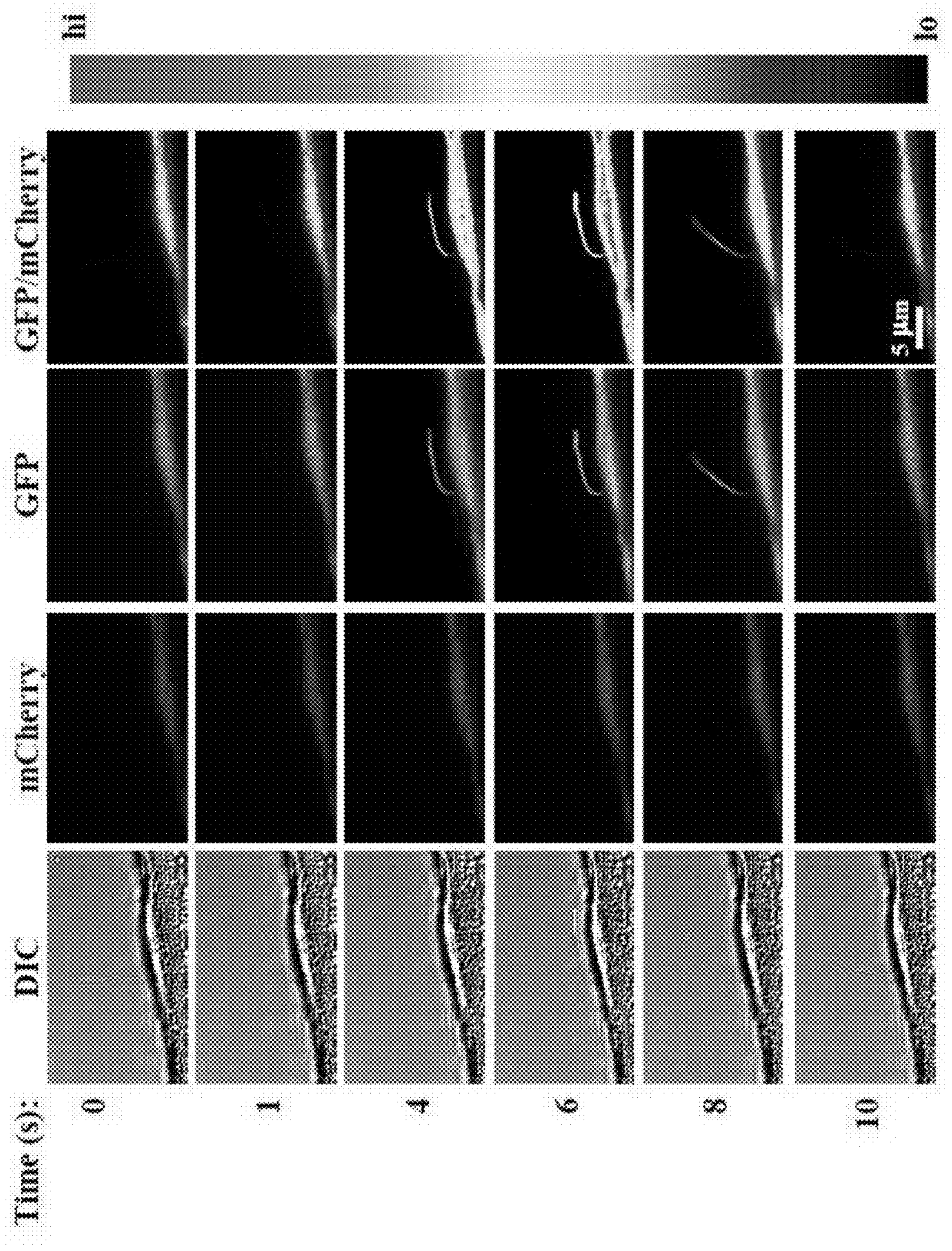
Figure 37A:
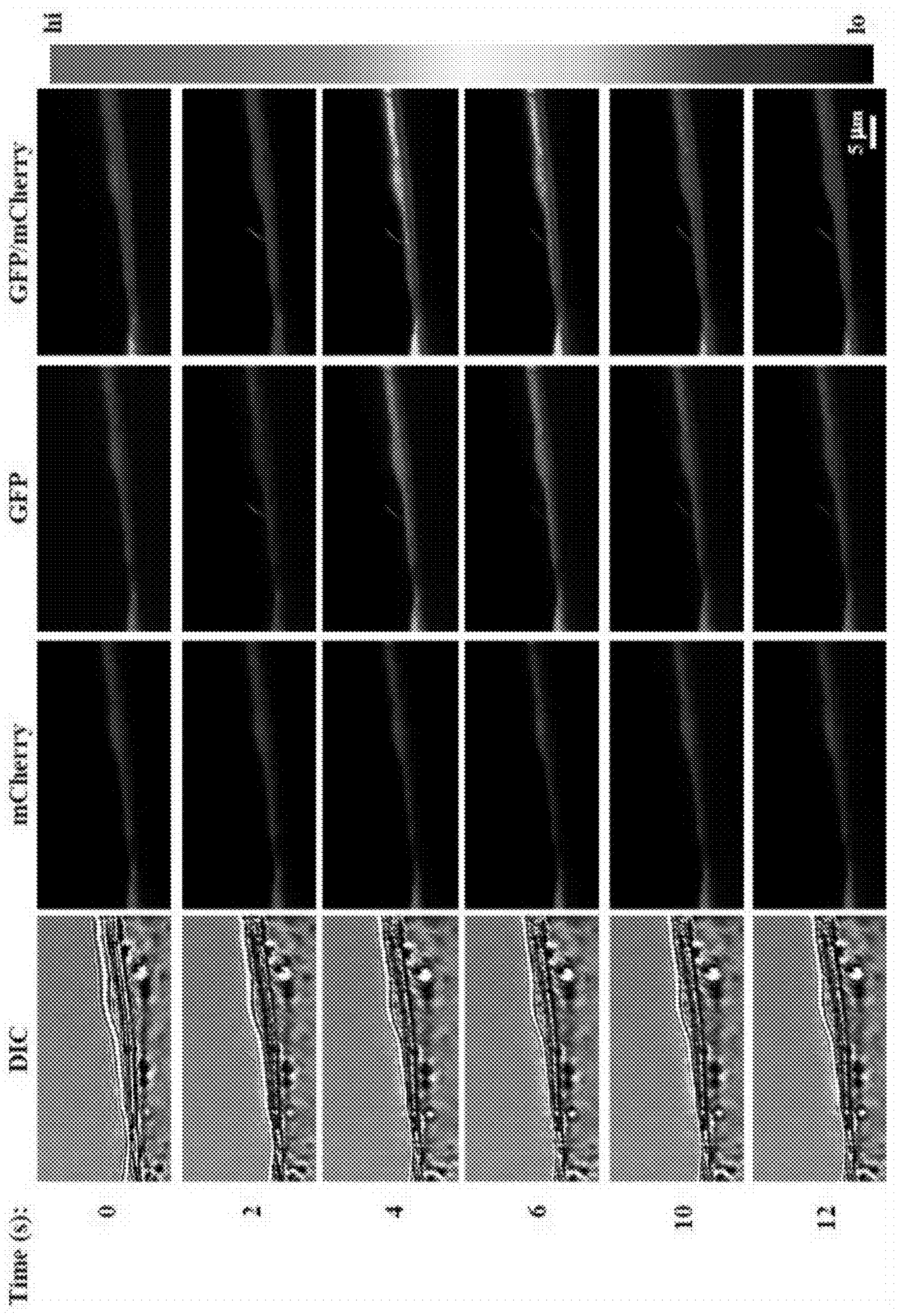
FIGS. 37A-B depict single-cell-single-cilium imaging for detecting intraciliary and cytosolic $Ca^{2+}$ levels in cells treated with the cCT-$Fe_2O_3$—NPs (FIG. 37A) CT-$Fe_2O_3$—NPs (FIG. 37B) and challenged with flow. 5HT$_6$-mCherry-G-GECO1.0 was expressed in the cilioplasm and cytoplasm. Three sets of images (DIC, mCherry and GFP) were captured at 30 fps. DIC was used to track cilia movement, mCherry was used to normalize motion artefacts, GFP was used to measure changes in $Ca^{2+}$ signals, and the GFP/mCherry ratio (pseudocolored) indicates normalized $Ca^{2+}$ levels to avoid potential artefacts. gradient After treatment with the cCT-$Fe_2O_3$-NPs or CT-$Fe_2O_3$—NPs, the cell was challenged with sub-minimal shear stress (0.5 dyn/cm$^2$). n=4 sample per group in each study.
Figure 37B:
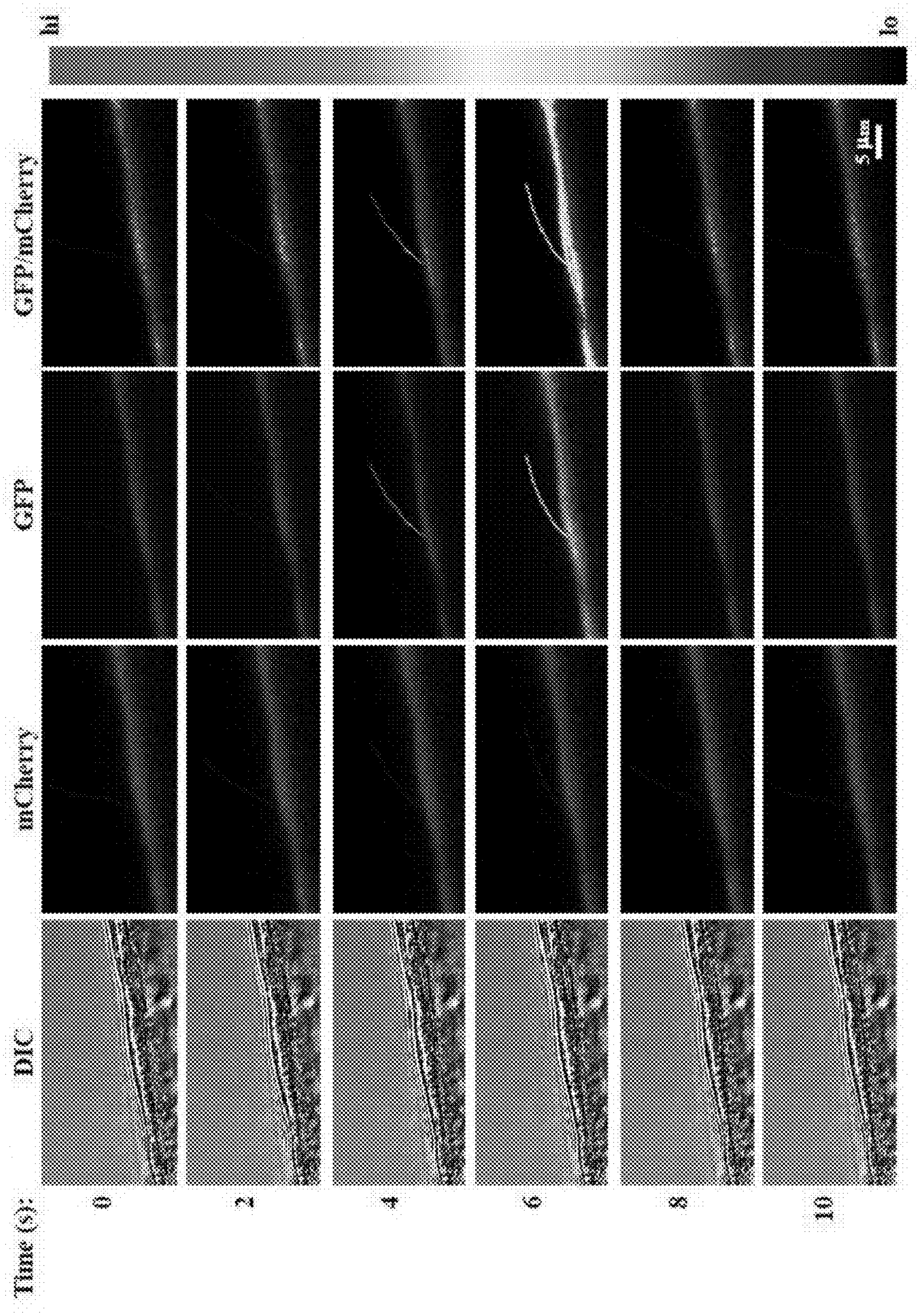
Figure 38A:
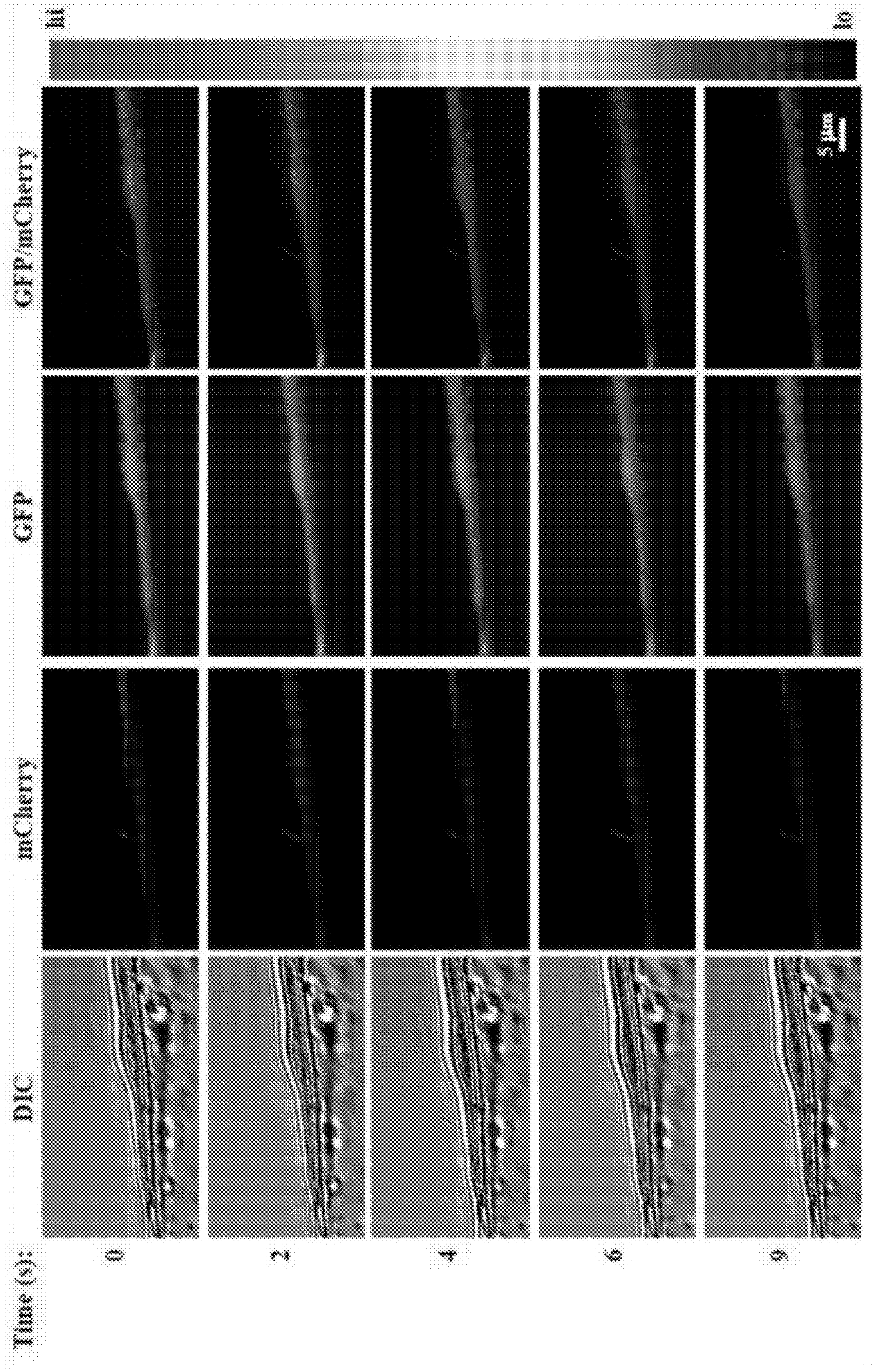
FIGS. 38A-B depict single-cell-single-cilium imaging for detecting intraciliary and cytosolic $Ca^{2+}$ levels in cells treated with the cCT-M-$Fe_2O_3$—NPs (FIG. 38A) or CT-M-$Fe_2O_3$—NPs (FIG. 38B) and challenged with a magnetic field. 5HT$_6$-mCherry-G-GECO1.0 was expressed in the cilioplasm and cytoplasm. Three sets of images (DIC, mCherry and GFP) were captured at 30 fps. DIC was used to track cilia movement, mCherry was used to normalize motion artefacts, GFP was used to measure changes in $Ca^{2+}$ signals, and the GFP/mCherry ratio (pseudocolored) indicates normalized $Ca^{2+}$ levels to avoid potential artefacts. The gradient bar indicates $Ca^{2+}$ levels. After treatment with the cCT-M-$Fe_2O_3$—NPs or CT-M-$Fe_2O_3$—NPs, an oscillating magnetic field (1.35 T) was applied. N=4 samples per group in each study.
Figure 38B:
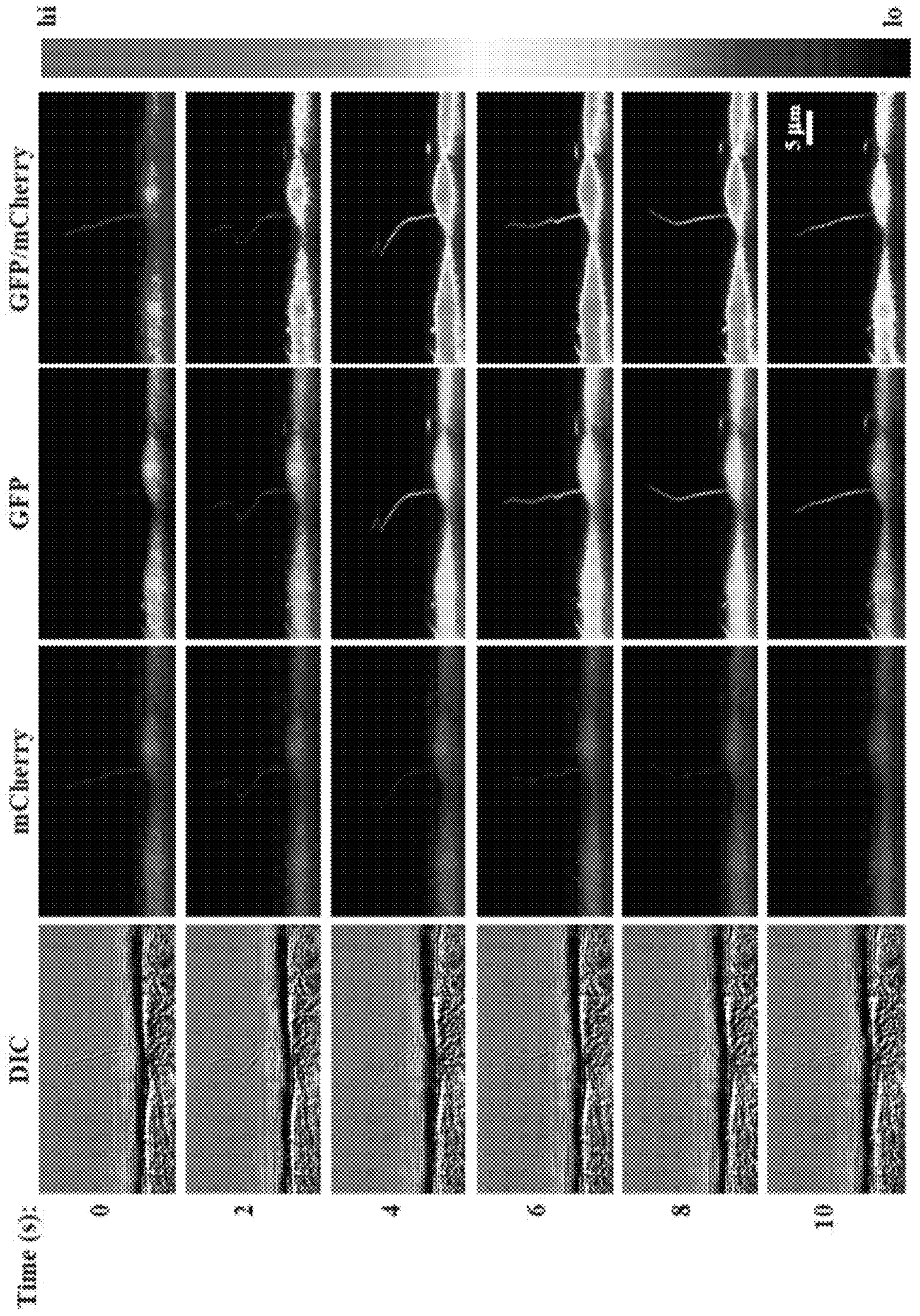

The function of primary cilia is also associated with nitric oxide (NO) production. The deflection of primary cilia with the magnetic field was sufficient to evoke a sustained release of NO in renal epithelial cells (FIGS. 35C and 35D). On the other hand, shear stress induced only a burst of NO release, suggesting that the CT-M-$Fe_2O_3$—NPs induced more pronounced NO production than the CT-$Fe_2O_3$—NPs.

Figure 28F:
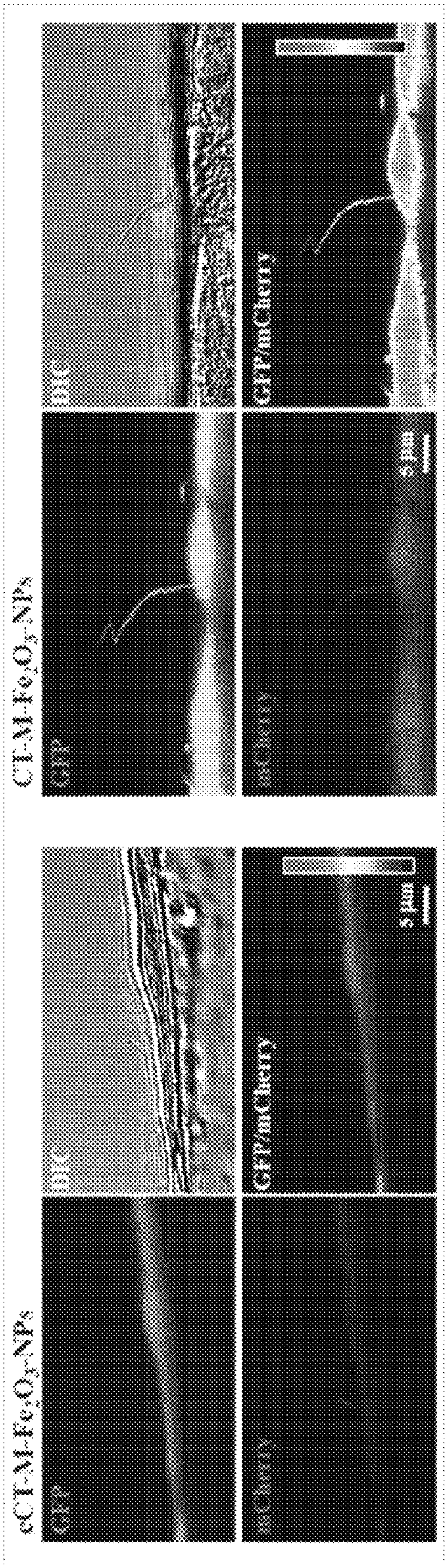
Figure 28G:
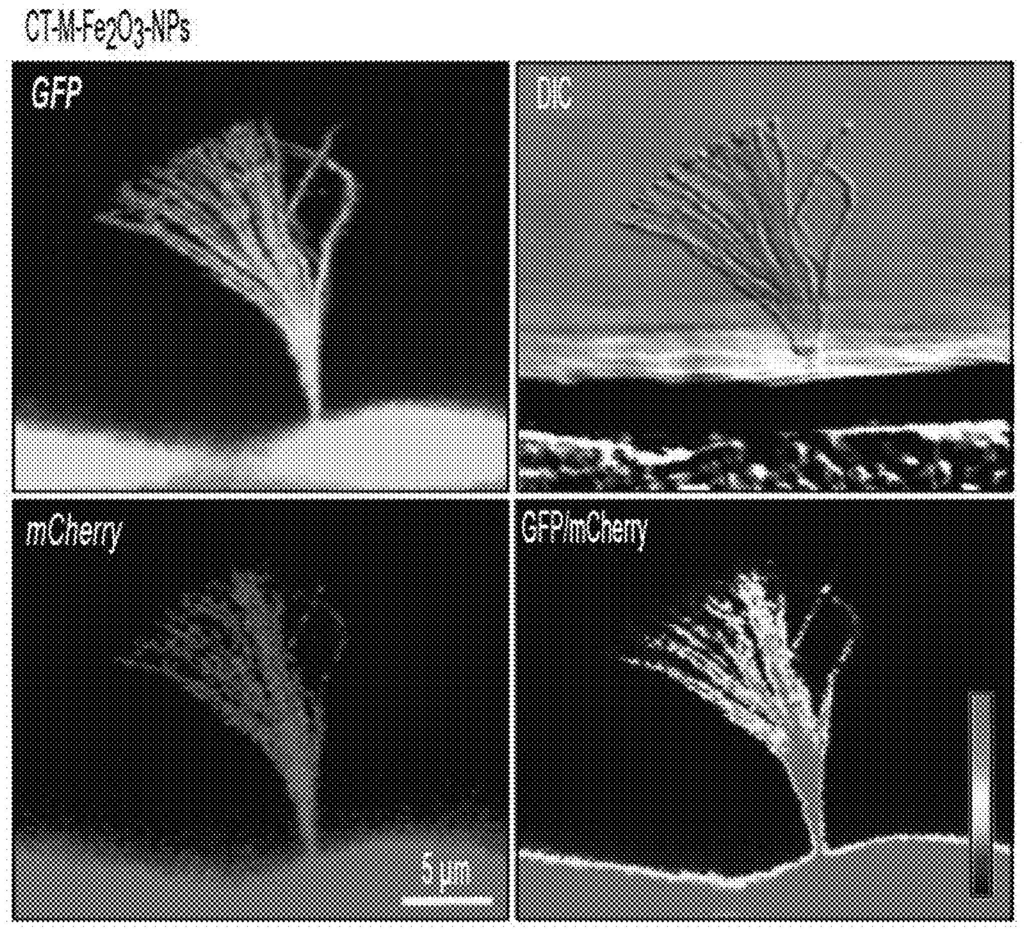
Figure 28H:
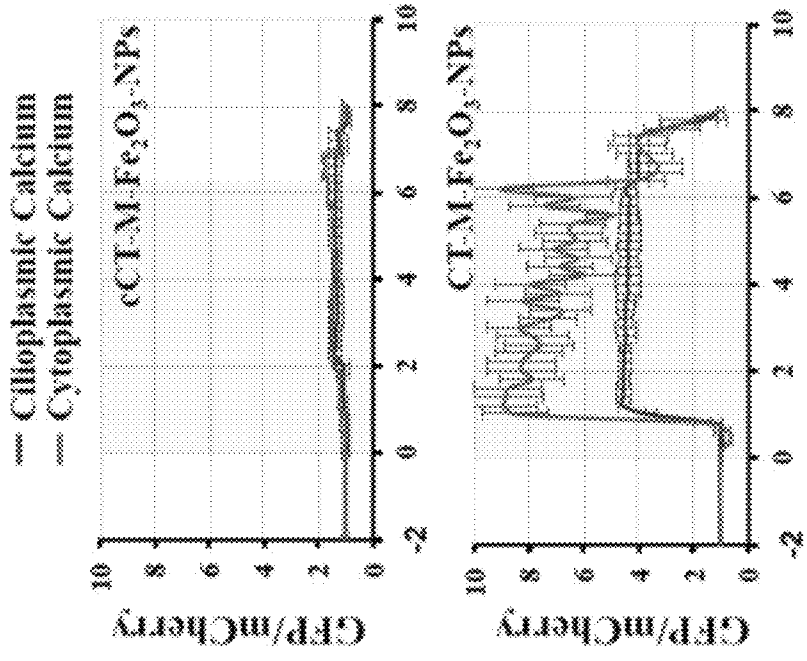
Figure 28I:
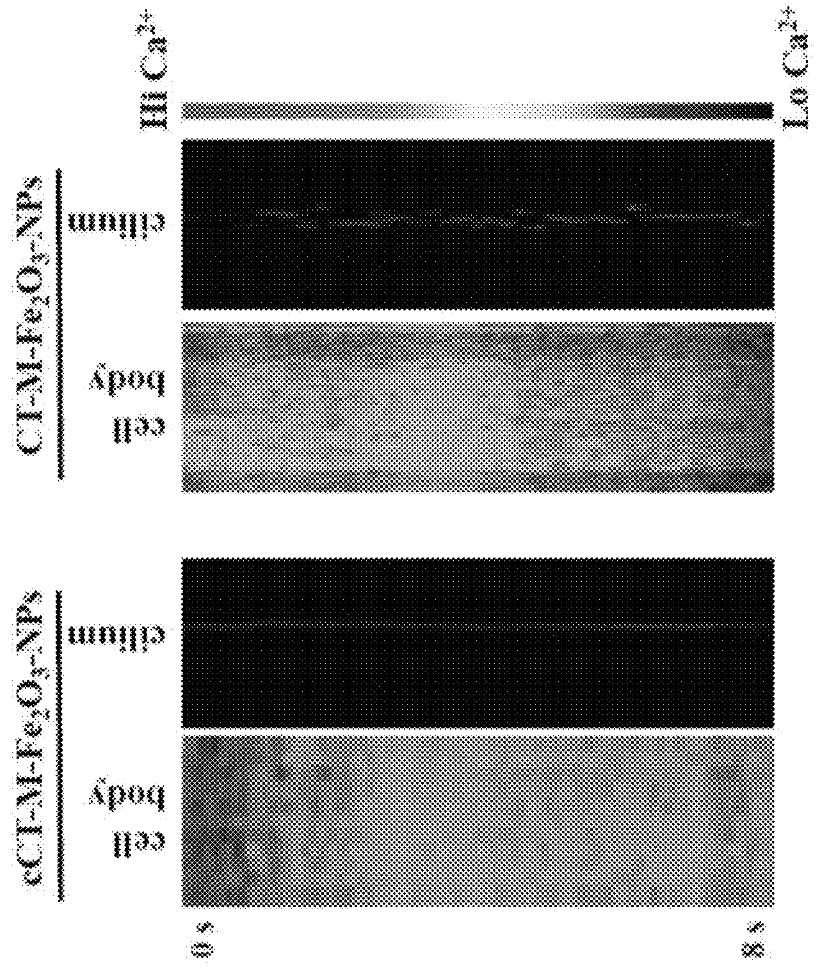
Figures 39A, 39B:
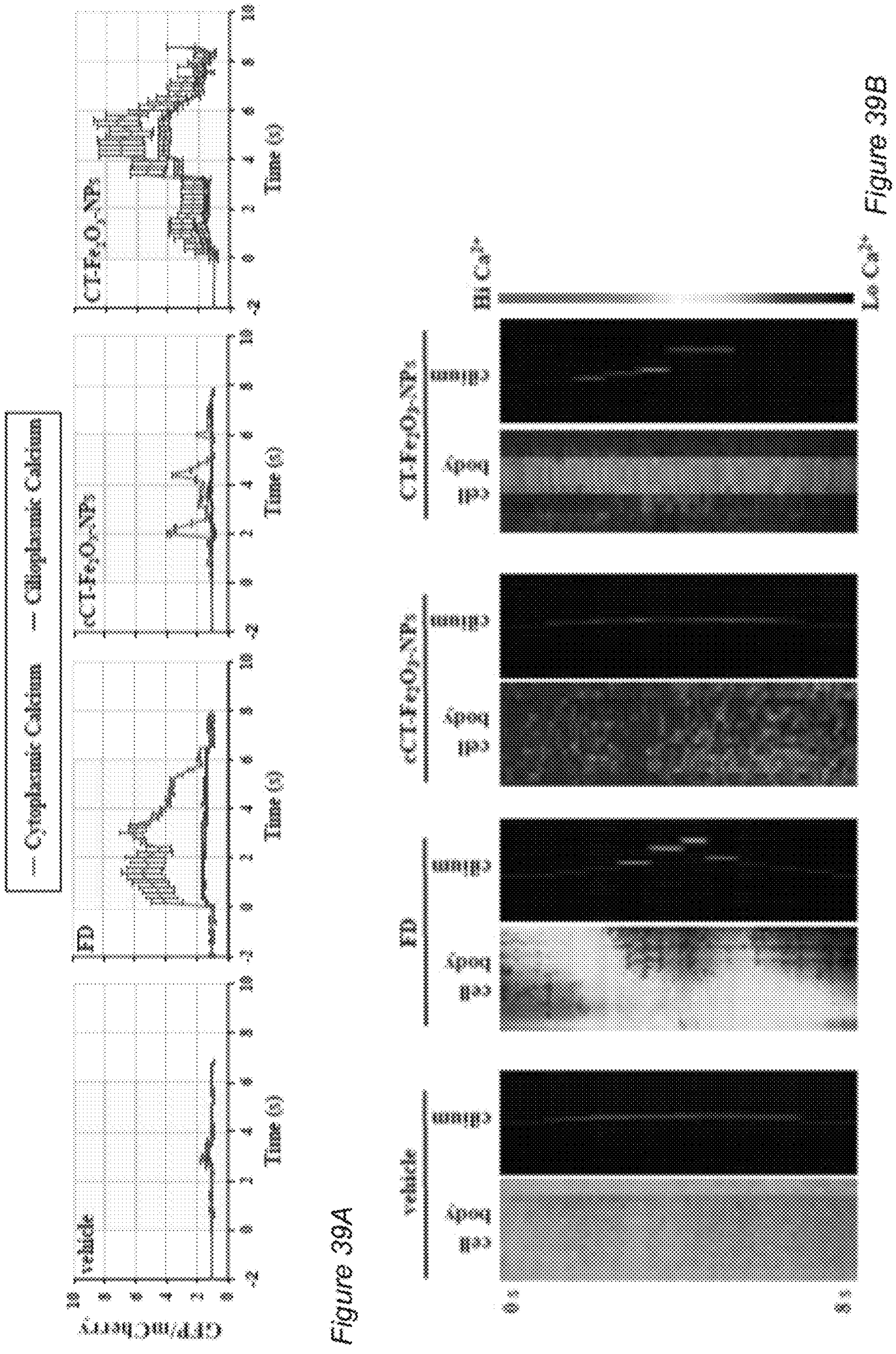
FIGS. 39A-C depict Kymograph analyses of ciliary and cellular $Ca^{2+}$ traces.
Figure 39C:
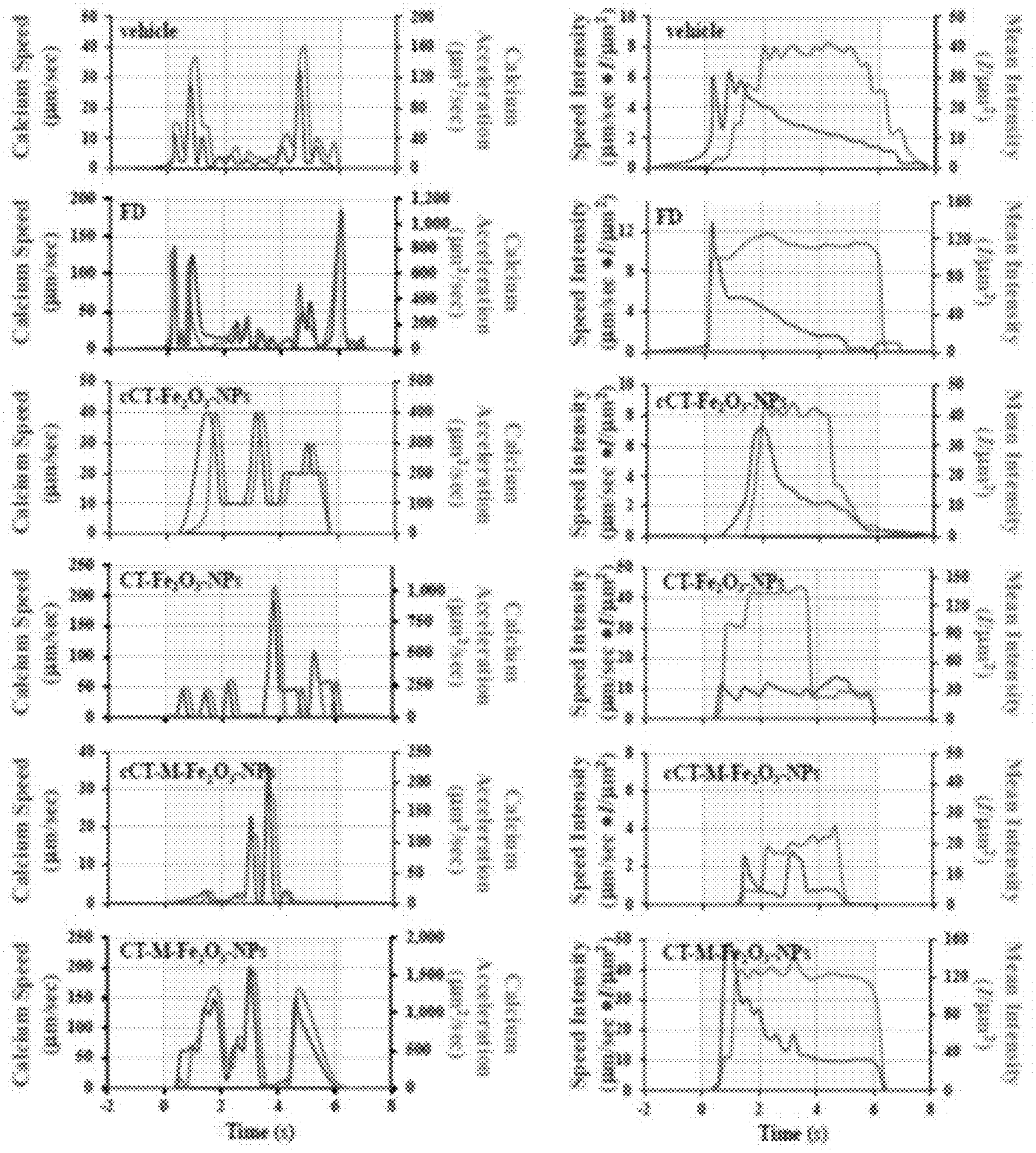

In addition to cytosolic $Ca^{2+}$ and NO, the presence of intraciliary $Ca^{2+}$ signalling has been used to assess the mechanosensing function of primary cilia. We used the ciliary $Ca^{2+}$ reporter 5HT6-mCherry-G-GECO1.0 in a single-cell-single-cilium setup to examine the potential effects of the CT-$Fe_2O_3$—NPs on ciliary $Ca^{2+}$ signalling. The CT-$Fe_2O_3$—NPs were not tagged with fluorescence markers in these studies to avoid fluorescence interference. The $Ca^{2+}$ reporter was distributed homogenously throughout the cell, including the cilium. The application of a magnetic field produced significant cilium bending and a sustained increase in $Ca^{2+}$ signalling in both the cilioplasm and cytoplasm in the CT-M-$Fe_2O_3$—NP-treated cells compared to those in the control cCT-M-$Fe_2O_3$—NP-treated cells (FIGS. 28F-28H). On the other hand, the CT-$Fe_2O_3$—NPs and their corresponding controls, including fenoldopam-alone, induced less of an increase in the intraciliary $Ca^{2+}$ signalling (FIGS. S36-S39A). While the mCherry signal is commonly used to indicate a signal artefact of the 5HT6-mCherry-G-GECO1.0 reporter, kymograph analyses were also performed to confirm that the calculated GFP/mCherry signal did not contain a green fluorescent protein (GFP) artefact or noise independent from mCherry (FIGS. 28I and 39B). A single trace from a cilium indicated that the speed and acceleration of the $Ca^{2+}$ signal or GFP/mCherry signals peaked when the cilium was fully bent. Changes in the speed and acceleration of the $Ca^{2+}$ signal were required for changes in the intensity of the GFP/mCherry signals (FIG. 39C). This finding indicated that the observed $Ca^{2+}$ signals were not a movement artefact, because a movement artefact would not require the speed and acceleration of the signal to dictate changes in the signal intensity. Importantly, the CT-M-$Fe_2O_3$—NP-treated groups showed an increased intracellular $Ca^{2+}$ flux compared with the other groups.

Many signaling molecules have been localized in the intraciliary compartment or cilioplasm. The $Ca^{2+}$ signaling can also occur within cilioplasm, but this idea has remained controversial. While studies from independent laboratories have indicated that $Ca^{2+}$ signaling occurs in the cilia, another study has shown that cilia bending by fluid-shear does not involve intraciliary $Ca^{2+}$ changes. In these present studies, we thus explored if cilia bending with fluid-shear stress and magnetic field could induce intraciliary $Ca^{2+}$ increase. Because many cilia are short with lengths about 4.5±0.2 μm, we pharmacologically increased the size of cilia to 20.9±0.5 μm. Because empty magnification in image quantification is known to produce signal artefacts, the 4× increase in cilia length allowed us to study intraciliary $Ca^{2+}$ to avoid unnecessary empty magnification during data extraction and analysis. While the idea of primary cilia as $Ca^{2+}$ signalling compartments is unclear, it has been known for decades that fluid-shear stress can induce cytosolic $Ca^{2+}$ increase. We thus studied both cilioplasmic and cytosolic $Ca^{2+}$ concurrently within a single cell, using cytosolic $Ca^{2+}$ as the internal control. We observed that cilia bending with either fluid-flow or magnetic field always increased both cilioplasmic and cytosolic $Ca^{2+}$. Increase in $Ca^{2+}$ was never observed to occur only in cytosol or only in cilium. The validations with the mCherry signal and more advanced kymograph analysis indicated that no signal artefact was detected during the measurement. While the data suggested that a cilium could function as a $Ca^{2+}$ signaling compartment, a cilium can serve as a much more complex signaling compartment discreet from the cell body.

Mechanociliary Signalling of the CT-$Fe_2O_3$—NPs

Figure 29A:
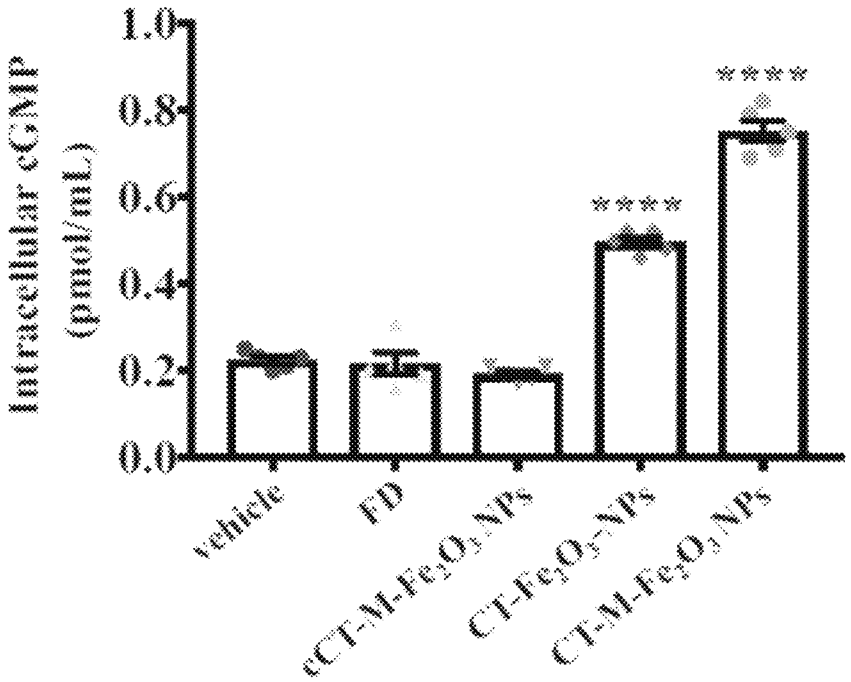
Figure 29B:
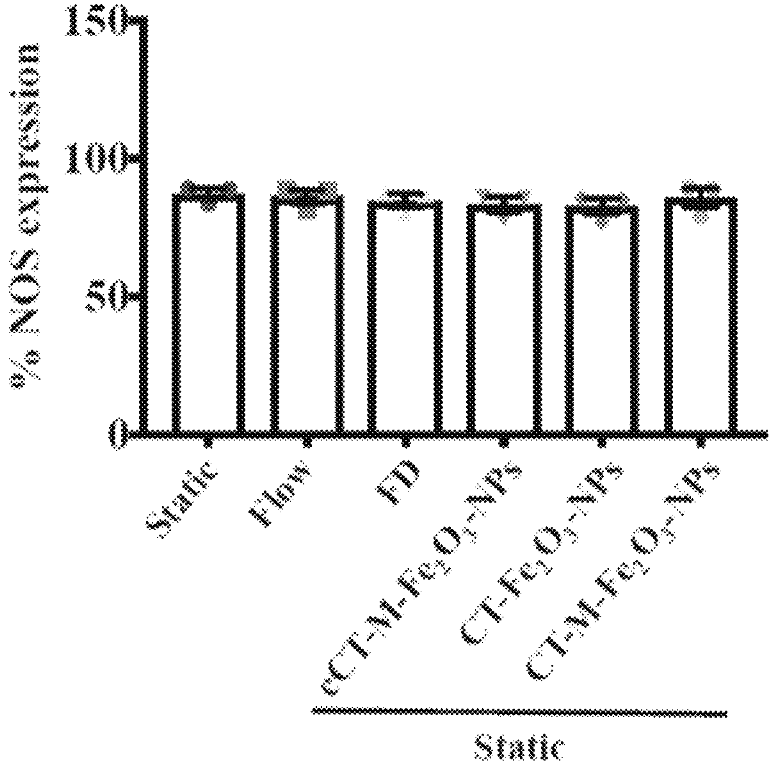
Figure 29C:
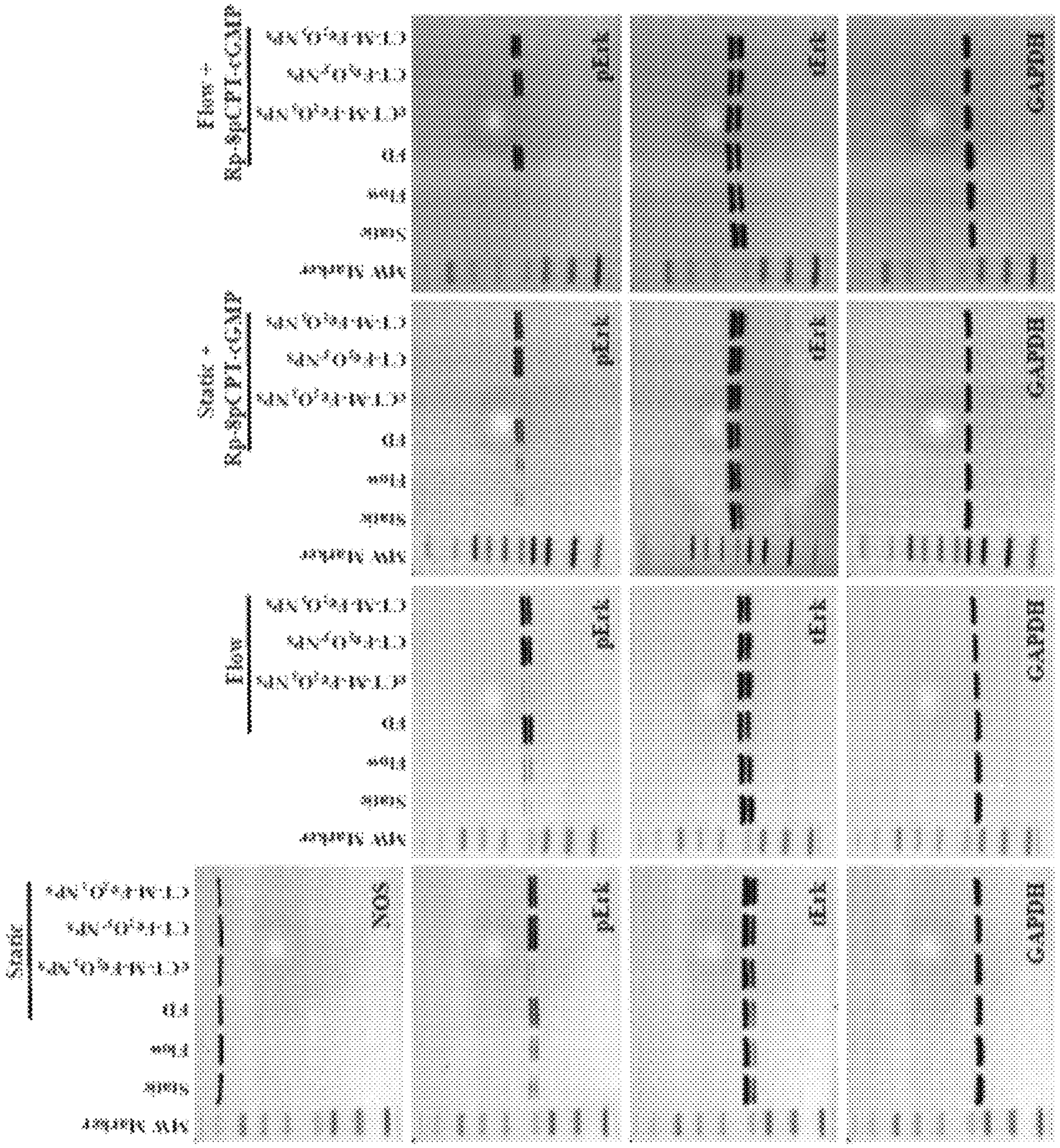

The importance of mechanociliary function was examined by monitoring intracellular cyclic guanosine monophosphate (cGMP) levels in renal epithelia to better understand the downstream signalling mechanism of NO. It was evidence that the CT-$Fe_2O_3$—NPs played a significant role in the $Ca^{2+}$/NO signalling pathway (FIG. 29A). Because NO synthase (NOS) was expressed at similar levels in different treatments (FIG. 29B), the effects of the NPs subjected to fluid flow (CT-$Fe_2O_3$—NPs) and the magnetic field (CT-M-$Fe_2O_3$—NPs) on cGMP-dependent kinase (PKG) and mitogen-activated protein kinase (MAPK) activity were examined (FIGS. 29C and 29D). Mechanical cilia activation through flow or chemical cilia activation by the CT-$Fe_2O_3$—NPs or fenoldopam-only increased ERK phosphorylation. Inhibition of PKG with Rp-8pCPT-cGMP reduced the flow-induced effect of NPs on ERK phosphorylation. Inhibition of PKG had little effect on ERK phosphorylation under static conditions, indicating that a cGMP-independent pathway may be involved in the chemosensory function of cilia and the increased cilia length. For example, increases in cilia length may depend on both cyclic nucleotide and ERK phosphorylation. Nonetheless, the most pronounced effects of NPs were observed when cells were challenged with fluid flow or a magnetic field (FIGS. 29C and 29D). While these studies were performed in a cell line, a validation study using isolated primary endothelia also produced a similar result (FIG. 40). Therefore, the CT-$Fe_2O_3$—NPs (containing fenoldopam) were involved in intracellular $Ca^{2+}$ signalling and NO synthesis, which further regulated MAPK activity through cGMP and PKG (FIG. 29E).

Although the transition zone (Y-shaped linkers) at the base of cilium prevents protein entering and exiting the cilium freely, the discreate signal transduction in the cell body and cilium may regulate signaling of one another. This is especially easy to understand if the second messenger involved NO, a gas that can easily permeate into other cellular compartments and surrounding cells. The data demonstrate that the fenoldopam-alone or CT-$Fe_2O_3$—NPs could enhance the NO-CAMP-PKG-ERK pathway in the presence of fluid-flow in renal epithelial cell line and primary cultured endothelial cells. Importantly, shear-stress induced NO biosynthesis is an important mechanism to reduce blood pressure via vasodilation effect.

Efficacy of the CT-$Fe_2O_3$—NPs in a Pkd2 Ciliopathy Zebrafish Model

Figure 30B:
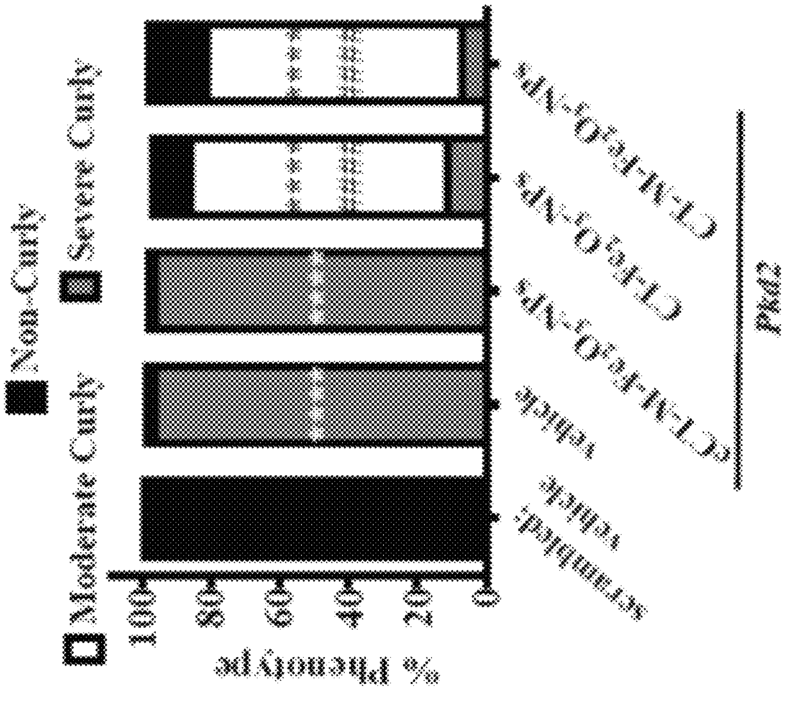
Figure 30C:
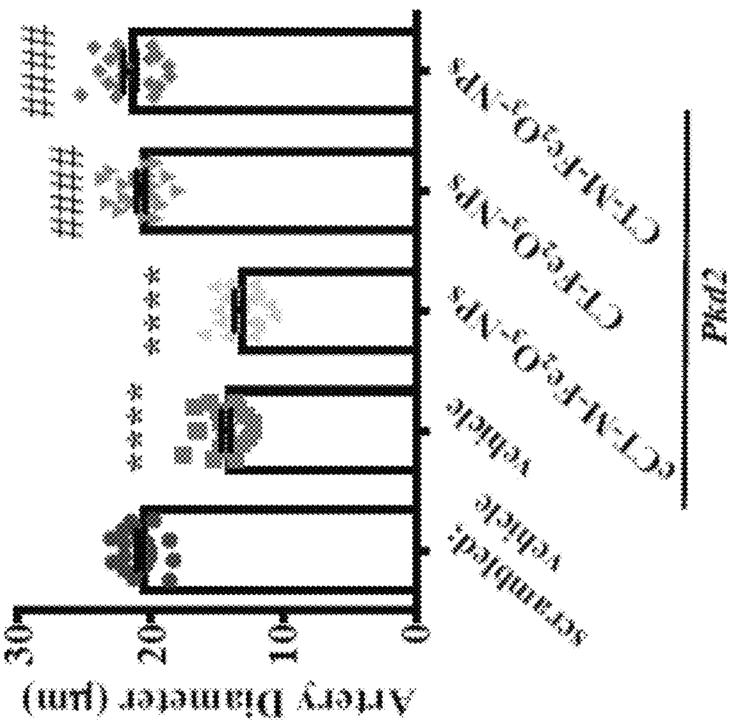
Figure 30D:
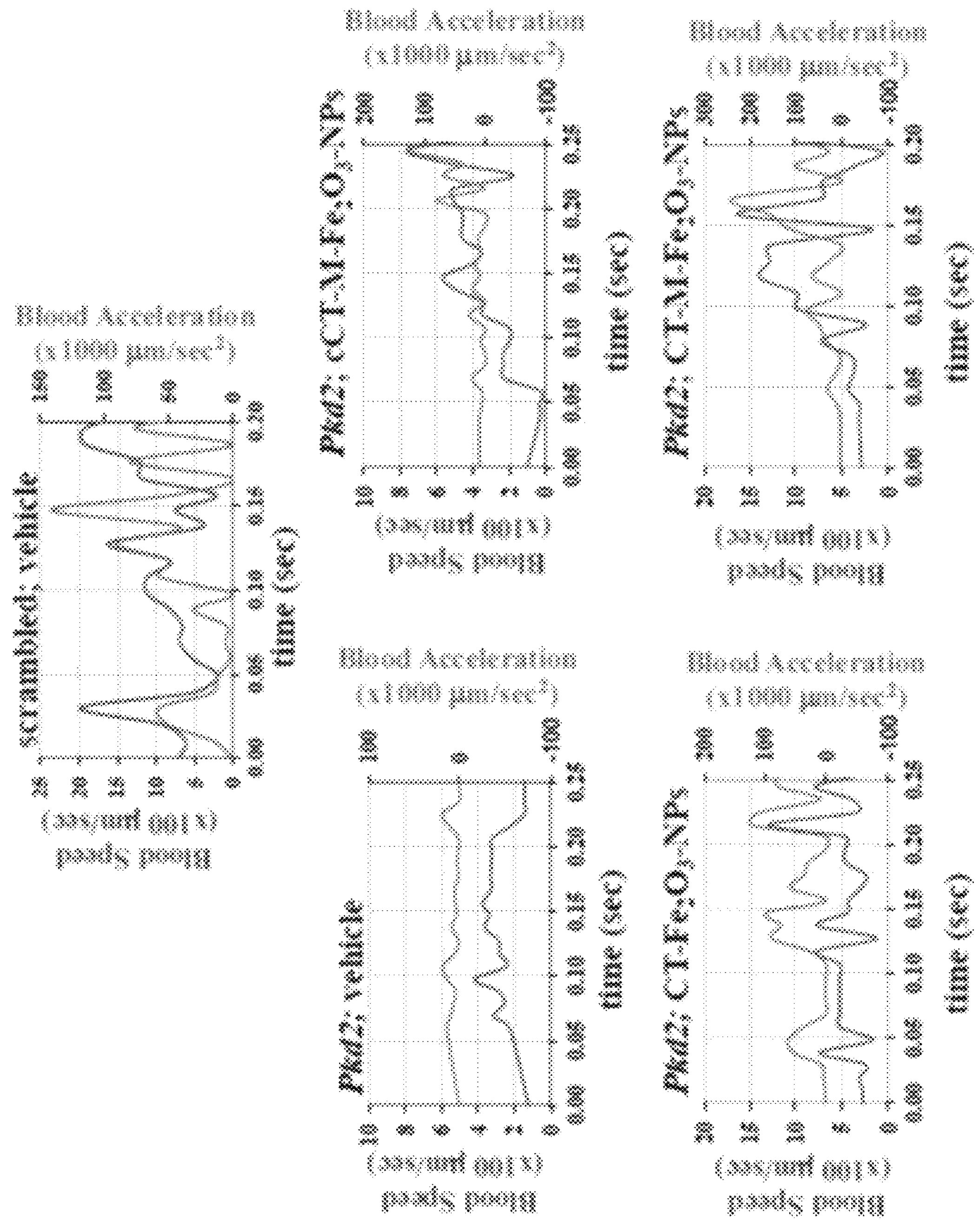
Figure 30E:
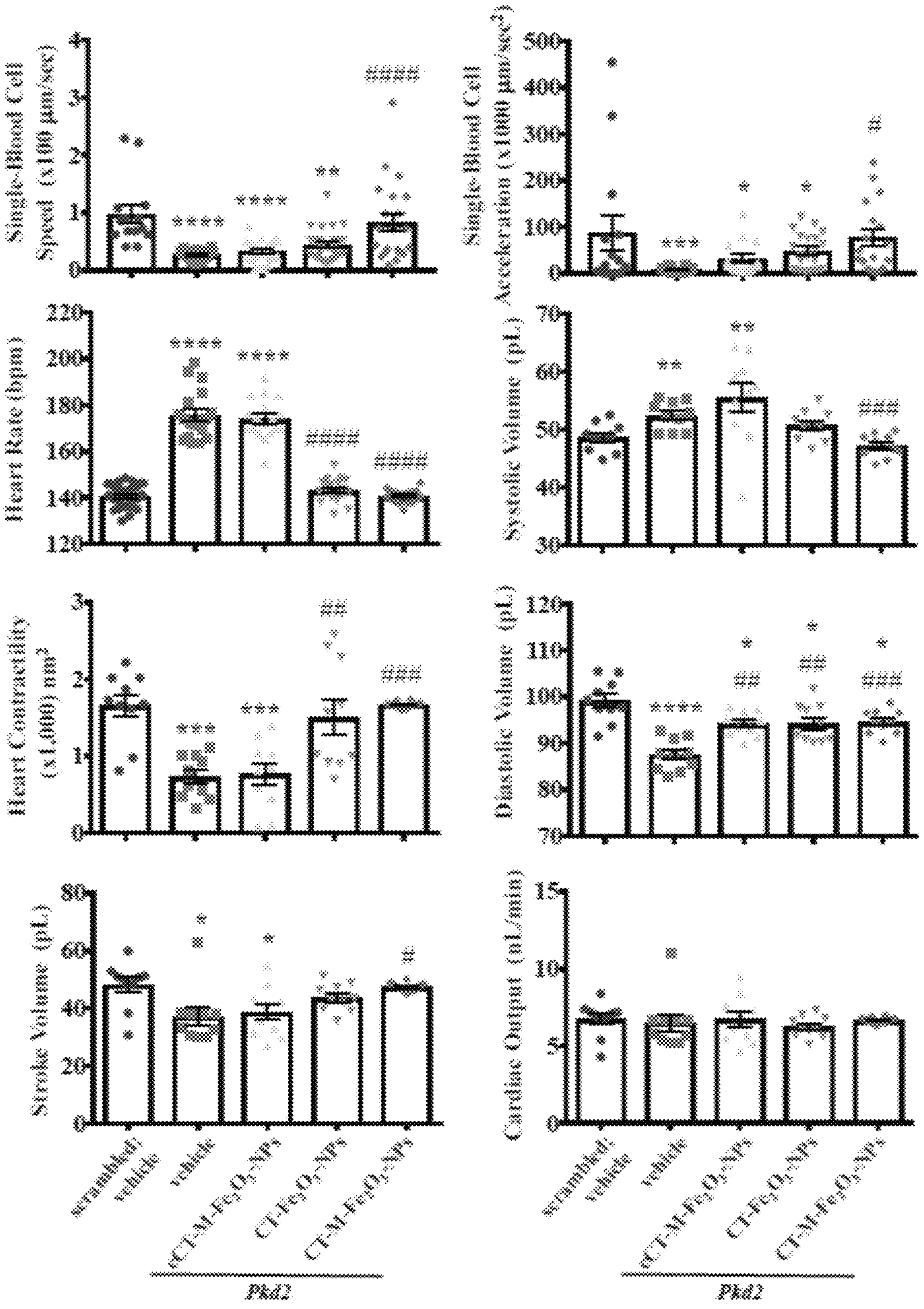

Because the PKG and MAPK signalling pathways have been independently implicated in cardiovascular function, the CT-$Fe_2O_3$—NPs were tested for their effectiveness in vivo. Pkd2 zebrafish were used as a ciliopathy model because their phenotypes, including the curly tail and cystic kidney phenotypes, have been well characterized. The CT-$Fe_2O_3$—NPs significantly rescued the curly tail (FIGS. 30A and 30B) and kidney phenotypes (FIG. 41A). Application of the CT-M-$Fe_2O_3$—NPs provided no further apparent improvement compared with that of the CT-$Fe_2O_3$-NPs. The curly tail phenotype might be an indication of abnormal osteogenesis, probably due to limited blood flow to the tail. We measured the blood vessel diameters to investigate this possibility. The significantly smaller diameter observed in Pkd2 fish might be attributed to vasoconstriction, which was improved by the CT-$Fe_2O_3$—NPs (FIG. 30C). The CT-M-$Fe_2O_3$—NPs did not provide a further improvement in vessel diameter. Blood flow was also examined in the blood vessels located in the dorsal region of the main artery within the medial-posterior lateral trunk. The speed and changes in speed (acceleration) of individual blood cells were significantly decreased in Pkd2 fish compared with those in control fish (FIGS. 30D, 30E). The CT-$Fe_2O_3$-NPs improved blood flow, and the CT-M-$Fe_2O_3$—NP-treated fish showed a further enhancement in blood flow that was similar to the normal control fish.

Improvements in blood flow are usually determined by not only the blood vessel function but also cardiac function. A significant decrease in cardiac contractility and stroke volume was observed in Pkd2 fish, although the overall cardiac output was not changed (FIG. 30E). This result was very likely due to an increase in heart rate, resulting in an increase in systolic volume per beat. The CT-$Fe_2O_3$—NPs corrected all the cardiac function parameters, which might have contributed to the less severe curly tail phenotype in the Pkd2 zebrafish. Similar to cell culture in vitro, the CT-$Fe_2O_3$—NPs specifically targeted primary cilia and effectively lengthened primary cilia in vivo. Cilia length was measured in vascular and cardiac cells (FIGS. 41B and 41C). Shorter cilia were consistently observed in cells of the Pkd2 artery, vein, and cardiac tissue. The CT-$Fe_2O_3$—NPs significantly lengthened the cilia in the blood vessels and heart. The application of a magnetic field to CT-$Fe_2O_3$—NP-treated fish did not result in any further effect on cilia length.

Figure 31A:
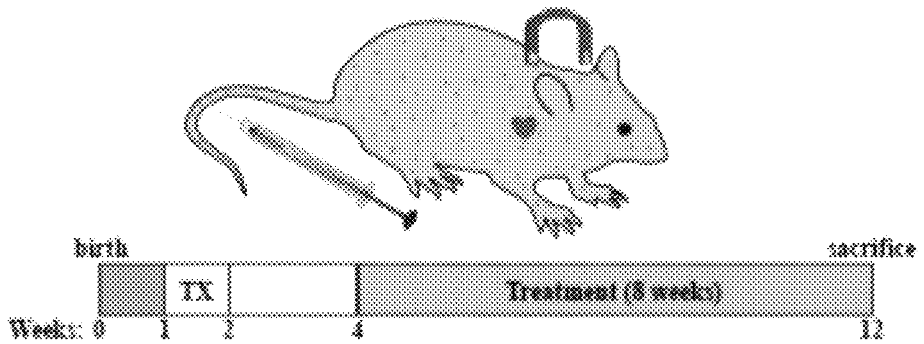
FIGS. 31A-H depict the use of CT-M-$Fe_2O_3$—NPs as a therapeutic delivery system in Tie2Cre•Pkd2$^{flox/flox}$ mice.
Figure 31B:
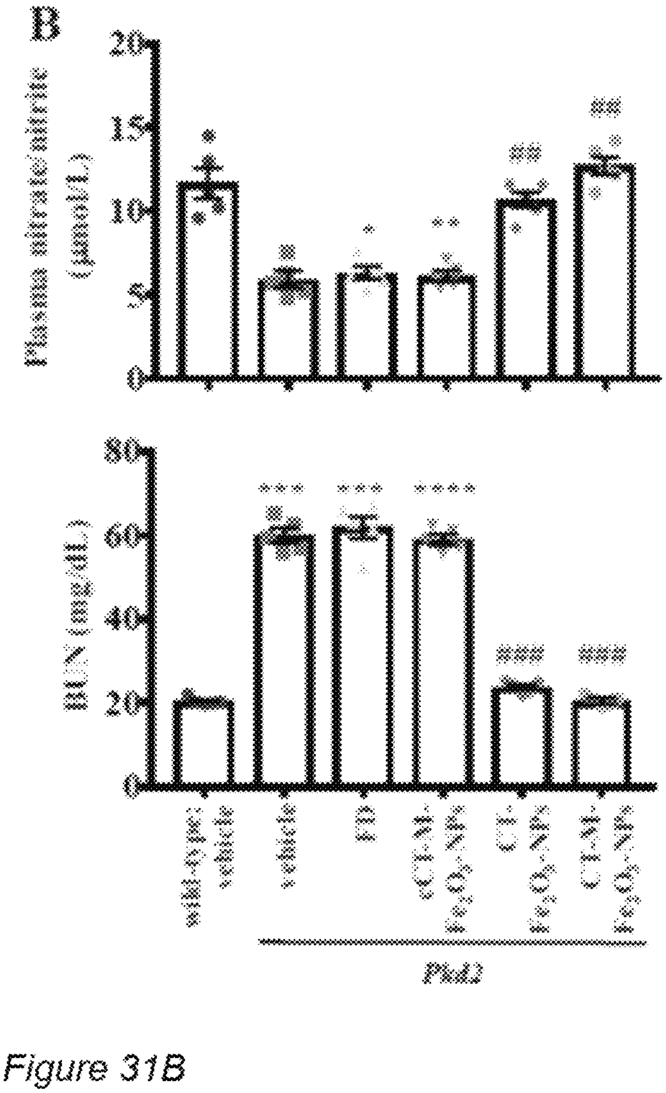
Figure 31C:
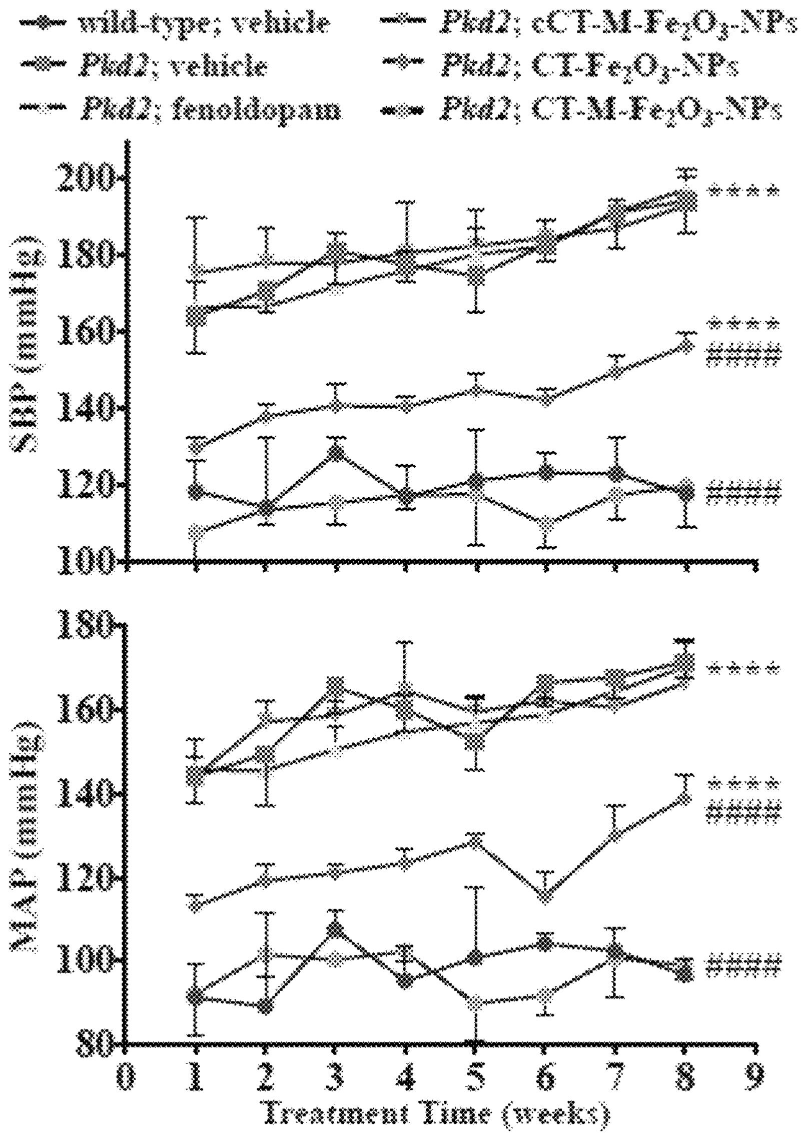

Effects of the CT-$Fe_2O_3$—NPs in Targeting Primary Cilia in a Pkd2 Mouse Model To validate the zebrafish results, we further investigated the effect of the CT-$Fe_2O_3$-NPs in targeting primary cilia by injecting them intravenously in the tail of an endothelial-specific Pkd2 mouse model for 8 weeks (FIG. 31A; Tie2Cre•Pkd2$^{flox/flox}$). Because the CT-$Fe_2O_3$—NPs increased NO production in cultured cells in vitro, we also evaluated plasma nitrate/nitrite in mouse ciliopathy model in vivo. Similar to patients with polycystic kidney disease (PKD), the plasma nitrate/nitrite level was decreased in the Pkd2 mice. The nitrate/nitrite level returned to normal in mice treated with the CT-$Fe_2O_3$—NPs (FIG. 31B). The blood urea nitrogen level was also corrected by the CT-$Fe_2O_3$—NPs (FIG. 31B). Similar to the endothelial-specific Pkd1 mice, elevated systolic and mean arterial pressures were observed in Pkd2 mice. The CT-$Fe_2O_3$—NPs significantly decreased the blood pressure of Pkd2 mice (FIG. 31C). The CT-M-$Fe_2O_3$—NPs decreased blood pressure further, and it became comparable to normal wild-type mice. The administration of fenoldopam-alone once every 3 days (a similar dosing regimen was used for the CT-$Fe_2O_3$—NPs) did not result in an overall decrease in systemic blood pressure.

Figure 31D:
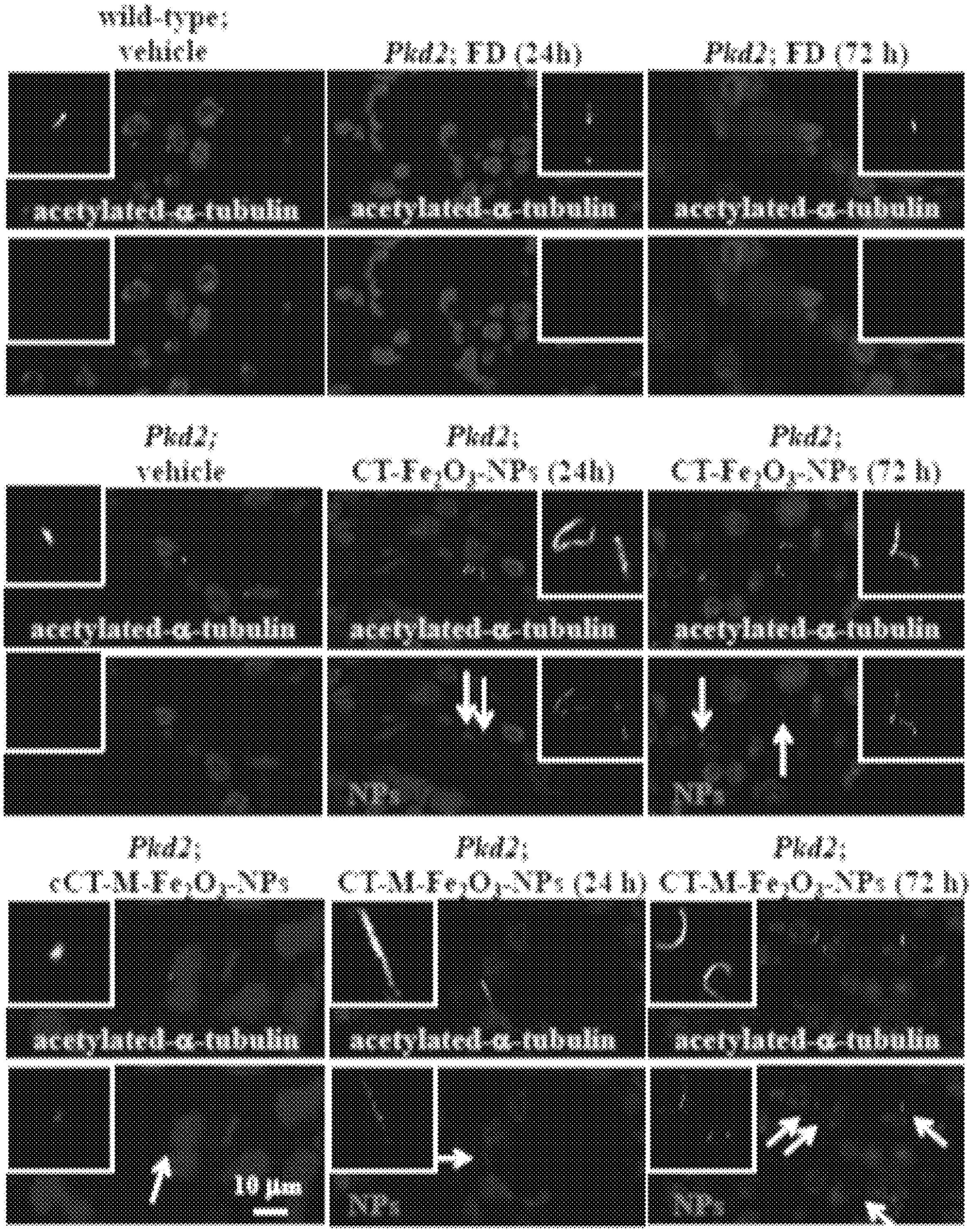
Figure 31E:
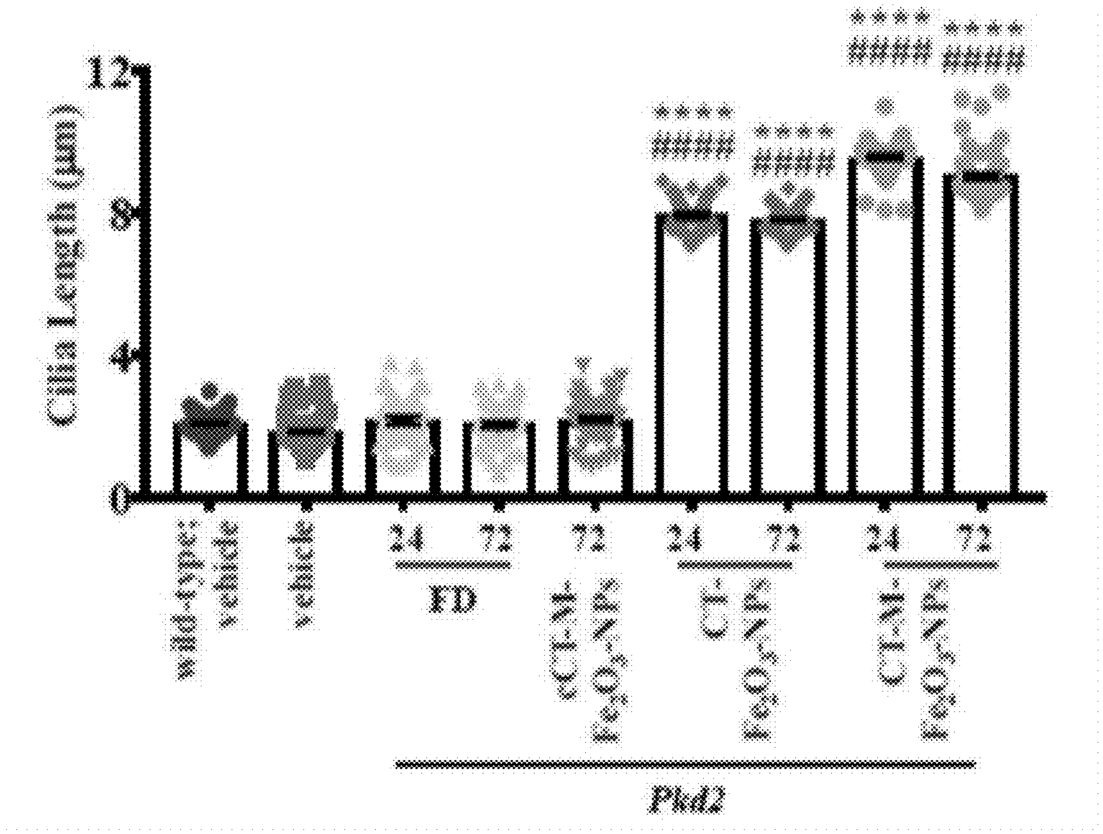
Figure 31F:
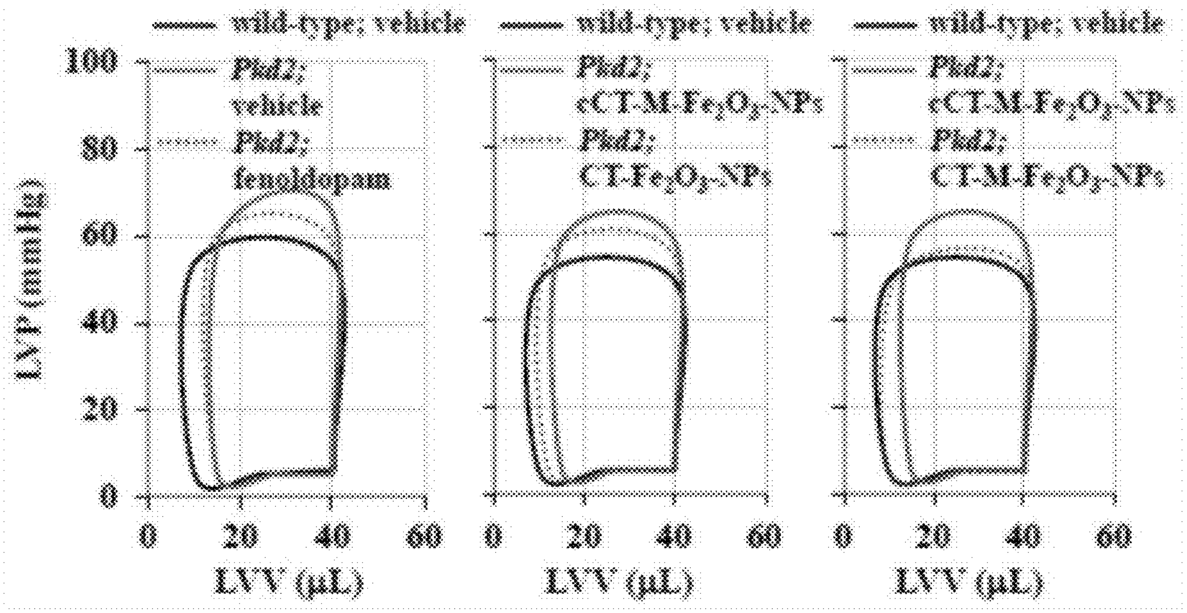
Figure 31G:
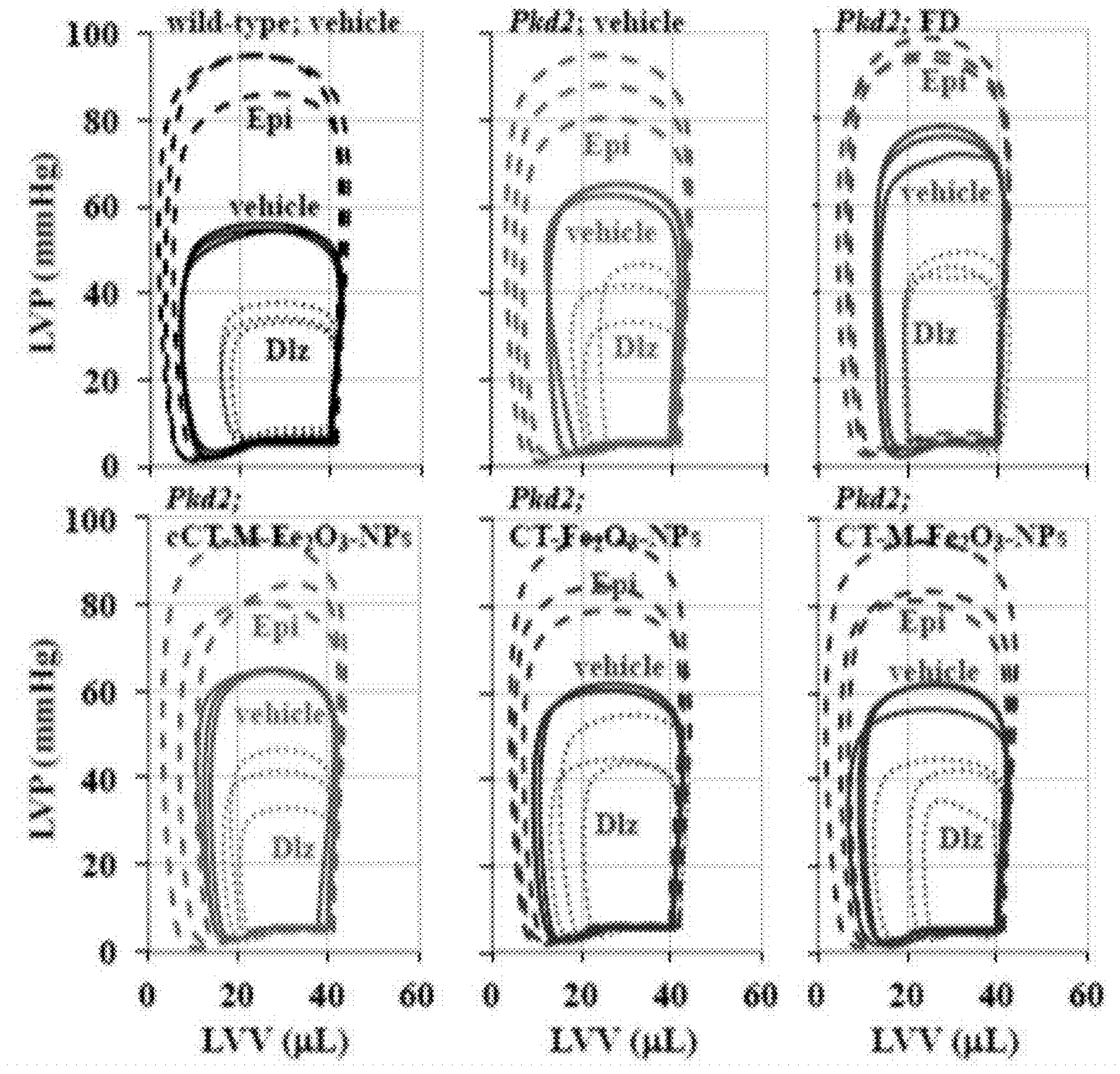
Figure 31H:
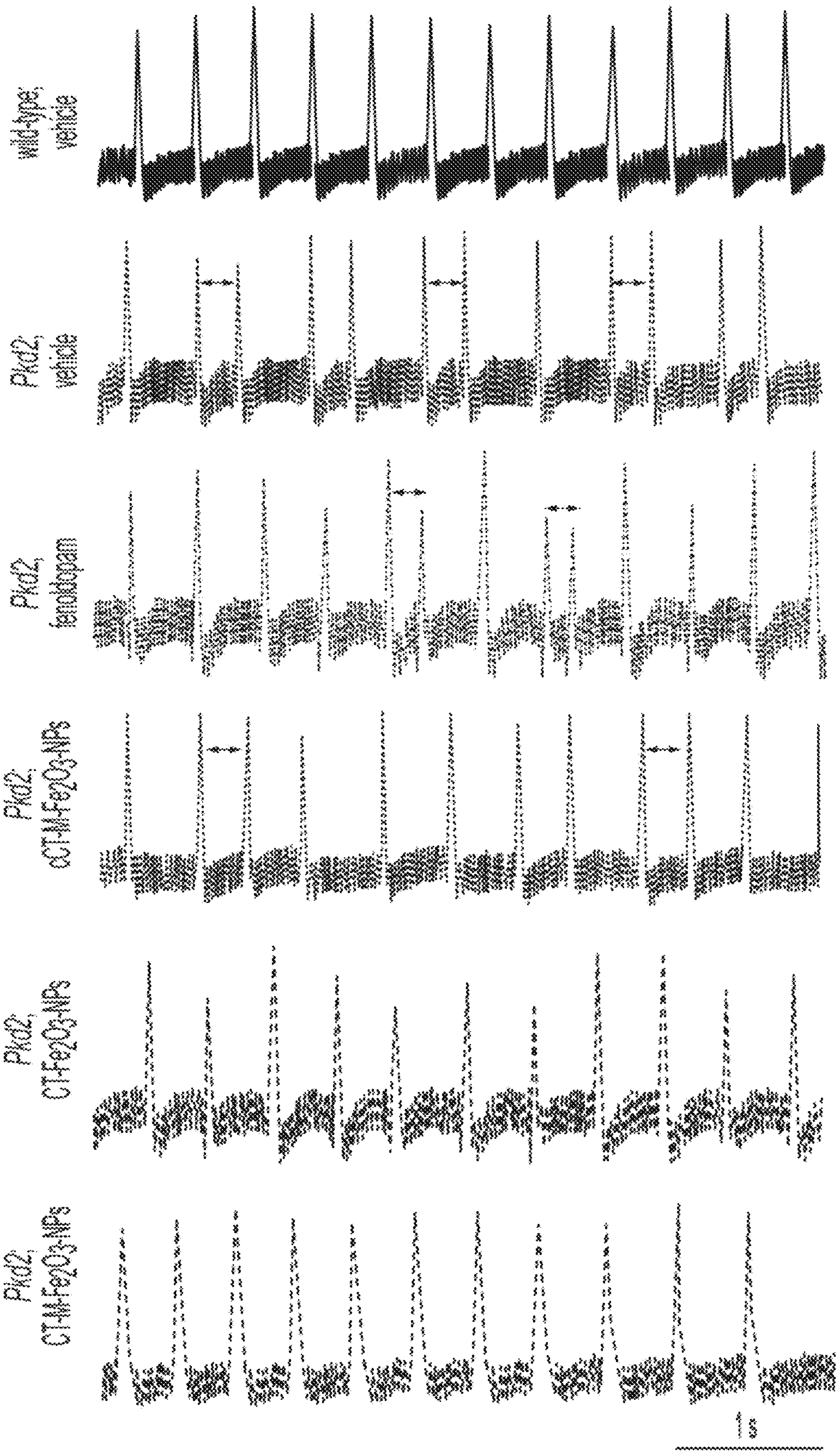

The in vivo cilia specificity of the CT-$Fe_2O_3$—NPs was examined in isolated femoral arteries (FIG. 31D). The localization of the CT-$Fe_2O_3$—NPs in the vascular endothelium was confirmed at 24 and 72 hours after the injections. Cilia length was significantly increased in mice treated with the CT-$Fe_2O_3$—NPs or CT-M-$Fe_2O_3$—NPs but not in mice that received a 30-minute infusion of fenoldopam (FIG. 31E). However, a continuous infusion of fenoldopam for 5 days increased the cilia length. At the end of the 8-week blood pressure studies, heart function was examined using an ex vivo isolated heart perfusion system to generate volume-pressure loops (FIG. 31F). This approach was required to separate the effect of neuronal regulation observed in zebrafish studies. The Pkd2 hearts displayed hypertrophy with compromised functions in left ventricle pressure, stroke volume, ejection fraction, and overall cardiac output, probably due to prolong hypertension (Table 5). Although the CT-$Fe_2O_3$—NPs significantly improved cardiac function in the Pkd2 mice, the CT-M-$Fe_2O_3$—NPs further improved heart function to a level comparable to the control wild-type mice (FIG. 31F). The hearts were also challenged with the pharmacological agents epinephrine and diltiazem to produce high and low contractile stresses, respectively, to evaluate the potential presence of more substantial abnormalities (FIG. 31G). However, all hearts responded well to these stressors (Tables 5-7). Importantly, when brought back to a normal heart rate, the Pkd2 mice exhibited a tendency towards arrhythmia, which was corrected by the CT-$Fe_2O_3$—NPs or CT-M-$Fe_2O_3$—NPs (FIG. 31H).

Figure 32A:
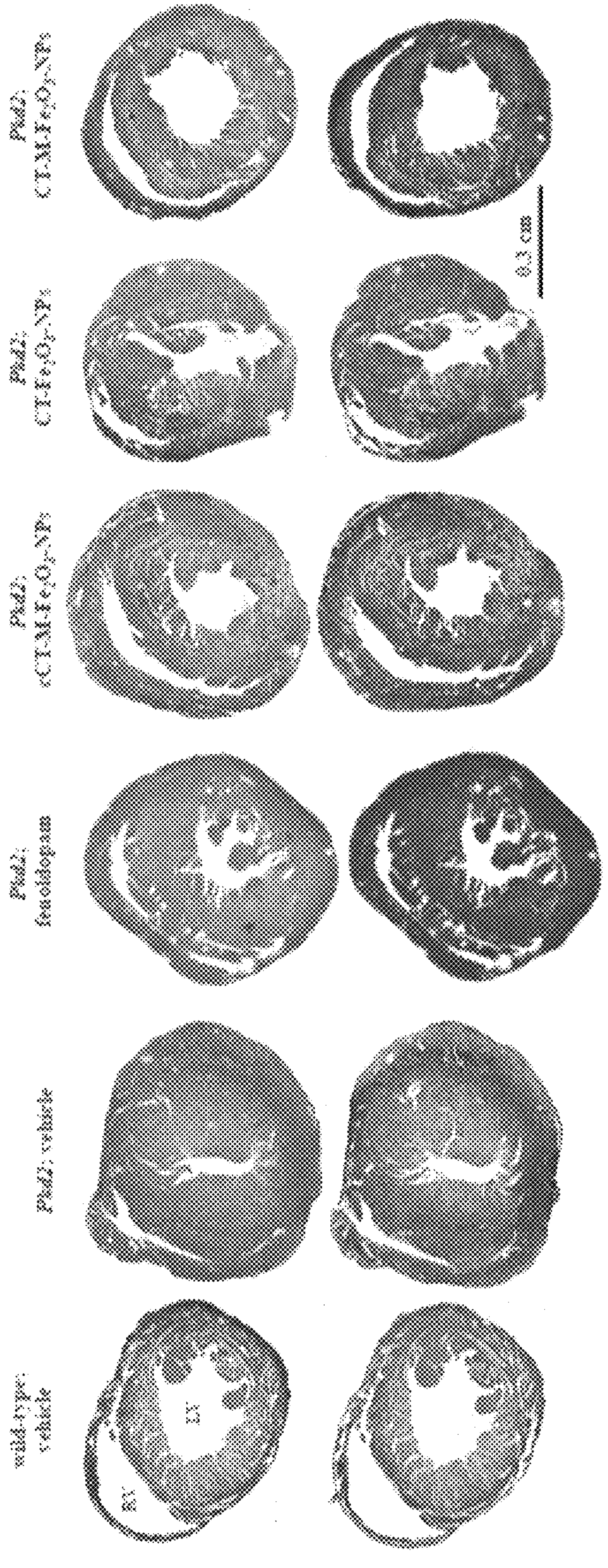
FIGS. 32A-F depicts that CT-$Fe_2O_3$—NPs increase the cilia length in Tie2Cre•Pkd2$^{flox/flox}$ mice and improve hypertrophy.
Figure 32B:
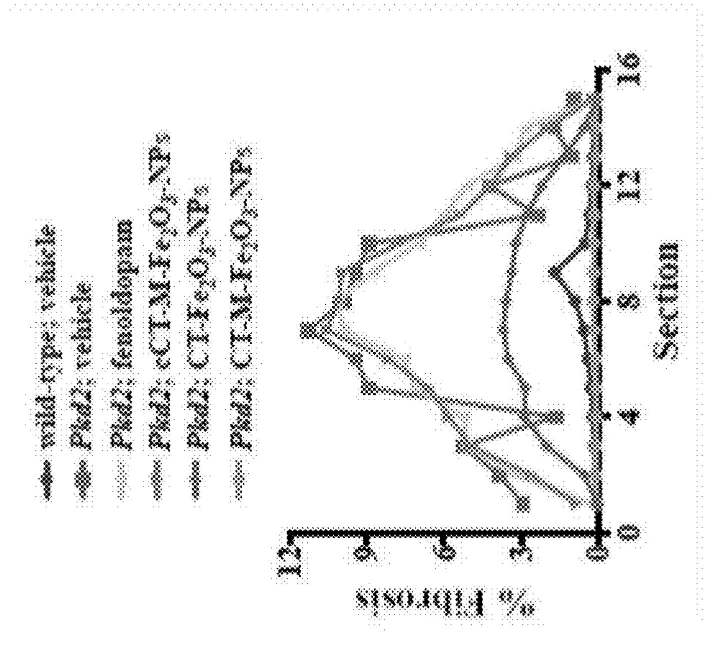
Figure 32C:
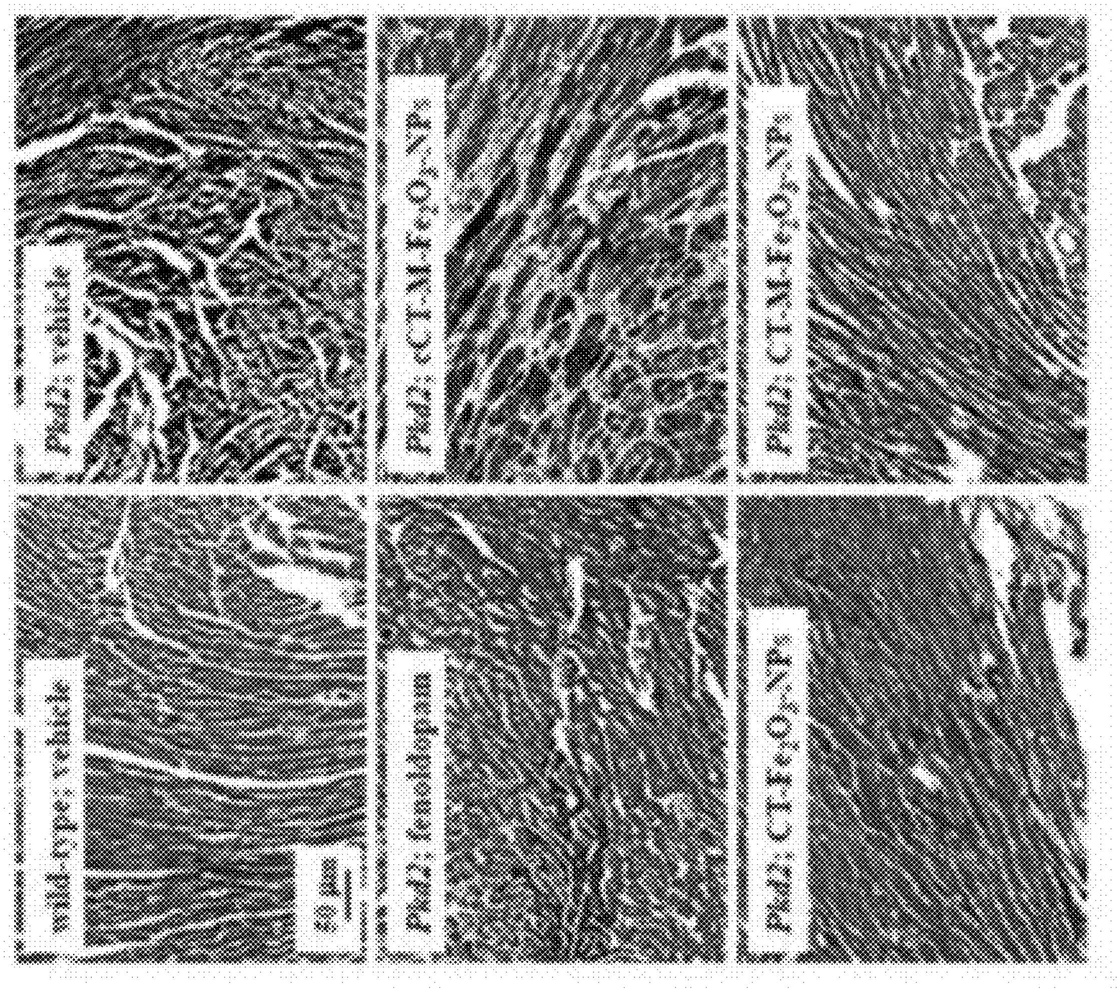
Figure 32D:
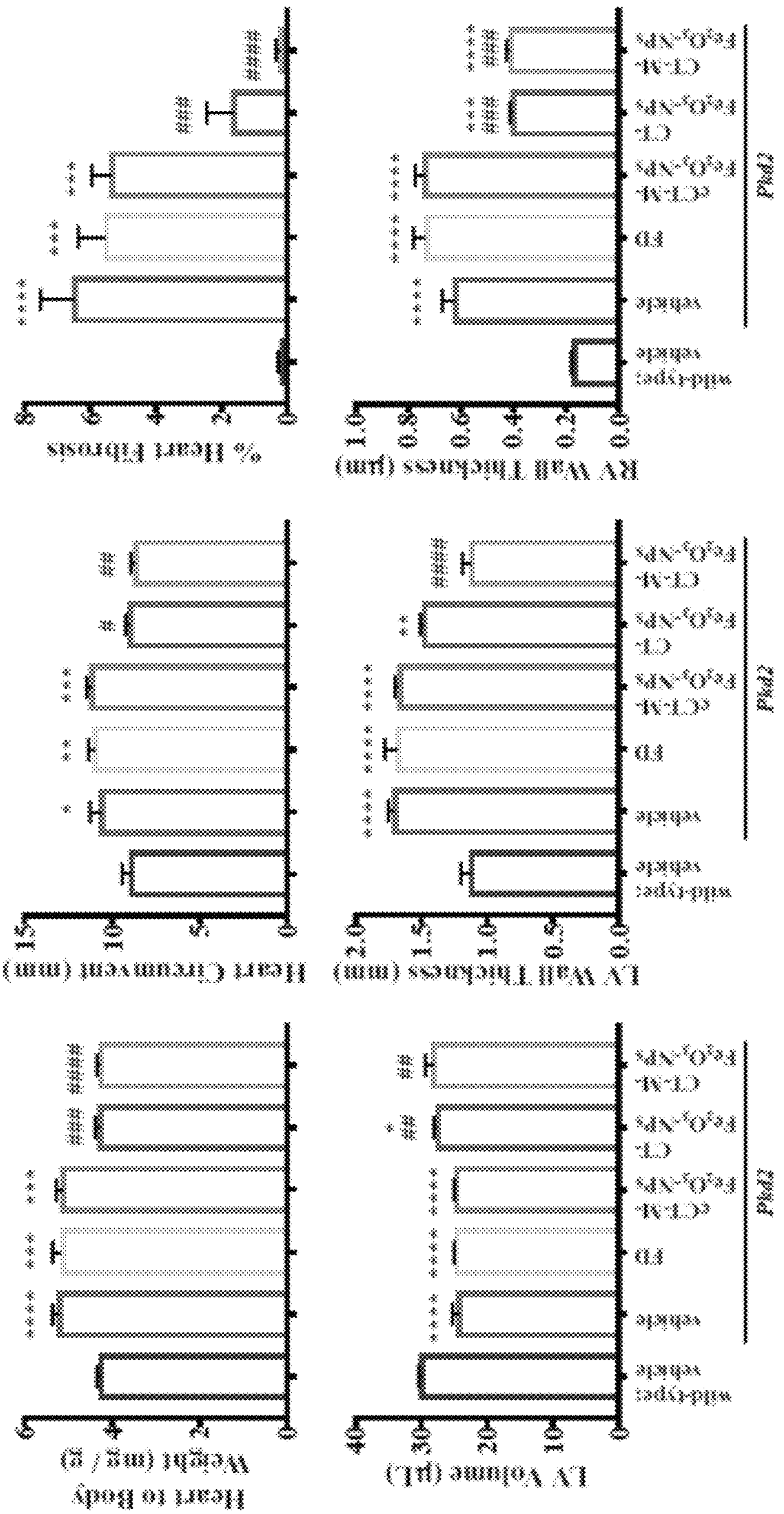
Figure 32E:
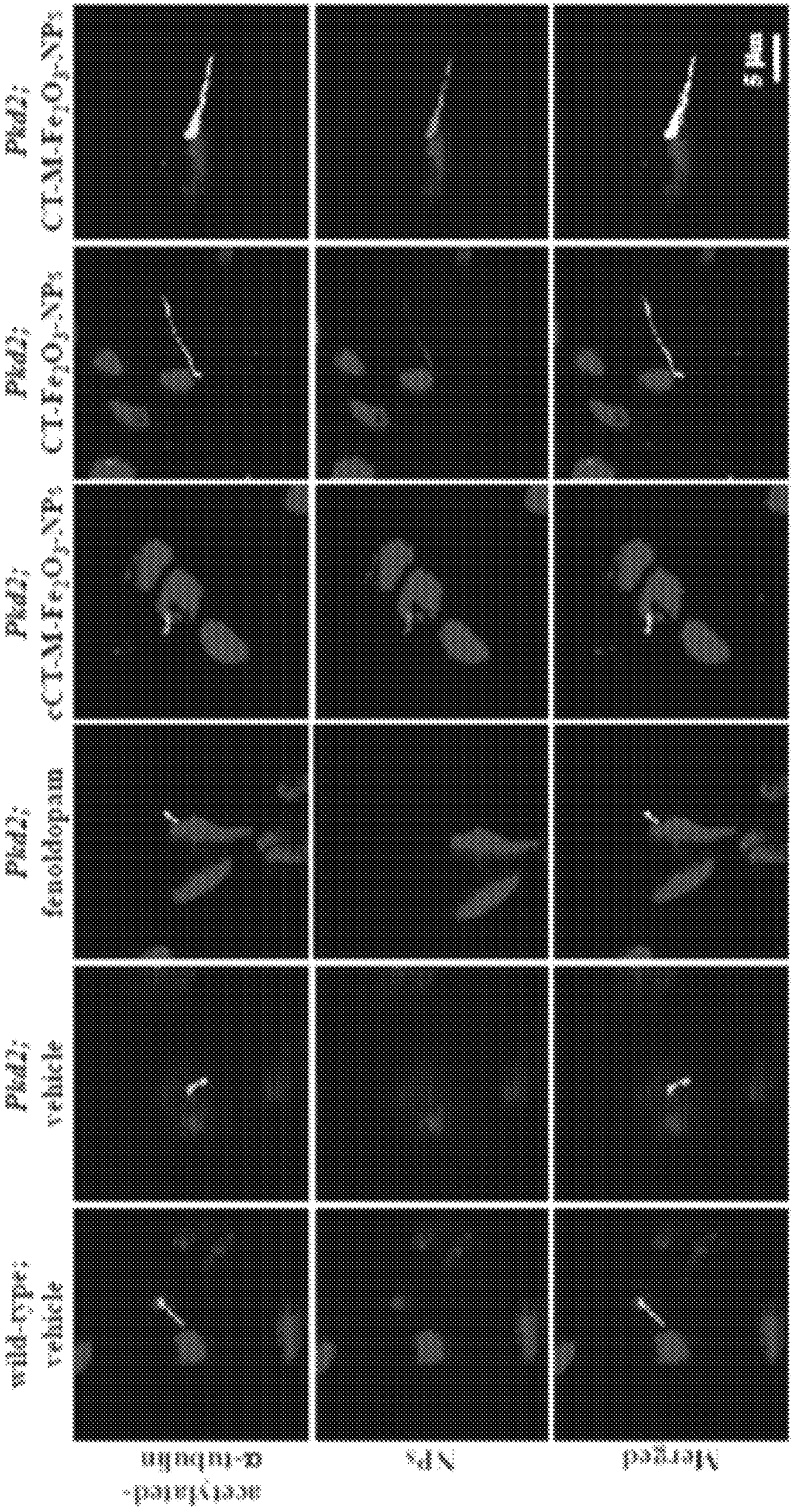
Figure 32F:
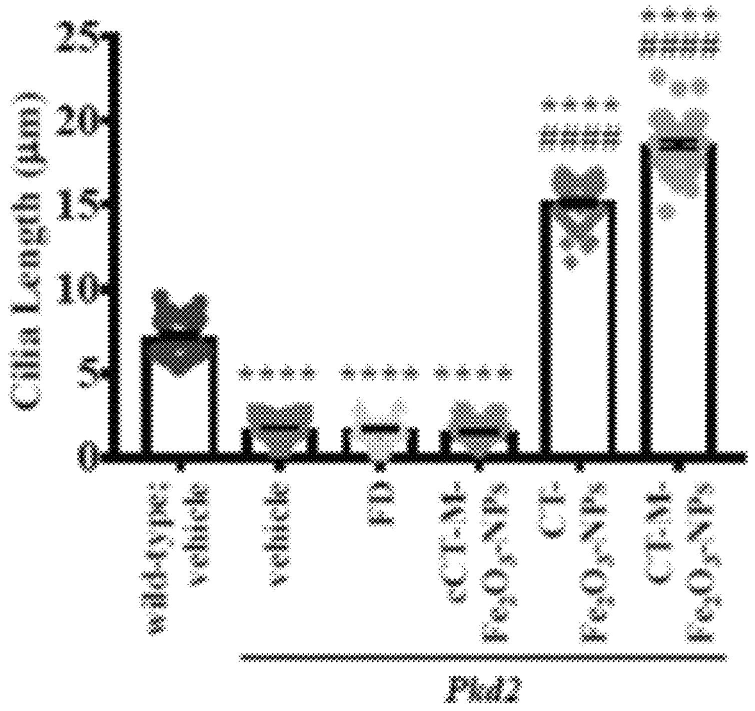

Consistent with the results of the functional studies, the Pkd2 mice were characterized by left ventricular hypertrophy, as indicated by an examination of consecutive heart sections stained with haematoxylin and eosin (H&E) and Masson's trichrome (FIG. 32A). Masson's trichrome staining also revealed cardiac fibrosis and myocyte enlargement. These characteristics, particularly cardiac fibrosis, were most apparent at the mid-section of the cross-sectional cardiac anatomy (FIGS. 32B and 32C). The CT-$Fe_2O_3$—NPs and CT-M-$Fe_2O_3$—NPs reduced cardiac hypertrophy and fibrosis in the Pkd2 mice (FIG. 32D). Based on different anatomical measurements, the CT-$Fe_2O_3$—NPs consistently improved the heart size and thickness of the heart wall. The use of the CT-M-$Fe_2O_3$—NPs in Pkd2 mice further improved the heart phenotype, and it became comparable to the control wild-type mice. Primary cilia are present in the heart and play an important role in heart diseases. Myocyte cilia were thus measured to further investigate the roles of the CT-$Fe_2O_3$—NPs (FIG. 32E). The CT-$Fe_2O_3$—NPs increased the cilia length in the Pkd2 mice, and the CT-M-$Fe_2O_3$—NPs did not further lengthen the primary cilia in the heart (FIG. 32F).

Fluorescence readings were quantified in the heart, kidneys, liver, spleen and lungs at 24- and 72-hours post-injection to examine the in vivo distribution of the CT-$Fe_2O_3$—NPs (FIG. 42A). The CT-$Fe_2O_3$—NPs were distributed throughout these organs. The liver, a metabolic and disposition organ, had relatively higher concentrations of the CT-$Fe_2O_3$—NPs, particularly within the first 24 hours. All organs were further screened by histopathology and showed no apparent toxicity resulting from the CT-$Fe_2O_3$—NPs (FIG. 42B). Separate hemanalyses and biochemistry studies on cellular biomarkers also did not indicate toxicity of the CT-M-$Fe_2O_3$—NPs in the liver, kidney, spleen and other tissues (Table 11). Although apparent morphological abnormalities were not observed in the liver, spleen or lung tissues, cysts formed in the kidneys and hypertrophy in the heart was observed. While isolated cysts were much smaller in mice subjected to the CT-$Fe_2O_3$—NPs, evidence of tubular sclerosis was detected in the Pkd2 kidneys (FIG.

42B). The cardiac and renal abnormalities might have resulted from prolonged hypertension.

Fenoldopam was used as an experimental agent in the present study due to its therapeutic potential; unfortunately, clinical use of fenoldopam is limited by its short-acting, non-selective activity and reflex tachycardia. With this cilia-targeted system, we were able to encapsulate and deliver fenoldopam to cilia more precisely and effectively. Based on the findings from these studies, a ciliopathy treatment should not depend on generating new drugs if existing drugs are able to be specifically targeted to cilia for achieving the maximum therapeutic outcome with no side effects. The cilia-targeted delivery system is an attractive means of achieving more targeted delivery of many other therapeutic pharmacological agents to treat various ciliopathies.

Validation of Fenoldopam-Only and CT-$Fe_2O_3$—NPs on Cilia Specificity

Figure 33B:
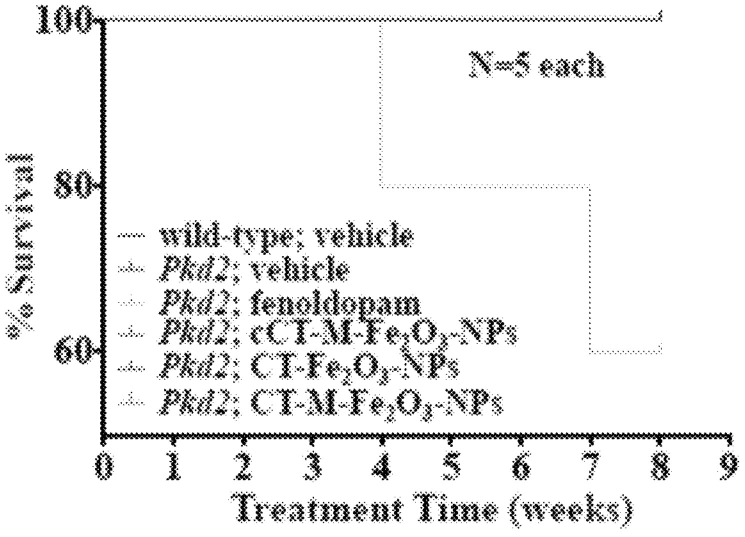
FIGS. 33A-F depict validation of effects of fenoldopam and CT-$Fe_2O_3$—NPs on cardiovascular functions.
Figure 33A:
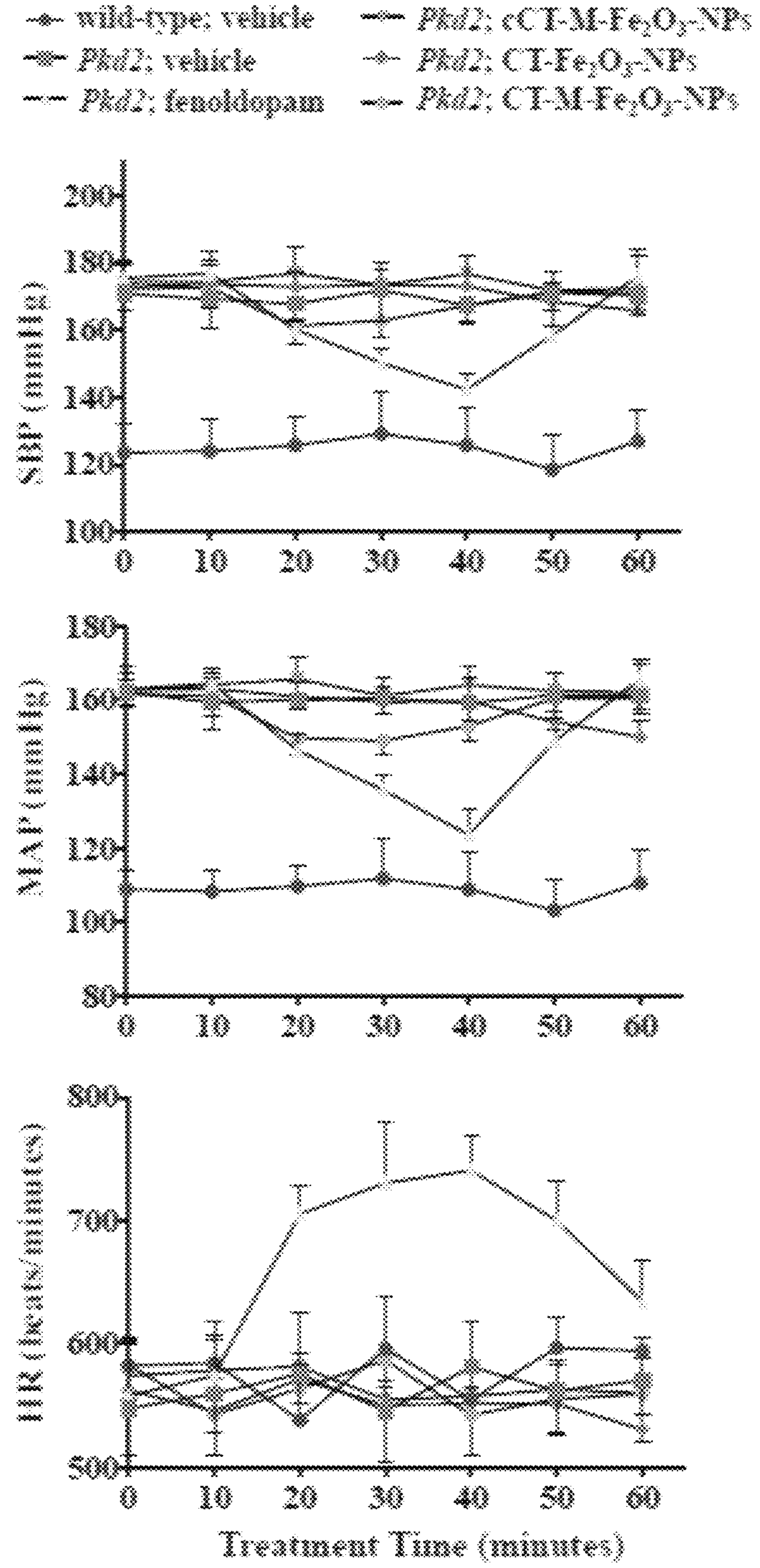
Figure 33C:
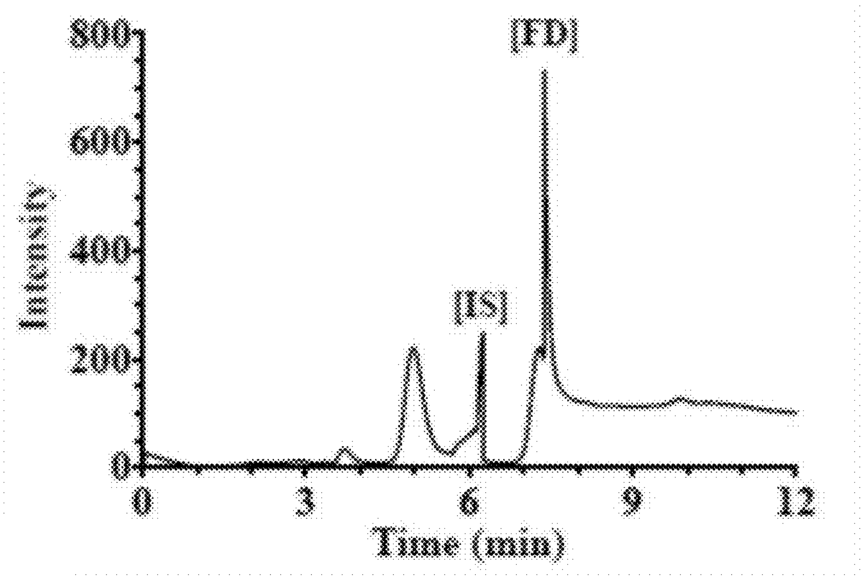
Figure 33D:
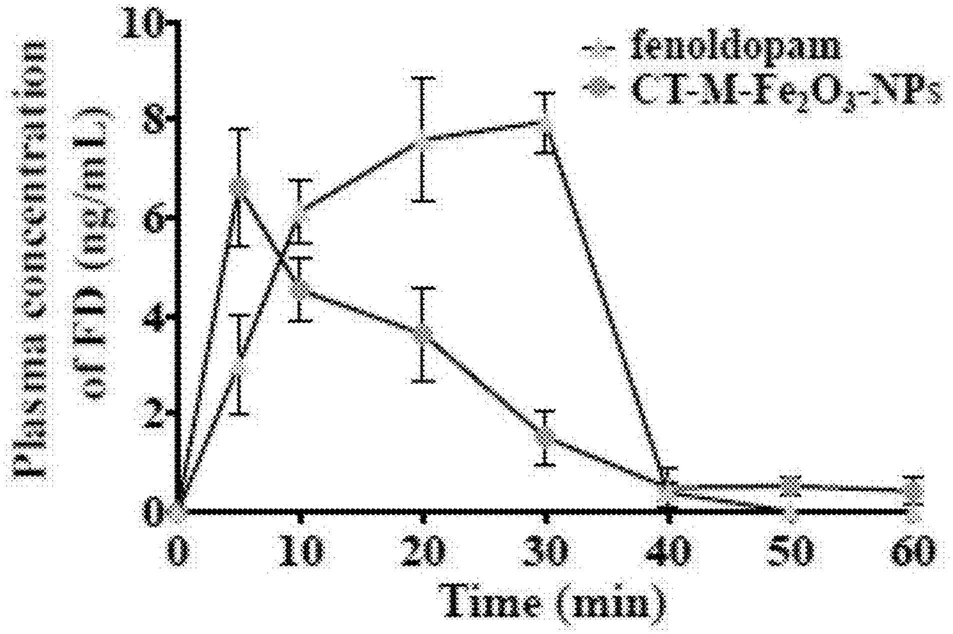

The infusion of fenoldopam-alone once every 3 days did not result in apparent changes in weekly-analysed blood pressure. To confirm that the fenoldopam was properly administered, we measured blood pressure for an hour after fenoldopam infusion (FIG. 33A). While fenoldopam-alone decreased blood pressure, its affect only lasted for approximately one hour. Unlike the CT-$Fe_2O_3$—NPs or CT-M-$Fe_2O_3$—NPs, fenoldopam-alone caused an immediate decrease in blood pressure, followed by reflex tachycardia. This observation was consistent with the short-acting property of fenoldopam. We also observed an increased in heart rate following fenoldopam-only injection. We speculated that the rebound in blood pressure and reflex tachycardia contributed to fenoldopam-induced mortality in hypertensive Pkd2 mice (FIG. 33B). Based on the pharmacological profiles obtained from fenoldopam- and CT-M-$Fe_2O_3$—NPs-treated mice, both fenoldopam and the NPs remained in the circulatory system during the infusion (FIGS. 33C and 33D). Together with the reflex tachycardia, these results reinforced the broad spectrum of fenoldopam effects in the cardiovascular system. These studies also indicated that unlike the slow-release CT-$Fe_2O_3$—NPs, repeated short-infusion of fenoldopam-alone every 3 days for 8 weeks was not beneficial for the in vivo experiments.

Figure 33E:
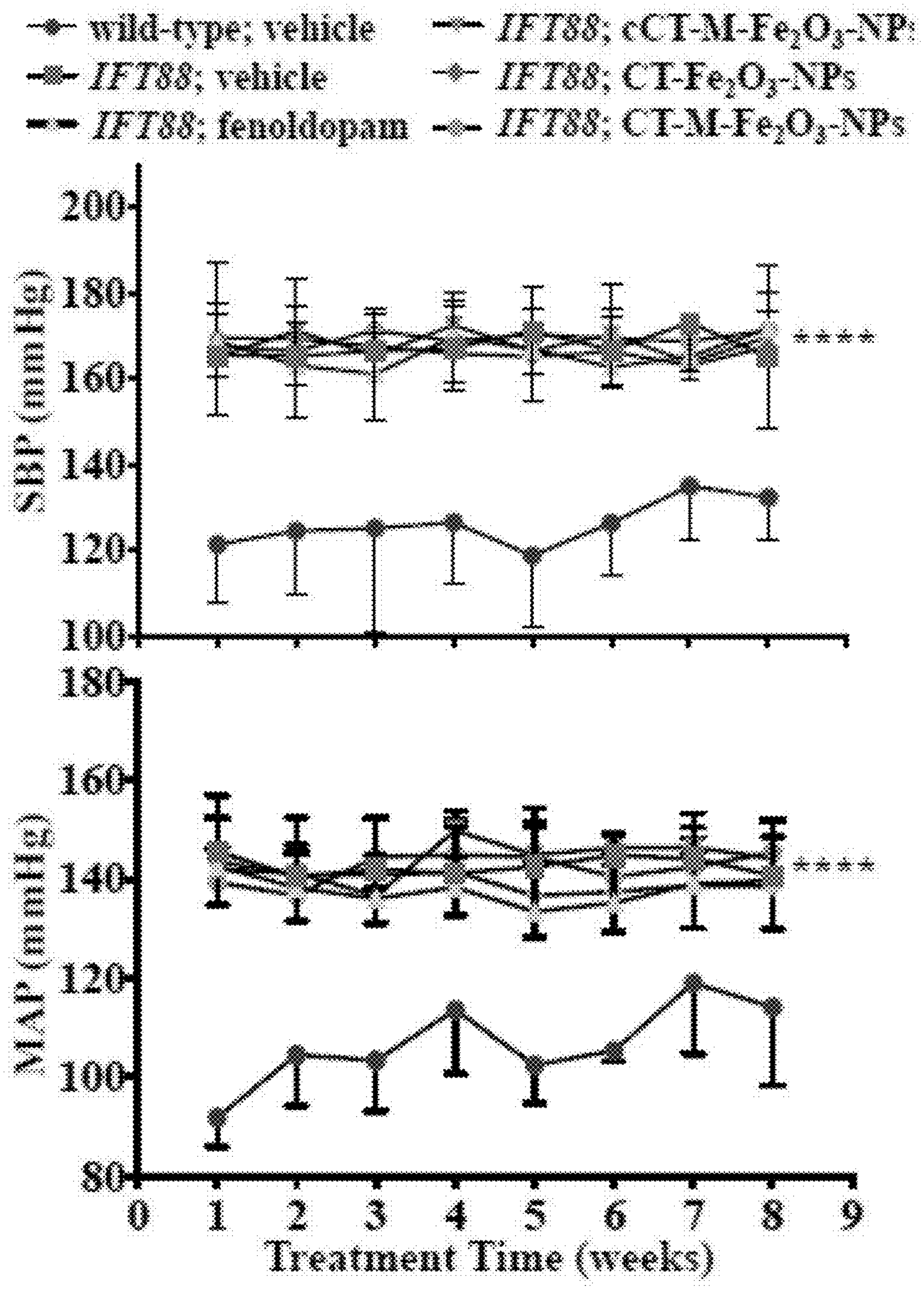
Figure 33F:
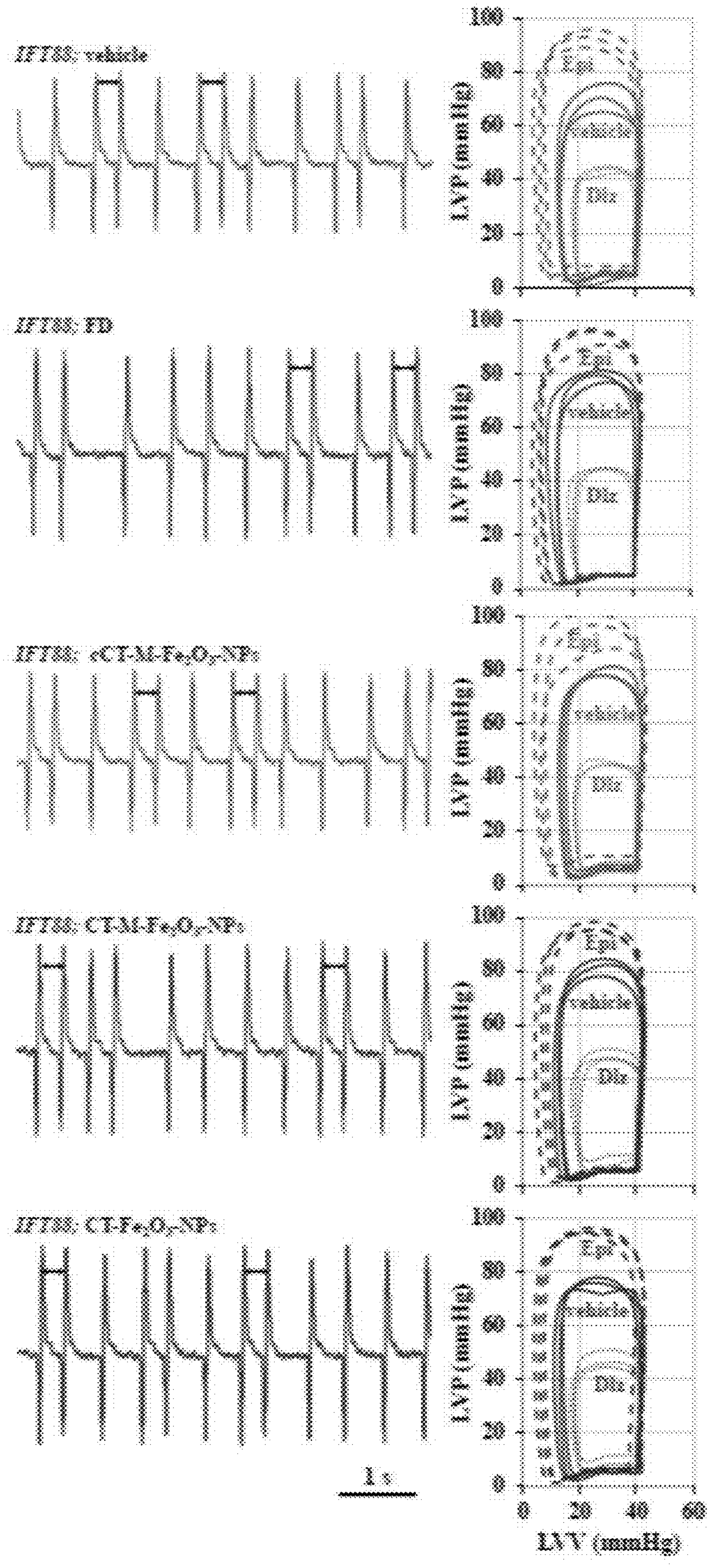

In separate studies, we utilized mice without vascular endothelial cilia (Tie2Cre•$IFT88^{flox/flox}$) to confirm that the CT-$Fe_2O_3$—NPs were specifically targeted to cilia. These mice exhibited vascular hypertension, and neither the CT-$Fe_2O_3$—NPs nor the CT-M-$Fe_2O_3$—NPs reduced blood pressure, indicating vascular endothelial specificity of the NPs (FIG. 33E). Parameters of heart function were also analysed (Tables 8-10). While IFT88 hearts responded well to the stresses, the hearts were susceptible to arrhythmia. Unlike arrhythmic Pkd2 heart, however, IFT88 hearts were characterized with an inverted PR interval arrhythmia (FIG. 33F). Unlike Pkd2 hearts, normal rhythmic and function of IFT88 hearts could not be corrected by the CT-$Fe_2O_3$—NPs, confirming the presence of cilia was required for the CT-$Fe_2O_3$—NP effect.

The in vivo studies also provided two surprising findings that had never been reported. First, the ciliopathy hypertensive model was associated with renal cyst formation. Second, ciliopathy hypertensive models were associated with cardiac arrhythmia. While the types of arrhythmia between Pkd2 and IFT88 were not identical, both were very susceptible to arrhythmia when heart pacing was withdrawn from the Working Heart system. On the other hand, hearts from wild-type mice would slowly reduce their contractility and/or heart rate. Hypertension is commonly associated with atrial and ventricular arrhythmias. Importantly, the CT-$Fe_2O_3$—NPs were able to reduce not only the blood pressure but also those complications associated with hypertension, such as renal cyst and cardiac arrhythmia. In these studies, we did not observe any significant effect between the CT-$Fe_2O_3$—NPs alone and the CT-$Fe_2O_3$—NPs with magnetic field (CT-M-$Fe_2O_3$—NPs). However, compared to the CT-$Fe_2O_3$—NPs, the CT-M-$Fe_2O_3$—NPs returned physiological functions or anatomical structures to the levels that were comparable to the normal healthy wild-type in either zebrafish or mice.

In summary, we have introduced a new approach to remotely control primary cilia. The cilia-targeted magnetic nanoparticles can be used to control non-motile primary cilia movement, cilia length and function. Compared to a short-acting drug-alone, the use of nanoparticle drug delivery is more superior in providing a more specific cellular target and provides a slow-release mechanism to avoid non-specific reflexes or other systemic adverse effects.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

TABLE 1

| | wild-type | | | Pkd2 | | |
|---|---|---|---|---|---|---|
| | vehicle | epinephrine | diltiazem | vehicle | epinephrine | diltiazem |
| HR (beat/min) | 144 ± 15 | 209 ± 16 | 72 ± 20 | 134 ± 17 | 230 ± 15 | 76 ± 9 |
| ESPVR (mmHg/μL) | 3.8 ± 0.2 | 10.0 ± 2.4 | 1.7 ± 0.3 | 3.9 ± 0.1 | 11.2 ± 1.7 | 2.0 ± 0.2 |
| EDPVR (mmHg/μL) | 0.15 ± 0.02 | 0.12 ± 0.01 | 0.13 ± 0.01 | 0.13 ± 0.01 | 0.13 ± 0.01 | 0.13 ± 0.01 |
| dP/dtmax (mmHg/s) | 5075 ± 123 | 16222 ± 808 | 3034 ± 332 | 4711 ± 157 | 16480 ± 356 | 2845 ± 954 |
| dP/dtmin (mmHg/s) | −2008 ± 200 | −3048 ± 114 | −1401 ± 59 | −1297 ± 144 | −3096 ± 81 | −1071 ± 358 |
| LV Pmax (mmHg) | 47.0 ± 1.1 | 81.1 ± 4.0 | 33.7 ± 3.7 | 43.6 ± 14.5 | 82.4 ± 1.8 | 31.6 ± 10.6 |
| LV ESP (mmHg) | 35.2 ± 0.9 | 60.8 ± 3.0 | 25.3 ± 2.8 | 32.7 ± 10.9 | 61.8 ± 1.3 | 23.7 ± 6.0 |
| LV EDP (mmHg) | 6.2 ± 0.6 | 5.1 ± 0.2 | 5.2 ± 0.1 | 4.0 ± 1.3 | 5.2 ± 0.1 | 4.0 ± 1.3 |
| LV ESV (μL) | 12.4 ± 0.4 | 8.5 ± 1.6 | 20.4 ± 0.9 | 11.6 ± 3.8 | 7.74 ± 1.2 | 15.6 ± 5.2 |
| LV EDV (μL) | 40.1 ± 0.1 | 41.2 ± 0.1 | 40.1 ± 0.1 | 30.1 ± 10.0 | 41.0 ± 0.2 | 30.3 ± 10.1 |
| SV (μL) | 27.7 ± 0.3 | 32.7 ± 1.7 | 19.7 ± 1.0 | 18.4 ± 6.1 | 16.6 ± 7.4 | 14.7 ± 5.0 |
| SW (mmHg · μL) | 1130 ± 16 | 2486 ± 292 | 562 ± 152 | 1304 ± 390 | 2283 ± 114 | 407 ± 23 |
| EF (%) | 69.0 ± 0.9 | 79.4 ± 4.0 | 49.1 ± 2.4 | 61.3 ± 0.9 | 81.3 ± 2.9 | 48.6 ± 3.0 |
| CO (μL/min) | 3987 ± 45 | 6828 ± 268 | 1772 ± 199 | 2473 ± 104 | 3829 ± 219 | 1324 ± 455 |

HR, heart rate;
ESPVR and EDPVR, end-systolic and end-diastolic pressure volume relation, respectively;
dP/dtmax and dP/dtmin, maximum rate of left ventricle (LV) pressure rise and fall, respectively;
Pmax, systolic pressure;
ESP, end-systolic pressure;
EDP, end-diastolic pressure;
ESV, end-systolic volume;
EDV, end-diastolic volume;
SV, stroke volume;
SW, stroke work;
EF, ejection fraction;
CO, cardiac output.

TABLE 2

| | Pkd2; CT-DAu-NPs | | | Pkd2; CT-PLGA-NPs | | |
|---|---|---|---|---|---|---|
| | vehicle | epinephrine | diltiazem | vehicle | epinephrine | diltiazem |
| HR (beat/min) | 136 ± 16 | 207 ± 19 | 94 ± 10 | 143 ± 11 | 210 ± 18 | 89 ± 13 |
| ESPVR (mmHg/μL) | 4.4 ± 0.10 | 9.8 ± 1.30 | 1.8 ± 0.33 | 4.3 ± 0.14 | 9.2 ± 2.50 | 2.5 ± 0.59 |
| EDPVR (mmHg/μL) | 0.14 ± 0.01 | 0.14 ± 0.01 | 0.13 ± 0.01 | 0.15 ± 0.02 | 0.19 ± 0.03 | 0.17 ± 0.02 |
| dP/dtmax (mmHg/s) | 5900 ± 320 | 16134 ± 594 | 3356 ± 188 | 5758 ± 233 | 15364 ± 757 | 3776 ± 347 |
| dP/dtmin (mmHg/s) | −1851 ± 99 | −3451 ± 226 | −1403 ± 132 | −2008 ± 199 | −4646 ± 283 | −1793 ± 427 |
| LV Pmax (mmHg) | 54.6 ± 0.3 | 80.7 ± 3.0 | 37.3 ± 2.1 | 53.3 ± 2.1 | 76.8 ± 3.8 | 42.0 ± 3.9 |
| LV ESP (mmHg) | 41.0 ± 0.2 | 60.5 ± 2.2 | 28.0 ± 1.6 | 40.0 ± 1.5 | 57.6 ± 2.8 | 31.5 ± 2.9 |
| LV EDP (mmHg) | 5.7 ± 0.1 | 5.8 ± 0.4 | 5.2 ± 0.1 | 6.2 ± 0.6 | 7.7 ± 1.0 | 6.6 ± 0.8 |
| LV ESV (μL) | 12.4 ± 0.3 | 8.5 ± 1.0 | 21.8 ± 2.7 | 12.4 ± 0.4 | 8.5 ± 0.9 | 18.8 ± 2.8 |
| LV EDV (μL) | 40.0 ± 0.1 | 39.9 ± 0.2 | 40.2 ± 0.5 | 40.1 ± 0.1 | 40.0 ± 0.3 | 40.0 ± 0.1 |
| SV (μL) | 27.7 ± 0.3 | 31.4 ± 1.1 | 18.4 ± 2.2 | 27.7 ± 0.3 | 31.5 ± 0.6 | 21.2 ± 2.9 |

TABLE 2-continued

| | Pkd2; CT-DAu-NPs | | | Pkd2; CT-PLGA-NPs | | |
|---|---|---|---|---|---|---|
| | vehicle | epinephrine | diltiazem | vehicle | epinephrine | diltiazem |
| SW (mmHg · μL) | 1353 ± 52 | 2354 ± 307 | 590 ± 19 | 1305 ± 25 | 2177 ± 118 | 749 ± 53 |
| EF (%) | 69.1 ± 0.8 | 78.7 ± 2.6 | 45.9 ± 6.2 | 69.1 ± 0.9 | 78.8 ± 2.0 | 53.0 ± 7.1 |
| CO (μL/min) | 3767 ± 55 | 6510 ± 448 | 1654 ± 221 | 3975 ± 34 | 6615 ± 110 | 1910 ± 37 |

HR, heart rate;
ESPVR and EDPVR, end-systolic and end-diastolic pressure volume relation, respectively;
dP/dtmax and dP/dtmin, maximum rate of left ventricle (LV) pressure rise and fall, respectively;
Pmax, systolic pressure;
ESP, end-systolic pressure;
EDP, end-diastolic pressure;
ESV, end-systolic volume;
EDV, end-diastolic volume;
SV, stroke volume;
SW, stroke work;
EF, ejection fraction;
CO, cardiac output.

TABLE 3

| | Pkd2; Fenoldopam | | |
|---|---|---|---|
| | vehicle | epinephrine | diltiazem |
| HR (beat/min) | 140 ± 24 | 219 ± 44 | 98 ± 9 |
| ESPVR (mmHg/μL) | 4.4 ± 0.1 | 9.7 ± 0.9 | 2.3 ± 0.1 |
| EDPVR (mmHg/μL) | 0.13 ± 0.01 | 0.16 ± 0.01 | 0.14 ± 0.01 |
| dP/dtmax (mmHg/s) | 7157 ± 211 | 16864 ± 85 | 4020 ± 643 |
| dP/dtmin (mmHg/s) | −1624 ± 24 | −3843 ± 277 | −1537 ± 97 |
| LV Pmax (mmHg) | 66.3 ± 2.0 | 84.3 ± 0.4 | 44.7 ± 0.7 |
| LV ESP (mmHg) | 49.7 ± 1.5 | 63.2 ± 0.3 | 33.5 ± 0.5 |
| LV EDP (mmHg) | 5.0 ± 0.1 | 6.4 ± 0.5 | 5.7 ± 0.2 |
| LV ESV (μL) | 15.0 ± 0.1 | 8.9 ± 0.8 | 19.5 ± 0.6 |
| LV EDV (pL) | 40.0 ± 0.1 | 39.9 ± 0.1 | 40.3 ± 0.8 |
| SV (μL) | 24.9 ± 0.1 | 31.1 ± 0.7 | 20.8 ± 0.8 |
| SW (mmHg · μL) | 1530 ± 20 | 2417 ± 28 | 812 ± 29 |
| EF (%) | 62.5 ± 0.2 | 77.7 ± 2.0 | 51.6 ± 1.4 |
| CO (μL/min) | 3486 ± 81 | 6810 ± 347 | 1873 ± 70 |

HR, heart rate;
ESPVR and EDPVR, end-systolic and end-diastolic pressure volume relation, respectively;
dP/dtmax and dP/dtmin, maximum rate of left ventricle (LV) pressure rise and fall, respectively;
Pmax, systolic pressure;
ESP, end-systolic pressure;
EDP, end-diastolic pressure;
ESV, end-systolic volume;
EDV, end-diastolic volume;
SV, stroke volume;
SW, stroke work;
EF, ejection fraction;
CO, cardiac output.

TABLE 4

| Analytes | Vehicle | CT-DAu-NPs | CT-PLGA-NPs |
|---|---|---|---|
| ALB (g/dL) | 3.4 ± 0.9 | 3.1 ± 0.7 | 3.3 ± 0.6 |
| ALP (U/L) | 56 ± 32 | 38 ± 34 | 59 ± 28 |
| ALT (U/L) | 32 ± 1.6 | 36 ± 1.8 | 45 ± 1.4 |
| AMY (U/L) | 789 ± 43 | 730 ± 41 | 843 ± 51 |
| TBIL (mg/dL) | 0.3 ± 0.1 | 0.3 ± 0.3 | 0.3 ± 0.2 |
| CA (mg/dL) | 9.3 ± 0.8 | 10.2 ± 0.7 | 10.6 ± 0.5 |
| PHOS (mg/dL) | 8.1 ± 2.1 | 9.8 ± 3.3 | 9.0 ± 2.7 |
| CRE (mg/dL) | 0.2 ± 0.06 | 0.3 ± 0.2 | 0.2 ± 0.07 |
| GLU (mg/dL) | 291 ± 54 | 189 ± 65 | 327 ± 57 |
| $Na^+$ (mmol/L) | 149 ± 2.1 | 158 ± 1.9 | 150 ± 2.0 |
| $K^+$ (mmol/L) | 4.9 ± 0.9 | 6.5 ± 0.9 | 5.8 ± 0.6 |
| TP (g/dL) | 4.6 ± 0.6 | 4.4 ± 0.7 | 5.2 ± 0.5 |
| GLOB (g/dL) | 1.4 ± 0.4 | 1.8 ± 0.4 | 1.3 ± 0.2 |

ALB, albumin;
ALP, alkaline phosphatase;
ALT, alanine aminotransferase;
AMY, amylase;
TBIL, total bilirubin;
CA, calcium;
PHOS, phosphorus;
CRE, creatinine;
GLU, glucose;
$Na^+$, sodium;
$K^+$, potassium;
TP, total protein;
GLOB, globulin.

TABLE 5

| | wild-type | | | Pkd2 | | |
|---|---|---|---|---|---|---|
| | vehicle | epinephrine | diltiazem | vehicle | epinephrine | diltiazem |
| HR (beat/min) | 143 ± 14 | 209 ± 15 | 72 ± 19 | 134 ± 17 | 227 ± 17 | 76 ± 9 |
| ESPVR (mmHg/μL) | 5.0 ± 0.04 | 12.4 ± 3.25 | 1.6 ± 0.12 | 3.78 ± 0.07 | 8.02 ± 2.32 | 2.10 ± 0.28 |
| EDPVR (mmHg/μL) | 0.14 ± 0.01 | 0.13 ± 0.01 | 0.18 ± 0.01 | 0.13 ± 0.01 | 0.13 ± 0.01 | 0.13 ± 0.01 |
| dP/dtmax (mmHg/s) | 5408 ± 52 | 16013 ± 524 | 2775 ± 501 | 6285 ± 96 | 14480 ± 453 | 3475 ± 293 |
| dP/dtmin (mmHg/s) | 1765 ± 130 | −3127 ± 85 | −1294 ± 129 | −1735 ± 97 | −3096 ± 82 | −1419 ± 281 |
| LV Pmax (mmHg) | 50.1 ± 0.5 | 80.1 ± 5.1 | 38.2 ± 0.1 | 58.2 ± 0.1 | 72.4 ± 7.3 | 38.6 ± 3.3 |
| LV ESP (mmHg) | 37.5 ± 0.4 | 60.0 ± 3.8 | 23.1 ± 0.4 | 43.6 ± 0.1 | 54.3 ± 5.4 | 29.0 ± 2.5 |
| LV EDP (mmHg) | 5.4 ± 0.4 | 5.2 ± 0.1 | 4.8 ± 2.4 | 5.4 ± 0.1 | 5.2 ± 0.1 | 5.3 ± 0.1 |
| LV ESV (μL) | 10.1 ± 0.1 | 6.8 ± 0.2 | 12.7 ± 0.6 | 15.4 ± 0.3 | 10.1 ± 1.8 | 18.9 ± 1.2 |
| LV EDV (μL) | 40.3 ± 0.1 | 41.2 ± 0.5 | 40.0 ± 0.1 | 40.1 ± 0.1 | 40.9 ± 0.2 | 40.3 ± 0.2 |
| SV (μL) | 30.3 ± 0.1 | 34.3 ± 1.9 | 14.0 ± 0.7 | 24.7 ± 0.3 | 30.9 ± 2.1 | 21.4 ± 1.3 |
| SW (mmHg · μL) | 1345 ± 38 | 2566 ± 394 | 365 ± 83 | 1304 ± 17 | 2078 ± 121 | 715 ± 17 |

TABLE 5-continued

| | wild-type | | | Pkd2 | | |
|---|---|---|---|---|---|---|
| | vehicle | epinephrine | diltiazem | vehicle | epinephrine | diltiazem |
| EF (%) | 74.8 ± 0.1 | 83.3 ± 3.6 | 52.5 ± 2.7 | 61.6 ± 0.7 | 75.4 ± 4.6 | 53.1 ± 3.1 |
| CO (μL/min) | 4338 ± 21 | 7158 ± 299 | 1261 ± 139 | 3310 ± 51 | 7017 ± 703 | 1928 ± 118 |

HR, heart rate;
ESPVR and EDPVR, end-systolic and end-diastolic pressure volume relation, respectively;
dP/dtmax and dP/dtmin, maximum rate of left ventricle (LV) pressure rise and fall, respectively;
Pmax, systolic pressure;
ESP, end-systolic pressure;
EDP, end-diastolic pressure;
ESV, end-systolic volume;
EDV, end-diastolic volume;
SV, stroke volume;
SW, stroke work;
EF, ejection fraction;
CO, cardiac output.

TABLE 6

| | Pkd2; Fenoldopam | | |
|---|---|---|---|
| | vehicle | epinephrine | diltiazem |
| HR (beat/min) | 136 ± 26 | 216 ± 47 | 94 ± 11 |
| ESPVR (mmHg/μL) | 4.6 ± 0.04 | 9.8 ± 0.88 | 2.21 ± 0.03 |
| EDPVR (mmHg/μL) | 0.13 ± 0.01 | 0.16 ± 0.01 | 0.14 ± 0.01 |
| dP/dtmax (mmHg/s) | 7524 ± 71 | 17130 ± 239 | 4020 ± 642 |
| dP/dtmin (mmHg/s) | −1625 ± 27 | −3844 ± 278 | −1537 ± 97 |
| LV Pmax (mmHg) | 69.7 ± 0.7 | 85.6 ± 1.2 | 44.7 ± 0.7 |
| LV ESP (mmHg) | 52.2 ± 0.5 | 64.2 ± 0.9 | 35.5 ± 0.5 |
| LV EDP (mmHg) | 5.0 ± 0.1 | 6.4 ± 0.5 | 5.7 ± 0.2 |
| LV ESV (μL) | 15.0 ± 0.1 | 8.9 ± 0.8 | 20.2 ± 0.1 |
| LV EDV (μL) | 40.0 ± 0.1 | 39.9 ± 0.1 | 40.0 ± 0.4 |
| SV (μL) | 25.0 ± 0.1 | 31.0 ± 0.8 | 19.8 ± 0.3 |
| SW (mmHg · μL) | 1616 ± 70 | 2569 ± 53 | 772 ± 10 |
| EF (%) | 62.5 ± 0.2 | 77.7 ± 2.0 | 49.5 ± 0.3 |
| CO (μL/min) | 3402 ± 92 | 6707 ± 373 | 1783 ± 32 |

HR, heart rate; ESPVR and EDPVR, end-systolic and end-diastolic pressure volume relation, respectively;
dP/dtmax and dP/dtmin, maximum rate of left ventricle (LV) pressure rise and fall, respectively;
Pmax, systolic pressure;
ESP, end-systolic pressure;
EDP, end-diastolic pressure;
ESV, end-systolic volume;
EDV, end-diastolic volume;
SV, stroke volume;
SW, stroke work;
EF, ejection fraction;
CO, cardiac output.

TABLE 7

| | Pkd2; CT-$Fe_2O_3$-NPs | | | Pkd2; CT-M-$Fe_2O_3$-NPs | | |
|---|---|---|---|---|---|---|
| | vehicle | epinephrine | diltiazem | vehicle | epinephrine | diltiazem |
| HR (beat/min) | 143 ± 16 | 239 ± 13 | 92 ± 15 | 117 ± 19 | 252 ± 34 | 82 ± 9 |
| ESPVR (mmHg/L) | 4.4 ± 0.09 | 9.3 ± 1.31 | 2.2 ± 0.25 | 4.6 ± 0.22 | 10.5 ± 2.63 | 1.9 ± 0.40 |
| EDPVR (mmHg/μL) | 0.14 ± 0.01 | 0.14 ± 0.01 | 0.04 ± 0.01 | 0.12 ± 0.01 | 0.13 ± 0.01 | 0.12 ± 0.01 |
| dP/dtmax (mmHg/s) | 5900 ± 38 | 15499 ± 857 | 3454 ± 137 | 5813 ± 178 | 15283 ± 940 | 3348 ± 180 |
| dP/dtmin (mmHg/s) | −1767 ± 43 | −3498 ± 159 | −1497 ± 62 | −1603 ± 365 | −3146 ± 186 | −1290 ± 159 |
| LV Pmax (mmHg) | 54.6 ± 0.4 | 77.5 ± 4.3 | 39.4 ± 1.5 | 53.8 ± 1.6 | 76.4 ± 4.7 | 37.2 ± 2.0 |
| LV ESP (mmHg) | 41.0 ± 0.3 | 58.1 ± 3.2 | 28.8 ± 1.1 | 40.4 ± 1.2 | 57.3 ± 3.5 | 27.9 ± 1.5 |
| LV EDP (mmHg) | 5.4 ± 0.1 | 5.8 ± 0.3 | 5.5 ± 0.1 | 5.0 ± 0.3 | 5.2 ± 0.1 | 4.8 ± 0.1 |
| LV ESV (μL) | 12.4 ± 0.3 | 8.5 ± 0.8 | 17.8 ± 2.3 | 11.7 ± 0.9 | 7.9 ± 1.3 | 21.0 ± 3.0 |
| LV EDV (μL) | 40.4 ± 0.1 | 40.8 ± 0.6 | 40.8 ± 0.6 | 40.1 ± 0.2 | 40.8 ± 0.5 | 40.4 ± 0.1 |
| SV (μL) | 27.9 ± 0.3 | 32.3 ± 0.4 | 23.0 ± 2.6 | 28.4 ± 1.0 | 32.8 ± 1.8 | 19.5 ± 3.1 |
| SW (mmHg · μL) | 1372 ± 41 | 2313 ± 78 | 755 ± 172 | 1388 ± 83 | 2337 ± 69 | 632 ± 25 |

TABLE 7-continued

| | Pkd2; $CT-Fe_2O_3$-NPs | | | Pkd2; $CT-M-Fe_2O_3$-NPs | | |
|---|---|---|---|---|---|---|
| | vehicle | epinephrine | diltiazem | vehicle | epinephrine | diltiazem |
| EF (%) | 69.1 ± 0.8 | 79.1 ± 1.7 | 56.3 ± 5.9 | 70.7 ± 2.3 | 80.5 ± 3.5 | 48.2 ± 7.8 |
| CO (μL/min) | 3989 ± 45 | 7718 ± 566 | 2071 ± 401 | 3334 ± 201 | 8279 ± 122 | 1754 ± 279 |

HR, heart rate;
ESPVR and EDPVR, end-systolic and end-diastolic pressure volume relation, respectively;
dP/dtmax and dP/dtmin, maximum rate of left ventricle (LV) pressure rise and fall, respectively;
Pmax, systolic pressure;
ESP, end-systolic pressure;
EDP, end-diastolic pressure;
ESV, end-systolic volume;
EDV, end-diastolic volume;
SV, stroke volume;
SW, stroke work;
EF, ejection fraction;
CO, cardiac output.

TABLE 8

| | IFT88 | | | IFT88; Fenoldopam | | |
|---|---|---|---|---|---|---|
| | vehicle | epinephrine | diltiazem | vehicle | epinephrine | diltiazem |
| HR (beat/min) | 140 ± 23 | 213 ± 24 | 101 ± 17 | 144 ± 32 | 241 ± 22 | 104 ± 20 |
| ESPVR (mmHg/μL) | 4.3 ± 0.3 | 10.0 ± 1.2 | 2.0 ± 0.01 | 5.4 ± 0.7 | 10.0 ± 1.1 | 2.1 ± 0.1 |
| EDPVR (mmHg/μL) | 0.12 ± 0.01 | 0.16 ± 0.02 | 0.14 ± 0.01 | 0.13 ± 0.01 | 0.13 ± 0.01 | 0.13 ± 0.01 |
| dP/dtmax (mmHg/s) | 7142 ± 429 | 16797 ± 383 | 3635 ± 157 | 7819 ± 140 | 17206 ± 578 | 3619 ± 111 |
| dP/dtmin (mmHg/s) | −1538 ± 41 | −3795 ± 548 | −1475 ± 218 | −1658 ± 190 | −3180 ± 120 | −1372 ± 330 |
| LV Pmax (mmHg) | 66.1 ± 4.0 | 84.0 ± 2.0 | 40.4 ± 0.2 | 72.4 ± 1.3 | 56.0 ± 0.3 | 40.2 ± 0.1 |
| LV ESP (mmHg) | 49.6 ± 3.0 | 63.0 ± 1.5 | 30.3 ± 0.1 | 54.3 ± 1.0 | 64.5 ± 0.2 | 30.2 ± 0.1 |
| LV EDP (mmHg) | 4.7 ± 0.1 | 6.3 ± 1.0 | 5.5 ± 0.4 | 5.1 ± 0.1 | 5.3 ± 0.2 | 5.1 ± 0.1 |
| LV ESV (μL) | 15.5 ± 0.3 | 8.7 ± 1.1 | 20.0 ± 0.2 | 13.8 ± 1.4 | 8.7 ± 0.9 | 19.4 ± 0.7 |
| LV EDV (μL) | 40.4 ± 0.2 | 40.2 ± 0.1 | 40.1 ± 0.1 | 40.1 ± 0.1 | 40.2 ± 0.1 | 40.0 ± 0.1 |
| SV (μL) | 24.9 ± 0.1 | 35.5 ± 1.0 | 20.1 ± 0.1 | 26.3 ± 1.4 | 31.4 ± 0.8 | 20.6 ± 0.7 |
| SW (mmHg · μL) | 1528 ± 63 | 2448 ± 121 | 701 ± 97 | 1767 ± 56 | 2538 ± 16 | 725 ± 20 |
| EF (%) | 61.6 ± 0.4 | 78.5 ± 2.7 | 50.1 ± 0.1 | 65.5 ± 3.5 | 78.2 ± 2.2 | 51.6 ± 1.7 |
| CO (μL/min) | 3478 ± 121 | 6717 ± 247 | 1808 ± 71 | 3780 ± 437 | 7590 ± 176 | 1857 ± 137 |

HR, heart rate;
ESPVR and EDPVR, end-systolic and end-diastolic pressure volume relation, respectively;
dP/dtmax and dP/dtmin, maximum rate of left ventricle (LV) pressure rise and fall, respectively;
Pmax, systolic pressure;
ESP, end-systolic pressure;
EDP, end-diastolic pressure;
ESV, end-systolic volume;
EDV, end-diastolic volume;
SV, stroke volume;
SW, stroke work;
EF, ejection fraction;
CO, cardiac output.

TABLE 9

| | IFT88; $cCT-Fe_2O_3$-NPs | | | IFT88; $CT-M-Fe_2O_3$-NPs | | |
|---|---|---|---|---|---|---|
| | vehicle | epinephrine | diltiazem | vehicle | epinephrine | diltiazem |
| HR (beat/min) | 153 ± 34 | 257 ± 30 | 108 ± 25 | 166 ± 26 | 266 ± 21 | 106 ± 34 |
| ESPVR (mmHg/μL) | 4.5 ± 0.1 | 10.0 ± 1.5 | 2.1 ± 0.1 | 4.9 ± 0.1 | 10.1 ± 1.1 | 2.2 ± 0.1 |
| EDPVR (mmHg/μL) | 0.16 ± 0.02 | 0.19 ± 0.04 | 0.18 ± 0.03 | 0.15 ± 0.01 | 0.14 ± 0.01 | 0.21 ± 0.04 |
| dP/dtmax (mmHg/s) | 7754 ± 186 | 17428 ± 497 | 3741 ± 110 | 7615 ± 168 | 17190 ± 199 | 3999 ± 159 |
| dP/dtmin (mmHg/s) | −2045 ± 263 | −4648 ± 882 | −1914 ± 561 | −1981 ± 180 | −3439 ± 229 | −2227 ± 902 |
| LV Pmax (mmHg) | 71.8 ± 1.7 | 87.1 ± 2.5 | 41.6 ± 1.2 | 70.5 ± 1.6 | 86.0 ± 0.5 | 43.3 ± 1.8 |
| LV ESP (mmHg) | 53.8 ± 1.3 | 65.4 ± 1.9 | 31.2 ± 0.9 | 52.9 ± 1.5 | 64.5 ± 1.4 | 32.5 ± 1.3 |
| LV EDP (mmHg) | 6.3 ± 0.8 | 7.7 ± 1.5 | 7.1 ± 1.0 | 6.1 ± 0.6 | 5.7 ± 0.4 | 8.2 ± 1.7 |
| LV ESV (μL) | 16.0 ± 0.6 | 9.0 ± 1.0 | 20.2 ± 0.1 | 14.5 ± 0.5 | 8.7 ± 0.9 | 19.4 ± 0.6 |
| LV EDV (μL) | 40.1 ± 0.1 | 40.7 ± 0.4 | 40.1 ± 0.1 | 41.2 ± 0.4 | 40.0 ± 1.3 | 40.1 ± 0.1 |
| SV (L) | 24.2 ± 0.6 | 31.7 ± 0.7 | 19.9 ± 0.1 | 26.7 ± 0.4 | 31.3 ± 1.9 | 20.7 ± 0.6 |

TABLE 9-continued

| | IFT88; cCT-$Fe_2O_3$-NPs | | | IFT88; CT-M-$Fe_2O_3$-NPs | | |
|---|---|---|---|---|---|---|
| | vehicle | epinephrine | diltiazem | vehicle | epinephrine | diltiazem |
| SW (mmHg · µL) | 1582 ± 45 | 2519 ± 113 | 688 ± 45 | 1720 ± 14 | 2507 ± 67 | 724 ± 77 |
| EF (%) | 60.2 ± 1.5 | 77.9 ± 2.4 | 49.7 ± 0.2 | 64.9 ± 0.9 | 78.1 ± 2.8 | 51.5 ± 1.4 |
| CO (µL/min) | 3711 ± 198 | 8147 ± 212 | 1794 ± 12 | 4439 ± 103 | 8317 ± 401 | 1859 ± 19 |

HR, heart rate;
ESPVR and EDPVR, end-systolic and end-diastolic pressure volume relation, respectively;
dP/dtmax and dP/dtmin, maximum rate of left ventricle (LV) pressure rise and fall, respectively;
Pmax, systolic pressure;
ESP, end-systolic pressure;
EDP, end-diastolic pressure;
ESV, end-systolic volume;
EDV, end-diastolic volume;
SV, stroke volume;
SW, stroke work;
EF, ejection fraction;
CO, cardiac output.

TABLE 10

| | IFT88; CT-$Fe_2O_3$-NPs | | |
|---|---|---|---|
| | vehicle | epinephrine | diltiazem |
| HR (beat/min) | 145 ± 39 | 243 ± 32 | 104 ± 24 |
| ESPVR (mmHg/µL) | 5.1 ± 0.4 | 9.7 ± 1.4 | 2.2 ± 0.1 |
| EDPVR (mmHg/µL) | 0.13 ± 0.01 | 0.14 ± 0.01 | 0.21 ± 0.04 |
| dP/dtmax (mmHg/s) | 7966 ± 203 | 17265 ± 184 | 3966 ± 105 |
| dP/dtmin (mmHg/s) | −1738 ± 97 | −3483 ± 239 | −2252 ± 806 |
| LV Pmax (mmHg) | 73.8 ± 1.9 | 86.3 ± 0.9 | 44.1 ± 1.2 |
| LV ESP (mmHg) | 55.3 ± 1.4 | 64.7 ± 0.7 | 33.1 ± 0.9 |
| LV EDP (mmHg) | 5.4 ± 0.3 | 5.8 ± 0.4 | 8.3 ± 1.5 |
| LV ESV (µL) | 14.5 ± 0.8 | 9.3 ± 1.3 | 19.8 ± 0.7 |
| LV EDV (µL) | 40.3 ± 0.3 | 40.2 ± 0.1 | 40.5 ± 0.2 |
| SV (µL) | 25.9 ± 0.6 | 30.9 ± 1.2 | 20.6 ± 0.6 |
| SW (mmHg · µL) | 1769 ± 40 | 2488 ± 62 | 737 ± 63 |
| EF (%) | 64.1 ± 1.7 | 76.9 ± 3.1 | 50.9 ± 1.6 |
| CO (µL/min) | 3754 ± 244 | 7513 ± 378 | 1856 ± 140 |

HR, heart rate;
ESPVR and EDPVR, end-systolic and end-diastolic pressure volume relation, respectively;
dP/dtmax and dP/dtmin, maximum rate of left ventricle (LV) pressure rise and fall, respectively;
Pmax, systolic pressure;
ESP, end-systolic pressure;
EDP, end-diastolic pressure;
ESV, end-systolic volume;
EDV, end-diastolic volume;
SV, stroke volume;
SW, stroke work;
EF, ejection fraction;
CO, cardiac output.

TABLE 11

| Analytes | Vehicle | CT-M-$Fe_2O_3$-NPs |
|---|---|---|
| WBC ($\times 10^9$/L) | 9.9 ± 2.4 | 9.4 ± 3.1 |
| LYM ($\times 10^9$/L) | 9.1 ± 2.6 | 9.0 ± 2.9 |
| MON ($\times 10^9$/L) | 0.09 ± 0.01 | 0.08 ± 0.03 |
| NEU ($\times 10^9$/L) | 0.41 ± 0.19 | 0.45 ± 0.23 |

TABLE 11-continued

| Analytes | Vehicle | CT-M-$Fe_2O_3$-NPs |
|---|---|---|
| RBC ($\times 10^{12}$/L) | 9.94 ± 0.3 | 9.82 ± 0.4 |
| HGB (g/dL) | 13.9 ± 1.2 | 13.8 ± 1.8 |
| HCT (%) | 42.1 ± 0.6 | 42.0 ± 0.8 |
| MCV (fl) | 43.0 ± 5.2 | 41.3 ± 4.3 |
| ALB (g/dL) | 3.5 ± 0.7 | 3.2 ± 0.9 |
| ALP (U/L) | 47 ± 38 | 49 ± 27 |
| ALT (U/L) | 34 ± 1.5 | 29 ± 1.9 |
| AMY (U/L) | 801 ± 46 | 803 ± 38 |
| TBIL (mg/dL) | 0.3 ± 0.2 | 0.3 ± 0.2 |
| CA (mg/dL) | 10.2 ± 0.9 | 8.7 ± 0.6 |
| PHOS (mg/dL) | 7.9 ± 1.9 | 7.8 ± 2.3 |
| CRE (mg/dL) | 0.2 ± 0.07 | 0.3 ± 0.1 |
| GLU (mg/dL) | 304 ± 53 | 287 ± 43 |
| $Na^+$ (mmol/L) | 163 ± 2.4 | 155 ± 1.8 |
| $K^+$ (mmol/L) | 4.4 ± 0.7 | 4.5 ± 0.7 |
| TP (g/dL) | 5.1 ± 0.4 | 4.7 ± 0.9 |
| GLOB (g/dL) | 1.7 ± 0.6 | 1.2 ± 0.2 |

WBC, white blood cell;
LYM, lymphocyte;
MON, monocyte;
NEU, neutrophil;
RBC, red blood cell;
HGB, hemoglobin;
HCT, hematocrit;
MCV, mean corpuscular volume;
ALB, albumin;
ALP, alkaline phosphatase;
ALT, alanine aminotransferase;
AMY, amylase;
TBIL, total bilirubin;
CA, calcium;
PHOS, phosphorus;
CRE, creatinine;
GLU, glucose;
$Na^+$, sodium;
$K^+$, potassium;
TP, total protein;
GLOB, globulin.

What is claimed is:

1. A composition comprising:

cilia-targeting nanoparticles consisting of a core polymeric nanoparticle, a polyethylene glycol (PEG) coating on the core polymeric nanoparticle, a cilia-targeting antibody, a fatty acid coating between the core polymeric nanoparticle and the PEG coating, and a pharmaceutical agent.

2. The composition according to claim 1, wherein the core polymeric nanoparticle is a poly lactic-co-glycolic acid (PLGA) nanoparticle.

3. The composition according to claim 1, wherein the fatty acid coating is oleic acid.

4. The composition according to claim 1, wherein the core polymeric nanoparticle is biocompatible.

5. The composition according to claim 1, wherein the PEG is an activated PEG.

6. The composition according to claim 5, wherein the activated PEG has a molecular weight from 3,000 to 10,000 daltons.

7. The composition according to claim 6, wherein the activated PEG has a molecular weight from 4,000 to 8,000 daltons.

8. The composition according to claim 1, wherein the cilia-targeting antibody is specific for dopamine-receptor type-5.

9. A method of treating a ciliopathy in a subject in need thereof comprising administering to a subject having a ciliopathy the cilia-targeting nanoparticles according to claim 1.

10. The method according to claim 9, wherein the ciliopathy is a kidney disorder, a liver disorder, or a cardiovascular disorder.

11. The method according to claim 9, wherein the ciliopathy is Alström syndrome, Bardet-Biedl syndrome, Joubert syndrome, Meckel-Gruber syndrome, nephronophthisis, orofaciodigital syndrome, Senior-Loken syndrome, polycystic kidney disease (ADPKD and ARPKD), primary ciliary dyskinesia (Kartagener syndrome), asphyxiating thoracic dysplasia (Jeune syndrome), Marden-Walker syndrome, situs inversus/isomerism, conorenal syndrome, Ellis-van Creveld syndrome, juvenile mycoclonic epilepsy, polycystic liver disease, and retinitis pigmentosa.

12. The method according to claim 9, wherein the ciliopathy is treated by reducing hypertension.

13. The method according to claim 9, wherein the pharmaceutical agent is a dopamine receptor agonist.

14. A nanoparticle delivery formulation for targeting cilia comprising:

a plurality of cilia-targeting nanoparticles consisting of a core polymeric nanoparticle, a polyethylene glycol (PEG) coating on the core polymeric nanoparticle, a cilia-targeting antibody, a fatty acid coating between the core polymeric nanoparticle and the PEG coating, and a pharmaceutical agent.

15. A nanoparticle delivery formulation for ciliopathy treatment comprising:

a plurality of cilia-targeting nanoparticles consisting of a core polymeric nanoparticle, a polyethylene glycol (PEG) coating on the core polymeric nanoparticle, a cilia-targeting antibody, a fatty acid coating between the core polymeric nanoparticle and the PEG coating, and a dopamine receptor agonist.

* * * * *